US011046728B2

(12) United States Patent
Martinez Botella et al.

(10) Patent No.: US 11,046,728 B2
(45) Date of Patent: Jun. 29, 2021

(54) NEUROACTIVE STEROIDS, COMPOSITIONS, AND USES THEREOF

(71) Applicant: Sage Therapeutics, Inc., Cambridge, MA (US)

(72) Inventors: Gabriel Martinez Botella, Wayland, MA (US); Boyd L. Harrison, Princeton Junction, NJ (US); Albert Jean Robichaud, Boston, MA (US); Francesco G. Salituro, Marlborough, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/393,396

(22) Filed: Apr. 24, 2019

(65) Prior Publication Data
US 2020/0017542 A1 Jan. 16, 2020

Related U.S. Application Data

(60) Division of application No. 15/698,151, filed on Sep. 7, 2017, now Pat. No. 10,323,059, which is a continuation of application No. 14/906,043, filed as application No. PCT/US2014/047246 on Jul. 18, 2014, now abandoned.

(60) Provisional application No. 61/856,592, filed on Jul. 19, 2013.

(51) Int. Cl.
*C07J 41/00* (2006.01)
*A61K 45/06* (2006.01)
*A61K 31/56* (2006.01)
*A61K 31/565* (2006.01)
*A61K 31/567* (2006.01)
*C07J 1/00* (2006.01)
*C07J 5/00* (2006.01)
*C07J 11/00* (2006.01)
*C07J 21/00* (2006.01)
*C07J 31/00* (2006.01)
*C07J 51/00* (2006.01)
*C07J 71/00* (2006.01)

(52) U.S. Cl.
CPC .......... *C07J 41/0094* (2013.01); *A61K 31/56* (2013.01); *A61K 31/565* (2013.01); *A61K 31/567* (2013.01); *A61K 45/06* (2013.01); *C07J 1/0011* (2013.01); *C07J 1/0022* (2013.01); *C07J 5/0053* (2013.01); *C07J 11/00* (2013.01); *C07J 21/008* (2013.01); *C07J 31/006* (2013.01); *C07J 51/00* (2013.01); *C07J 71/001* (2013.01)

(58) Field of Classification Search
CPC .................................................. C07J 41/0094
See application file for complete search history.

(56) References Cited

U.S. PATENT DOCUMENTS

| | | | |
|---|---|---|---|
| 2,856,415 | A | 10/1958 | Mihina |
| 3,169,134 | A | 2/1965 | Klimstra et al. |
| 3,206,459 | A | 9/1965 | Cross |
| 3,580,937 | A | 5/1971 | Campbell et al. |
| 3,943,124 | A | 3/1976 | Phillipps et al. |
| 3,983,111 | A | 9/1976 | Phillipps et al. |
| 3,998,829 | A | 12/1976 | Phillips et al. |
| 4,029,777 | A | 6/1977 | Engelfried et al. |
| 4,071,625 | A | 1/1978 | Grunwell et al. |
| 4,179,336 | A | 12/1979 | Weber et al. |
| 4,192,871 | A | 3/1980 | Phillipps et al. |
| 4,389,345 | A | 6/1983 | Lenz |
| 5,593,983 | A | 1/1997 | Campbell |
| 5,721,227 | A | 2/1998 | Melloni et al. |
| 5,925,630 | A | 7/1999 | Upasani et al. |
| 5,935,545 | A | 8/1999 | Leary et al. |

(Continued)

FOREIGN PATENT DOCUMENTS

| | | |
|---|---|---|
| CA | 2831054 A1 | 12/2013 |
| CN | 1190404 A | 8/1998 |

(Continued)

OTHER PUBLICATIONS

Phillips et al (1978): STN International (Columbus, Ohio), HCAPLUS database, Accession No. 1978: 38078.*

(Continued)

*Primary Examiner* — Golam M Shameem
(74) *Attorney, Agent, or Firm* — Honigman LLP; Andrew N. Weber; Jonathan P. O'Brien

(57) ABSTRACT

Described herein are neuroactive steroids of the Formula (I):

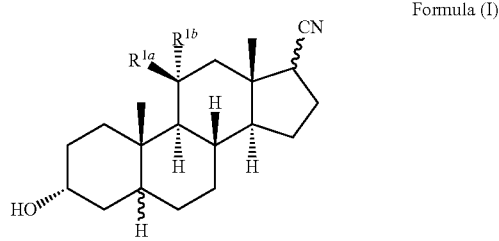

Formula (I)

or a pharmaceutically acceptable salt thereof; wherein $R^{1a}$ and $R^{1b}$ are as defined herein. Such compounds are envisioned, in certain embodiments, to behave as GABA modulators. The present invention also provides pharmaceutical compositions comprising a compound of the present invention and methods of use and treatment, e.g., such for inducing sedation and/or anesthesia.

14 Claims, 8 Drawing Sheets

(56) References Cited

U.S. PATENT DOCUMENTS

| | | | |
|---|---|---|---|
| 5,939,545 | A | 8/1999 | Upasani et al. |
| 6,133,280 | A | 10/2000 | Brodie et al. |
| 6,143,736 | A | 11/2000 | Upasani et al. |
| 6,277,838 | B1 | 8/2001 | Upasani et al. |
| 6,717,002 | B2 | 4/2004 | Yano et al. |
| 6,844,456 | B2 | 1/2005 | Covey |
| 7,064,116 | B2 | 6/2006 | Calogeropoulou et al. |
| 7,781,421 | B2 | 8/2010 | Covey et al. |
| 8,759,330 | B2 | 6/2014 | Covey et al. |
| 8,939,545 | B2 | 1/2015 | Tunmore et al. |
| 9,156,876 | B2 | 10/2015 | Covey |
| 9,365,611 | B2 | 6/2016 | Martinez Botella et al. |
| 9,512,165 | B2 | 12/2016 | Martinez Botella et al. |
| 9,630,986 | B2 | 4/2017 | Covey et al. |
| 9,725,481 | B2 | 8/2017 | Martinez Botella et al. |
| 9,765,110 | B2 | 9/2017 | Covey |
| 10,246,482 | B2 | 4/2019 | Harrison et al. |
| 10,323,059 | B2 * | 6/2019 | Martinez Botella ... A61K 31/56 |
| 2002/0091112 | A1 | 7/2002 | Menzenbach et al. |
| 2005/0176976 | A1 | 8/2005 | Calogeropoulou et al. |
| 2006/0094696 | A1 | 5/2006 | Leese et al. |
| 2007/0014719 | A1 | 1/2007 | Reading et al. |
| 2008/0269183 | A1 | 10/2008 | Mellon et al. |
| 2009/0048218 | A1 | 2/2009 | Kuhnke et al. |
| 2010/0152840 | A1 | 6/2010 | Seguin et al. |
| 2010/0234335 | A1 | 9/2010 | Gravanis et al. |
| 2010/0317638 | A1 | 12/2010 | Covey et al. |
| 2011/0152840 | A1 | 6/2011 | Lee et al. |
| 2011/0172242 | A1 | 7/2011 | Helton et al. |
| 2014/0017675 | A1 | 1/2014 | Ito |
| 2014/0050789 | A1 | 2/2014 | Rogawski et al. |
| 2014/0094619 | A1 | 4/2014 | Runyon et al. |
| 2014/0148412 | A1 | 5/2014 | Hogenkamp |
| 2014/0235600 | A1 | 8/2014 | Covey et al. |
| 2014/0249120 | A1 | 9/2014 | Covey et al. |
| 2014/0275241 | A1 | 9/2014 | Covey |
| 2015/0291654 | A1 | 10/2015 | Upasani et al. |
| 2015/0315230 | A1 | 11/2015 | Covey et al. |
| 2016/0068563 | A1 | 3/2016 | Martinez Botella et al. |
| 2016/0083418 | A1 | 3/2016 | Martinez Botella et al. |
| 2016/0108080 | A1 | 4/2016 | Martinez Botella et al. |
| 2016/0229887 | A1 | 8/2016 | Martinez Botella et al. |
| 2017/0233433 | A1 | 8/2017 | Martinez Botella et al. |
| 2017/0246191 | A1 | 8/2017 | Martinez Botella et al. |
| 2018/0071315 | A1 | 3/2018 | Cashman et al. |
| 2019/0160078 | A1 | 5/2019 | Masuoka et al. |

FOREIGN PATENT DOCUMENTS

| | | | |
|---|---|---|---|
| CN | 101412742 A | | 4/2009 |
| CN | 101624414 A | | 1/2010 |
| CN | 104136452 A | | 11/2014 |
| CN | 108727453 A | | 11/2018 |
| DE | 2330342 A1 | | 1/1974 |
| DE | 2526373 A1 | | 12/1976 |
| DE | 2700267 A1 | | 7/1977 |
| DE | 2632677 A1 | | 1/1978 |
| EP | 0104489 A1 | | 4/1984 |
| EP | 0554436 A1 | | 8/1993 |
| EP | 0656365 A1 | | 6/1995 |
| EP | 0701444 A1 | | 3/1996 |
| EP | 1038880 A2 | | 9/2000 |
| FR | 1994 M | | 9/1963 |
| GB | 1380246 A | | 1/1975 |
| GB | 1430942 A | | 4/1976 |
| GB | 1494097 A | | 12/1977 |
| GB | 1538869 A | | 1/1979 |
| GB | 1570394 A | | 7/1980 |
| GB | 1581234 A | | 12/1980 |
| GB | 1581235 A | | 12/1980 |
| RU | 2194712 C2 | | 12/2002 |
| RU | 2243232 C2 | | 12/2004 |
| RU | 2010100334 A | | 7/2011 |
| RU | 2675855 C2 | | 12/2018 |
| WO | 1991016897 A1 | | 11/1991 |
| WO | 9303732 A1 | | 3/1993 |
| WO | 9305786 A1 | | 4/1993 |
| WO | 9318053 A1 | | 9/1993 |
| WO | 9427608 A1 | | 12/1994 |
| WO | 1995021617 A1 | | 8/1995 |
| WO | 1996003421 A1 | | 2/1996 |
| WO | 1996016076 A1 | | 5/1996 |
| WO | 9640043 A2 | | 12/1996 |
| WO | 9805337 A1 | | 2/1998 |
| WO | 0066614 A1 | | 11/2000 |
| WO | 2005051972 A1 | | 6/2005 |
| WO | 2005105822 A2 | | 11/2005 |
| WO | 2006037016 A2 | | 4/2006 |
| WO | 2006131392 A1 | | 12/2006 |
| WO | 2008151745 A1 | | 12/2008 |
| WO | 2008157460 A1 | | 12/2008 |
| WO | 2010003391 A2 | | 1/2010 |
| WO | 2010054158 A2 | | 5/2010 |
| WO | 2010107815 A1 | | 9/2010 |
| WO | 2012013816 A1 | | 2/2012 |
| WO | 2012083090 A2 | | 6/2012 |
| WO | 2012109752 A1 | | 8/2012 |
| WO | 2012110010 A1 | | 8/2012 |
| WO | 2012116290 A2 | | 8/2012 |
| WO | 2013019711 A2 | | 2/2013 |
| WO | 2013036835 A1 | | 3/2013 |
| WO | 2013056181 A1 | | 4/2013 |
| WO | 2013188792 A2 | | 12/2013 |
| WO | 2013192097 A1 | | 12/2013 |
| WO | 2014058736 A1 | | 4/2014 |
| WO | 2014071449 A1 | | 5/2014 |
| WO | 2014100228 A1 | | 6/2014 |
| WO | 2014108808 A2 | | 7/2014 |
| WO | 2014122480 A1 | | 8/2014 |
| WO | 2014169831 A1 | | 10/2014 |
| WO | 2014169832 A1 | | 10/2014 |
| WO | 2014169833 A1 | | 10/2014 |
| WO | 2014169836 A1 | | 10/2014 |
| WO | 2015010054 A2 | | 1/2015 |
| WO | 2015027227 A1 | | 2/2015 |
| WO | 2015180679 A1 | | 12/2015 |
| WO | 2015195962 A1 | | 12/2015 |
| WO | 2016036724 A1 | | 3/2016 |
| WO | 2016061527 A1 | | 4/2016 |
| WO | 2016061537 A1 | | 4/2016 |
| WO | 2016082789 A1 | | 6/2016 |
| WO | 2016123056 A1 | | 8/2016 |
| WO | 2016131414 A1 | | 8/2016 |
| WO | 2016134301 A2 | | 8/2016 |
| WO | 2016209847 A1 | | 12/2016 |
| WO | 2017044659 A1 | | 3/2017 |
| WO | 2017066626 A1 | | 4/2017 |
| WO | 2017087864 A1 | | 5/2017 |
| WO | 2017156103 A1 | | 9/2017 |
| WO | 2017156418 A1 | | 9/2017 |
| WO | 2018013613 A1 | | 1/2018 |
| WO | 2018013615 A1 | | 1/2018 |
| WO | 2018039378 A1 | | 3/2018 |
| WO | 2019018119 A1 | | 1/2019 |
| WO | 2019045121 A1 | | 3/2019 |
| WO | 2019051264 A1 | | 3/2019 |
| WO | 2019094724 A1 | | 5/2019 |

OTHER PUBLICATIONS

Knox et al., "Steroids. CCLXXVIII. Reductions of 19-substituted androst-4-en-3-ones and related compounds", Journal of Organic Chemistry, 1965, vol. 30, No. 7, pp. 2198-2205.

Krafft et al., "Synthesis of the C/D/E and A/B Rings of Xestobergsterol—(A)", Journal of Organic Chemistry, American Chemical Society, vol. 64, No. 7, (1999), pp. 2475-2485.

Krishnan et al., "Neurosteroid Analogues. Chapter 17. Inverted Binding Orientations of Androsterone Enantiomers at the Steroid Potentiation Site on γ-Aminobutyric Acid Type A Receptors", Journal of Medicinal Chemistry, 2012, vol. 55, No. 3, pp. 1334-1345.

Lehmann et al., "Schweinegallensäuren Der Abbau von Hyocholsäure zu Pregnanderivaten", vol. 32, No. 3-4, (1966), pp. 217-224.

(56) References Cited

OTHER PUBLICATIONS

Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Mariangela et al., "The influence of neuroactive steroid lipophilicity on gabaa receptor modulation: Evidence for a low-affinity interaction", Journal of Neurophysiology, 2009, vol. 102, No. 2, pp. 1254-1264.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Möhler, "The GABA system in anxiety and depression and its therapeutic potential", Neuropharmacology, (2012) 62; pp. 42-53.
Nicoletti et al., "Synthesis and GABAA receptor activity of 6-oxa-analogs of neurosteroids", Steroids, Elsevier Science Publishers 2000, vol. 65, No. 6, pp. 349-356.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem CID: 70249446, [database online], created Dec. 1, 2012 [retrieved on Mar. 21, 2018]. Retrieved from the National Center for Biotechnology Information, PubChem Compound Database, using internet URL: <https://pubchem.ncbi.nlm.nikgovicompound/70249446>.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.
Rogawski et al., "Neuroactive Steroids for the Treatment of Status Epilepticus", Epilepsia (2013), vol. 54, No. 6, pp. 93-98.
Rongone et al., "In vivo metabolism of d-homotestosterone", Steroids, vol. 1, No. 6, 1963, pp. 664-669.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fff1f35-fc4c-4eb2-9456-3228ec891a59; [retrieved on Dec. 21, 2018].
Santaniello & Caspi, "Reduction of certain steroidal 19-sulfonic esters with metal hydrides", J. of Ster. Biochem, 1976, vol. 7, No. 3, pp. 223-227.
Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.
Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GADA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Shu et al., "Characteristics of concatemeric GABM receptors containing alpha4/d subunits expressed in Xenopus oocytes" British Journal of Pharmacology (2012) 165, 2228-2243.
Shu et al., "Photodynamic effects of steroid-conjugated fluorophores on gabaa receptors", Molecular Pharmacology, 2009, vol. 76, No. 4, pp. 754-765.
Slavíková et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16-Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.

(56) References Cited

OTHER PUBLICATIONS

Stastna et al., "The use of symmetry in enantioselective synthesis: Four pairs of chrysene enantiomers prepared from 19-nortestosterone", Org. Biomol. Chem., 2011, vol. 9, pp. 4685-4694.
Sunõl et al., "Activity of b-nor analogues of neurosteroids on the gabaa receptor in primary neuronal cultures", Journal of Medicinal Chemistry, 2006, vol. 49, No. 11, pp. 3225-3234.
Supplemental European Search Report, European Patent Application No. 14826212.4, dated Feb. 16, 2017.
Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids. VII. Preparation of of androstan-3(b)-ol-7-one from from dehydroisoandrosterone", Journal of Biological Chemistry, 1946, vol. 165, pp. 677-685.
Hewett et al., "Amino steroids. Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten and bela,gamma-ngesalligten, homoallylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz[e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/018748 dated Aug. 29, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for Corresponding International Application No. PCT/US2018/050012 dated Dec. 7, 2018.
International Search Report and Written Opinion for Corresponding International Application No. PCT/US2018/051048 dated Jan. 11, 2019.
International Search Report and Written Opinion for Corresponding International Application No. PCT/US2018/064546 dated Apr. 9, 2019.
International Search Report and Written Opinion for Corresponding International Application No. PCT/US2019/036848 dated Aug. 22, 2019.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report and Written Opinion for International Application No. PCT/US2018/067277 dated May 24, 2019.
International Search Report and Written Opinion for International Application No. PCT/US2018/067306 dated May 28, 2019.
International Search Report and Written Opinion for International Application No. PCT/US2019/013315 dated Jun. 14, 2019.
International Search Report for International Application No. PCT/US2012/060136 dated Mar. 27, 2013.
Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.

(56) References Cited

OTHER PUBLICATIONS

Jungmann et al., "7-Keto-5b-ätiansäure-Derivate. über Gallensäuren and verwandte Stoffe, 51. Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7-dideoxyxestobergsterol A", Chem. & Pharm. Bulletin, 2000, vol. 48, No. 10, pp. 1480-1483.
Kanes et al., "A multiple-ascending dose study of the neuroactive steroid Sage-217", Biological Psychiatry, vol. 81, No. 10, 2017, pp. S347.
Kanes et al., "A single-ascending dose study of the neuroactive steroid Sage-217", Biological Psychiatry, vol. 81, No. 10, 2017, pp. S31.
Kasal et al., "Neurosteroid analogues: synthesis of 6-aza-allopregnanolone", Tetrahedron, Elsevier Science Publishers, 2005, vol. 61, No. 9, pp. 2269-2278.
Katona et al., "Neurosteroid analogues. 12. Potent enhancement of GABA-mediated chloride currents at GABAA receptors by ent-androgens", European Journal of Medicinal Chemistry, 2008, vol. 43, No. 1, pp. 107-113.
Adams et al., "The estrogenic activity and enzymic oxidation of 17b-estradiol-17a-d1", Steroids, Elsevier Science Publishers, (1965), pp. 75-84.
Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Anonymous: "Archive History for NCT03000530", Aug. 4, 2017, Retrieved from the Internet: <URL:https://www.clinicaltrials.gov/ct2/his> tory/NCT03000530?V-_6=View#StudyPageTop; [retrieved on Nov. 20, 2018].
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, BE., "Rett Syndrome Medication" [online], Updated Feb. 6, 2017, [retrieved on May 3, 2018]. Retrieved from the website Medscape, using Internet URL: <https://emedicine.medscape.com/article/916377-medication>.
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-y1)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp A-J.
CAS Registry No. 1040410-23-8 [Database Registry in STN]; STN Entry Date: Aug. 12, 2008; Chemical Name: 1-((3S,8R,9S,10S,13S,14S,17S)-3-hydroxy-10,13-dimethyl-2,3,4,5,8,9,10,11,12,13,14,15,16,17-tetradecahydro-1H-cyclopenta[a]phenanthren-17-yl)ethan-1-one.
CAS Registry No. 162882-77-1 [Database Registry in STN]; STN Entry Date: May 11, 1995; Chemical Name: (3a,5b)-3-Hydroxy-3-methyl-19-norpregnan-20-one.

CAS Registry No. 162883-68-3 [Database Registry in STN]; STN Entry Date: May 11, 1995; Chemical Name: 19-Norpregnan-20-one, 3-hydroxy-3-methyl-, (3a,5a)-.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Chen et al., "The mechanism investigation in substitution of 21-bromo-3a-hydroxy-3b-methoxymethy1-5a-pregnan-20-one with nucleophiles", Steroids, vol. 71, (2006), pp. 942-948.
Chodounska et al., "Epalons: Synthesis of 3a, 7a-Dihydroxy-5a-Pregnan-20-One", Collection Symposium Series, vol. 63, No. 10, (1998), pp. 1543-1548.
D'hulst et al., "Expression of the GABAergic system in animal models for fragile X syndrome and fragile X associated tremor/ataxia syndrome (FXTAS)", Brain Research, 2008, vol. 1253, pp. 176-183.
Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Database Medline, US National Library of Medicine, Bethesda, MD, 1984, Welling: "Intentions affecting drug absorption", Database accession No. NLM6388952, abstract.
Deluca et al., "Synthesis of 3b-Hydroxy[21-14C]-5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, p. IX.
Durán et al., "Synthesis of 6-thia analogs of the natural neurosteroid allopregnanolone", Tetrahedron, Elsevier Science Publishers, 2006, vol. 62, No. 20, pp. 4762-4768.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Eimon et al., "Brain activity patterns in high-throughput electrophysiology screen predict both drug efficacies and side effects", Nature Communications, (2018) 9:219, pp. 1-14.
Evers et al., "A Synthetic 18-Norsleroid Distinguishes Between Two Neuroactive Steroid Binding Sites on GABAA receptors", Journal of Pharmacology and Experimental Therapeutics, 2010, vol. 333, No. 2, pp. 404-413.
Extended European Search Report for application PCT/CN2014075593 dated Aug. 26, 2016.
Extended European Search Report for application PCT/CN2014075594 dated Aug. 26, 2016.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrance Perturbation and Anesthetic Activity", Molecular Pharmacology, 1985, vol. 27, pp. 624-629.
Gasior et al., "Neuroactive steroids: potential therapeutic use in neurological and psychiatric disorders", Trends in Pharmacological Science, (1999), vol. 20, No. 3, pp. 107-112.
Gottesmann, "GABA Mechanisms and Sleep", Neuroscience, (2002), vol. 111, No. 2, pp. 231-239.
Green et al., "The nonfeminizing enantiomer of 17b-estradiol exerts protective effects in neuronal cultures and a rat model of cerebral ischemia", Endocrinology, 2001, vol. 142, pp. 400-406.

(56) References Cited

OTHER PUBLICATIONS

Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al.,"Sage-217 in Major Depressive Disorder: A Multicenter, Randomized, Double-Blind, Phase 2 3Iacebo-Controlled Trial", European Nueuropsychopharmacology, vol. 29, 2019, pp. S59-S-60, Abstract.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Han et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkins et al., "The synthetic neuroactive steroid SGE-516 reduces seizure burden and improves survival in a Dravet syndrome mouse model", Science Reports, (2017), pp. 1-8.
Hawkinson et al., "3a-Hydroxy-3b-trifluoromethy1-5a-pregnan-20-one (Co-2-1970): A Partial Agonist at the Neuroactive Steroid Site of the y-Aminobutyric acidA Receptor" Molecular Pharmacology (1996) vol. 49, pp. 897-906.
U.S. Appl. No. 15/681,983, filed Aug. 21, 2017, Ravindra B. Upasani et al., Issued.
U.S. Appl. No. 15/698,151, filed Sep. 7, 2017, Gabriel Martinez Botella et al., Issued.
U.S. Appl. No. 15/143,312, filed Apr. 29, 2016, Gabriel Martinez Botella et al., Issued.
U.S. Appl. No. 14/785,192, filed Oct. 16, 2015, Gabriel Martinez Botella et al., Issued.
U.S. Appl. No. 15/273,125, filed Sep. 22, 2016, Gabriel Martinez Botella et al., Issued.
U.S. Appl. No. 16/007,556, filed Jun. 13, 2018, Gabriel Martinez Botella et al., Pending.
U.S. Appl. No. 14/785,171, filed Jun. 16, 2015, Gabriel Martinez Botella et al., Issued.
U.S. Appl. No. 15/297,845, filed Oct. 19, 2016, Gabriel Martinez Botella et al., Issued.
U.S. Appl. No. 16/020,641, filed Jun. 27, 2018, Gabriel Martinez Botella et al., Issued.
U.S. Appl. No. 14/785,175, filed Oct. 16, 2015, Gabriel Martinez Botella et al., Issued.
U.S. Appl. No. 15/639,702, filed, Jun. 30, 2017, Gabriel Martinez Botella et al., Issued.
U.S. Appl. No. 14/913,920, filed Feb. 23, 2016, Gabriel Martinez Botella et al., Pending.
U.S. Appl. No. 14/132,386, filed Dec. 18, 2013, Albert Jean Robichaud et al., Issued.
U.S. Appl. No. 14/652,717, filed Dec. 18, 2013, Albert Jean Robichaud et al., Issued.
U.S. Appl. No. 15/586,853, filed May 4, 2017, Albert Jean Robichaud et al., Pending.
U.S. Appl. No. 15/459,492, filed Mar. 15, 2017 Albert Jean Robichaud et al., Issued.
U.S. Appl. No. 15/314,565, filed Nov. 29, 2016, Gabriel Martinez Botella et al., Pending.
U.S. Appl. No. 15/319,503, filed Dec. 16, 2016, Boyd L. Harrison et al., Issued.
U.S. Appl. No. 16/269,779, filed Feb. 7, 2019, Boyd L. Harrison et al., Pending.
U.S. Appl. No. 15/519,480, filed Apr. 14, 2017, Gabriel Martinez Botella et al., Pending.
U.S. Appl. No. 16/206,472, filed Nov. 30, 2018, Gabriel Martinez Botella et al., Pending.
U.S. Appl. No. 16/365,123, filed Mar. 26, 2019, Gabriel Martinez Botella et al., Pending.
U.S. Appl. No. 15/552,201, filed Aug. 18, 2017, Albert Jean Robichaud et al., Granted.
U.S. Appl. No. 15/777,394, filed May 18, 2018, James J. Doherty, Pending.
U.S. Appl. No. 16/316,851, filed Jan. 10, 2019, Albert Jean Robichaud et al., Pending.
U.S. Appl. No. 16/316,853, filed Jan. 10, 2019, Albert Jean Robichaud et al., Pending.
U.S. Appl. No. 16/326,977, filed Feb. 21, 2019, Paul Steven Watson et al., Pending.
Tsai et al., "Synthesis and antiproliferative activity of 3a-hydroxyl-3b-methoxymethy1-5a-pregnan-20-one with a C-21 hydrophilic substituent", Heteroatom Chemistry, (2017), pp. 1-9.
Upasani et al., "3a-Hydroxy-3β-(phenylethyny1)-5β-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethy1-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Veleiro et al., "Structure-activity relationships of neuroactive steroids acting on the gabaa receptor", Current Medicinal Chemistry, 2009, vol. 16, No. 4, pp. 455-472.
Welling, "Interactions affecting drug absorption", Clinical Pharmacokinetics, vol. 9, No. 5, Sep. 1984 (Sep. 1984), pp. 404-434.
Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethy1-195-alcohols", Journal of the Chemical Society [Section] C: Organic, 1969, vol. 6, pp. 947-951.

(56) References Cited

OTHER PUBLICATIONS

Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.

Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs", Journal of Organic Chemistry, 1973, vol. 38 No. 7, pp. 1280-1283.

Wu "A New Classification of Prodrugs: Regulatory Perspectives", Pharmaceuticals, 2009, vol. 2, pp. 77-81.

Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal chemistry, (2005). vol. 48, pp. 3051-3059.

Zonana et al., "The Neurobiology of Postpartum Depression", CNS Spectrums, (2005), pp. 792-799, 805.

Zorumski et al., "Enantioselective Modulation of GABAergic Synaptic Transmission by Steroids and Benz[dindenes in Hippocampal Microcultures", Synapse, (1998), vol. 29, pp. 162-171.

\* cited by examiner

NEUROACTIVE STEROIDS, COMPOSITIONS, AND USES THEREOF

CROSS-REFERENCE TO RELATED APPLICATIONS

This application is a divisional of U.S. Ser. No. 15/698,151 filed Sep. 7, 2017, which is a continuation of U.S. Ser. No. 14/906,043 filed Jan. 19, 2016, which is a national stage application under 35 U.S.C. § 371 of International Application No. PCT/US2014/047246 filed Jul. 18, 2014, which claims priority under 35 U.S.C. § 119(e) to U.S. provisional patent application, U.S. Ser. No. 61/856,592, filed Jul. 19, 2013, the contents of each of which are incorporated herein by reference.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids (Lan, N. C. et al., *Neurochem. Res.* 16:347-356 (1991)).

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232:1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy,* 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet,* 1235-1237 (1956)). A more direct correlation has been observed with a reduction in progesterone metabolites (Rosciszewska et al., *J. Neurol. Neurosurg. Psych.* 49:47-51 (1986)). In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy,* 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium,* Raven Press, New York (1984), pp. 279-282, and Dalton, K.,

*Premenstrual Syndrome and Progesterone Therapy*, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Provided herein are 17-cyano substituted neuroactive steroids comprising at least one substituent at one or more positions 2, 4, and/or 11 on the steroid scaffold, and designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

In one aspect, the present invention provides compounds of Formula (I):

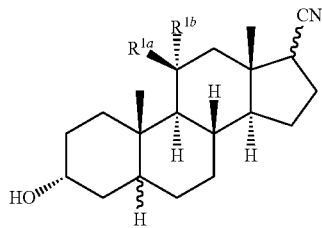

Formula (I)

wherein $R^{1a}$ is hydrogen, halo, alkyl, alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —S(O)$_{0-2}R^a$, —S(O)$_{0-2}$O$R^a$, or —S(O)$_{0-2}$N($R^b$)($R^c$); $R^{1b}$ is H, halo, hydroxy, alkyl, alkoxy, —C(O)$R^a$, —C(O)N($R^b$)($R^c$), —C(O)O$R^a$, —N($R^d$)($R^e$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$); wherein one of $R^{1a}$ and $R^{1b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^d$ and $R^e$ is hydrogen, substituted methyl or $C_2$-$C_6$ alkyl, or $R^d$ and $R^e$, together with the nitrogen atom to which they are attached, form a 3-7-membered (e.g., 5-7-membered) heterocyclic ring.

The present invention also provides pharmaceutical compositions comprising a compound of the present invention and methods of use and treatment, e.g., such for inducing sedation and/or anesthesia.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry* (University Science Books, Sausalito, 1999); Smith and March, *March's Advanced Organic Chemistry*, 5$^{th}$ Ed. (John Wiley & Sons, Inc., New York, 2001); Larock, *Comprehensive Organic Transformations* (VCH Publishers, Inc., New York, 1989); and Carruthers, *Some Modern Methods of Organic Synthesis*, 3$^{rd}$ Ed. (Cambridge University Press, Cambridge, 1987).

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compounds described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including 160 and 180; and the like.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analog" means one analog or more than one analog.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 8 carbon atoms ("$C_{2-8}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH═CHCH$_2$—, —CH$_2$—CH═CH—). Exemplary substituted alkenylene groups, e.g., substituted with one or more alkyl (methyl) groups, include but are not limited to, substituted ethylene (—C(CH$_3$)═CH—, —CH═C (CH$_3$)—), substituted propylene (e.g., —C(CH$_3$) ═CHCH$_2$—, —CH═C(CH$_3$)CH$_2$—, —CH═CHCH (CH$_3$)—, —CH═CHC(CH$_3$)$_2$—, —CH(CH$_3$)— CH═CH—, —C(CH$_3$)$_2$—CH═CH—, —CH$_2$—C(CH$_3$) ═CH—, —CH$_2$—CH═C(CH$_3$)—), and the like.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 8 carbon atoms ("C$_{2-8}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_2$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C$_{2-10}$ alkynyl. In certain embodiments, the alkynyl group is substituted C$_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_2$ s alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and 1 or 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and 1 or 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

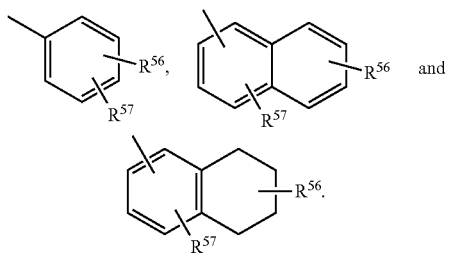

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

Other representative aryl groups having a fused heterocyclyl group include the following:

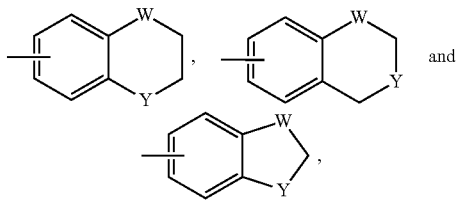

wherein each W is selected from C(R$^{66}$)$_2$, NR$^{66}$, O, and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

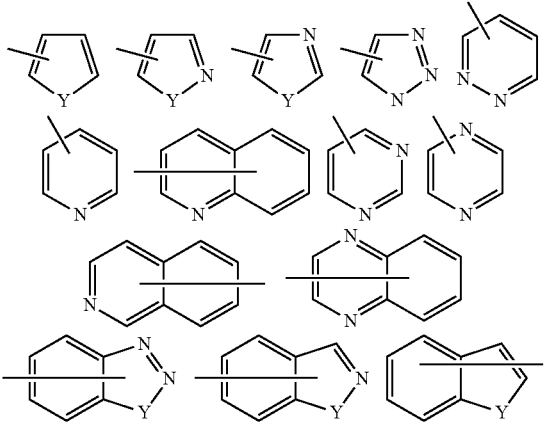

wherein each Y is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

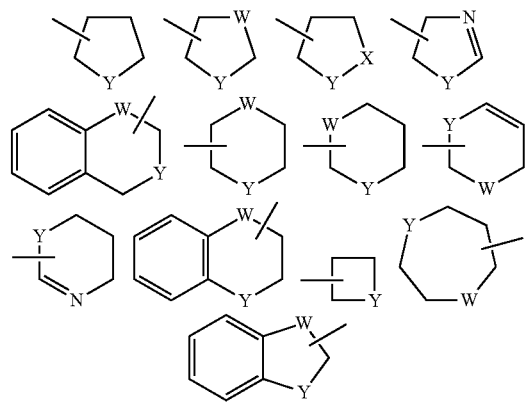

wherein each W is selected from CR$^{67}$, C(R$^{67}$)$_2$, NR$^{67}$, O, and S; and each Y is selected from NR$^{67}$, O, and S; and R$^{67}$ is independently hydrogen, C$_1$-C$_8$ alkyl, C$_3$-C$_{10}$ cycloalkyl, 4-10 membered heterocyclyl, C$_6$-C$_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R$^{23}$ is independently hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and hexylcarbonylamino. Particular exemplary "acylamino" groups are —NR$^{24}$C(O)—C$_1$-C$_8$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)—(CH$_2$)$_t$(C$_3$-C$_{10}$ cycloalkyl), and —NR$^{24}$C(O)—(CH$_2$)$_t$(4-10 membered heterocyclyl), wherein t is an integer from 0 to 4, and each R$^{24}$ independently represents H or C$_1$-C$_8$ alkyl. In certain embodiments, R$^{25}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl; provided at least one of R$^{25}$ and R$^{26}$ is other than H.

"Acyloxy" refers to a radical —OC(O)R$^{27}$, where R$^{27}$ is hydrogen, substituted or unsubstitued alkyl, substituted or unsubstitued alkenyl, substituted or unsubstitued alkynyl, substituted or unsubstitued carbocyclyl, substituted or unsubstitued heterocyclyl, substituted or unsubstitued aryl, or substituted or unsubstitued heteroaryl, as defined herein. Representative examples include, but are not limited to, formyl, acetyl, cyclohexylcarbonyl, cyclohexylmethylcarbonyl, benzoyl, and benzylcarbonyl. In certain embodiments, R$^{28}$ is C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstitued alkynyl, substituted or unsubstitued carbocyclyl, substituted or unsubstituted heterocyclyl, substituted or unsubstituted aryl, or substituted or unsubstitued heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$-. Exemplary "substituted alkoxy" groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein R$^{38}$ is hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, substituted or unsubstitued heteroaryl, or an amino protecting group, wherein at least one of R$^{38}$ is not a hydrogen. In certain embodiments, each R$^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$ (4-10 membered heterocyclyl), wherein t is an integer from 0 to 4, for instance 1 or 2, each R$^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N(R$^{62}$)$_2$ wherein each R$^{62}$ is independently hydrogen, substituted or unsubstituted alkyl, substituted or unsubstitued alkenyl, substituted or unsubstituted alkynyl, substituted or unsubstitued carbocyclyl, substituted or unsubstituted heterocyclyl, substituted or unsubstituted aryl, substituted or unsubstitued heteroaryl, or an amino protecting group, wherein at least one of R$^{62}$ is not a hydrogen. In certain embodiments, R$^{62}$ is selected from H, C$_1$-C$_8$ alkyl, C$_3$-C$_{10}$ cycloalkyl, 4-10 membered heterocyclyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocyclyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; provided that at least one R$^{62}$ is other than H.

Exemplary "substituted carbamoyl" groups include, but are not limited to, —C(O) NR$^{64}$—C$_1$-C$_8$ alkyl, —C(O)NR$^{64}$—(CH$_2$)$_t$(C$_6$-C$_{10}$ aryl), —C(O)N$^{64}$—(CH$_2$)$_t$(5-10 membered heteroaryl), —C(O)NR$^{64}$—(CH$_2$)$_t$(C$_3$-C$_{10}$ cycloalkyl), and —C(O)NR$^{64}$—(CH$_2$)$_t$(4-10 membered heterocyclyl), wherein t is an integer from 0 to 4, each R$^{64}$ independently represents H or C$_1$-C$_8$ alkyl and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C=C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{32}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_6$ m aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_W$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_W$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14-membered heteroaryl, or two R$^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14-membered heterocyclyl, C$_{6-14}$ aryl, and 5-14-membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis* (T. W. Greene and P. G. M. Wuts, 3$^{rd}$ Ed., John Wiley & Sons, 1999), incorporated herein by reference.

Exemplary amino protecting groups include, but are not limited to amide groups (e.g., —C(=O)R$^{aa}$), which include, but are not limited to, formamide and acetamide; carbamate groups (e.g., —C(=O)OR$^{aa}$), which include, but are not limited to, 9-fluorenylmethyl carbamate (Fmoc), f-butyl carbamate (BOG), and benzyl carbamate (Cbz); sulfonamide groups (e.g., —S(=O)$_2$R$^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis* (T. W. Greene and P. G. M. Wuts, 3$^{rd}$ Ed., John Wiley & Sons, 1999), incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$) R$^{aa}$, —C(=NR$^{bb}$)OR$^{aa}$, —C(=NR$^{bb}$)N(R$^{bb}$)$_2$, —S(=O) R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis* (T. W. Greene and P. G. M. Wuts, 3$^{rd}$ Ed., John Wiley & Sons, 1999), incorporated herein by reference.

These and other exemplary substituents are described in more detail in the Detailed Description, Examples, and Claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

Figure 1:
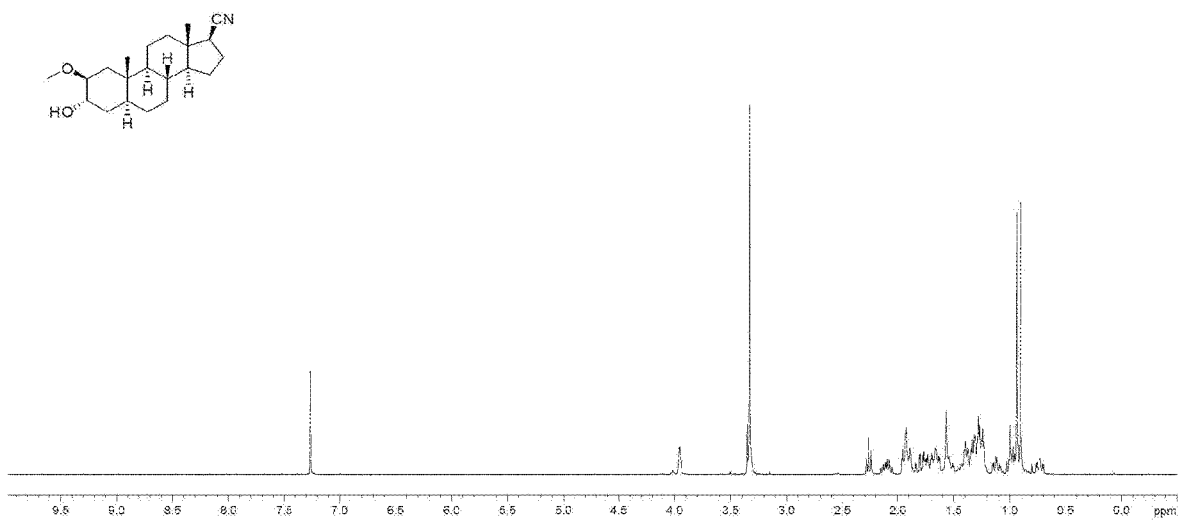
FIGS. 1-12 depict representative $^1$H NMR spectra of exemplary compounds described herein.

As generally described herein, the present invention provides 17-cyano substituted neuroactive steroids comprising at least one substituent at one or more positions 2, 4, or 11 on the steroid scaffold, and designed, for example, to act as GABA modulators. In some embodiments, the present invention provides 17-cyano substituted neuroactive steroids comprising at least one substituent at one or more positions 2, 4, and 11 on the steroid scaffold. In certain embodiments, such compounds are envisioned to be useful as therapeutic agents for the inducement of anesthesia and/or sedation in a subject. In certain embodiments, such compounds are envisioned to be useful as therapeutic agents for treating a CNS-related disorder.

In one aspect, provided is a compound of Formula (I):

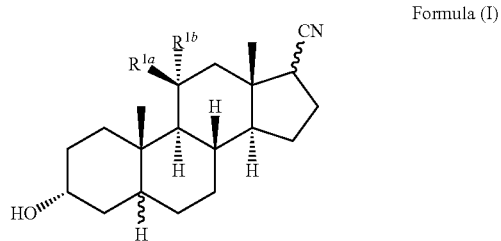

Formula (I)

wherein $R^{1a}$ is hydrogen, halo, alkyl, alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —S(O)$_{0-2}R^a$, —S(O)$_{0-2}$O$R^a$, or —S(O)$_{0-2}$N($R^b$)($R^c$); $R^{1b}$ is hydrogen, halo, hydroxy, alkyl, alkoxy, —C(O)$R^a$, —C(O)N($R^b$)($R^c$), —C(O)O$R^a$, —N($R^d$)($R^e$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$); wherein one of $R^{1a}$ and $R^{1b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^d$ and $R^e$ is hydrogen, substituted methyl or $C_2$-$C_6$ alkyl, or $R^d$ and $R^e$, taken together with the nitrogen atom to which they are attached, form a 3-7-membered (e.g., 5-7-membered) heterocyclic ring.

In some embodiments, $R^{1a}$ is hydrogen and $R^{1b}$ is hydroxy, alkyl, or alkoxy. In some embodiments, $R^{1b}$ is hydroxy or alkoxy. In embodiments, $R^{1b}$ is hydroxy. In some embodiments, $R^{1b}$ is methoxy. In some embodiments, $R^{1b}$ is alkyl.

In some embodiments, $R^{1b}$ is hydrogen and $R^{1a}$ is alkyl or alkoxy. In some embodiments, $R^{1a}$ is alkoxy. In some embodiments, $R^{1a}$ is methoxy.

In some embodiments, the compound is of the Formula (Ia):

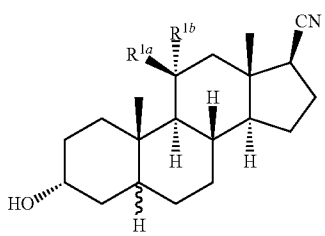

Formula (Ia)

wherein $R^{1a}$ is hydrogen, halo, alkyl, alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —S(O)$_{0-2}R^a$, —S(O)$_{0-2}$O$R^a$, or —S(O)$_{0-2}$N($R^b$)($R^c$); $R^{1b}$ is hydrogen, halo, hydroxy, alkyl, alkoxy, —C(O)$R^a$, —C(O)N($R^b$)($R^c$), —C(O)O$R^a$, —N($R^d$)($R^e$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$); wherein one of $R^{1a}$ and $R^{1b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^d$ and $R^e$ is hydrogen, substituted methyl or $C_2$-$C_6$ alkyl, or $R^d$ and $R^e$, taken together with the nitrogen atom to which they are attached, form a 3-7-membered (e.g., 5-7-membered) heterocyclic ring.

In some embodiments, $R^{1a}$ is hydrogen and $R^{1b}$ is hydroxy, alkyl, or alkoxy. In some embodiments, $R^{1b}$ is hydroxy or alkoxy. In some embodiments, $R^{1b}$ is hydroxy. In some embodiments, $R^{1b}$ is methoxy. In some embodiments, $R^{1b}$ is alkyl.

In some embodiments, $R^{1b}$ is hydrogen and $R^{1a}$ is alkyl or alkoxy. In some embodiments, $R^{1a}$ is alkoxy. In some embodiments, $R^{1a}$ is methoxy.

In some embodiments, the compound is of the Formula (Ib):

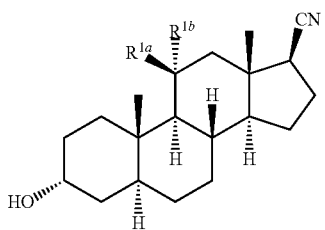

Formula (Ib)

wherein $R^{1a}$ is hydrogen, halo, alkyl, alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —S(O)$_{0-2}R^a$, —S(O)$_{0-2}$O$R^a$, or —S(O)$_{0-2}$N($R^b$)($R^c$); $R^{1b}$ is hydrogen, halo, hydroxy, alkyl, alkoxy, —C(O)$R^a$, —C(O)N($R^b$)($R^c$), —C(O)O$R^a$, —N($R^d$)($R^e$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$); wherein one of $R^{1a}$ and $R^{1b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^d$ and $R^e$ is hydrogen, substituted methyl or $C_2$-$C_6$ alkyl, or $R^d$ and $R^e$, taken together with the nitrogen atom to which they are attached, form a 3-7-membered (e.g., 5-7-membered) heterocyclic ring.

In some embodiments, $R^{1a}$ is hydrogen and $R^{1b}$ is hydroxy, alkyl, or alkoxy. In some embodiments, $R^{1b}$ is hydroxy or alkoxy. In some embodiments, $R^{1b}$ is hydroxy. In some embodiments, $R^{1b}$ is methoxy. In some embodiments, $R^{1b}$ is alkyl.

In some embodiments, $R^{1b}$ is hydrogen and $R^{1a}$ is alkyl or alkoxy. In some embodiments, $R^{1a}$ is alkoxy. In some embodiments, $R^{1a}$ is methoxy.

In one aspect, provided is a compound selected from:

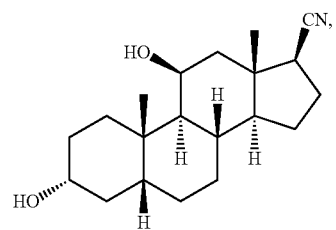

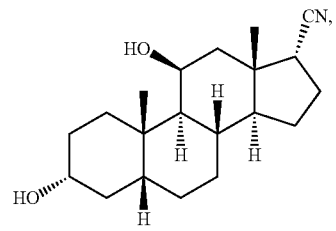

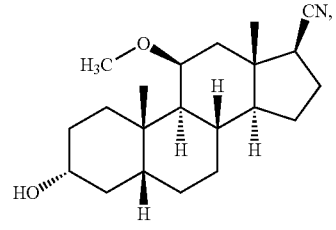

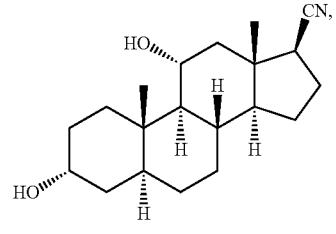

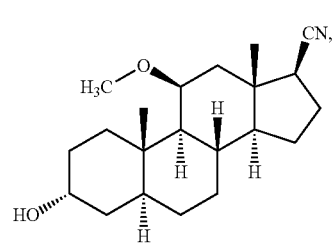

-continued

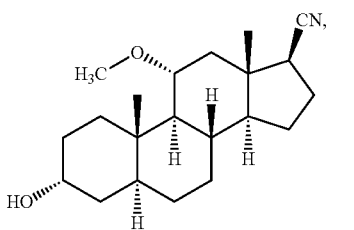

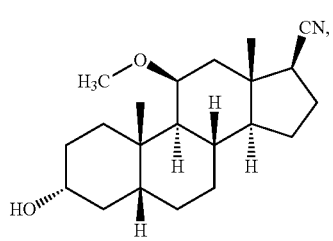

In some embodiments, the compound is selected from:

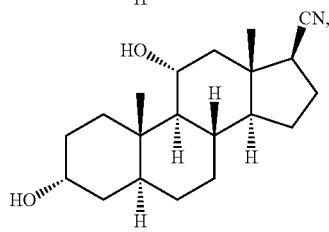

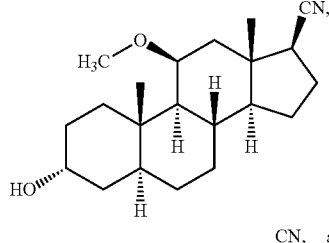

-continued

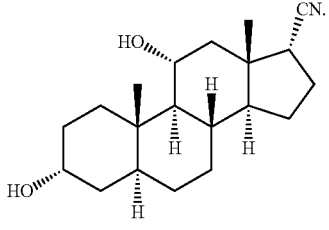

In some embodiments, the compound is selected from:

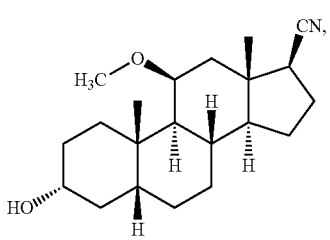

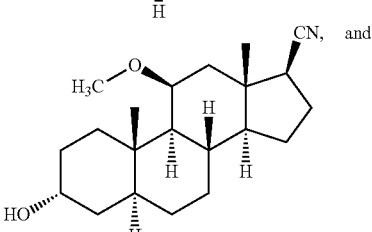

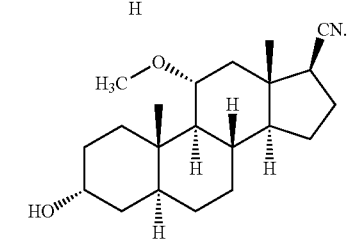

In one aspect, provided is a compound of the Formula (II):

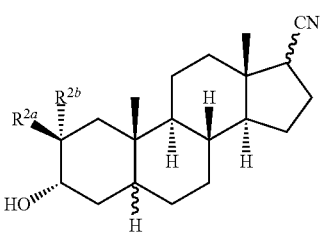

Formula (II)

wherein $R^{2a}$ is hydrogen, halo (e.g., chloro, fluoro, bromo, iodo), hydroxy, alkyl, methoxy, substituted ethoxy, $C_3$-$C_6$ alkoxy, —C(O)$R^a$, —C(O)N($R^b$)($R^c$), —C(O)O$R^a$, —N($R^f$)($R^g$), —OC(O)N($R^b$)($R^c$), —OC(O)O$R^a$, —OC(O)$R^a$, —S(O)$_{0\text{-}2}R^a$, —S(O)$_{0\text{-}2}$O$R^a$, or —S(O)$_{0\text{-}2}$N($R^b$)($R^c$); $R^{2b}$ is hydrogen, halo, hydroxy, alkyl, methoxy, substituted ethoxy, $C_3$-$C_6$ alkoxy, —C(O)$R^a$, —C(O)N($R^b$)($R^c$), —C(O)O$R^a$, —N($R^b$)($R^c$), —OC(O)N($R^b$)($R^c$), —OC(O)O$R^a$, —OC(O)$R^a$, —S(O)$_{0\text{-}2}R^a$, —S(O)$_{0\text{-}2}$O$R^a$, or —S(O)$_{0\text{-}2}$N($R^b$)($R^c$); wherein one of $R^{2a}$ and $R^{2b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^f$ and $R^g$ is independently hydrogen or $C_1$-$C_6$ alkyl, or $R^f$ and $R^g$, taken together with the nitrogen atom to which they are attached, form a 3-7-membered (e.g., 5-7-membered) heterocyclic ring optionally comprising one additional heteroatom selected from nitrogen, oxygen and sulfur.

In some embodiments, $R^{2a}$ is hydrogen and $R^{2b}$ is alkyl. In some embodiments, $R^{2b}$ is alkyl. In some embodiments, $R^{2b}$ is methyl. In some embodiments, $R^{2b}$ is methoxy.

In some embodiments, $R^{2b}$ is hydrogen and $R^{2a}$ is alkyl, methoxy, substituted ethoxy, or $C_3$-$C_6$ alkoxy. In some embodiments, $R^{2a}$ is alkyl. In some embodiments, $R^{2a}$ is methyl. In some embodiments, $R^{2a}$ is ethyl. In some embodiments, $R^{2a}$ is methoxy. In some embodiments, $R^{2a}$ is —$OCF_3$. In some embodiments, $R^{2a}$ is substituted ethoxy. In some embodiments, $R^{2a}$ is —$OCH_2CH_2OMe$. In some embodiments, $R^{2a}$ is —$OCH_2CH_2OH$. In some embodiments, $R^{2a}$ is —$OCH_2CF_3$. In some embodiments, $R^{2a}$ is $C_3$-$C_6$ alkoxy. In some embodiments, $R^{2a}$ is propoxy. In some embodiments, $R^{2a}$ is —$OCH(CH_3)_2$. In some embodiments, $R^{2a}$ is —$OCH_2CH(CH_3)_2$. In some embodiments, $R^{2a}$ is cyclopropoxy.

In some embodiments, the compound is of the Formula (IIa):

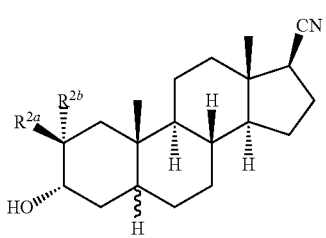

Formula (IIa)

wherein $R^{2a}$ is hydrogen, halo (e.g., chloro, fluoro, bromo, iodo), hydroxy, alkyl, methoxy, substituted ethoxy, $C_3$-$C_6$ alkoxy, —$C(O)R^a$, —$C(O)N(R^b)(R^c)$, —$C(O)OR^a$, —$N(R^f)(R^g)$, —$OC(O)N(R^b)(R^c)$, —$OC(O)OR^a$, —$OC(O)R^a$, —$S(O)_{0-2}R^a$, —$S(O)_{0-2}OR^a$, or —$S(O)_{0-2}N(R^b)(R^c)$; $R^{2b}$ is hydrogen, halo, hydroxy, alkyl, methoxy, substituted ethoxy, $C_3$-$C_6$ alkoxy, —$C(O)R^a$, —$C(O)N(R^b)(R^c)$, —$C(O)OR^a$, —$N(R^b)(R^c)$, —$OC(O)N(R^b)(R^c)$, —$OC(O)OR^a$, —$OC(O)R^a$, —$S(O)_{0-2}R^a$, —$S(O)_{0-2}OR^a$, or —$S(O)_{0-2}N(R^b)(R^c)$; wherein one of $R^{2a}$ and $R^{2b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^f$ and $R^g$ is independently hydrogen or $C_1$-$C_6$ alkyl, or $R^f$ and $R^g$, taken together with the nitrogen atom to which they are attached, form a 3-7-membered (e.g., 5-7-membered) heterocyclic ring optionally comprising one additional heteroatom selected from nitrogen, oxygen and sulfur.

In some embodiments, $R^{2a}$ is hydrogen and $R^{2b}$ is alkyl. In some embodiments, $R^{2b}$ is alkyl. In some embodiments, $R^{2b}$ is methyl. In some embodiments, $R^{2b}$ is methoxy.

In some embodiments, $R^{2b}$ is hydrogen and $R^{2a}$ is alkyl, methoxy, substituted ethoxy, or $C_3$-$C_6$ alkoxy. In some embodiments, $R^{2a}$ is alkyl. In some embodiments, $R^{2a}$ is methyl. In some embodiments, $R^{2a}$ is ethyl. In some embodiments, $R^{2a}$ is methoxy. In some embodiments, $R^{2a}$ is —$OCF_3$. In some embodiments, $R^{2a}$ is substituted ethoxy. In some embodiments, $R^{2a}$ is —$OCH_2CH_2OMe$. In some embodiments, $R^{2a}$ is —$OCH_2CH_2OH$. In some embodiments, $R^{2a}$ is —$OCH_2CF_3$. $C_3$-$C_6$ alkoxy. In some embodiments, $R^{2a}$ is propoxy. In some embodiments, $R^{2a}$ is —$OCH(CH_3)_2$. In some embodiments, $R^{2a}$ is —$OCH_2CH(CH_3)_2$. In some embodiments, $R^{2a}$ is cyclopropoxy.

In some embodiments, the compound is of the Formula (IIb):

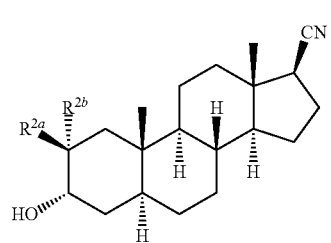

Formula (IIb)

wherein $R^{2a}$ is hydrogen, halo (e.g., chloro, fluoro, bromo, iodo), hydroxy, alkyl, methoxy, substituted ethoxy, $C_3$-$C_6$ alkoxy, —$C(O)R^a$, —$C(O)N(R^b)(R^c)$, —$C(O)OR^a$, —$N(R^f)(R^g)$, —$OC(O)N(R^b)(R^c)$, —$OC(O)OR^a$, —$OC(O)R^a$, —$S(O)_{0-2}R^a$, —$S(O)_{0-2}OR^a$, or —$S(O)_{0-2}N(R^b)(R^c)$; $R^{2b}$ is hydrogen, halo, hydroxy, alkyl, methoxy, substituted ethoxy, $C_3$-$C_6$ alkoxy, —$C(O)R^a$, —$C(O)N(R^b)(R^c)$, —$C(O)OR^a$, —$N(R^b)(R^c)$, —$OC(O)N(R^b)(R^c)$, —$OC(O)OR^a$, —$OC(O)R^a$, —$S(O)_{0-2}R^a$, —$S(O)_{0-2}OR^a$, or —$S(O)_{0-2}N(R^b)(R^c)$; wherein one of $R^{2a}$ and $R^{2b}$ is hydrogen; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; and each $R^f$ and $R^g$ is independently hydrogen or $C_1$-$C_6$ alkyl, or $R^f$ and $R^g$, taken together with the nitrogen atom to which they are attached, form a 3-7-membered (e.g., 5-7-membered) heterocyclic ring optionally comprising one additional heteroatom selected from nitrogen, oxygen and sulfur.

In some embodiments, $R^{2a}$ is hydrogen and $R^{2b}$ is alkyl. In some embodiments, $R^{2b}$ is alkyl. In some embodiments, $R^{2b}$ is methyl. In some embodiments, $R^{2b}$ is methoxy.

In some embodiments, $R^{2b}$ is hydrogen and $R^{2a}$ is alkyl, methoxy, substituted ethoxy, or $C_3$-$C_6$ alkoxy. In some embodiments, $R^{2a}$ is alkyl. In some embodiments, $R^{2a}$ is methyl. In some embodiments, $R^{2a}$ is ethyl. In some embodiments, $R^{2a}$ is methoxy. In some embodiments, $R^{2a}$ is —$OCF_3$. In some embodiments, $R^{2a}$ is substituted ethoxy. In some embodiments, $R^{2a}$ is —$OCH_2CH_2OMe$. In some embodiments, $R^{2a}$ is —$OCH_2CH_2OH$. In some embodiments, $R^{2a}$ is —$OCH_2CF_3$. $C_3$-$C_6$ alkoxy. In some embodiments, $R^{2a}$ is propoxy. In some embodiments, $R^{2a}$ is —$OCH(CH_3)_2$. In some embodiments, $R^{2a}$ is —$OCH_2CH(CH_3)_2$. In some embodiments, $R^{2a}$ is cyclopropoxy.

In one aspect, provided is a compound selected from:

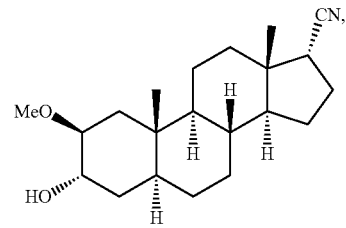

31
-continued
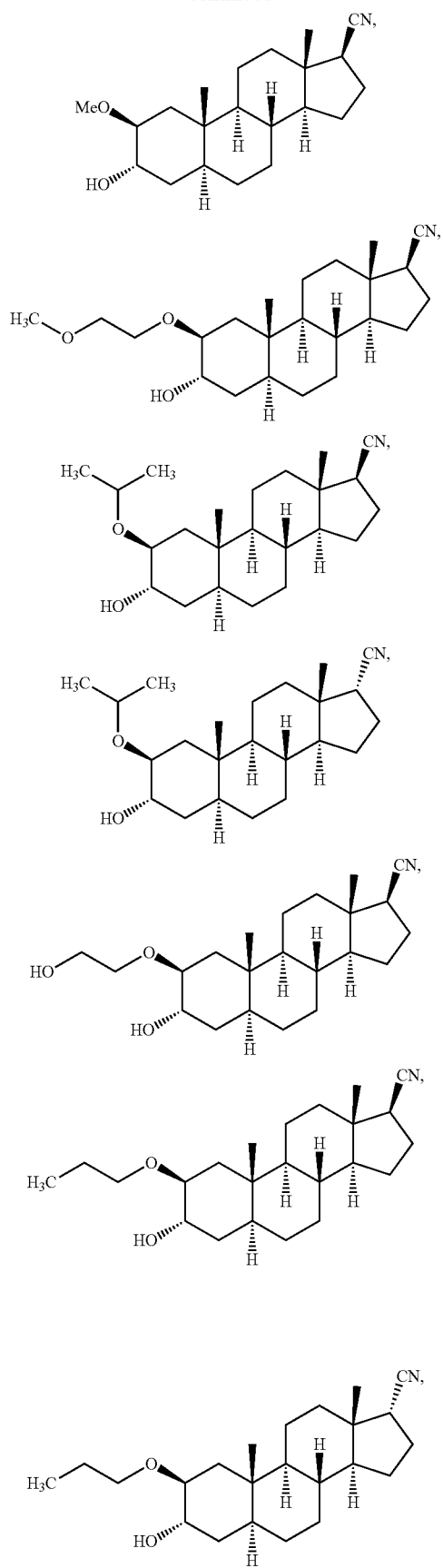
32
-continued
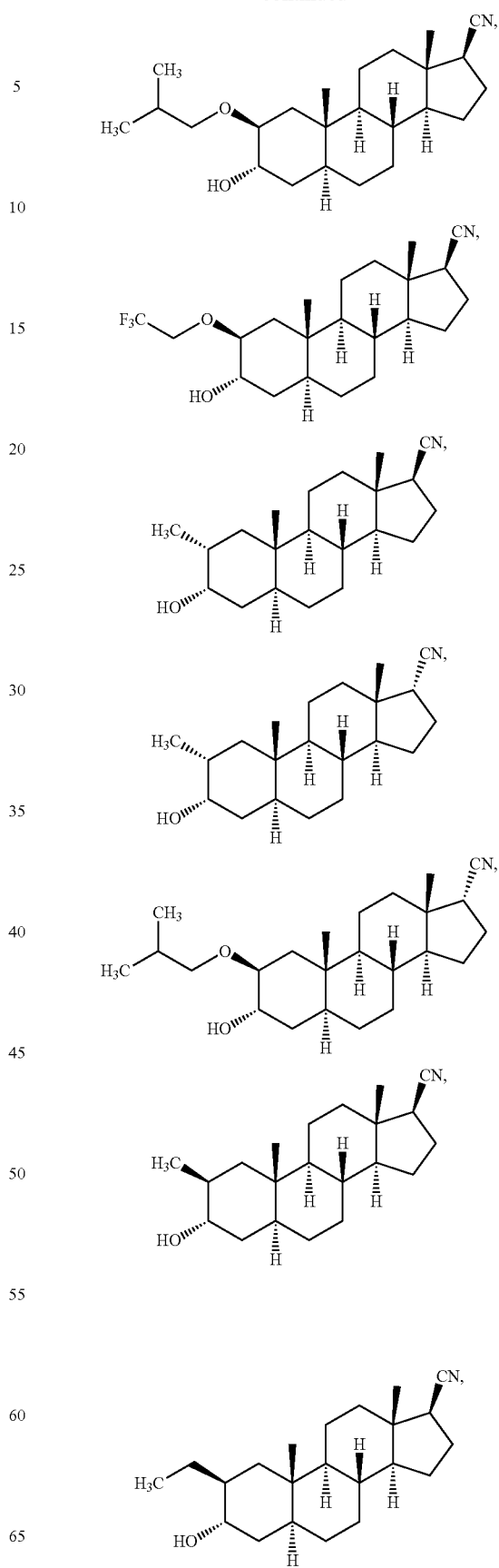

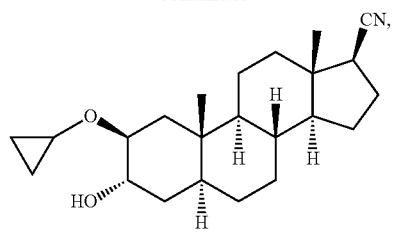
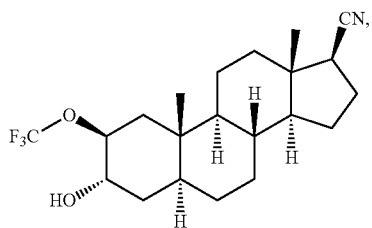
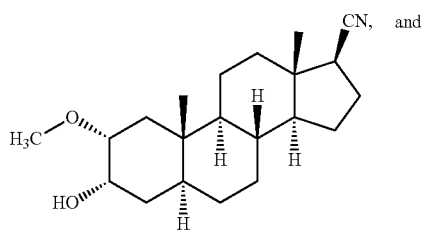
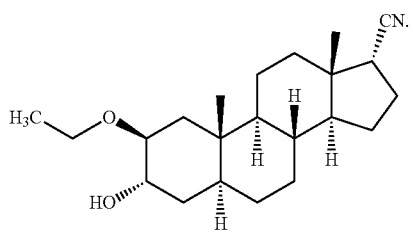
In some embodiments, the compound is selected from:
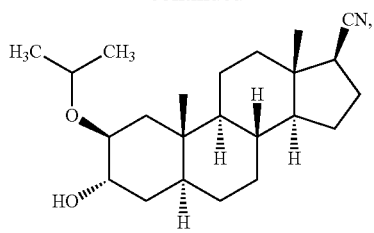
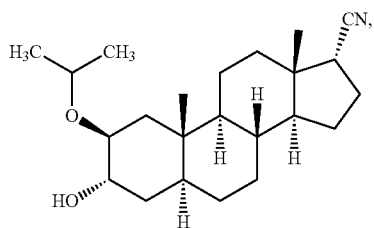
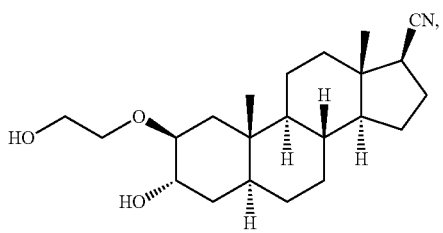
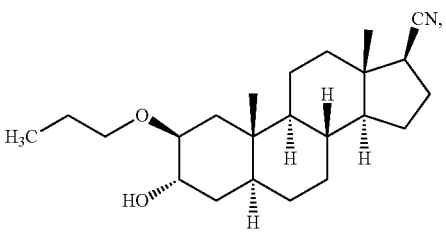
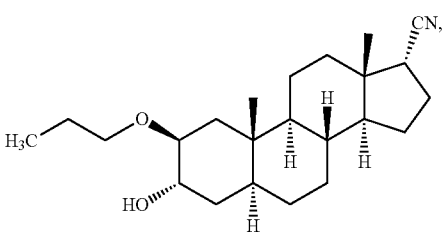
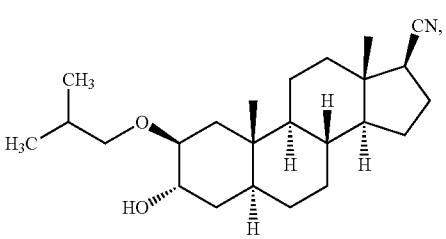
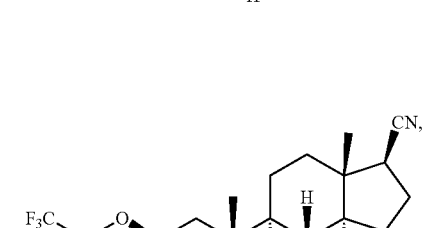
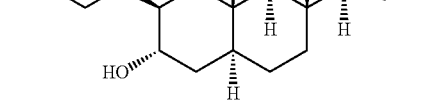

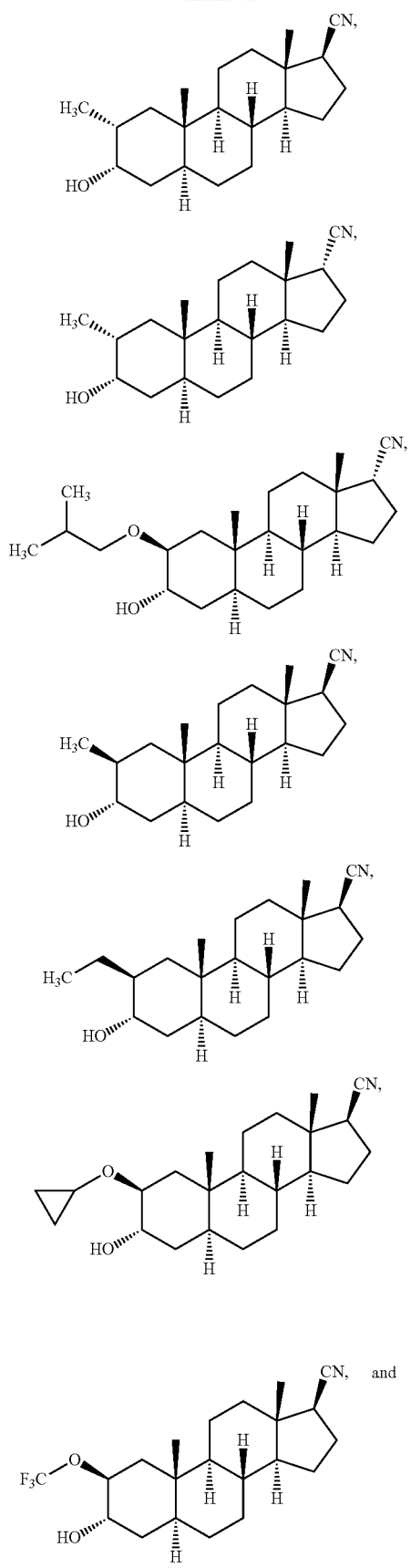
In some embodiments, the compound is selected from:
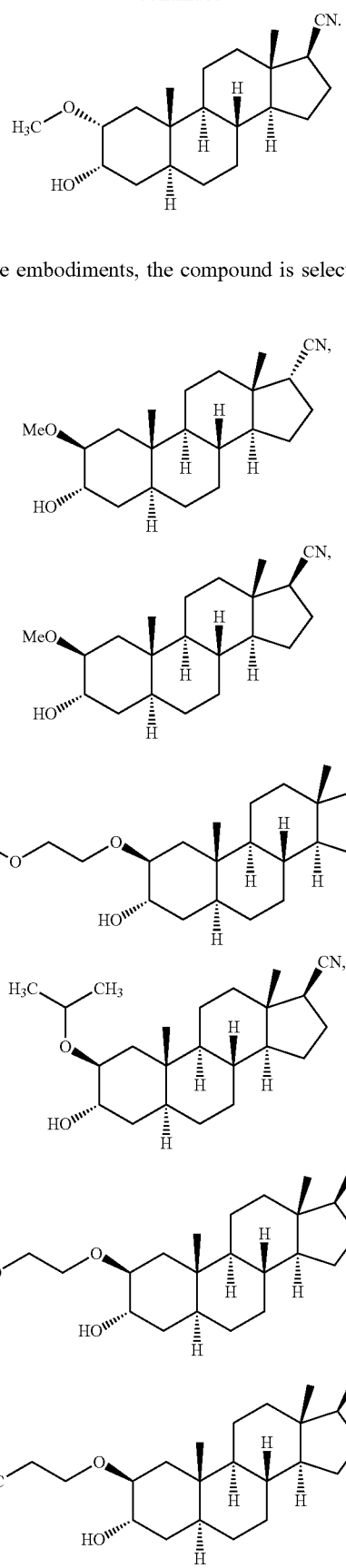

37

-continued

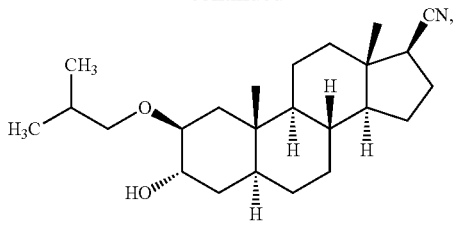

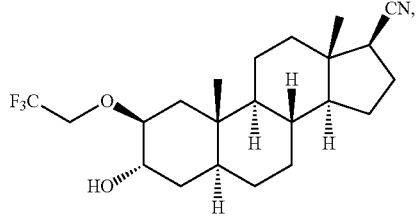

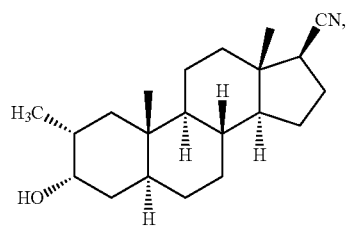

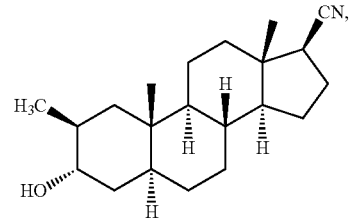

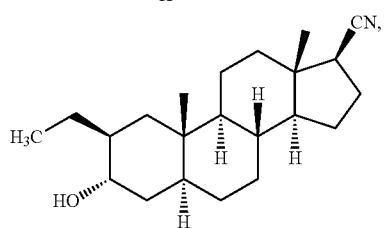

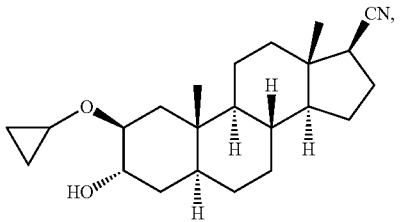

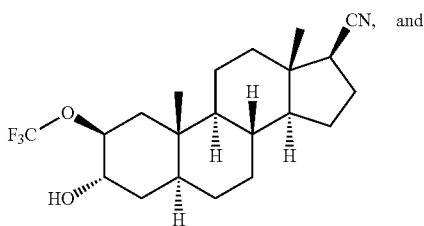 and

38

-continued

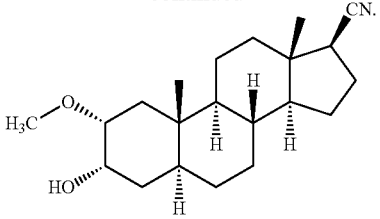

In one aspect, provided is a compound of the Formula (III):

Formula (III)

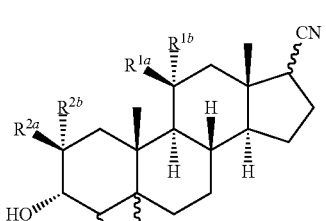

wherein one of $R^{1a}$ and $R^{1b}$ is halo (e.g., chloro, fluoro, bromo, iodo), hydroxy, alkyl, alkoxy, —C(O)$R^a$, —C(O)N($R^b$)($R^c$), —C(O)O$R^a$, —N($R^h$)($R^i$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$), and the other one is hydrogen; or $R^{1a}$ and $R^{1b}$ are taken together with the carbon to which they are attached to form C(=O); one of $R^{2a}$ and $R^{2b}$ is chloro, fluoro, hydroxy, alkyl, alkoxy, —C(O)$R^a$, —C(O)N($R^b$)($R^c$), —C(O)O$R^a$, —N($R^f$)($R^g$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$), and the other one is hydrogen; $R^3$ is hydrogen or $C_1$-$C_6$ alkyl; each $R^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form 3-7-membered (e.g., 5-7-membered) heterocyclic ring; each $R^f$ and $R^g$ is independently hydrogen or $C_1$-$C_6$ alkyl, or $R^f$ and $R^g$, taken together with the nitrogen atom to which they are bound to form a 3-7-membered (e.g., 5-7-membered) heterocyclic ring optionally comprising one additional heteroatom selected from nitrogen, oxygen and sulfur; and each $R^h$ is unsubstituted $C_1$-$C_4$ alkyl; each $R^i$ is hydrogen, substituted methyl or $C_2$-$C_6$ alkyl, or $R^h$ and $R^i$, together with the nitrogen atom to which they are attached, form a 3-7-membered (e.g., 5-7-membered) heterocyclic ring.

In some embodiments, $R^{1a}$ is hydrogen and $R^{1b}$ is hydroxy, alkyl, or alkoxy.

In some embodiments, $R^{1b}$ is hydrogen and $R^{1a}$ is hydroxy, alkyl, or alkoxy. In some embodiments, $R^{1a}$ is hydroxy. In some embodiments, $R^{1a}$ is alkoxy. In some embodiments, $R^{1a}$ is methoxy.

In some embodiments, $R^{1a}$ and $R^{1b}$ are taken together with the carbon to which they are attached to form C(=O).

In some embodiments, $R^{2a}$ is hydrogen and $R^{2b}$ is hydroxy, alkyl, or alkoxy. In some embodiments, $R^{2b}$ is hydroxy. In some embodiments, $R^{2b}$ is alkyl. In some embodiments, $R^{2b}$ is methyl. In some embodiments, $R^{2b}$ is alkoxy.

In some embodiments, $R^{2b}$ is hydrogen and $R^{2a}$ is hydroxy, alkyl, or alkoxy. In some embodiments, $R^{2a}$ is hydroxy. In some embodiments, $R^{2a}$ is alkyl. In some embodiments, $R^{2a}$ is methyl. In some embodiments, $R^{2a}$ is alkoxy. In some embodiments, $R^{2a}$ is methoxy. In some embodiments, $R^{2a}$ is ethoxy. In some embodiments, $R^{2a}$ is propoxy. In some embodiments, $R^{2a}$ is —OCH$_2$CH$_2$OCH$_3$. In some embodiments, $R^{2a}$ is —OCH(CH$_3$)$_2$.

In some embodiments, $R^3$ is alkyl (e.g., $C_1$-$C_6$ alkyl) or alkoxy (e.g., $C_1$-$C_6$ alkoxy).

In some embodiments, the compound is a compound of Formula (IIIa):

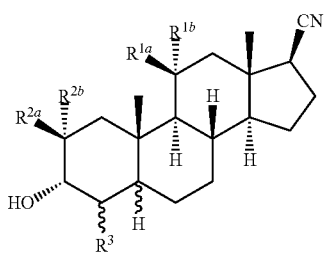

Formula (IIIa)

wherein one of $R^{1a}$ and $R^{1b}$ is halo, hydroxy, alkyl, alkoxy, —C(O)R$^a$, —C(O)N(R$^b$)(R$^c$), —C(O)OR$^a$, —N(R$^h$)(R$^i$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$), and the other one is hydrogen; or $R^{1a}$ and $R^{1b}$ are taken together with the carbon to which they are attached to form C(=O); one of $R^{2a}$ and $R^{2b}$ is halo (e.g., chloro, fluoro, bromo, iodo), hydroxy, alkyl, alkoxy, —C(O)R$^a$, —C(O)N(R$^b$)(R$^c$), —C(O)OR$^a$, —N(R$^f$)(R$^g$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$), and the other one is hydrogen; $R^3$ is hydrogen or $C_1$-$C_6$ alkyl; each R$^a$ is hydrogen or $C_1$-$C_6$ alkyl; each R$^b$ and R$^c$ is independently hydrogen or $C_1$-$C_6$ alkyl, or R$^b$ and R$^c$, taken together with the nitrogen atom to which they are attached, form 3-7-membered (e.g., 5-7-membered) heterocyclic ring; each R$^f$ and R$^g$ is independently hydrogen or $C_1$-$C_6$ alkyl, or R$^f$ and R$^g$, taken together with the nitrogen atom to which they are attached, form a 3-7-membered (e.g., 5-7-membered) heterocyclic ring optionally comprising one additional heteroatom selected from nitrogen, oxygen and sulfur; and each R$^h$ is unsubstituted $C_1$-$C_4$ alkyl; each R$^1$ is hydrogen, substituted methyl or $C_2$-$C_6$ alkyl, or R$^h$ and R$^i$, together with the nitrogen atom to which they are attached, form a 3-7-membered (e.g., 5-7-membered) heterocyclic ring.

In some embodiments, $R^{1a}$ is hydrogen and $R^{1b}$ is hydroxy, alkyl, or alkoxy.

In some embodiments, $R^{1b}$ is hydrogen and $R^{1a}$ is hydroxy, alkyl, or alkoxy. In some embodiments, $R^{1a}$ is hydroxy. In some embodiments, $R^{1a}$ is alkoxy. In some embodiments, $R^{1a}$ is methoxy.

In some embodiments, $R^{1a}$ and $R^{1b}$ are taken together with the carbon to which they are attached to form C(=O).

In some embodiments, $R^{2a}$ is H and $R^{2b}$ is hydroxy, alkyl, or alkoxy. In some embodiments, $R^{2b}$ is hydroxy. In some embodiments, $R^{2b}$ is alkyl. In some embodiments, $R^{2b}$ is methyl. In some embodiments, $R^{2b}$ is alkoxy.

In some embodiments, $R^{2b}$ is H and $R^{2a}$ is hydroxy, alkyl, or alkoxy. In some embodiments, $R^{2a}$ is hydroxy. In some embodiments, $R^{2a}$ is alkyl. In some embodiments, $R^{2a}$ is methyl. In some embodiments, $R^{2a}$ is alkoxy. In some embodiments, $R^{2a}$ is methoxy. In some embodiments, $R^{2a}$ is ethoxy. In some embodiments, $R^{2a}$ is propoxy. In some embodiments, $R^{2a}$ is —OCH$_2$CH$_2$OCH$_3$. In some embodiments, $R^{2a}$ is —OCH(CH$_3$)$_2$.

In some embodiments, $R^3$ is hydrogen. In some embodiments, $R^3$ is $C_1$-$C_6$ alkyl.

In some embodiments, the compound is a compound of Formula (IIIb):

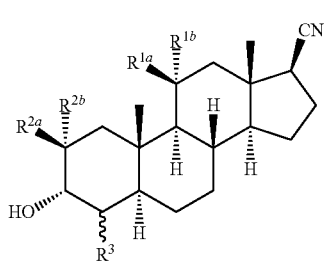

Formula (IIIb)

wherein one of $R^{1a}$ and $R^{1b}$ is halo (e.g., chloro, fluoro, bromo, iodo), hydroxy, alkyl, alkoxy, —C(O)R$^a$, —C(O)N(R$^b$)(R$^c$), —C(O)OR$^a$, —N(R$^h$)(R$^i$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$), and the other one is hydrogen; or $R^{1a}$ and $R^{1b}$ are taken together with the carbon to which they are attached to form C(=O); one of $R^{2a}$ and $R^{2b}$ is halo (e.g., chloro, fluoro, bromo, iodo), hydroxy, alkyl, alkoxy, —C(O)R$^a$, —C(O)N(R$^b$)(R$^c$), —C(O)OR$^a$, —N(R$^f$)(R$^g$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$), and the other one is hydrogen; $R^3$ is hydrogen or $C_1$-$C_6$ alkyl; each R$^a$ is hydrogen or $C_1$-$C_6$ alkyl; each R$^b$ and R$^c$ is independently hydrogen or $C_1$-$C_6$ alkyl, or R$^b$ and R$^c$, taken together with the nitrogen atom to which they are attached, form 3-7-membered (e.g., 5-7-membered) heterocyclic ring; each R$^f$ and R$^g$ is independently hydrogen or $C_1$-$C_6$ alkyl, or R$^f$ and R$^g$, taken together with the nitrogen atom to which they are attached, form a 3-7-membered (e.g., 5-7-membered) heterocyclic ring optionally comprising one additional heteroatom selected from nitrogen, oxygen and sulfur; and each R$^h$ is unsubstituted $C_1$-$C_4$ alkyl; each R$^1$ is hydrogen, substituted methyl or $C_2$-$C_6$ alkyl, or R$^h$ and R$^i$, together with the nitrogen atom to which they are attached, form a 3-7-membered (e.g., 5-7-membered) heterocyclic ring.

In some embodiments, $R^{1a}$ is hydrogen and $R^{1b}$ is hydroxy, alkyl, or alkoxy.

In some embodiments, $R^{1b}$ is hydrogen and $R^{1a}$ is hydroxy, alkyl, or alkoxy. In some embodiments, $R^{1a}$ is hydroxy. In some embodiments, $R^{1a}$ is alkoxy. In some embodiments, $R^{1a}$ is methoxy.

In some embodiments, $R^{1a}$ and $R^{1b}$ are taken together with the carbon to which they are attached to form C(=O).

In some embodiments, $R^{2a}$ is H and $R^{2b}$ is hydroxy, alkyl, or alkoxy. In some embodiments, $R^{2b}$ is hydroxy. In some embodiments, $R^{2b}$ is alkyl. In some embodiments, $R^{2b}$ is methyl. In some embodiments, $R^{2b}$ is alkoxy.

In some embodiments, $R^{2b}$ is H and $R^{2a}$ is hydroxy, alkyl, or alkoxy. In some embodiments, $R^{2a}$ is hydroxy. In some embodiments, $R^{2a}$ is alkyl. In some embodiments, $R^{2a}$ is methyl. In some embodiments, $R^{2a}$ is alkoxy. In some embodiments, $R^{2a}$ is methoxy. In some embodiments, $R^{2a}$ is ethoxy. In some embodiments, $R^{2a}$ is propoxy. In some embodiments, $R^{2a}$ is —OCH$_2$CH$_2$OCH$_3$. In some embodiments, $R^{2a}$ is —OCH(CH$_3$)$_2$.

In some embodiments, R³ is hydrogen. In some embodiments, R³ is $C_1$-$C_6$ alkyl.
In one aspect, provided is a compound selected from:
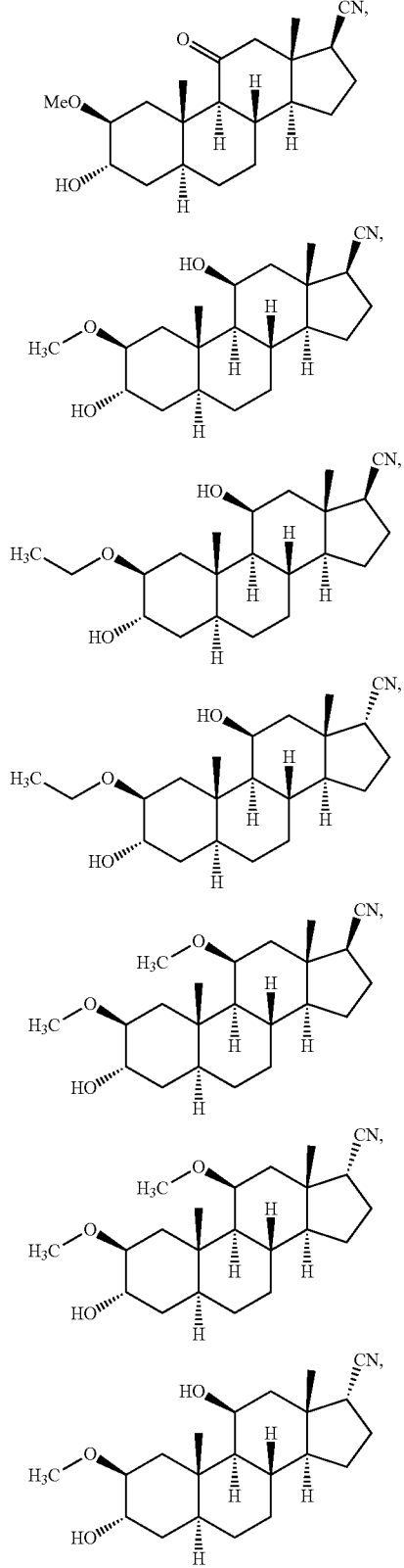
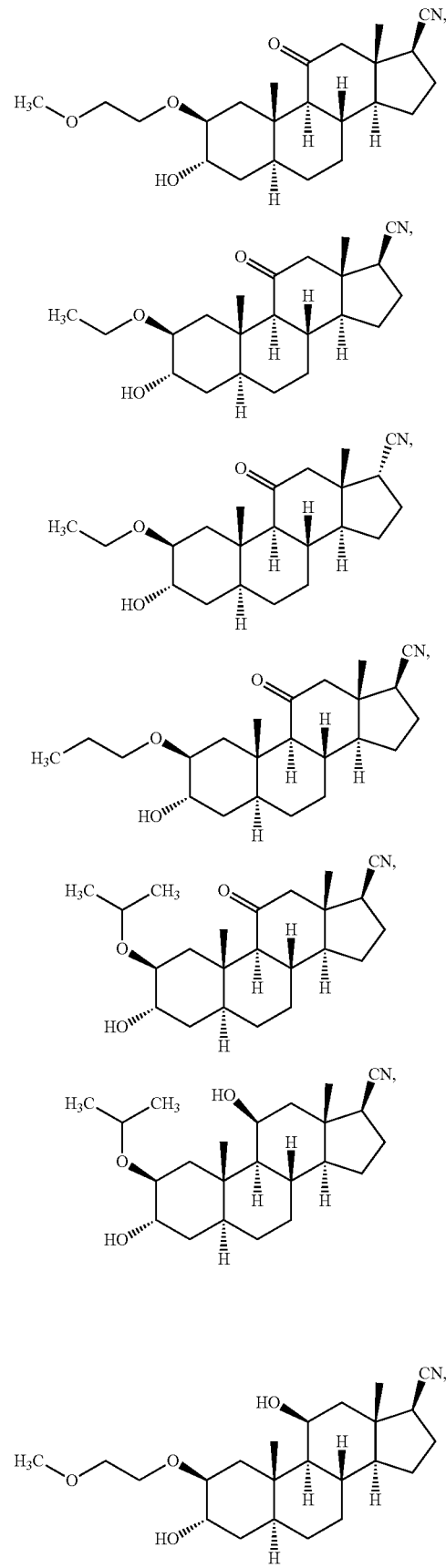

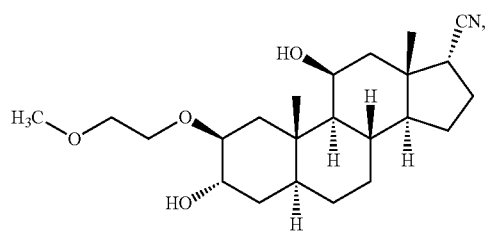
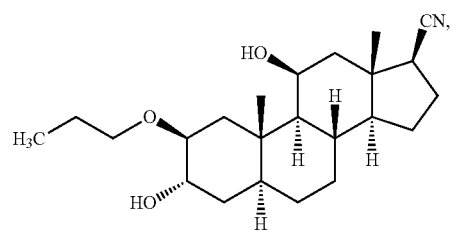
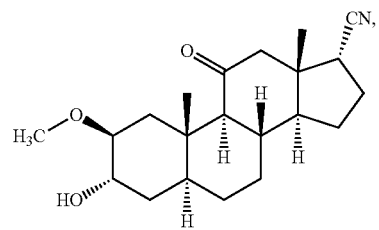
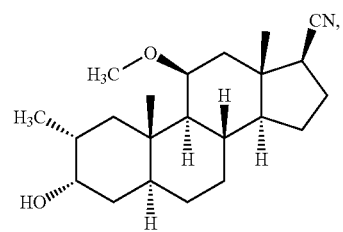
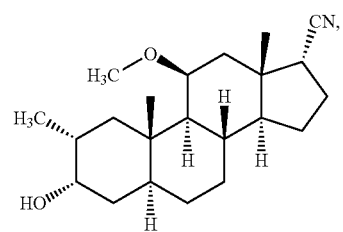
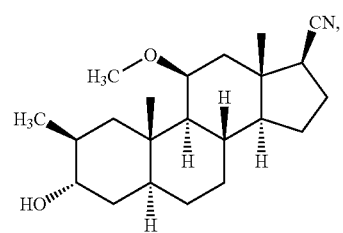
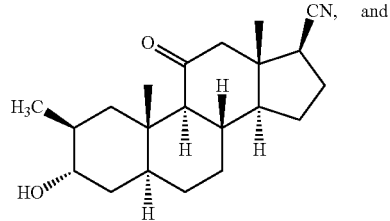
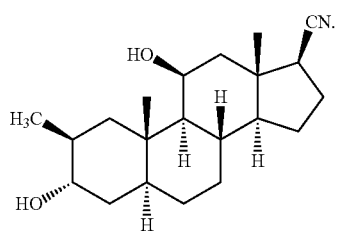
In one aspect, provided is a compound selected from:
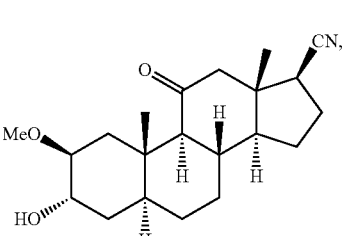
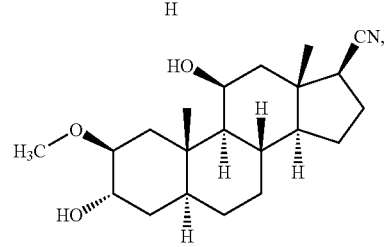
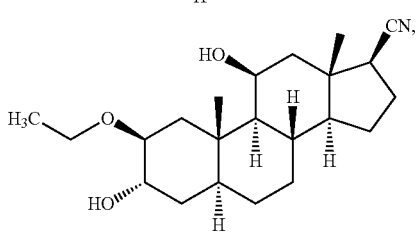
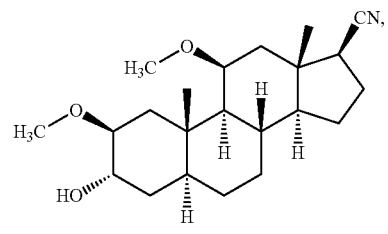
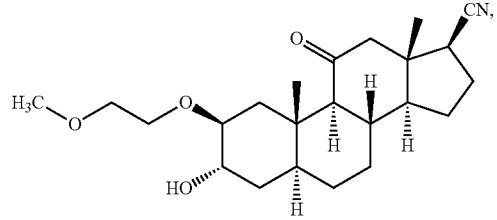
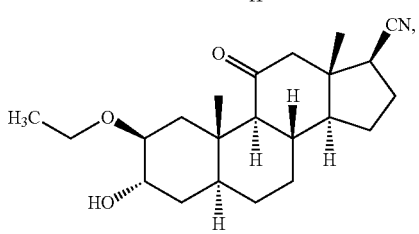

-continued

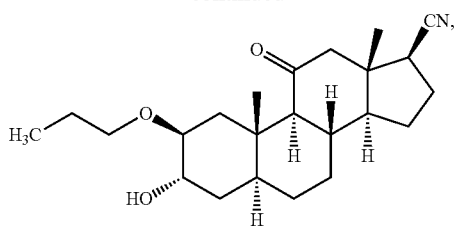

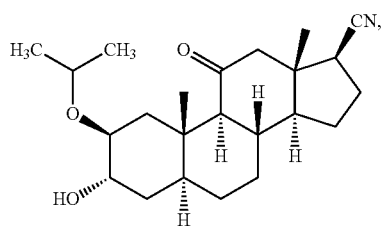

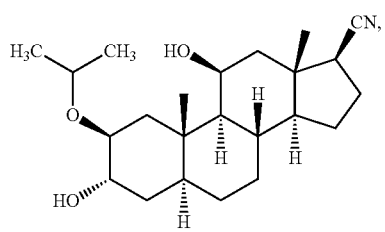

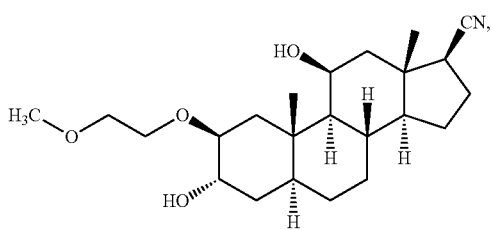

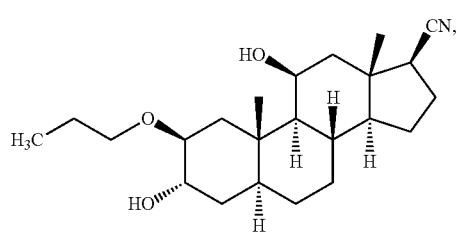

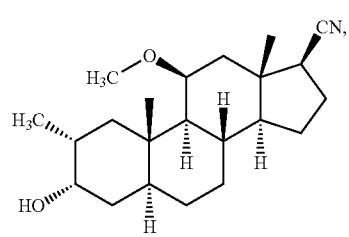

-continued

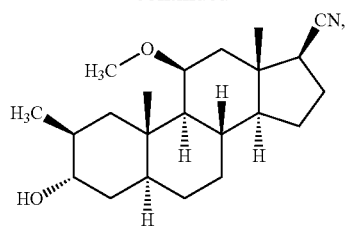

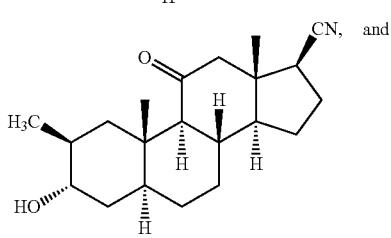

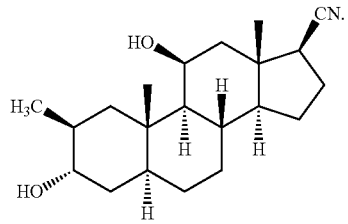

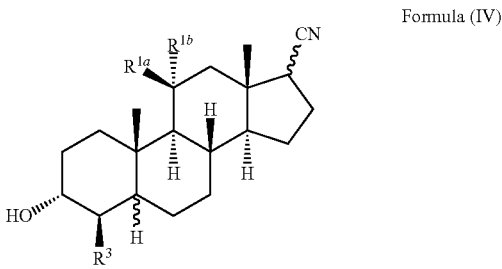

In one aspect, provided is a compound of the Formula (IV):

Formula (IV)

wherein one of $R^{1a}$ and $R^{1b}$ is halo, hydroxy, alkyl, alkoxy, —C(O)R$^a$, —C(O)N(R$^b$)(R$^c$), —C(O)OR$^a$, —N(R$^b$)(R$^c$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$), and the other one is hydrogen; or $R^{1a}$ and $R^{1b}$ are taken together with the carbon to which they are attached to form C(=O); $R^3$ is alkyl or alkoxy; each R$^a$ is hydrogen or C$_1$-C$_6$ alkyl; each R$^b$ and R$^c$ is independently hydrogen or C$_1$-C$_6$ alkyl, or R$^b$ and R$^c$, together with the nitrogen atom to which they are bound to form a 3-7-membered (e.g., 5-7-membered) heterocyclic ring.

In some embodiments, $R^{1b}$ is hydrogen and $R^{1a}$ is hydroxy, alkyl, or alkoxy. In some embodiments, $R^{1a}$ is hydroxy. In some embodiments, $R^{1a}$ is alkyl. In some embodiments, $R^{1a}$ is alkoxy. In some embodiments, $R^{1a}$ is methoxy.

In some embodiments, $R^{1a}$ and $R^{1b}$ are taken together with the carbon to which they are attached to form C(=O).

In some embodiments, $R^3$ is alkyl. In some embodiments, $R^3$ is methyl.

In some embodiments, provided is a compound selected from:

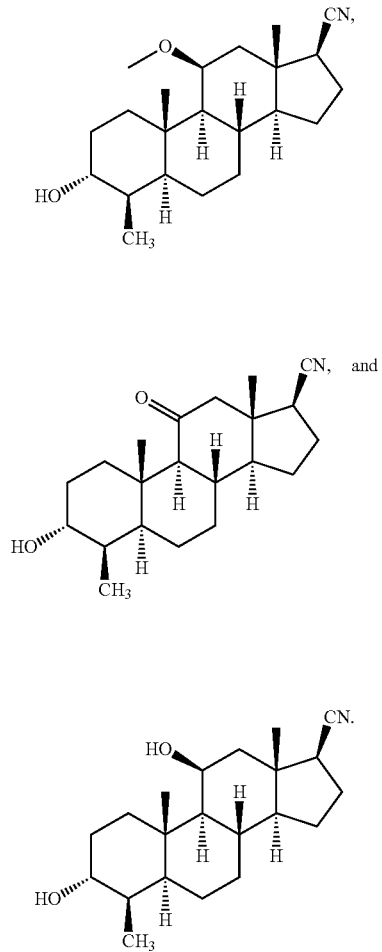

In one aspect, provided is a compound of the Formula (V):

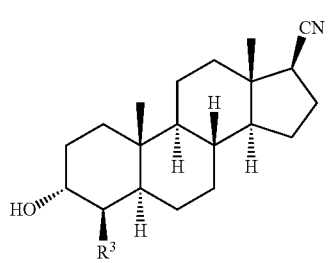

Formula (V)

wherein R³ is alkyl or alkoxy.

In some embodiments, R³ is alkyl. In some embodiments, R³ is methyl or ethyl.

In some embodiments, provided is a compound selected from:

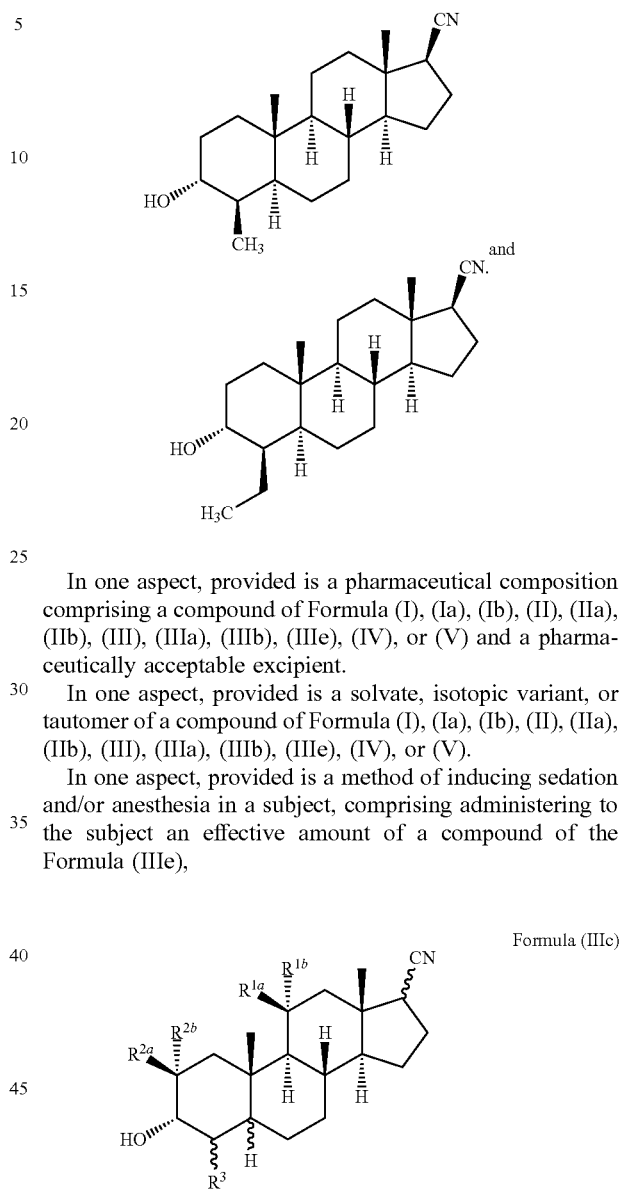

In one aspect, provided is a pharmaceutical composition comprising a compound of Formula (I), (Ia), (Ib), (II), (IIa), (IIb), (III), (IIIa), (IIIb), (IIIe), (IV), or (V) and a pharmaceutically acceptable excipient.

In one aspect, provided is a solvate, isotopic variant, or tautomer of a compound of Formula (I), (Ia), (Ib), (II), (IIa), (IIb), (III), (IIIa), (IIIb), (IIIe), (IV), or (V).

In one aspect, provided is a method of inducing sedation and/or anesthesia in a subject, comprising administering to the subject an effective amount of a compound of the Formula (IIIe),

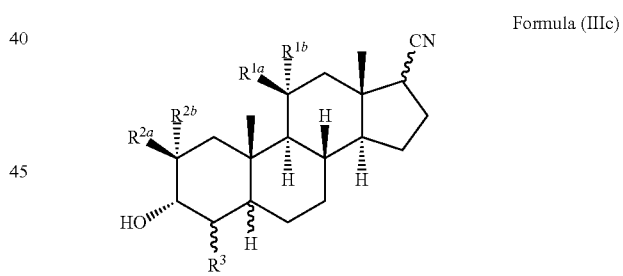

Formula (IIIc)

a pharmaceutically acceptable salt or a pharmaceutical composition thereof,
wherein one of $R^{1a}$ and $R^{1b}$ is halo (e.g., chloro, fluoro, bromo, iodo), hydroxy, alkyl, alkoxy, —C(O)R$^a$, —C(O)N(R$^b$)(R$^c$), —C(O)OR$^a$, —N(R$^b$)(R$^c$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$); or $R^{1a}$ and $R^{1b}$ are optionally taken together with the carbon to which they are attached to form C(=O); one of $R^{2a}$ and $R^{2b}$ is halo (e.g., chloro, fluoro, bromo, iodo), hydroxy, alkyl, methoxy, substituted ethoxy, $C_3$-$C_6$ alkoxy, —C(O)R$^a$, —C(O)N(R$^b$)(R$^c$), —C(O)OR$^a$, —N(R$^f$)(R$^g$), —OC(O)N(R$^b$)(R$^c$), —OC(O)OR$^a$, —OC(O)R$^a$, —S(O)$_{0-2}$R$^a$, —S(O)$_{0-2}$OR$^a$, or —S(O)$_{0-2}$N(R$^b$)(R$^c$), wherein one of $R^{1a}$, $R^{1b}$, $R^{2a}$, and $R^{2b}$ is not hydrogen, and when $R^{1a}$ and $R^{1b}$ are taken together with the carbon to which they are attached to form C(=O), one of $R^{2a}$ and $R^{2b}$ is hydrogen; R³ is hydrogen or $C_1$-$C_6$ alkyl; each R$^a$ is hydrogen or $C_1$-$C_6$ alkyl; each $R^b$ and $R^c$ is independently hydrogen or $C_1$-$C_6$ alkyl, or $R^b$ and $R^c$, taken together with the nitrogen atom to which they are attached, form a 3-7-membered (e.g., 5-7-membered) heterocyclic ring; each $R^f$ and $R^g$ is independently hydrogen or $C_1$-$C_6$ alkyl, or $R^f$ and $R^g$, taken together with the nitrogen atom to which they are attached, form a 3-7-membered (e.g., 5-7-membered) heterocyclic ring optionally comprising one additional heteroatom selected from nitrogen, oxygen and sulfur; and each $R^j$ and $R^k$ is independently hydrogen, substituted methyl, or $C_3$-$C_6$ alkyl, or $R^j$ and $R^k$, taken together with the nitrogen atom to which they are attached, form a 3-7-membered (e.g., 5-7-membered) heterocyclic ring optionally comprising one additional heteroatom selected from nitrogen, oxygen and sulfur.

In some embodiments, $R^{1a}$ is hydrogen and $R^{1b}$ is hydroxy, alkyl, or alkoxy. In some embodiments, $R^{1b}$ is hydroxy. In some embodiments, $R^{1b}$ is alkyl. In some embodiments, $R^{1b}$ is methyl or ethyl. In some embodiments, $R^{1b}$ is alkoxy. In some embodiments, $R^{1b}$ is methoxy. In some embodiments, $R^{1b}$ is ethoxy. In some embodiments, $R^{1b}$ is propoxy.

In some embodiments, $R^{1b}$ is hydrogen and $R^{1a}$ is hydroxy, alkyl, or alkoxy. In some embodiments, $R^{1a}$ is hydroxy. In some embodiments, $R^{1a}$ is alkyl. In some embodiments, $R^{1a}$ is methyl or ethyl. In some embodiments, $R^{1a}$ is alkoxy. In some embodiments, $R^{1a}$ is methoxy.

In some embodiments, $R^{1a}$ is ethoxy. In some embodiments, $R^{1a}$ is propoxy.

In some embodiments, $R^{1a}$ and $R^{1b}$ are taken together with the carbon to which they are attached to form C(=O).

In some embodiments, $R^{2a}$ is hydrogen and $R^{2b}$ is hydroxy, alkyl, methoxy, substituted ethoxy, or $C_3$-$C_6$ alkoxy. In some embodiments, $R^{2b}$ is methoxy. In some embodiments, $R^{2b}$ is —$OCF_3$. In some embodiments, $R^{2b}$ is substituted ethoxy. In some embodiments, $R^{2b}$ is —$OCH_2CH_2OMe$. In some embodiments, $R^{2b}$ is —$OCH_2CH_2OH$. In some embodiments, $R^{2b}$ is —$OCH_2CF_3$. In some embodiments, $R^{2b}$ is $C_3$-$C_6$ alkoxy. In some embodiments, $R^{2b}$ is propoxy. In some embodiments, $R^{2b}$ is —$OCH(CH_3)_2$. In some embodiments, $R^{2b}$ is —$OCH_2CH(CH_3)_2$. In some embodiments, $R^{2b}$ is cyclopropoxy.

In some embodiments, $R^{2b}$ is hydrogen and $R^{2a}$ is methoxy. In some embodiments, $R^{2a}$ is —$OCF_3$. In some embodiments, $R^{2a}$ is substituted ethoxy. In some embodiments, $R^{2a}$ is —$OCH_2CH_2OMe$. In some embodiments, $R^{2a}$ is —$OCH_2CH_2OH$. In some embodiments, $R^{2a}$ is —$OCH_2CF_3$. In some embodiments, $R^{2a}$ is $C_3$-$C_6$ alkoxy. In some embodiments, $R^{2a}$ is propoxy. In some embodiments, $R^{2a}$ is —$OCH(CH_3)_2$. In some embodiments, $R^{2a}$ is —$OCH_2CH(CH_3)_2$. In some embodiments, $R^{2a}$ is cyclopropoxy.

In some embodiments, $R^3$ is hydrogen. In some embodiments, $R^3$ is $C_1$-$C_6$ alkyl.

In some embodiments, the compound is administered by intravenous administration.

In some embodiments, the compound is administered in combination with another therapeutic agent.

In one aspect, provided is a method for treating disorders related to GABA function in a subject in need thereof, the method comprising administering to the subject a therapeutically effective amount of a compound, a pharmaceutically acceptable salt thereof, or pharmaceutical composition of a compound as described herein (e.g., a compound of Formula (I), (Ia), (Ib), (II), (IIa), (IIb), (III), (IIIa), (IIIb), (IIIe), (IV), or (V)).

In one aspect, provided is a method of administering an effective amount of a compound, a pharmaceutically acceptable salt thereof, or pharmaceutical composition of one of a compound as described herein (e.g., a compound of Formula (I), (Ia), (Ib), (II), (IIa), (IIb), (III), (IIIa), (IIIb), (IIIe), (IV), or (V)), to a subject in need thereof, wherein the subject experiences sedation and/or anesthesia within two hours.

In some embodiments, the subject is a mammal. In some embodiments, the subject is a human.

In some embodiments, the method of administering is intravenous administration.

In some embodiments, the subject experiences sedation and/or anesthesia within one hour of administration. In some embodiments, the subject experiences sedation and/or anesthesia instanteously.

Pharmaceutical Compositions

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

Injection dose levels range from about 0.1 mg/kg/hour to at least 10 mg/kg/hour, all for from about 1 to about 120 hours and from about 24 to about 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient. An exemplary composition may be, for example, dissolved or suspended in a buffered sterile saline injectable aqueous medium to a concentration of approximately 5 mg/mL.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ Edition (Lippincott Williams & Wilkins, 2005).

Methods of Use and Treatment

As generally described herein, the present invention is directed to 17-cyano substituted neuroactive steroids comprising at least one substituent at one or more positions 2, 4, and/or 11 on the steroid scaffold, designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., *European Journal of Pharmacology*, 136:419-423 (1987)) demonstrated that certain 3α-hydroxylated steroids are orders of magnitude more potent as modulators of the GABA receptor complex (GRC) than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In one aspect, the present invention provides a method for treating disorders related to GABA function in a subject in need thereof, the method comprising administering to the subject a therapeutically effective amount of a compound as described herein, a pharmaceutically acceptable salt thereof, or a pharmaceutical composition comprising one of a compound as described herein.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of administering an effective amount of a compound of the present invention, to a subject in need thereof, wherein the subject experiences sedation and/or anesthesia within two hours of administration. In some embodiments, the subject experiences sedation and/or anesthesia within one hour of administration. In some embodiments, the subject experiences sedation and/or anesthesia instanteously.

In yet another aspect, provided is a method of cognition enhancement or treating memory disorder by administering to the subject a therapeutically effective amount of a compound of the present invention. In certain embodiments, the disorder is Alzheimer's disease.

In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses.

Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Anxiety Disorders

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

In one aspect, the present invention provides a method for treating epilepsy or status or status epilepticus in a subject, comprising administering to the subject a therapeutically effective amount of a compound as described herein, a pharmaceutically acceptable salt thereof, or a pharmaceutical composition comprising one of a compound as described herein.

The compounds and compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Synthetic Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, $3^{rd}$ Edition (John Wiley & Sons, New York, 1999), and references cited therein.

The compounds provided herein may be isolated and purified by known standard procedures. Such procedures include (but are not limited to) recrystallization, column chromatography, HPLC, or supercritical fluid chromatography (SFC). The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Figure 2:
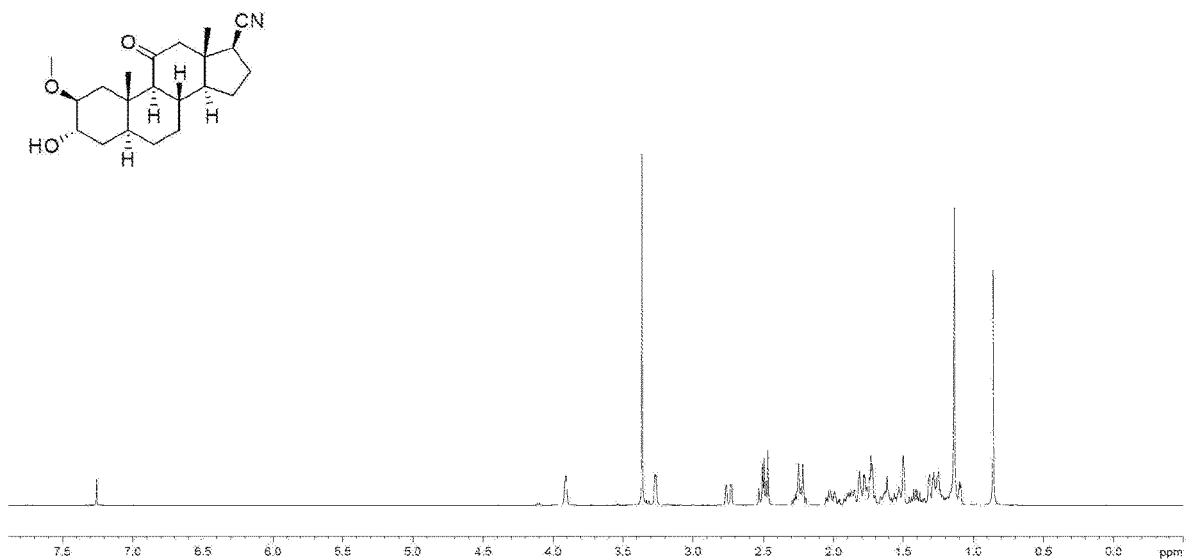
Figure 3:
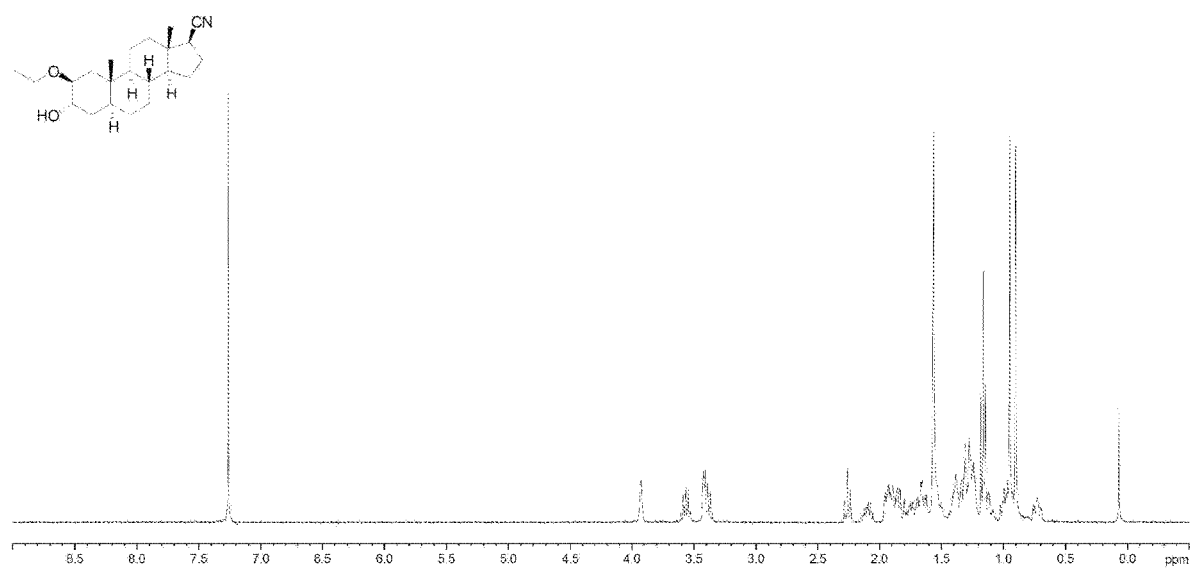
Figure 4:
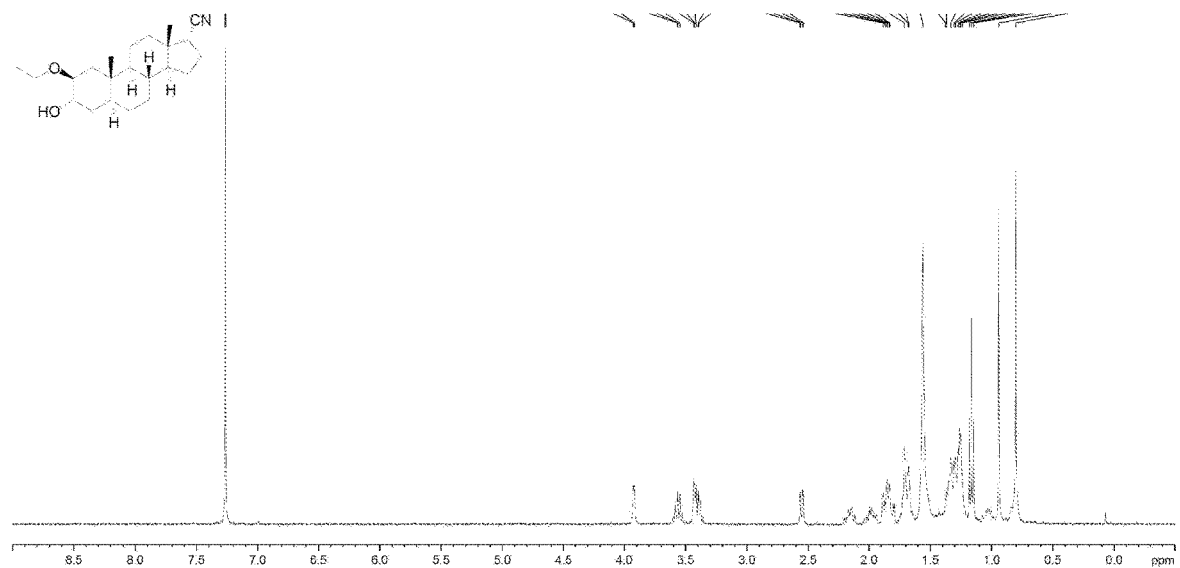
Figure 5:
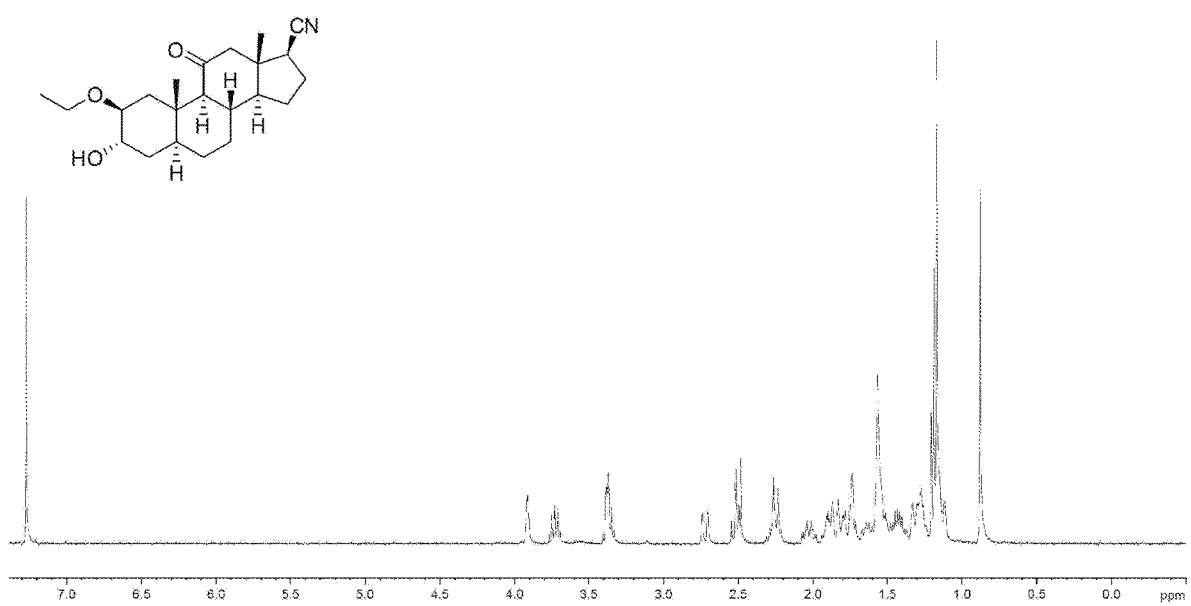
Figure 6:
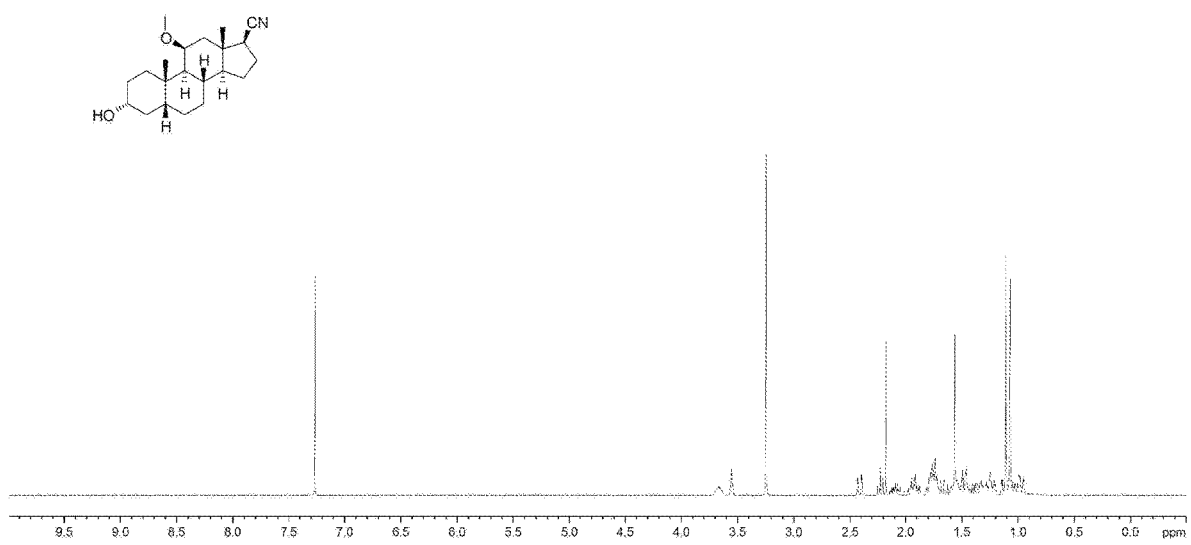
Figure 7:
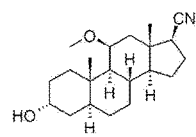
Figure 7:
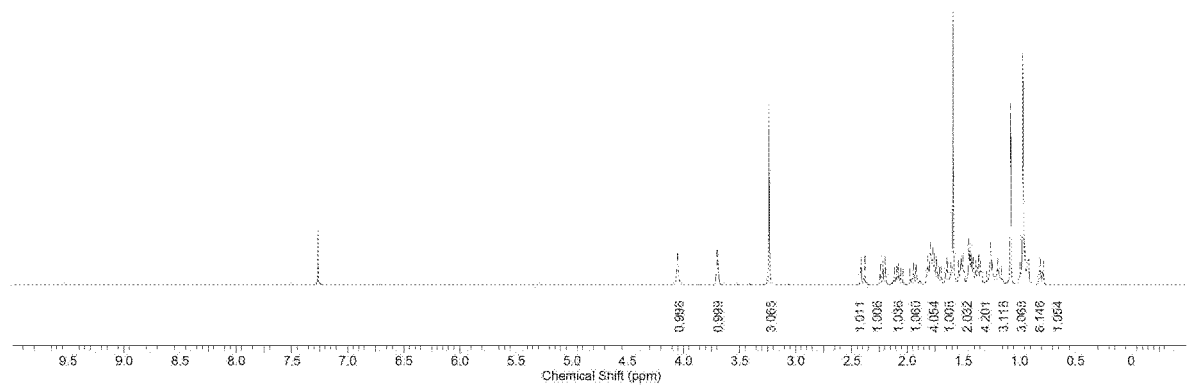
Figure 8:
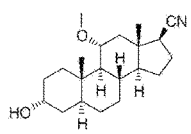
Figure 8:
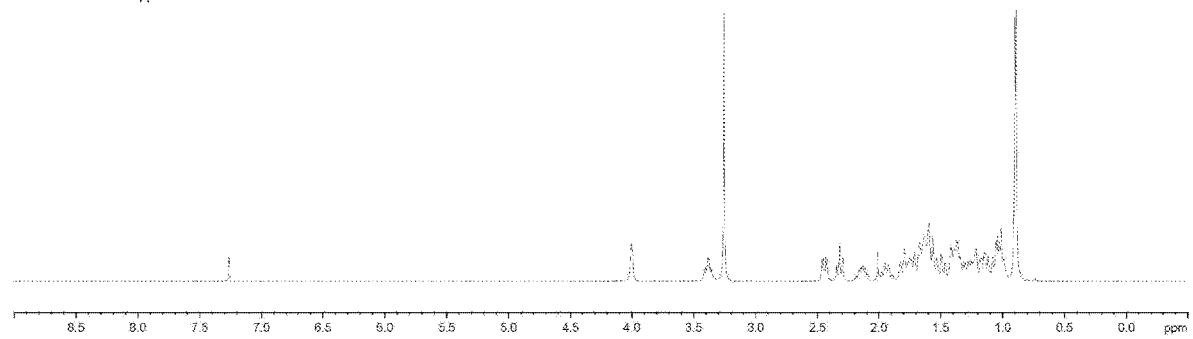
Figure 9:
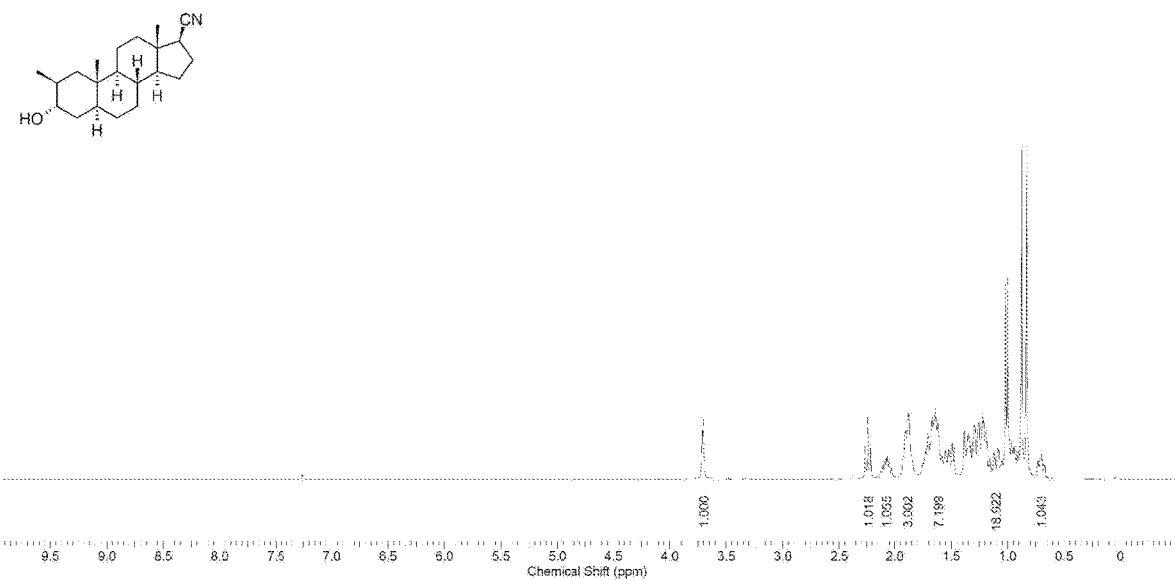
Figure 10:
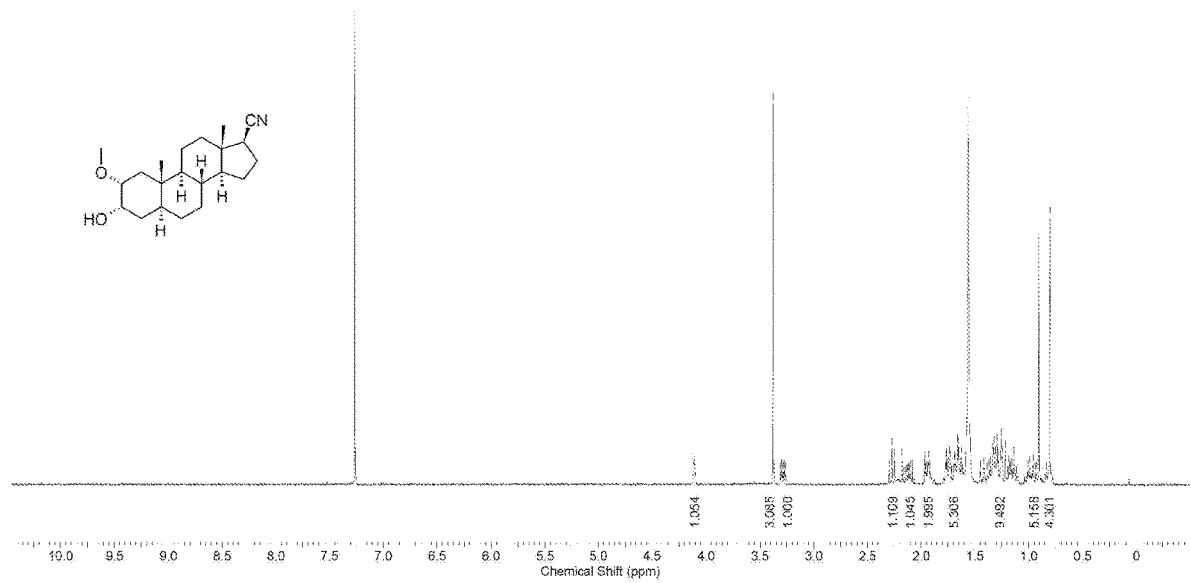
Figure 11:
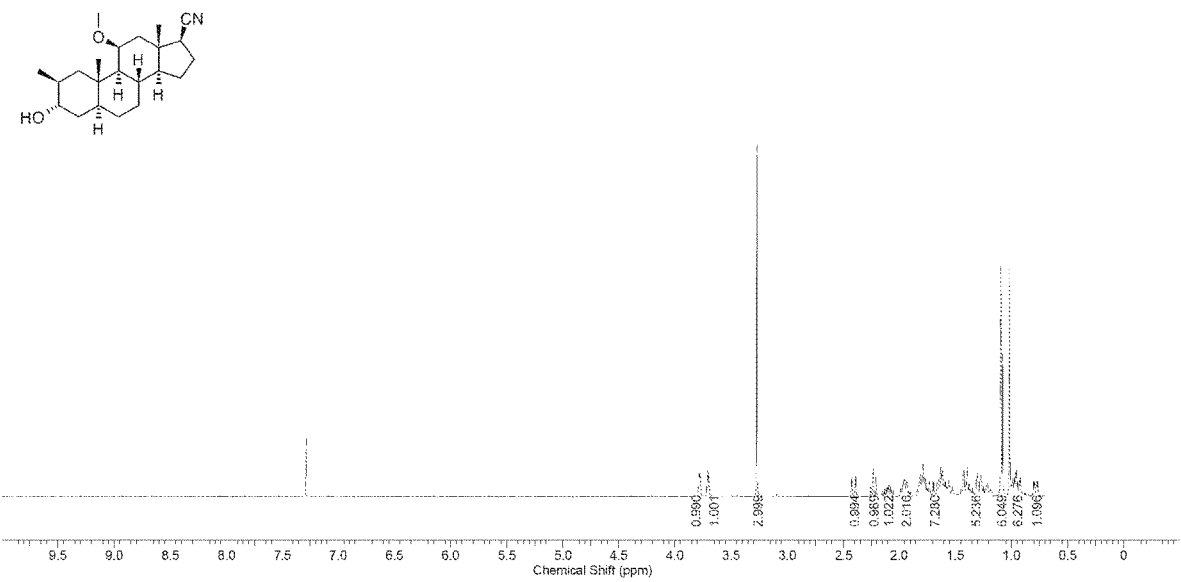
Figure 12:
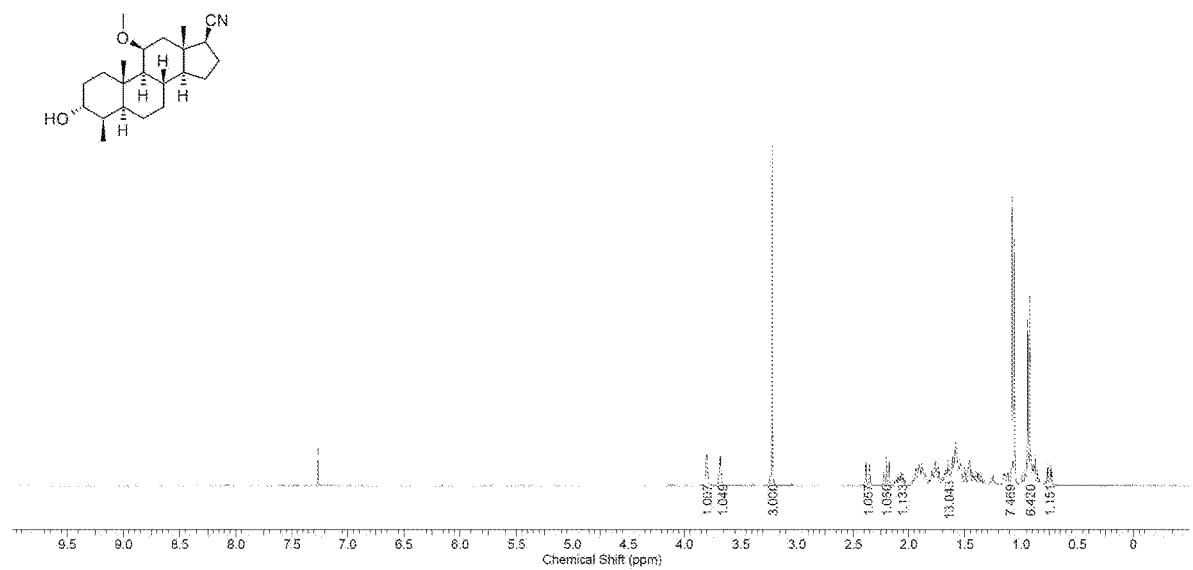

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm. Copies of full $^1$H-NMR spectrum for representative examples are provided in FIGS. 1-12.

Exemplary general method for preparative HPLC: Column: Waters RBridge prep 10 μm C18, 19*250 mm. Mobile phase: acetonitrile, water ($NH_4HCO_3$) (30 L water, 24 g $NH_4HCO_3$, 30 mL $NH_3.H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6×50 mm, 3.5 μm at 45° C.

Example 1. Synthesis of Compounds 1 and 2
Synthesis of A1 and A2 Intermediates
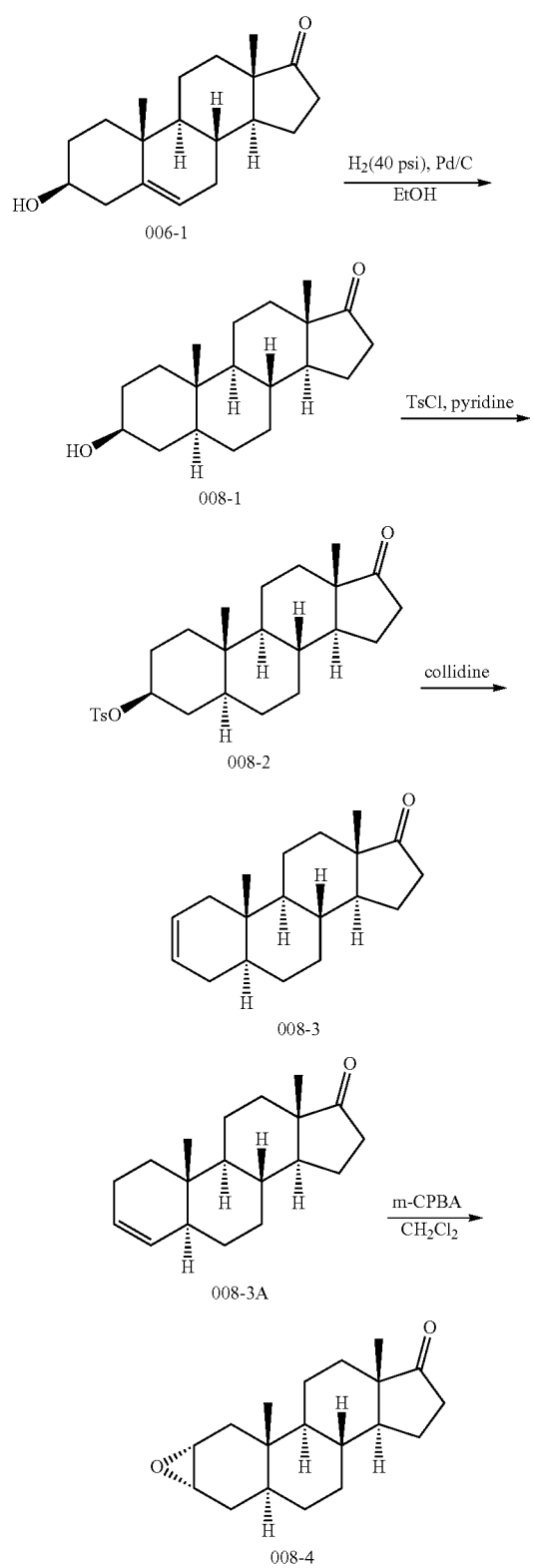
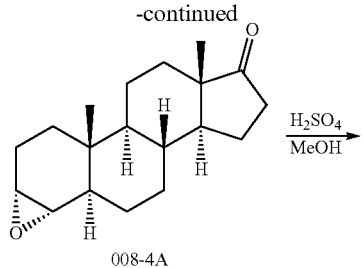
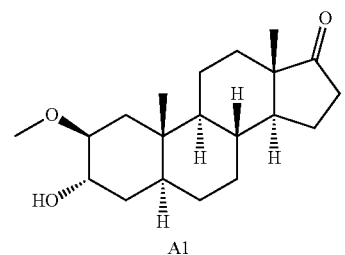
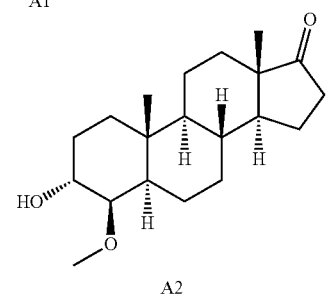
Synthesis of Compounds 1 and 2
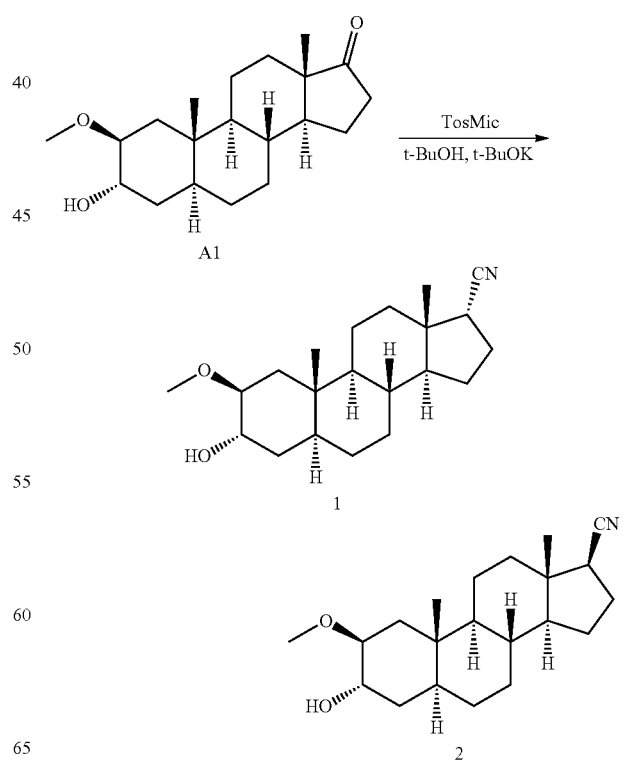

To a solution of 006-1, dehydroepiandrosterone (11 g, 38.17 mmol) in EtOH (150 mL) was added 10% Pd/C (1.1 g). Then the mixture was stirred under $H_2$ (40 psi) at 40° C. for 12 hours. TEC showed the starting material was consumed completely. The mixture was filtered and the filtrate was concentrated under vacuum to give 008-1 (11 g, 99%) as a white solid. $^1$H NMR (008-1): (400 MHz, CDCl$_3$) δ 3.59-3.51 (m, 1H), 2.46-2.39 (m, 1H), 2.10-2.01 (m, 1H), 1.92-1.81 (m, 1H), 1.80-0.94 (m, 19H), 0.85 (s, 3H), 0.82 (s, 3H), 0.69-0.62 (m, 1H).

To a solution of 008-1 (11 g, 37.8 mmol) in dry pyridine (150 mL) was added p-TsCl (11.4 g, 68.2 mmol) in portions. The mixture was stirred at 40° C. for 6 hours. Water was added slowly, then a white solid precipitated. The white solid was filtered, and washed with aqueous HCl (200 mL*3, 1M), followed by water (200 mL*3). The solid was dried to give 008-2 (13 g, 77%) as a white solid. $^1$H NMR (008-2): (400 MHz, CDCl$_3$) δ 7.78 (d, J=8.4 Hz, 2H), 7.32 (d, 7=8.0 Hz, 1H), 4.44-4.38 (m, 1H), 2.46-2.39 (m, 4H), 2.10-2.00 (m, 1H), 1.94-1.87 (m, 1H), 1.80-1.45 (m, 12H), 1.29-0.89 (m, 8H), 0.83 (s, 3H), 0.80 (s, 3H), 0.67-0.61 (m, 1H).

To a stirred solution of collidine (150 mL) was added 008-2 (12.0 g, 27.0 mmol). The mixture was stirred at 150° C. for 4 hours. TLC showed the starting material was consumed completely. The reaction mixture was treated with aqueous $H_2SO_4$ (500 mL, 10%) and a solid precipitated. The solid was filtered, washed with $H_2SO_4$ (500 mL×3, 10%) and water, and dried to give the crude product. Purification by column chromatography on silica gel (eluent: petroleum ether:ethyl acetate=100:1 to 50:1) afforded the mixture of 008-3 and 008-3A (7.2 g, 98%, 008-3:008-3A=3.5:1, confirmed by H-NMR) as a white solid. $^1$H NMR (008-3 and 008-3A): (400 MHz, CDCl$_3$) δ 5.61-5.59 (m, 2H), 2.47-2.40 (m, 1H), 2.11-1.60 (m, 10H), 1.59-1.20 (m, 9H), 0.99-0.95 (m, 1H), 0.87 (m, 3H), 0.79-0.75 (m, 4H).

To a stirred solution of the mixture of 008-3 and 008-3A (7.2 g, 26.4 mmol) in $CH_2Cl_2$ (100 mL) was added m-CPBA (6.8 g, 39.6 mmol) in portions at 0° C. The mixture was stirred at 0° C. for 1 hour, then at room temperature for 12 hours. The solvent was removed and the residue diluted with EtOAc; then the solution was washed successively with a saturated aqueous solution of $Na_2SO_3$ (200 mL) and a saturated aqueous solution of $Na_2CO_3$ (200 mL), dried over $MgSO_4$, filtered and evaporated to dryness. The crude product was purified by column chromatography on silica gel (eluent: petroleum ether:ethyl acetate=50:1 to 30:1) to give the mixture of 008-4 and 008-4A (7.0 g, 94.7%) as a white solid. $^1$H NMR (008-4 and 008-4A): (400 MHz, CDCl$_3$) δ 3.16-3.15 (m, 1H), 3.12-3.11 (m, 1H), 2.46-2.39 (m, 1H), 2.08-2.01 (m, 1H), 1.94-0.90 (m, 19H), 0.87-0.85 (m, 3H), 0.79-0.77 (m, 3H), 0.69-0.68 (m, 1H).

A solution of the mixture of 008-4 and 008-4A (3.0 g, 10.4 mmol) in MeOH (30 mL) was treated with 5 drops of $H_2SO_4$ (98%) at room temperature. After 1 hour, TLC showed the starting material was consumed completely. The reaction mixture was treated with aqueous $NaHCO_3$ and extracted with EtOAc. The organic layer was washed with brine, dried over $MgSO_4$, filtered and evaporated to dryness. The crude product was purified by flash column chromatography on silica gel (eluent: petroleum ether:ethyl acetate=15:1 to 10:1) to give the A1 (1.7 g, 51%) and A2 (0.5 g, 15%) as a white solid. $^1$H NMR (A1): (400 MHz, CDCl$_3$) δ 3.95-3.93 (m, 1H), 3.35-3.33 (m, 4H), 2.46-2.39 (m, 1H), 2.10-1.66 (m, 7H), 1.62-1.18 (m, 11H), 1.05-0.98 (m, 1H), 0.95 (s, 3H), 0.85 (s, 3H), 0.79-0.73 (m, 1H). $^1$H NMR (A2): (400 MHz, CDCl$_3$) δ 4.02-4.01 (m, 1H), 3.30 (s, 3H), 3.03-3.02 (m, 1H), 2.46-2.39 (m, 1H), 2.11-1.60 (m, 7H), 1.59-1.43 (m, 4H), 1.33-0.99 (m, 7H), 0.97 (s, 3H), 0.85 (s, 3H), 0.77-0.70 (m, 1H).

To a stirred solution of t-BuOK (3.5 g, 31.2 mmol) in BuOH (20 mL) was added of a solution of A1 (1.0 g, 3.12 mmol) in ethylene glycol dimethyl ether (20 mL) under $N_2$. A solution of TosMic (2.5 g, 12.48 mmol) in ethylene glycol dimethyl ether (10 mL) was added dropwise. The reaction mixture was stirred at room temperature for 12 hours and then treated with aqueous sodium chloride followed by hydrochloric acid (2 M) until acidic. The mixture was extracted with $CH_2Cl_2$, and the organic layer was washed with brine, dried over anhydrous $Na_2SO_4$, and concentrated to get a residue, which was purified by flash column chromatography on silica gel (eluent: petroleum ether:ethyl acetate=15:1 to 10:1) to give the 2 (250 mg, 24%) and 1 (110 mg, 11%) as a white solid. $^1$H NMR (2): (400 MHz, CDCl$_3$) δ 3.95-3.93 (m, 1H), 3.35-3.33 (m, 4H), 2.28-2.23 (m, 1H), 2.11-2.04 (m, 1H), 1.96-1.54 (m, 8H), 1.42-1.23 (m, 8H), 1.15-0.98 (m, 2H), 0.93 (s, 3H), 0.90 (s, 3H), 0.76-0.69 (m, 1H). $^1$H NMR (1): (400 MHz, CDCl$_3$) δ 3.95-3.93 (m, 1H), 3.35-3.30 (m, 4H), 2.57-2.54 (dd, $J_1$=2.0 Hz, $J_2$=7.2 Hz, 1H), 2.17-2.12 (m, 1H), 2.00-1.57 (m, 9H), 1.40-1.22 (m, 10H), 1.04-1.00 (m, 1H), 0.95 (s, 3H), 0.93-0.83 (m, 1H), 0.80 (s, 3H).

Example 2. Synthesis of Compounds 3 and 38

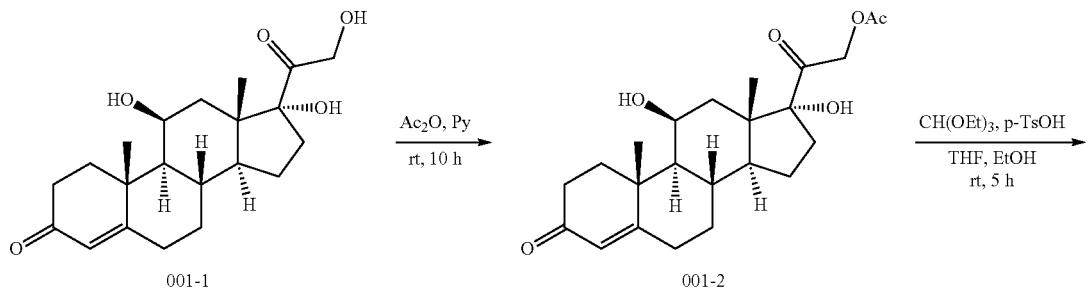

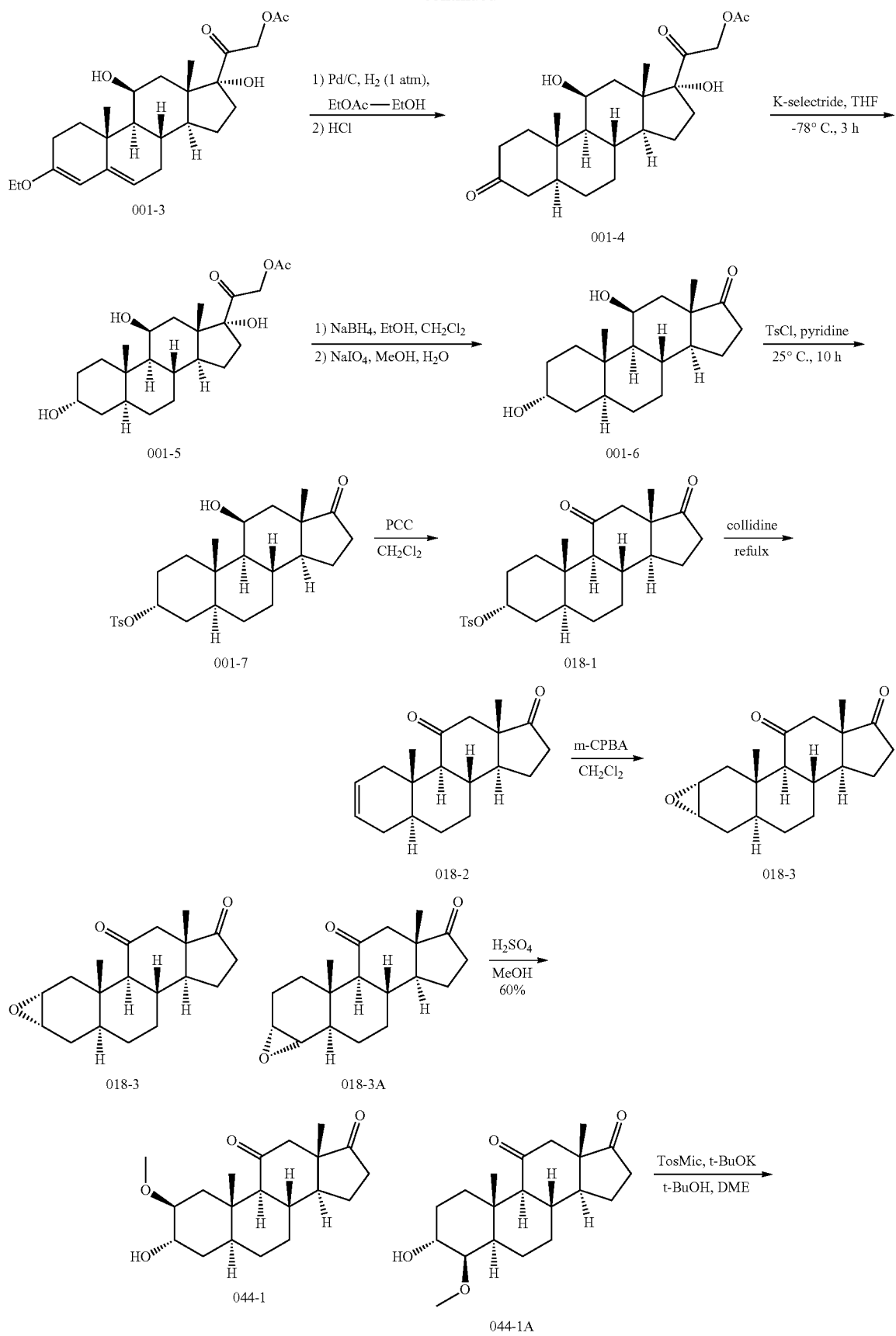

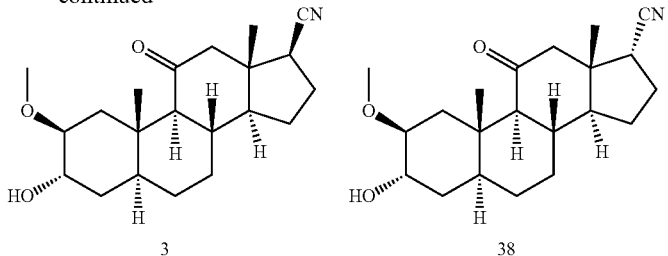

To a solution of 001-1 (20 g, 55 mmol) in pyridine (200 mL) was added dropwise Ac$_2$O (8.45 g, 82.8 mmol), then the mixture was stirred at room temperature over night. TLC (petroleum ether:ethyl acetate=1:1) showed that the starting material was consumed completely.

The mixture was poured into water (1.5 L) with stirring. The resulting solid was collected by filtration and washed with 500 mL of HCl (1 M), followed by water (500 mL×3). The solid was dried by lyophilization, and 001-2 (19.1 g, 85.9%) was obtained as a white solid. $^1$H NMR (001-2): (400 MHz, CDCl$_3$) δ 5.68 (s, 1H), 5.03 (d, J=17.6 Hz, 1H), 4.84 (d, J=17.6 Hz, 1H), 4.48-4.47 (m, 1H), 2.81-2.77 (m, 1H), 2.57-2.20 (m, 5H), 2.17 (s, 3H), 2.17-1.97 (m, 3H), 1.91-1.79 (m, 2H), 1.76-1.64 (m, 2H), 1.54-1.46 (m, 2H), 1.42 (s, 3H), 1.30-1.07 (m, 3H), 0.98 (s, 3H), 0.90-0.89 (m, 1H).

To a solution of 001-2 (17 g, 42 mmol) in EtOH (19 mL) and THF (190 mL) was added CH(OEt)$_3$ (38.6 mL, 231 mmol) and p-TsOH (463 mg, 2.31 mmol). The mixture was stirred at 20° C. for 4 h. TLC (petroleum ether:ethyl acetate=1:1) showed that the starting material was consumed completely. Then the mixture was diluted with EtOAc (200 mL), and washed with aqueous NaHCO$_3$ solution. The organic phase was dried over Na$_2$SO$_4$ and evaporated to give the crude product, which was purified by column chromatography on silica gel (eluent: petroleum ether:ethyl acetate=7:1) to afford 001-3 (12 g, 66.0%) as white solid, $^1$H NMR (001-3): (300 MHz, DMSO) δ 5.39 (s, 1H), 5.13-5.07 (m, 2H), 5.07-5.01 (m, 1H), 4.77-4.71 (d, J=23.4 Hz, 1H), 4.27 (m, 1H), 4.18-4.17 (m, 1H), 3.73-3.67 (m, 2H), 2.50-2.19 (m, 2H), 2.09 (s, 3H), 2.03-1.92 (m, 4H), 1.80-1.60 (m, 4H), 1.52-1.39 (m, 1H), 1.47-1.12 (m, 6H), 1.09 (s, 3H), 0.95-0.92 (m, H), 0.74 (s, 3H).

To a solution of 001-3 (1 g, 2.31 mmol) in EtOAc (20 mL) and EtOH (20 mL) was added 10% Pd/C (100 mg). The mixture was stirred at 20° C. for 30 min under H$_2$ (1 atm), then the mixture was filtered. To the resulting solution was added aqueous HCl (12%, 50 mL) and stirred for 20 min. The mixture was extracted with EtOAc (50 mL). The organic phase was washed with aqueous NaHCO$_3$ solution (50 mL). The organic phase was dried over Na$_2$SO$_4$ and evaporated to give the crude product, which was purified by column chromatography on silica gel (eluent: petroleum ether:ethyl acetate=2:1) to afford the 001-4 (605 mg, 64.4%) as a white solid. $^1$H NMR (001-4): (400 MHz, CDCl$_3$) δ 5.04 (d, J=17.2 Hz, 1H), 4.83 (d, J=17.2 Hz, 1H), 4.45-4.44 (m, 1H), 2.75-2.65 (m, 1H), 2.52-2.40 (m, 1H), 2.35-2.20 (m, 3H), 2.18 (s, 3H), 2.10-2.02 (m, 2H), 2.00-1.78 (m, 3H), 1.78-1.60 (m, 3H), 1.58-1.30 (m, 6H), 1.26 (s, 3H), 0.94 (s, 3H), 0.83-0.79 (m, 1H).

To a solution of 001-4 (5.3 g, 13.05 mmol) in THL (50 mL) was added dropwise a solution of K-selectride (19.34 mL, 19.34 mmol, 1M in THE) at −78° C. The mixture was stirred at −78° C. for 3 h. Then the mixture was quenched with H$_2$O$_2$ (0.4 mL). The mixture was extracted with EtOAc (80 mL) and H$_2$O (80 mL). The organic phase was washed with aqueous NaHCO$_3$ solution (100 mL). The organic phase was dried over Na$_2$SO$_4$ and evaporated to give the crude product (5.9 g), which was used in the next step without purification.

To a solution of 001-5 (5.9 g, 14.46 mmol) in EtOH (33 mL) and CH$_2$Cl$_2$ (33 mL) was added NaBH$_4$ (1.1 g, 28.92 mmol) in portions. The mixture was stirred at 15° C. over night. The reaction mixture was quenched with acetone (33 mL) and H$_2$O (33 mL). To the mixture was added MeOH (200 mL), H$_2$O (200 mL) and NaIO$_4$ (12.26 g, 57.56 mmol), then the mixture was stirred at 60° C. over night. The mixture was cooled to room temperature and extracted with EtOAc (3×100 mL). The combined organic phase was dried over Na$_2$SO$_4$ and evaporated to give the crude product, which was purified by column chromatography on silica gel (eluent: petroleum ether:ethyl acetate=2:1) to afford the 001-6 (2.5 g, 62%, two step) as a white solid. $^1$H NMR (001-6): (400 MHz, CDCl$_3$) δ 4.45-4.40 (m, 1H), 4.10-4.05 (m, 1H), 2.50-2.43 (m, 1H), 2.01-1.90 (m, 5H), 1.78-1.35 (m, 12H), 1.28-1.22 (m, 4H), 1.10 (s, 3H), 1.04 (s, 3H), 0.93-0.83 (m, 4H).

To a solution of 001-6 (2.5 g, 8.17 mmol) in pyridine (25 mL) was added TsCl (2.33 g, 12.25 mmol). The mixture was stirred at 25° C. for 10 h. TLC showed most of starting material was consumed. The reaction was extracted with EtOAc (50 mL×2), washed with brine (50 mL), the organic phase dried over Na$_2$SO$_4$ and evaporated to give the crude product, which was purified by column chromatography on silica gel (ethyl acetate/petroleum ether=1/4) to afford 001-7 (2 g, 53%) as a white solid. $^1$H NMR (001-7): (400 MHz, CDCl$_3$) δ 7.78 (d, 7=8.0 Hz, 2H), 7.32 (d, 7=8.0 Hz, 2H), 4.43-4.37 (m, 1H), 4.35-4.30 (m, 1H), 2.44 (s, 3H), 2.00-1.68 (m, 8H), 1.62-1.57 (m, 3H), 1.54-1.38 (m, 3H), 1.35-1.14 (m, 5H), 1.12 (s, 3H), 1.03 (s, 3H), 1.01-0.95 (m, 2H).

To a solution of 001-7 (8.0 g, 17.39 mmol) in CH$_2$Cl$_2$ (100 mL) was added PCC (7.5 g, 34.8 mmol) in portions at room temperature, then the reaction mixture was stirred overnight. TLC (petroleum ether:ethyl acetate=1:1) showed that the reaction was complete. The mixture was filtered off, the filtrate was concentrated to give crude product, which was purified by flash chromatography eluting with (petroleum ether:ethyl acetate=3:1) to give 018-1 (6.5 g, 81%) as a white solid.

Compound 018-1 (12 g, 26.2 mmol) was dissolved in collidine (40 mL), then the solution was heated to 130° C. and maintained at the temperature for 2 h. TLC (petroleum ether:ethyl acetate=3:1) showed that the reaction was complete. After the mixture was recovered to ambient temperature, it was poured into H$_2$SO$_4$ aqueous solution (10%). The solution was extracted with ethyl acetate (100 mL×3). The combined organic layer was washed with saturated NaHCO₃ solution and brine. The organic layer was dried over anhydrous Na₂SO₄ and concentrated the solvent to give almost pure 018-2 (7.0 g, 93.0%) as a white solid. $^1$H NMR (018-2): (400 MHz, CDCl₃) δ 5.65-5.50 (m, 2H), 2.85-2.75 (m, 1H), 2.57-2.50 (m, 1H), 2.45-2.40 (m, 2H), 2.39-2.13 (m, 3H), 2.11-2.07 (m, 1H), 1.96-1.74 (m, 3H), 1.65-1.60 (m, 2H), 1.51-1.48 (m, 1H), 1.28-1.18 (m, 4H), 0.98 (s, 3H), 0.84 (s, 3H).

To a solution of 018-2 (7.0 g, 24.3 mmol) in CH₂Cl₂ (50 mL) was added m-CPBA (6.3 g, 36.5 mmol) in portions. The resulting mixture was stirred at 10° C. for 20 h. TLC (petroleum ether:ethyl acetate=3:1) showed that few starting material was always existed. Then saturated Na₂SO₃ solution (100 mL) was added into the solution. The organic layer was washed with saturated NaHCO₃ solution and brine. The organic layer was dried over anhydrous Na₂SO₄ and concentrated the solvent. The residue was purified by flash chromatography eluting with (petroleum ether:ethyl acetate=10:1) to give 018-3 (4.8 g, 66%) as white solid. $^1$HNMR (018-3): (400 MHz, CDCl₃) δ 3.17-3.10 (m, 2H), 2.84-2.78 (m, 1H), 2.56-2.22 (m, 4H), 2.10-2.00 (m, 2H), 1.98-1.80 (m, 3H), 1.74-1.58 (m, 3H), 1.42-1.05 (m, 5H), 0.98 (s, 3H), 0.82 (s, 3H).

To a solution of the mixture of 018-3 and 018-3A (0.9 g, 3 mmol) in MeOH (10 mL) was added H₂SO₄ (5 drops, 98%). The mixture was stirred at 20° C. for 2 hours. TLC showed the starting material was consumed completely. The mixture was quenched with NaHCO₃ aqueous (40 mL). The mixture was extracted with EtOAc (20 mL×2) and washed with brine (20 mL). The organic phase was dried over Na₂SO₄ and concentrated to give the crude product, which was purified by column chromatography on silica gel (petroleum ethenediyl acetate=4:1) to give the pure 044-1 (200 mg, 20%) and the mixture of 044-1 and 044-1A (400 mg, 40%) as a white solid. $^1$H NMR (044-1): (300 MHz, CDCl3) δ 3.96-3.90 (m, 1H), 3.37 (s, 3H), 3.31-3.23 (m, 1H), 2.80-2.71 (m, 1H), 2.59-2.47 (m, 1H), 2.45-2.37 (m, 1H), 2.34-2.23 (m, 2H), 2.20-2.15 (m, 1H), 2.14-2.04 (m, 1H), 1.98-1.71 (m, 5H), 1.68-1.57 (m, 1H), 1.44-1.39 (m, 1H), 1.38-1.23 (m, 4H), 1.17 (s, 3H), 1.15-1.09 (m, 1H), 0.82 (s, 3H).

To a stirred solution of t-BuOK (6.53 g, 58.35 mmol) in BuOH (50 mL) was added of a solution of the 044-1 (3.9 g, 11.67 mmol) in 1,2-dimethoxyethane (50 mL) under N₂. A solution of TosMic (3.41 g, 17.5 mmol) in 1,2-dimethoxyethane (30 mL) was then added dropwise. The mixture was stirred at room temperature for 4 hours. The mixture was treated with aqueous sodium chloride followed by hydrochloric acid (2 M) until pH=2. The mixture was extracted with CH₂Cl₂, and the organic layer was washed with brine, dried over anhydrous Na₂SO₄, then concentrated to get residue, which was purified by flash column chromatography on silica gel (eluent: petroleum ether:ethyl acetate=4:1) to give 3 (1.24 g, 32%) and 38 (0.75 g, 19%) as white solids. $^1$H NMR: (3) (300 MHz, CDCl₃) δ 3.92-3.89 (m, 1H), 3.30 (s, 3H), 3.30-3.25 (m, 1H), 2.78-2.73 (m, 1H), 2.55-2.47 (m, 2H), 2.29-2.17 (m, 2H), 2.08-1.92 (m, 1H), 1.90-1.82 (m, 1H), 1.80-1.68 (m, 4H), 1.67-1.59 (m, 1H), 1.58-1.48 (m, 2H), 1.47-1.32 (m, 1H), 1.30-1.23 (m, 3H), 1.17 (s, 3H), 1.10-1.09 (m, 1H), 0.87 (s, 3H). $^1$H NMR: (38) (300 MHz, CDCl₃) δ 3.95-3.90 (m, 1H), 3.37 (s, 3H), 3.30-3.25 (m, 1H), 2.78-2.70 (m, 2H), 2.52-2.45 (m, 1H), 2.33-2.30 (m, 1H), 2.30-1.21 (m, 1H), 2.20-2.19 (m, 1H), 2.07-1.92 (m, 2H), 1.88-1.78 (m, 3H), 1.77-1.68 (m, 1H), 1.55-1.50 (m, 1H), 1.49-1.26 (m, 7H), 1.13 (s, 3H), 0.88 (s, 3H).

Example 3. Synthesis of Compounds 47 and 48

Synthesis of Intermediates 039-1 and 051-1

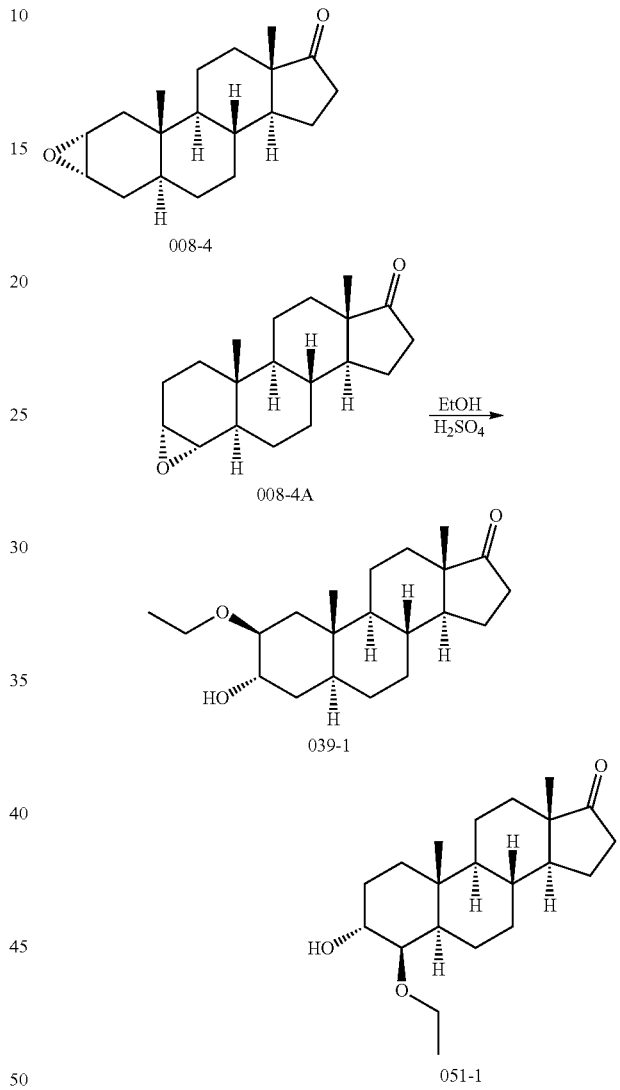

Synthesis of Compounds 47 and 48

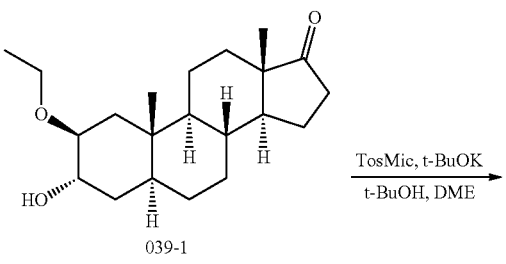

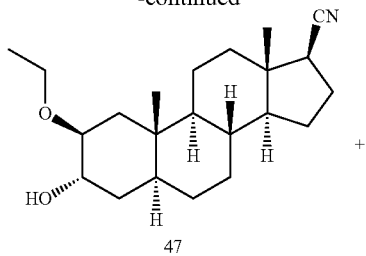

Example 4. Synthesis of Compound 4

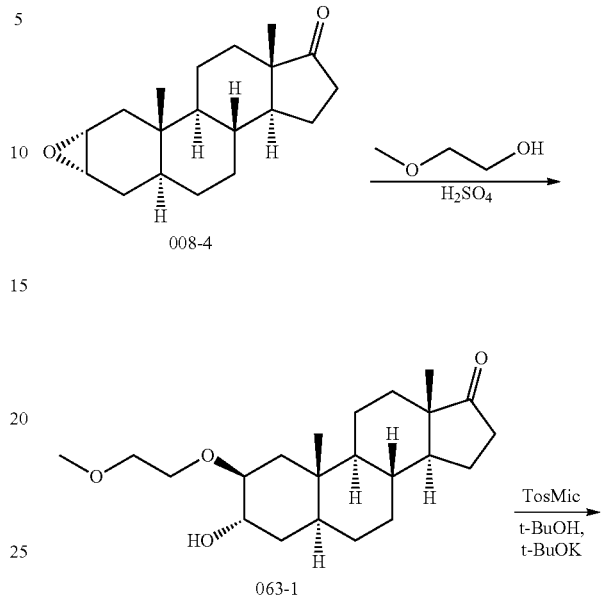

To a solution of the mixture of 008-4 and 008-4A (2.5 g, 8.68 mmol) in EtOH (75 mL) was added H₂SO₄ (10 drops, 98%). The mixture was stirred at 20° C. for 3 h. TEC showed the starting material was consumed completely. The mixture was quenched with aqueous NaHCO₃ (40 mL). The mixture was extracted with EtOAc (100 mL×2) and washed with aqueous NaCl (50 mL). The organic phase was dried over Na₂SO₄ and evaporated to give the crude product, which was purified by column chromatography on silica gel (ethyl acetate:petroleum ether=1:2) to afford the mixture of 039-1 and 051-1 (1.8 g, 60%) as a white solid.

To a solution of t-BuOK (1.47 g, 13.16 mmol) in t-BuOH (10 mL) was added a solution of 039-1 (440 mg, 1.32 mmol) in 1,2-dimethoxyethane (4 mL) dropwise at room temperature. Then a solution of TosMic (1.0 g, 5.1 mmol) in 1,2-dimethoxyethane (6 mL) was added dropwise to the mixture. The reaction mixture was warmed to room temperature and stirred for 4 hours. After the LCMS showed that the starting material was consumed completely, the mixture was quenched with aq. HCl solution and extracted with EtOAc (15 mL×3). The combined organic phases were dried over Na₂SO₄, and the solvent was evaporated to afford crude product. The crude product was purified by column chromatography on silica gel (eluent: petroleum ether:ethyl acetate=20:1) to give the products 47 (40.8 mg, 8.98%) and 48 (25.5 mg, 5.61%). $^1$H NMR (47): (400 MHz, CDCl₃) δ 3.96-3.92 (m, 1H), 3.61-3.52 (m, 1H), 3.45-3.35 (m, 2H), 2.32-2.22 (m, 1H), 2.18-2.05 (m, 1H), 2.00-1.60 (m, 7H), 1.45-1.20 (m, 9H), 1.20-1.05 (m, 4H), 1.05-0.91 (m, 5H), 0.88 (s, 3H), 0.80-0.71 (m, 1H). $^1$H NMR (48): (400 MHz, CDCl₃) δ 3.95-3.91 (m, 1H), 3.64-3.50 (m, 1H), 3.45-3.31 (m, 2H), 2.58-2.52 (m, 1H), 2.15-2.11 (m, 1H), 2.05-1.96 (m, 1H), 1.92-1.75 (m, 3H), 1.75-1.62 (m, 4H), 1.48-1.23 (m, 10H), 1.20-1.11 (m, 3H), 1.10-0.98 (m, 1H), 0.95 (s, 3H), 0.85-0.82 (m, 4H).

A solution of 008-4 (1.0 g, 3.46 mmol) in 2-methoxyethanol (10 mL) was treated with 3 drops of fuming H₂SO₄ at room temperature. After 1 hour, the reaction mixture was treated with aqueous NaHCO₃. The resulting solution was extracted with 2×100 mL of ethyl acetate and the organic layers combined and dried over anhydrous sodium sulfate. The organic phase was concentrated under vacuum. The crude product was purified by column chromatography on silica gel (petroleum ether:ethyl acetate=10:1) to give the product 063-1 (330 mg, 26%) as a white solid. $^1$H NMR (063-1): (400 MHz, CDCl₃) δ 3.97-3.96 (m, 1H), 3.67-3.63 (m, 1H), 3.53-3.51 (m, 3H), 3.50-3.45 (m, 1H), 3.38 (s, 3H), 2.46-2.41 (m, 1H), 1.92-1.65 (m, 8H), 1.54-1.21 (m, 11H), 1.02-0.98 (m, 1H), 0.96 (s, 3H), 0.85 (s, 3H), 0.78-0.75 (m, 1H).

To a stirred solution of t-BuOK (1.01 g, 9.00 mmol) in BuOH (3 mL) was added of a solution of 063-1 (330 mg, 0.90 mmol) in 1,2-dimethoxyethane (3 mL) under N₂. A solution of TosMic (720 mg, 3.60 mmol) in 1,2-dimethoxyethane (3 mL) was then added dropwise. The mixture was stirred at room temperature for 12 hours. The mixture was treated with aqueous sodium chloride followed by hydrochloric acid (2 M) until pH=2. The mixture was extracted with CH₂Cl₂, and the organic layer was washed with brine, dried over anhydrous sodium sulfate, then concentrated to give the crude product, which was purified by column chromatography on silica gel (eluent: petroleum ether:ethyl acetate=15:1 to 10:1) to give the 4 (25 mg, 12%). $^1$H NMR (4): (400 MHz, CDCl$_3$) δ 3.97-3.96 (m, 1H), 3.68-3.64 (m, 1H), 3.53-3.51 (m, 3H), 3.50-3.46 (m, 1H), 3.38 (s, 3H), 2.28-2.23 (m, 1H), 2.11-2.07 (m, 1H), 1.95-1.60 (m, 7H), 1.53-1.23 (m, 10H), 1.15-1.11 (m, 1H), 1.02-0.97 (m, 1H), 0.96 (s, 3H), 0.92 (s, 3H), 0.76-0.70 (m, 1H).

Example 5. Synthesis of Compounds 5 and 6

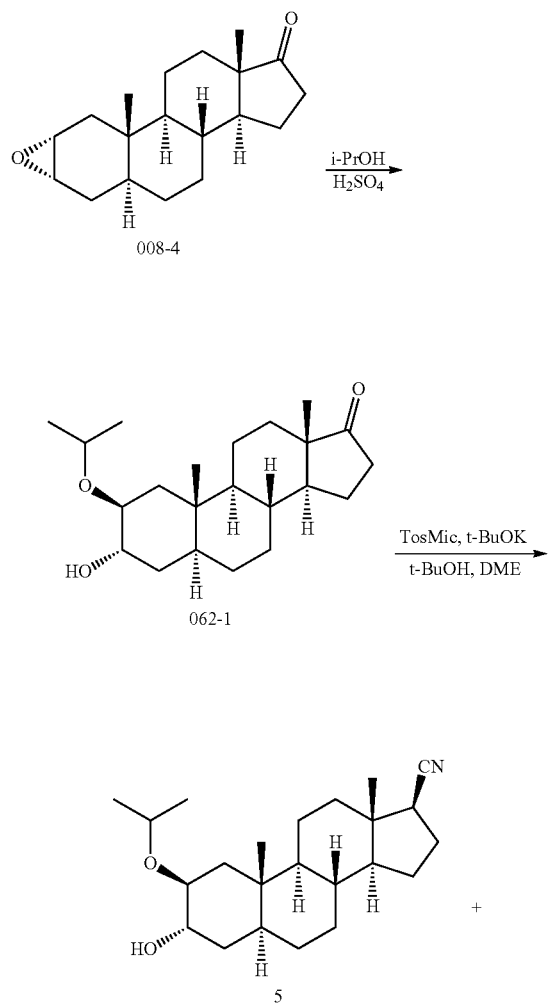

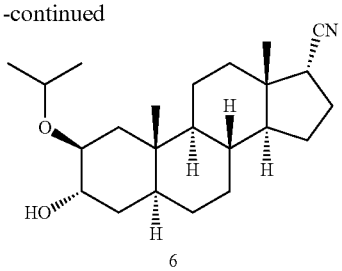

To a solution of 008-4 (2 g, 6.9 mmol) in isopropanol (20 mL) was added conc. H$_2$SO$_4$ (10 drops). The solution was stirred at room temperature for 3 h. After the TLC showed that the starting material was consumed completely, the mixture was quenched with aq.NaHCO$_3$, and extracted with EtOAc (25 mL×3). The combined organic layers were dried over Na$_2$SO$_4$, concentrated to give crude product, which was purified by column chromatography on silica gel (eluent: petroleum ether:ethyl acetate=20:1) to give 062-1 (430 mg, 17.77%) as white solid. $^1$H NMR (062-1): (400 MHz, CDCl$_3$) δ 3.85-3.80 (m, 1H), 3.70-3.60 (m, 1H), 3.50-3.45 (m, 1H), 2.50-2.35 (m, 1H), 2.10-1.75 (m, 5H), 1.35-1.25 (m, 9H), 1.15-1.06 (m, 5H), 0.95 (s, 3H), 0.85-0.86 (m, 9H), 0.8-0.7 (m, 1H).

To a solution of t-BuOK (1.38 g, 12.35 mmol) in t-BuOH (10 mL) was added a solution of 062-1 (430 mg, 1.23 mmol) in 1,2-Dimethoxyethane (4 mL) dropwise at room temperature. Then a solution of TosMic (964 mg, 4.94 mmol) in 1,2-Dimethoxyethane (6 mL) was added dropwise to the mixture. Then the reaction mixture was warmed to room temperature and stirred for 4 hours. After the LCMS showed that the starting material was consumed completely. The mixture was quenched with aq. HCl solution and extracted with EtOAc (15 mL*3). The combined organic phases were dried over Na$_2$SO$_4$, and the solvent was evaporated to afford crude product. The crude product was purified by column chromatography on silica gel (eluent: petroleum ether:ethyl acetate=20:1) to give the product 5 (27.1 mg, 6.1%) as a white powder and 6 (12.7 mg, 2.86%). $^1$H NMR (5): (400 MHz, CDCl$_3$) δ 3.87-3.80 (m, 1H), 3.68-3.60 (m, 1H), 3.52-3.46 (m, 1H), 2.30-2.20 (m, 1H), 2.15-2.05 (m, 1H), 2.0-1.6 (m, 7H), 1.55-1.45 (m, 2H), 1.45-1.19 (m, 9H), 1. 1.19-1.03 (m, 7H), 1.03-0.92 (m, 5H), 0.92-0.88 (m, 4H), 0.75-0.65 (m, 1H). $^1$H NMR (6): (400 MHz, CDCl$_3$) δ 3.86-3.80 (m, 1H), 3.68-3.60 (m, 1H), 3.52-3.47 (m, 1H), 2.58-2.52 (m, 1H), 2.20-2.10 (m, 1H), 2.00-1.90 (m, 1H), 1.90-1.60 (m, 7H), 1.55-1.45 (m, 2H), 1.45-1.20 (m, 9H), 1.20-1.05 (m, 6H), 1.05-1.00 (m, H), 0.95 (s, 3H), 0.85-0.75 (m, 4H).

Example 6. Synthesis of Compound 7

Synthesis of Intermediates 066-1 and 066-1A

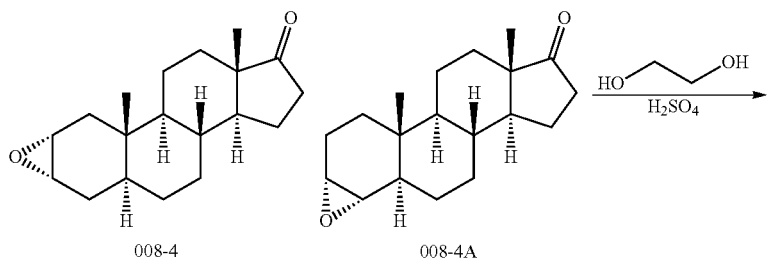

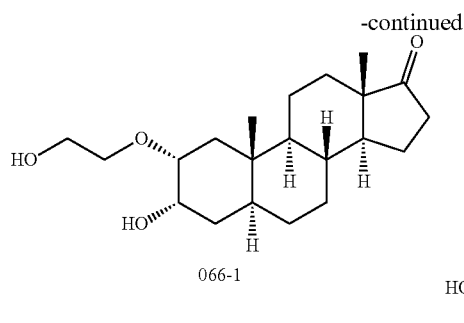

066-1

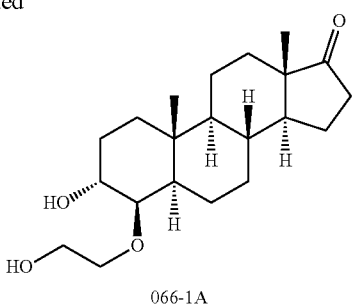

066-1A

Synthesis of Compound 7

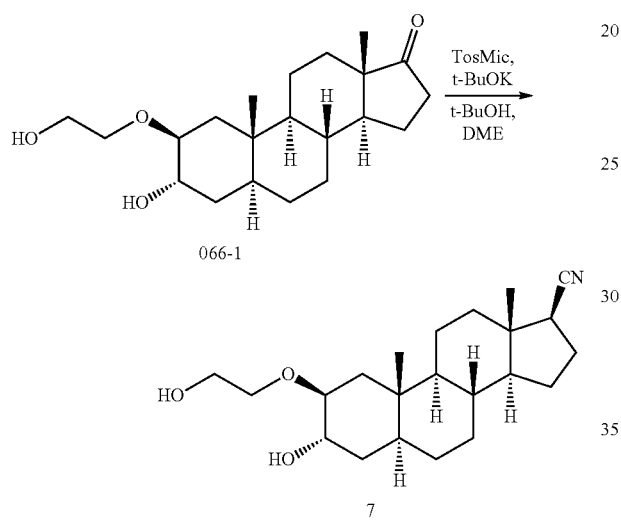

To a solution of the mixture 008-4 and 008-4A (4.0 g, 13.87 mmol) in THF (10 mL) was added ethane-1,2-diol (30 mL). Then 4 drops of fuming $H_2SO_4$ was added slowly. The mixture was stirred at room temperature for 1 hour. TLC (petroleum ether:ethyl acetate=1:3) indicated that the reaction was complete, then the reaction mixture was treated with aqueous $NaHCO_3$. The resulting solution was extracted with 3×100 mL of ethyl acetate and the organic layers combined and dried over anhydrous sodium sulfate. The organic phase was concentrated under vacuum. The crude product was purified by column chromatography on silica gel (petroleum ether:ethyl acetate=3:1) to give the product 066-1 (2.8 g, 57.6%) and 066-1A (0.6 g, 12.3%) as white solids. $^1$H NMR (066-1): (400 MHz, $CDCl_3$) δ 3.97-3.96 (m, 1H), 3.71-3.65 (m, 2H), 3.64-3.60 (m, 1H), 3.51-3.46 (m, 2H), 2.46-2.39 (m, 1H), 2.10-2.01 (m, 1H), 1.95-1.45 (m, 11H), 1.34-1.21 (m, 7H), 1.03-0.98 (m, 1H), 0.95 (s, 3H), 0.85 (s, 3H), 0.79-0.76 (m, 1H). $^1$H NMR (066-1A): (400 MHz, $CDCl_3$) δ 3.99-3.98 (m, 1H), 3.70-3.67 (m, 3H), 3.45-3.43 (m, 1H), 3.21-3.20 (m, 1H), 2.46-2.39 (m, 1H), 2.08-1.45 (m, 11H), 1.42-1.20 (m, 6H), 1.04-1.01 (m, 1H), 0.99-0.95 (m, 3H), 0.85 (s, 3H), 0.79-0.75 (m, 1H).

To a stirred solution of t-BuOK (1.28 g, 11.4 mmol) in t-BuOH (3 mL) was added of a solution of 066-1 (400 mg, 1.14 mmol) in 1,2-dimethoxyethane (3 mL) under $N_2$. A solution of TosMic (890 mg, 4.56 mmol) in 1,2-dimethoxyethane (3 mL) was then added dropwise. The mixture was stirred at room temperature for 12 hours. The mixture was treated with aqueous sodium chloride followed by hydrochloric acid (2 M) until acidic. The mixture was extracted with 3×100 mL of $CH_2Cl_2$, and the organic layer was washed with brine, dried over anhydrous sodium sulfate, then concentrated to get residue, which was purified by column chromatography on silica gel (petroleum ether:ethyl acetate=5:1 to 2:1) to give the crude product, then the crude product was purified by pre-HPLC to afford the 7 (60 mg, 14.5%). $^1$H NMR (7): (400 MHz, $CDCl_3$) δ 3.97-3.96 (m, 1H), 3.71-3.65 (m, 2H), 3.64-3.61 (m, 1H), 3.51-3.48 (m, 2H), 2.28-2.24 (m, 1H), 2.09-2.08 (m, 1H), 1.95-1.61 (m, 9H), 1.50-1.21 (m, 10H), 1.18-1.05 (m, 1H), 1.03-0.98 (m, 1H), 0.95 (s, 3H), 0.92 (s, 3H), 0.79-0.76 (m, 1H).

Example 7. Synthesis of Compounds 8 and 14

Synthesis of Intermediates A3 and A4

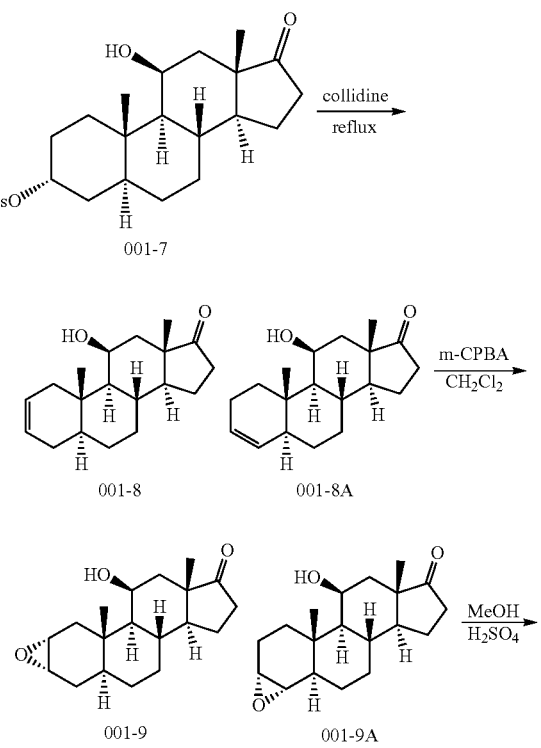

-continued

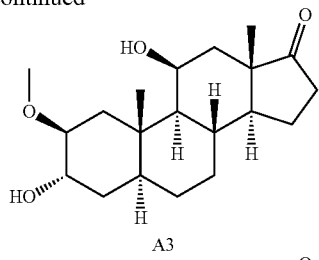

A3

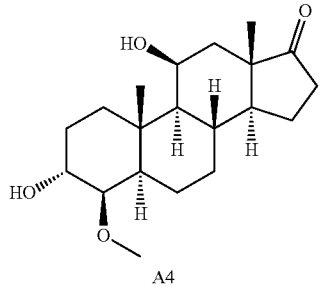

A4

Synthesis of Compounds 8 and 14

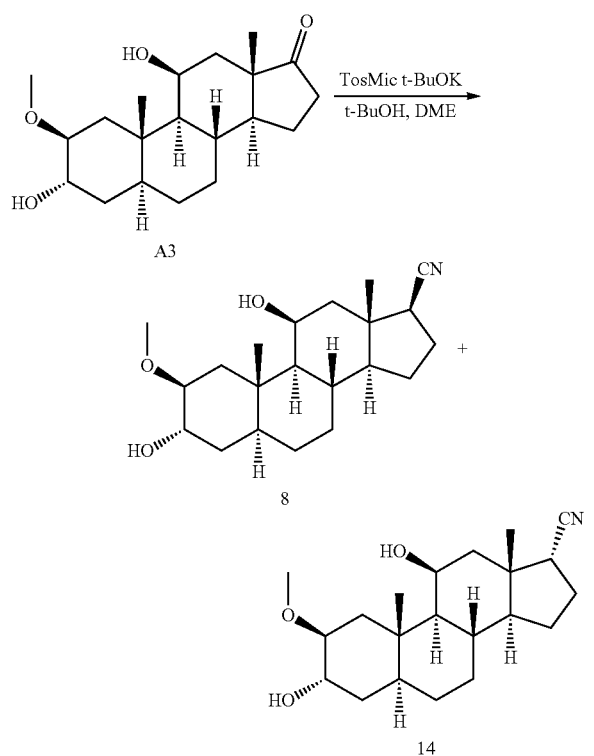

The solution of 001-7 (2 g, 4.35 mmol) in collidine (10 mL) was stirred at 140° C. for 4 h.

TLC showed the starting material was consumed completely. To the mixture was added $H_2SO_4$ (10 mL, 1 M) and extracted with EtOAc (30 mL×2) and aqueous NaCl (30 mL). The organic phase was dried over $Na_2SO_4$ and evaporated to give the crude product, which was purified by column chromatography on silica gel (ethyl acetate/petroleum ether=1/20) to afford the mixture of 001-8 and 001-8A (1.1 g, 88%) as white solid.

To a solution of the mixture of 001-8 and 001-8A (1.1 g, 3.82 mmol) in $CH_2Cl_2$ (10 mL) was added m-CPBA (0.99 g, 5.73 mmol) in portions at 0° C. The mixture was stirred at 0° C. for 1 h and warmed to room temperature and stirred over night. TLC showed the starting material was consumed completely. The mixture was quenched with aqueous $Na_2S_2O_3$ (30 mL) and aqueous $NaHCO_3$ (30 mL), extracted with EtOAc (30 mL×2) and washed with brine (30 mL). The organic phase was dried over $Na_2SO_4$ and evaporated to give the crude product, which was purified by column chromatography on silica gel (ethyl acetate/petroleum ether=1/15) to afford the mixture of 001-9 and 001-9A (1.0 g, 86%).

To a solution of the mixture of 001-9 and 001-9A (1 g, 3.29 mmol) in MeOH (25 mL) was added $H_2SO_4$ (10 drops, 98%). The mixture was stirred at 20° C. for 1 h. TLC showed the starting material was consumed completely. The mixture was quenched with aqueous $NaHCO_3$ (40 mL). The mixture was extracted with EtOAc (50 mL×2) and washed with brine (50 mL). The organic phase was dried over $Na_2SO_4$ and evaporated to give the crude product, which was purified by column chromatography on silica gel (ethyl acetate/petroleum ether=1/2) to afford A3 (550 mg, 42.6%) and A4 (240 mg, 18.6%) as white solid. $^1$H NMR (A3): (400 MHz, $CDCl_3$) δ 4.45-4.42 (m, 1H), 3.98-3.94 (m, 1H), 3.42-3.39 (m, 1H), 3.34 (s, 3H), 2.50-2.43 (m, 1H), 2.10-1.78 (m, 7H), 1.65-1.20 (m, 10H), 1.19 (s, 4H), 1.12 (s, 3H), 1.10-1.00 (m, 1H), 0.86-0.79 (m, 1H). $^1$H NMR (A4): (400 MHz, $CDCl_3$) δ 4.41-4.40 (m, 1H), 4.04-4.03 (m, 1H), 3.34 (s, 3H), 3.05-3.01 (m, 1H), 2.51-2.44 (m, 1H), 2.08-1.96 (m, 5H), 1.95-1.94 (m, 1H), 1.82-1.78 (m, 1H), 1.65-1.55 (m, 3H), 1.53-1.48 (m, 5H), 1.27 (s, 3H), 1.10 (s, 3H), 1.10-1.00 (m, 1H), 0.77-0.74 (m, 1H).

To a stirred solution of t-BuOK (830 mg, 7.4 mmol) in BuOH (4 mL) was added of a solution of A3 (250 mg, 0.74 mmol) in 1,2-dimethoxyethane (3 mL) under $N_2$. A solution of TosMic (290 mg, 1.48 mmol) in 1,2-dimethoxyethane (3 mL) was then added dropwise. The mixture was stirred at room temperature for 12 hours. The mixture was treated with aqueous sodium chloride followed by hydrochloric acid (2 M) until acidic. The mixture was extracted with $CH_2Cl_2$, and the organic layer was washed with brine, dried over anhydrous sodium sulfate, then concentrated to get residue, which was purified by column chromatography on silica gel (petroleum ether:ethyl acetate=10:1 to 8:1) to give the 8 (43 mg, 16%) and 14 (15 mg, 6%) as white powders. $^1$H NMR (8): (400 MHz, CDCl3) δ 4.40-4.39 (m, 1H), 3.96-3.95 (m, 1H), 3.37-3.34 (m, 4H), 2.22-2.18 (m, 1H), 2.11-1.76 (m, 8H), 1.53-1.52 (m, 1H), 1.46-1.18 (m, 7H), 1.14-1.13 (m, 6H), 1.00-0.94 (m, 1H), 0.80-0.77 (m, 1H). $^1$H NMR (14): (300 MHz, CDCl3) δ 4.48-4.46 (m, 1H), 3.96-3.95 (m, 1H), 3.35-3.33 (m, 4H), 2.55-2.51 (m, 1H), 2.20-2.16 (m, 1H), 2.05-1.59 (m, 8H), 1.50-1.22 (m, 7H), 1.21-1.18 (m, 1H), 1.15 (s, 3H), 1.03 (s, 3H), 0.92-0.83 (m, 1H).

Example 8. Synthesis of Compounds 9 and 15

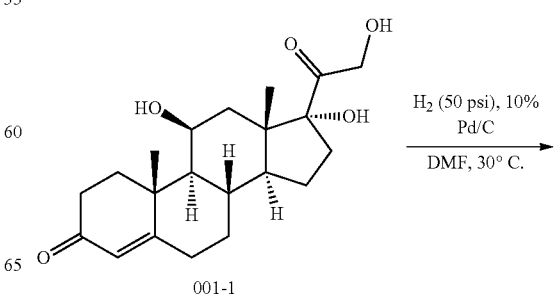

001-1

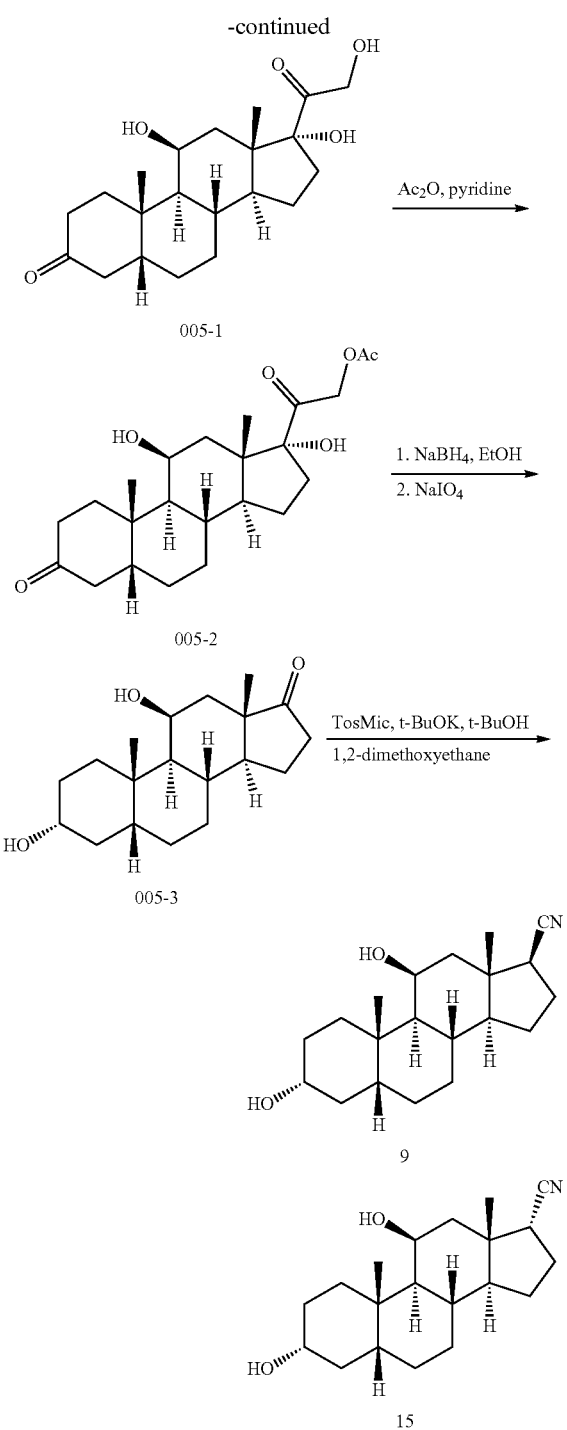

To a solution of compound 001-1 (4 g, 11.02 mmol) in DMF (50 mL) was added 10% Pd/C (400 mg). The mixture was stirred under H₂ (50 psi) at 30° C. overnight. Then the mixture was filtered and evaporated to give the crude product, which was purified by column chromatography on silica gel (ethyl acetate/petroleum ether=1/2) to afford the compound 005-1 (4 g, 100%) as a white solid. $^1$H NMR (005-1): (400 MHz, CDCl3) δ 5.06 (d, J=17.2 Hz, 1H), 4.83 (d, J=17.2 Hz, 1H), 4.45-4.40 (m, 1H), 2.79-2.62 (m, 1H), 2.35-2.34 (m, 1H), 2.27-2.21 (m, 3H), 2.13-1.96 (m, 3H), 2.83-1.80 (m, 2H), 1.76-1.72 (m, 1H), 1.67-1.63 (m, 2H), 1.63-1.59 (m, 1H), 1.51-1.42 (m, 3H), 1.27 (s, 3H), 1.23-1.21 (m, 1H), 1.20-1.17 (m, 1H), 0.96 (s, 3H).

To a solution of compound 005-1 (4 g, 11.02 mmol) in pyridine (40 mL) was added Ac₂O (2.2 g, 22 mmol). The mixture was stirred at room temperature overnight. The mixture was poured into cooled water (200 mL). The solid was collected by filtration and washed with 200 mL of HCl (1 M). The resulting solid was washed with water (100 mL×3). The solid was dried in air to give 005-2 (3.0 g, 69%) as a white solid used without further purification.

To a solution of compound 005-2 (2.4 g, 5.35 mmol) in EtOH (20 mL) and CH₂Cl₂ (20 mL) was added NaBH₄ (404 mg, 10.7 mmol). The mixture was stirred at 15° C. overnight. Then the mixture was quenched with acetone (20 mL) and H₂O (20 mL). NaIO₄ (3.3 g, 21.4 mmol) was added to the reaction mixture. The mixture was stirred at 30° C. overnight. Then the mixture was extracted with EtOAc (50 mL) and H₂O (50 mL). The organic phase was dried over Na₂SO₄ and evaporated to give the crude product, which was purified by column chromatography on silica gel (ethyl acetate/petroleum ether=1/2) to afford the compound 005-3 (1.3 g, 79.7%) as white solid. $^1$H NMR (005-3): (400 MHz, CDCl3) δ 4.42-4.29 (m, 1H), 3.67-3.56 (m, 1H), 2.51-2.44 (m, 1H), 2.10-1.94 (m, 5H), 1.73-1.65 (m, 2H), 1.62-1.50 (m, 5H), 1.48-1.37 (m, 5H), 1.19 (s, 3H), 1.10 (s, 3H), 0.96-0.82 (m, 2H).

To a solution of t-BuOK (2.2 g, 19.58 mmol) in t-BuOH (10 mL) was added dropwise a solution of compound 005-3 (600 mg, 1.958 mmol) in 1,2-dimethoxyethane (5 mL) at room temperature under N₂. The mixture was stirred at room temperature for 20 min. Then TosMic (574 mg, 2.94 mmol) in 1,2-dimethoxyethane (5 mL) was added dropwise and the mixture was stirred at room temperature for 3 hours. TLC (petroleum ether:ethyl acetate=3:1) showed that the reaction was completed. The reaction was quenched with water (50 mL). The resulting solution was extracted with 2×50 mL of ethyl acetate, the organic layers combined and dried over anhydrous sodium sulfate. The organic phase was concentrated under vacuum. The crude product was purified by column chromatography on silica gel (petroleum ether:ethyl acetate=5.5:1) to give the product 9 (170 mg, 23%) and 15 (200 mg, 27%) as a white solid. $^1$H NMR (9): (300 MHz, CDCl3) δ 4.22-4.18 (m, 1H), 3.66-3.55 (m, 1H), 2.19-2.12 (m, 1H), 2.06-1.55 (m, 10H), 1.49-1.12 (m, 9H), 1.11 (s, 3H), 1.08 (s, 3H), 1.05-0.94 (m, 2H). $^1$H NMR (15): (300 MHz, CDCl3) δ 4.31-4.24 (m, 1H), 3.68-3.51 (m, 1H), 2.52-2.45 (m, 1H), 2.19-1.41 (m, 16H), 1.31-1.17 (m, 5H), 1.11 (s, 3H), 1.08-1.02 (m, 1H), 0.96 (s, 3H).

Example 9. Synthesis of Compounds 10 and 11

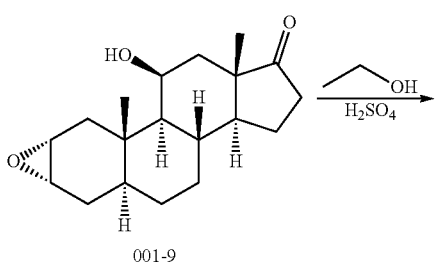

001-9

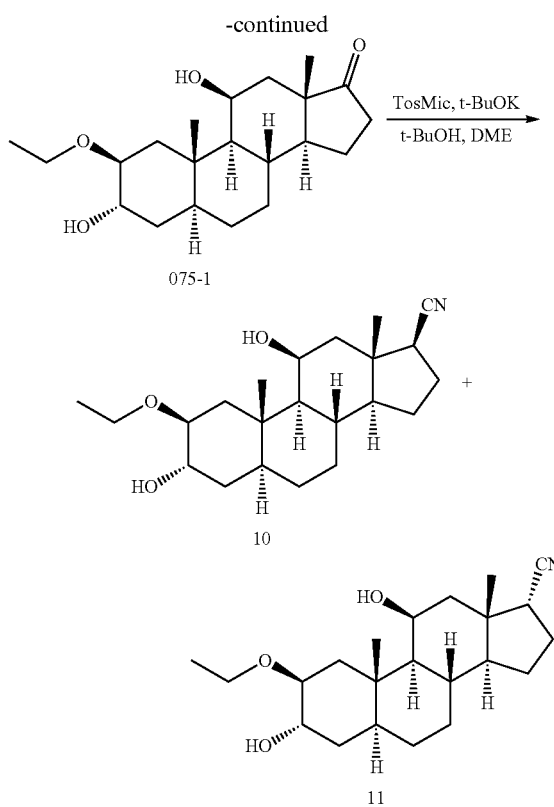

To a solution of 001-9 (500 mg, 1.64 mmol) in EtOH (10 mL) was added conc. $H_2SO_4$ (5 drops). The solution was stirred at room temperature for 3 h. TEC showed that the starting material was consumed completely. The mixture was quenched with aq.$NaHCO_3$ (20 mL), and extracted with EtOAc (15 mL×3). The combined organic layers were dried over $Na_2SO_4$, concentrated to give crude product, which was purified by column chromatography on silica gel (eluent: petroleum ether:ethyl acetate=6:1) to give 075-1 (160 mg, 28%) as a white solid. $^1H$ NMR (075-1): (400 MHz, CDCl3) δ 4.45-4.40 (m, 1H), 3.96-3.90 (m, 1H), 3.65-3.55 (m, 1H), 3.50-3.35 (m, 2H), 2.55-2.42 (m, 1H), 2.10-1.70 (m, 8H), 1.48-1.40 (m, 2H), 1.40-1.20 (m, 6H), 1.20-1.12 (m, 6H), 1.12-1.10 (m, 4H), 1.08-0.98 (m, 1H), 0.85-0.80 (m, 1H).

To a solution of t-BuOK (511.17 mg, 4.57 mmol) in t-BuOH (8 mL) was added a solution of 075-1 (160 mg, 0.56 mmol) in 1,2-dimethoxyethane (3 mL) dropwise at room temperature. Then a solution of TosMic (178.38 mg, 0.91 mmol) in 1,2-Dimethoxyethane (5 mL) was added dropwise to the mixture. The reaction mixture was warmed to room temperature and stirred for 4 hours. After LCMS showed that the starting material was consumed completely, the mixture was quenched with water and extracted with EtOAc (10 mL×3). The combined organic phases were dried over $Na_2SO_4$, and the solvent was evaporated to afford crude product. The crude product was purified by column chromatography on silica gel (eluent: petroleum ether:ethyl acetate=6:1) to give the product 10 (56.8 mg, 33.41%) as a white powder and 11 (32.8 mg, 19.29%). $^1H$ NMR (10): (400 MHz, $CDCl_3$) δ 4.45-4.35 (m, 1H), 3.98-3.90 (m, 1H), 3.65-3.55 (m, 1H), 3.50-3.35 (m, 2H), 2.25-2.15 (m, 1H), 2.10-1.80 (m, 8H), 1.45-1.10 (m, 19H), 1.05-0.95 (m, 1H), 0.82-0.75 (m, 1H). $^1H$ NMR (11): (400 MHz, $CDCl_3$) δ 4.5-4.45 (m, 1H), 3.98-3.90 (m, 1H), 3.65-3.55 (m, 1H), 3.50-3.35 (m, 2H), 2.56-2.50 (m, 1H), 2.25-2.15 (m, 1H), 2.00-1.80 (m, 7H), 1.45-1.15 (m, 16H), 1.05-1.02 (m, 4H), 0.95-0.85 (m, 1H).

Example 10. Synthesis of Compounds 12 and 13

Synthesis of Intermediates 003-5 and 003-5A

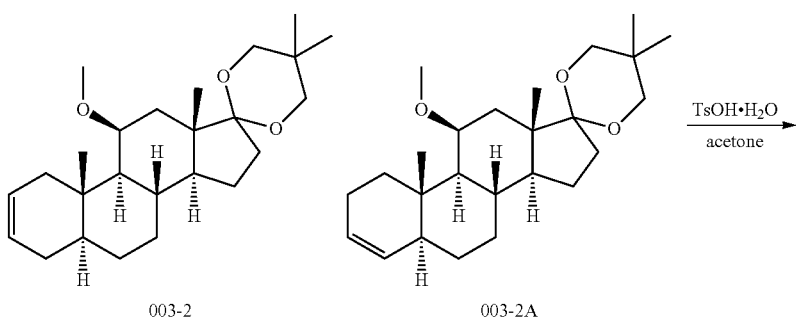

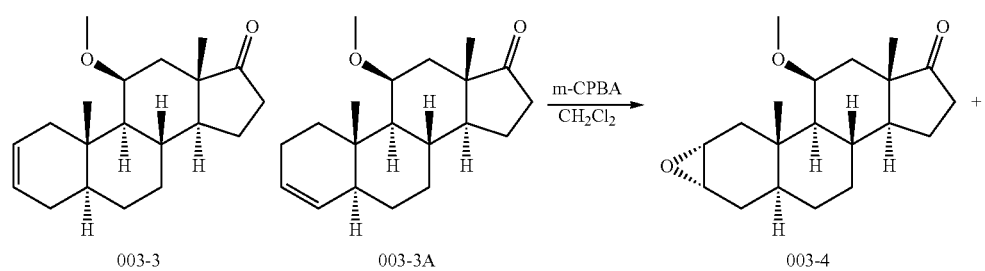

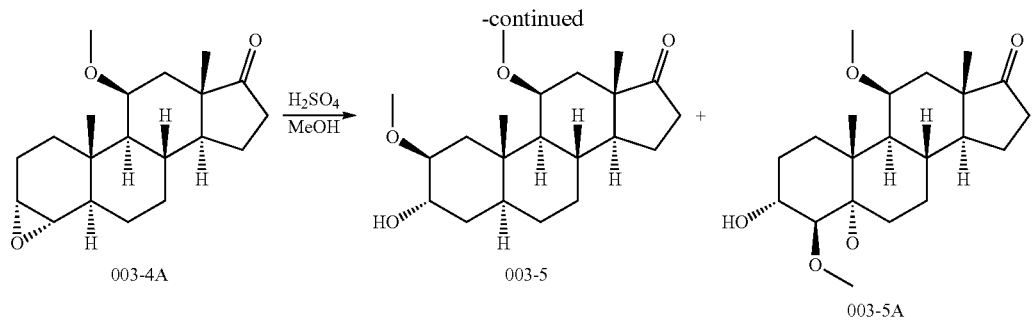

Synthesis of Compounds 12 and 13

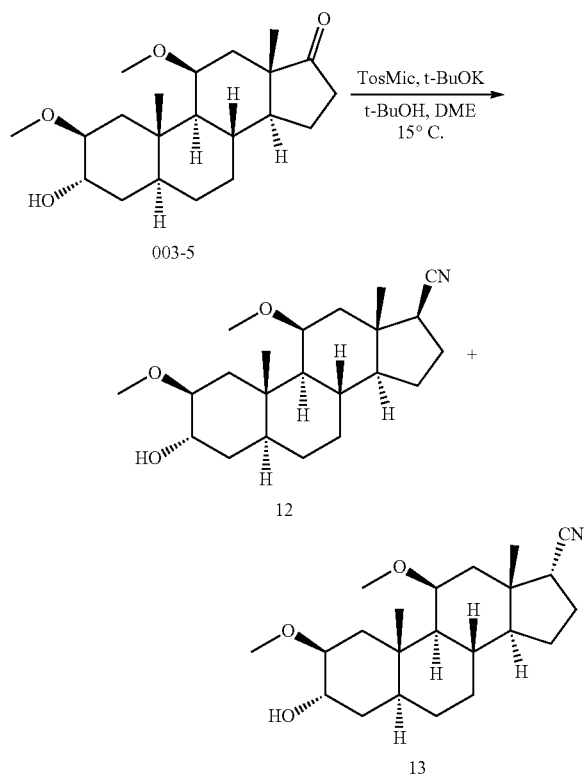

To a solution of mixture 003-2 and 003-2A (2.2 g, 5.67 mmol) in acetone (20 mL) was added TsOH.H₂O (975 mg, 5.67 mmol). The mixture was stirred at 10° C. for 3 h. TLC (petroleum ether:ethyl acetate=10:1) showed that the starting material was consumed completely. Then the mixture was quenched with aqueous NaHCO₃ solution (40 mL) and diluted with EtOAc (80 mL×2). The organic phase was dried over Na₂SO₄ and evaporated to give the mixture of 003-3 and 003-3A (2.1 g, crude) as yellow oil, which was used directly in the next step without any purification.

To a solution of mixture 003-3 and 003-3A (2.1 g, crude) in CH₂Cl₂ (20 mL) was added 3-chlorobenzoperoxoic acid (1.7 g, 10.43 mmol). The mixture was stirred at 10° C. for 3 h. TLC (petroleum ether:ethyl acetate=5:1) showed that the starting material was consumed completely. Then the mixture was quenched with a solution of Na₂S₂O₃/NaHCO₃ (3/1, 40 g) in water (40 mL) and extracted with EtOAc (70 mL×2). The organic phase was dried over Na₂SO₄ and evaporated to give the crude product, which was purified by column chromatography on silica gel (petroleum ether:ethyl acetate=20:1) to afford the mixture of 003-4 and 003-4A (1.35 g, 61%) as a white solid. ¹H NMR (003-4 and 003-4A): (400 MHz, CDCl3) δ 3.68-3.67 (m, 1H), 3.24 (s, 3H), 3.20-3.13 (m, 2H), 2.49-2.42 (m, 1H), 2.30-2.23 (m, 1H), 2.04-1.31 (m, 12H), 1.20-1.10 (m, 1H), 1.04-0.97 (m, 6H), 0.95-0.92 (m, 1H), 0.70-0.65 (m, 1H).

To a solution of mixture 003-4 and 003-4A (1 g, 3.1 mmol) in MeOH (25 mL) was added conc.H₂SO₄ (10 drops, 98%). The mixture was stirred at 10° C. for 2 h. TLC (petroleum ether:ethyl acetate=3:1) showed that the starting material was consumed completely. Then the mixture was quenched with a mixture aqueous NaHCO₃ solution (30 mL) and diluted with EtOAc (60 mL×2). The organic phase was dried over Na₂SO₄ and evaporated to give the crude product, which was purified by column chromatography on silica gel (petroleum ether:ethyl acetate=7:1) to afford 003-5 (600 mg, 55%) and 003-5A (250 mg, 25%) as white solid. ¹H NMR (003-5): (400 MHz, CDCl₃) δ 3.96-3.95 (m, 1H), 3.73-3.72 (m, 1H), 3.36-3.35 (m, 4H), 3.26 (s, 3H), 2.49-2.42 (m, 1H), 2.29-2.25 (m, 1H), 2.09-1.80 (m, 6H), 1.61-1.50 (m, 3H), 1.43-1.16 (m, 6H), 1.10 (s, 3H), 1.04 (s, 3H), 0.80-0.77 (m, 1H). ¹H NMR (003-5A): (400 MHz, CDCl₃) δ 4.03-4.01 (m, 1H), 3.71-3.69 (m, 1H), 3.35 (s, 3H), 3.20 (s, 3H), 3.02-3.01 (m, 1H), 2.49-2.42 (m, 1H), 2.27-2.23 (m, 1H), 2.07-2.00 (m, 4H), 1.91-1.79 (m, 1H), 1.60-1.21 (m, 8H), 1.19 (s, 3H), 1.02 (s, 3H), 0.99-0.97 (m, 1H), 0.74-0.71 (m, 1H).

To a stirred solution of t-BuOK (324 mg, 2.9 mmol) in BuOH (10 mL) was added of a solution of the 003-5 (100 mg, 0.29 mmol) in 1,2-dimethoxyethane (5 mL) under N₂. A solution of TosMic (84 mg, 0.43 mmol) in 1,2-dimethoxyethane was then added dropwise. The mixture was stirred at room temperature (15° C.) for 4 hours. The mixture was treated with aqueous sodium chloride followed by hydrochloric acid (2M) until acidic. The mixture was extracted with CH₂Cl₂, and the organic layer was washed with brine, dried over anhydrous Na₂SO₄, then concentrated to get residue, which was purified by column chromatography on silica gel (eluent: petroleum ether:ethyl acetate=8:1) and prep HPLC to give the 12 (25 mg, 24.3%) and 13 (20 mg, 19.4%) as a white solid. ¹H NMR (12): (400 MHz, CDCl₃) δ 3.97-3.93 (m, 1H), 3.72-3.68 (m, 1H), 3.39-3.32 (m, 4H), 3.23 (s, 3H), 2.44-2.38 (m, 1H), 2.23-2.18 (t, J=9.6 Hz, 1H), 2.12-2.02 (m, 1H), 1.97-1.88 (m, 2H), 1.86-1.72 (m, 4H), 1.53-1.17 (m, 9H), 1.09 (s, 3H), 1.07 (s, 3H), 0.97-0.90 (m, 3H), 0.79-0.72 (m, 1H). ¹H NMR (13): (400 MHz, CDCl₃) δ3.97-3.93 (m, 1H), 3.72-3.68 (m, 1H), 3.39-3.32 (m, 4H), 3.23 (s, 3H), 2.52-2.50 (m, 1H), 2.21-2.12 (m, 2H), 1.98-

1.71 (m, 6H), 1.60-1.43 (m, 3H), 1.41-1.18 (m, 8H), 1.07 (s, 3H), 1.04-0.99 (m, 1H), 0.96 (s, 3H), 0.89-0.84 (m, 1H).

Example 11. Synthesis of Compounds 16 and 18

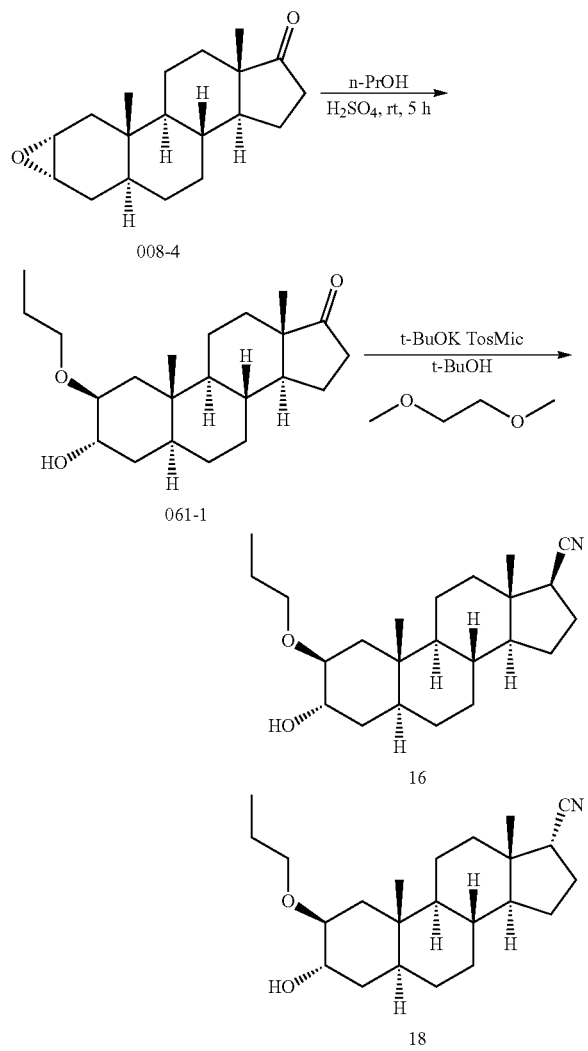

To a solution of 008-4 (1.0 g, 3.47 mmol) in n-PrOH (20 mL) was added H₂SO₄ (5 drops, 98%). The mixture was stirred at room temperature for 5 h. TLC (petroleum ether/ethyl acetate=3/1) showed that the starting material was consumed completely. The mixture was quenched with the addition of saturate NaHCO₃ aqueous (10 mL). The mixture was extracted with EtOAc (15 mL×3). The combined organic layers were washed with brine (20 mL) and dried over anhydrous Na₂SO₄ and concentrated to give crude product, which was purified by column chromatography on silica gel (petroleum ether/ethyl acetate=20/1) to afford pure 061-1 (360 mg, 30%) as a white solid. ¹H NMR (061-1): (400 MHz, CDCl₃) δ 3.89-3.97 (m, 1H), 3.37-3.49 (m, 2H), 3.26-3.32 (m, 1H), 2.39-2.48 (m, 1H), 2.01-2.11 (m, 1H), 1.73-1.97 (m, 6H), 1.14-1.71 (m, 22H), 0.71-1.05 (m, 16H).

To a solution of t-BuOK (1.16 g, 10.33 mmol) in t-BuOH (10 mL) was added 061-1 (0.36 g, 1.03 mmol) in 1,2-dimethoxyethane (7 mL) at room temperature under N₂ atmosphere. The mixture was stirred at room temperature for 30 min, then a solution of TosMic (0.405 g, 2.07 mmol) in 1,2-dimethoxyethane (7 mL) was added and the resulting solution was stirred at room temperature overnight. TLC (petroleum ether/ethyl acetate=3/1) showed the starting material was consumed completely. To the resulting mixture was added saturated aqueous NaCl (10 mL) and the resulting mixture was extracted with dichloromethane (20 mL×3). The combined organic layers were washed with brine (15 mL×2) and dried over anhydrous Na₂SO₄ and concentrated under vacuum to give crude product, which was purified by column chromatography on silica gel (petroleum ether/ethyl acetate=12/1) and further purified by Prep-HPLC to afford 16 (39.7 mg, 10.7%) and 18 (46.2 mg, 12.4%) as white solids. ¹H NMR (16): (400 MHz, CDCl₃) δ 3.89-3.96 (m, 1H), 3.41-3.47 (m, 1H), 3.37-3.42 (m, 1H), 3.26-3.32 (m, 1H), 2.22-2.39 (m, 1H), 2.03-2.15 (m, 1H), 1.88-1.95 (m, 2H), 1.81-1.87 (m, 2H), 1.60-1.79 (m, 3H), 1.48-1.59 (m, 5H), 1.19-1.44 (m, 9H), 1.02-1.17 (m, 1H), 0.77-1.02 (m, 11H), 0.68-0.75 (m, 1H). ¹H NMR (18): (400 MHz, CDCl₃) δ 3.89-3.95 (m, 1H), 3.37-3.48 (m, 2H), 3.27-3.32 (m, 1H), 2.52-2.56 (m, 1H), 2.11-2.21 (m, 1H), 1.92-2.01 (m, 2H), 1.77-1.89 (m, 3H), 1.62-1.76 (m, 4H), 1.19-1.40 (m, 10H), 0.95-1.09 (m, 1H), 0.86-0.97 (m, 5H), 0.76-0.87 (m, 4H).

Example 12. Synthesis of Compounds 17

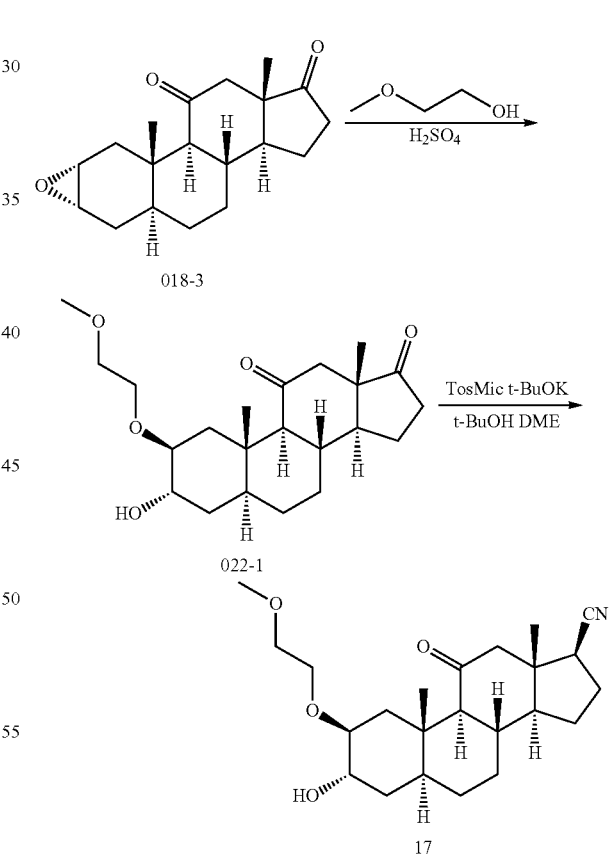

To a solution of 018-3 (950 mg, 3.13 mmol) in 2-methoxyethanol (15 mL) was added conc. H₂SO₄ (5 drops). The mixture was stirred at 30° C. for 2 hours. TLC (petroleum ether:ethyl acetate=1:1) showed that the reaction was completed. The solvent was evaporated and the residue was diluted with EtOAc (50 mL) and washed with aq.

NaHCO₃. The organic layer was dried over anhydrous Na₂SO₄ and concentrated the solvent. The residue was purified by flash column chromatography on silica gel (eluent: petroleum ether:ethyl acetate=3:1) to give 022-1 (680 mg, 57%) as white solid. ¹HNMR (022-1): (400 MHz, CDCl₃) δ 3.95-3.91 (m, 1H), 3.85-3.78 (m, 1H), 3.48-3.57 (m, 3H), 3.45-3.37 (m, 4H), 2.72-2.68 (m, 1H), 2.58-2.49 (m, 1H), 2.42-2.36 (m, 1H), 2.31-2.18 (m, 2H), 2.14-2.07 (m, 1H), 1.95-1.83 (m, 4H), 1.78-1.51 (m, 2H), 1.36-1.14 (m, 9H), 0.81 (s, 3H).

To a solution of t-BuOK (888 mg, 7.94 mmol) in t-BuOH (10 mL) was added dropwise a solution of 022-1 (300 mg, 0.79 mmol) in 1,2-dimethoxyethane (5 mL) at room temperature under N₂. The mixture was stirred at room temperature for 20 min. Then TosMic (300 mg, 1.58 mmol) in 1,2-dimethoxyethane (5 mL) was added dropwise. The mixture was stirred at room temperature for 3 hours. TLC (petroleum ether:ethyl acetate=3:1) showed that the reaction was completed. The reaction was quenched with water (50 mL). The resulting mixture was extracted with 2×100 mL of ethyl acetate, the organic layers combined and dried over anhydrous sodium sulfate. The organic phase was concentrated under vacuum and the crude product was purified by column chromatography on silica gel (petroleum ether:ethyl acetate=5.5:1) to give the product 17 (82 mg, 27%) as a yellow oil. ¹H NMR (17): (400 MHz, CDCl₃) δ 3.98-3.96 (m, 1H), 3.74-3.68 (m, 1H), 3.56-3.45 (m, 3H), 3.42-3.36 (m, 4H), 2.73-2.68 (m, 1H), 2.52-2.46 (m, 2H), 2.30-2.20 (m, 2H), 2.08-1.98 (m, 1H), 1.94-1.71 (m, 6H), 1.49-1.38 (m, 2H), 1.35-1.26 (m, 4H), 1.18-1.15 (m, 4H), 0.88 (s, 3H).

Example 13. Synthesis of Compounds 19 and 20

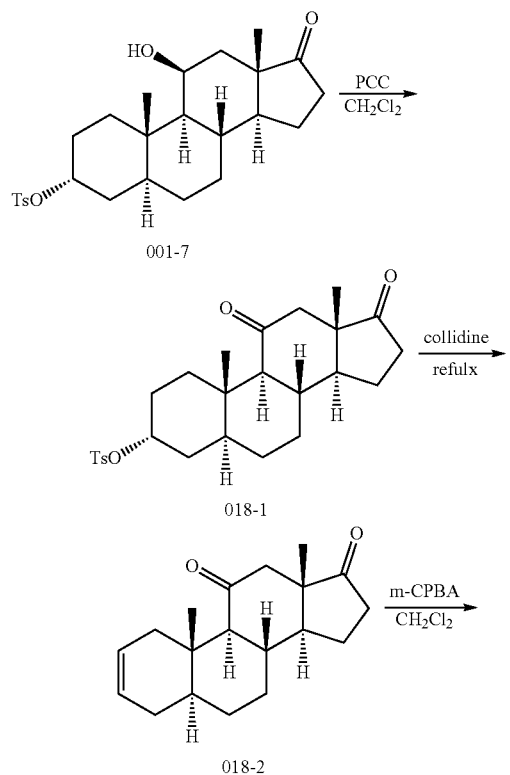

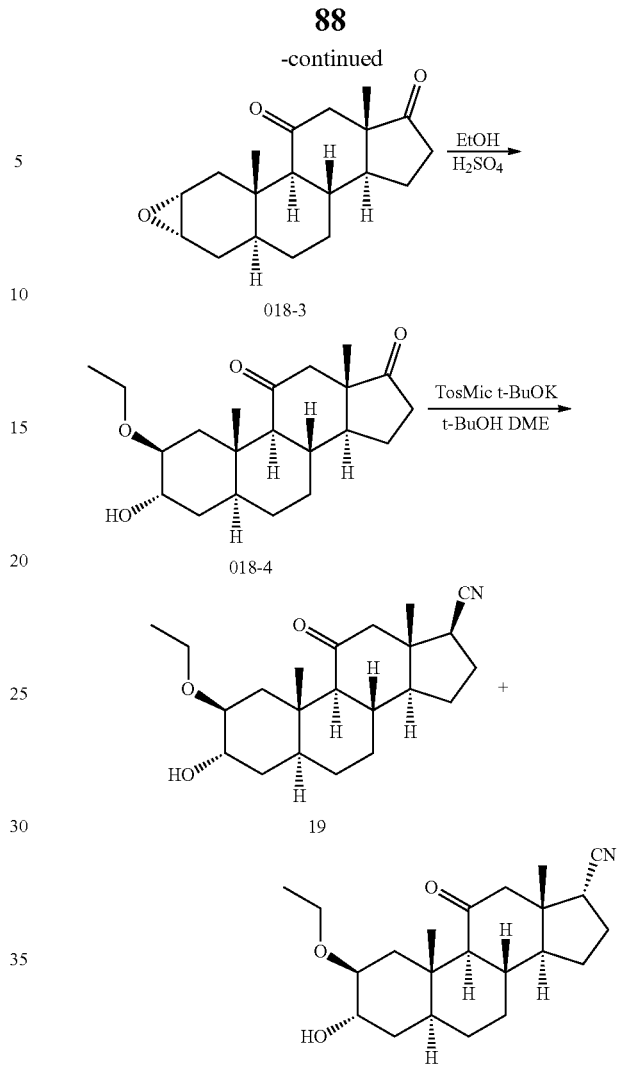

To a solution of 001-7 (8.0 g, 17.39 mmol) in CH₂Cl₂ (100 mL) was added PCC (7.5 g, 34.8 mmol) in portions at room temperature, then the reaction mixture was stirred overnight. TLC (petroleum ether:ethyl acetate=1:1) showed that the reaction was complete. The mixture was filtered off, the filtrate was concentrated to give crude product, which was purified by flash chromatography eluting with (petroleum ether:ethyl acetate=3:1) to give 018-1 (6.5 g, 81%) as a white solid.

Compound 018-1 (12 g, 26.2 mmol) was dissolved in collidine (40 mL), then the solution was heated to 130° C. and maintained at the temperature for 2 h. TLC (petroleum ether:ethyl acetate=3:1) showed that the reaction was complete. After the mixture was recovered to ambient temperature, it was poured into H₂SO₄ aqueous solution (10%). The solution was extracted with ethyl acetate (100 mL*3). The combined organic layer was washed with saturated NaHCO₃ solution and brine. The organic layer was dried over anhydrous Na₂SO₄ and concentrated the solvent to give almost pure 018-2 (7.0 g, 93.0%) as a white solid. ¹H NMR (018-2): (400 MHz, CDCl₃) δ 5.65-5.50 (m, 2H), 2.85-2.75 (m, 1H), 2.57-2.50 (m, 1H), 2.45-2.40 (m, 2H), 2.39-2.13 (m, 3H), 2.11-2.07 (m, 1H), 1.96-1.74 (m, 3H), 1.65-1.60 (m, 2H), 1.51-1.48 (m, 1H), 1.28-1.18 (m, 4H), 0.98 (s, 3H), 0.84 (s, 3H).

To a solution of 018-2 (7.0 g, 24.3 mmol) in CH$_2$Cl$_2$ (50 mL) was added m-CPBA (6.3 g, 36.5 mmol) in portions. The resulting mixture was stirred at 10° C. for 20 h. TLC (petroleum ether:ethyl acetate=3:1) showed that few starting material was always existed. Then saturated Na$_2$SO$_3$ solution (100 mL) was added into the solution. The organic layer was washed with saturated NaHCO$_3$ solution and brine. The organic layer was dried over anhydrous Na$_2$SO$_4$ and concentrated the solvent. The residue was purified by flash chromatography eluting with (petroleum ether:ethyl acetate=10:1) to give 018-3 (4.8 g, 66%) as white solid. $^1$HNMR (018-3): (400 MHz, CDCl$_3$) δ 3.17-3.10 (m, 2H), 2.84-2.78 (m, 1H), 2.56-2.22 (m, 4H), 2.10-2.00 (m, 2H), 1.98-1.80 (m, 3H), 1.74-1.58 (m, 3H), 1.42-1.05 (m, 5H), 0.98 (s, 3H), 0.82 (s, 3H).

To a solution of compound 018-3 (0.95 g, 3.13 mmol) in EtOH (20 mL) was added H$_2$SO$_4$ (98%, 5 drops). The mixture was stirred at 30° C. for 2 h. TLC (petroleum ether:ethyl acetate=1:1) showed that the reaction was complete. The mixture was quenched with aq. NaHCO$_3$ and extracted with ethyl acetate (30 mL×2). The combined organic layer was dried over anhydrous Na$_2$SO$_4$ and concentrated the solvent. The residue was purified by flash chromatography eluting with (petroleum ether:ethyl acetate=6:1) to give 018-4 (500 mg, 47%) as white solid. $^1$H NMR (018-4): (400 MHz, CDCl$_3$) δ 3.95-3.91 (m, 1H), 3.76-3.69 (m, 1H), 3.40-3.31 (m, 2H), 2.73-2.69 (m, 1H), 2.56-2.49 (m, 1H), 2.42-2.20 (m, 3H), 2.12-2.07 (m, 1H), 1.96-1.60 (m, 5H), 1.42-1.12 (m, 12H), 0.72 (s, 3H).

Into an over-dried flask was added t-BuOH (5 mL) and t-BuOK (644 mg, 5.70 mmol). It was evaporated and filled with N$_2$. Then TosMic (224 mg, 1.14 mmol) in 1,2-dimethoxyethane (4 mL) was added and the mixture became yellow. Compound 018-4 (200 mg, 0.57 mmol) in 1,2-dimethoxyethane (4 mL) was added into the suspension. The resulting mixture was stirred at room temperature (10° C.) for 16 h. TLC (petroleum ether:ethyl acetate=1:1) showed that the reaction was completed. Water was added and the mixture was stirred then extracted with ethyl acetate (50 mL×3). The combined organic layers were washed with brine, dried over anhydrous Na$_2$SO$_4$ and concentrated under vacuum. The residue was purified by flash column chromatography on silica gel (petroleum ether:ethyl acetate=6:1) to give 19 (43 mg, 21%) and 20 (14 mg, 7%) as white solid. $^1$H NMR (19): (400 MHz, CDCl$_3$) δ 3.91-3.86 (m, 1H), 3.74-3.66 (m, 1H), 3.40-3.30 (m, 2H), 2.73-2.68 (m, 1H), 2.53-2.44 (m, 2H), 2.30-2.18 (m, 2H), 2.08-1.95 (m, 1H), 1.93-1.70 (m, 5H), 1.68-1.58 (m, 1H), 1.51-1.40 (m, 2H), 1.33-1.22 (m, 3H), 1.20-1.11 (m, 8H), 0.87 (s, 3H). $^1$H NMR (20): (400 MHz, CDCl$_3$) δ 3.92-3.88 (m, 1H), 3.76-3.69 (m, 1H), 3.41-3.33 (m, 2H), 2.78-2.65 (m, 2H), 2.65-2.54 (m, 1H), 2.38-2.30 (m, 1H), 2.28-2.10 (m, 2H), 2.04-1.92 (m, 2H), 1.90-1.70 (m, 4H), 1.42-1.26 (m, 6H), 1.21-1.14 (m, 7H), 0.78 (s, 3H).

Example 14. Synthesis of Compound 21

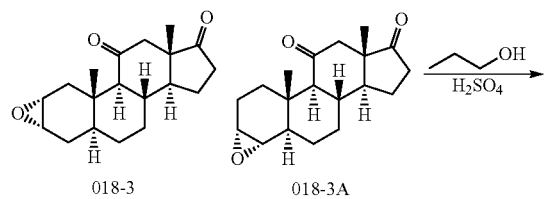

018-3    018-3A

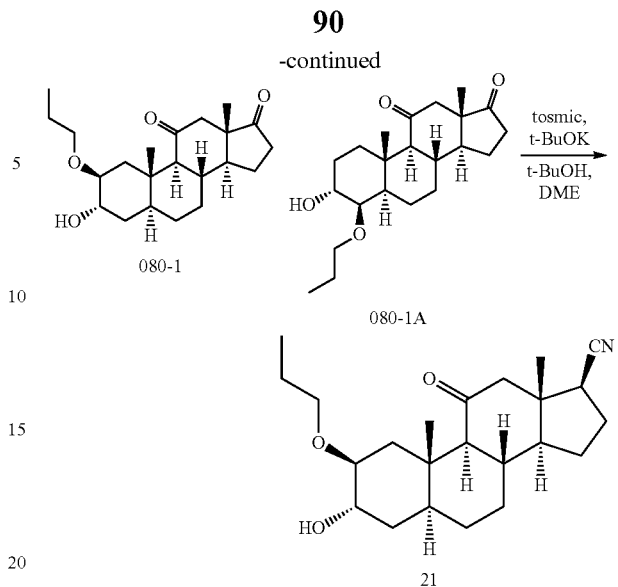

080-1

080-1A

21

To a solution of the mixture of 018-3 and 018-3A (500 mg, 1.65 mmol) in 1-propanol (10 mL) was added H$_2$SO$_4$ (5 drops, 98%). The mixture was stirred at 15° C. for 3 h. TLC showed the starting material was consumed completely. The mixture was quenched with NaHCO$_3$ aqueous (20 mL), extracted with EtOAc (20 mL×2) and aqueous NaCl (20 mL). The organic phase was dried over Na$_2$SO$_4$ and evaporated to give the crude product, which was purified by silica gel column (petroleum ethenediyl acetate=6:1) to give the mixture of 080-1 and 080-1A (250 mg, 41.7%) as a white solid.

To a stirred solution of t-BuOK (773 mg, 6.9 mmol) in BuOH (10 mL) was added of a solution of the mixture of 080-1 and 080-1A (250 mg, 0.69 mmol) in 1,2-dimethoxyethane (5 mL) under N$_2$. A solution of TosMic (269 mg, 1.38 mmol) in 1,2-dimethoxyethane (5 mL) was then added dropwise. The mixture was stirred at room temperature for 16 h. To the mixture was added water (20 mL), extracted with EtOAc. The organic layer was washed with brine, dried over anhydrous Na$_2$SO$_4$, then concentrated to get a residue, which was purified by flash column chromatography on silica gel (eluent: petroleum ether:ethyl acetate=8:1) and prep HPLC to give the 21 (40.4 mg, 15.6%) as a white solid. $^1$H NMR (21): (300 MHz, CDCl3) δ 3.94-3.89 (m, 1H), 3.64-3.57 (m, 1H), 3.36-3.32 (m, 1H), 3.29-3.22 (m, 1H), 2.74-2.67 (m, 1H), 2.55-2.47 (m, 2H), 2.28-2.20 (m, 2H), 2.03-1.70 (m, 6H), 1.66-1.58 (m, 3H), 1.53-1.49 (m, 2H), 1.48-1.23 (m, 6H), 1.16 (s, 3H), 1.12-1.09 (m, 1H), 0.92 (t, J=9 Hz, 3H), 0.87 (s, 3H).

Example 15. Synthesis of Compound 22

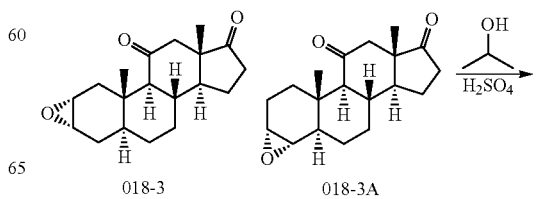

018-3    018-3A

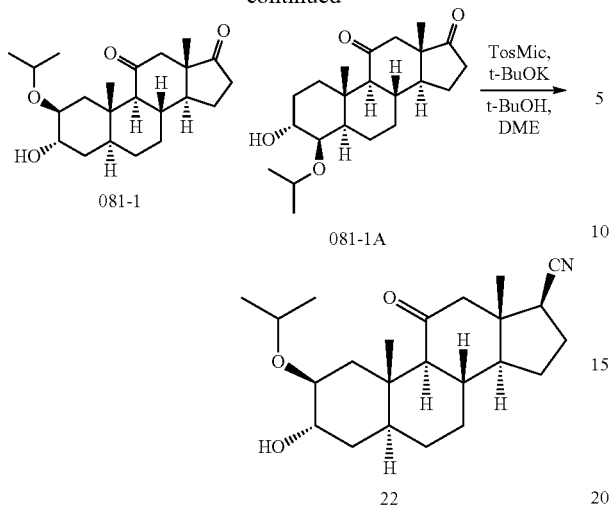

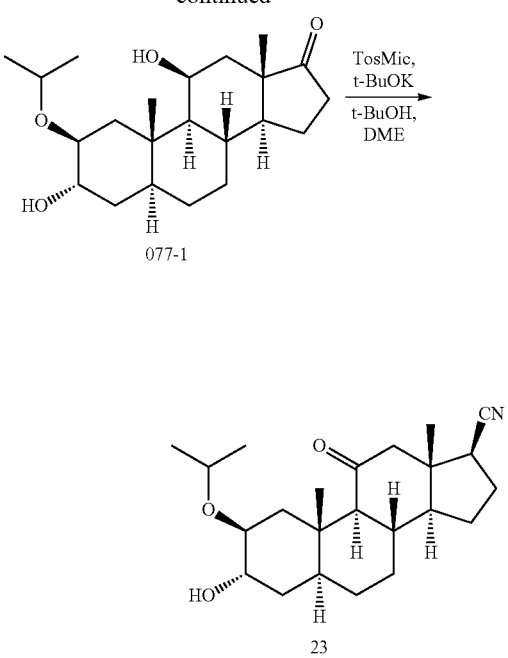

To a solution of the mixture of 018-3 and 018-3A (500 mg, 1.65 mmol) in isopropanol (10 mL) was added $H_2SO_4$ (5 drops, 98%). The mixture was stirred at 15° C. for 3 h. TLC showed the starting material was consumed completely. The mixture was quenched with $NaHCO_3$ aqueous (20 mL). The mixture was extracted with EtOAc (20 mL×2) and aqueous NaCl (20 mL). The organic phase was dried over $Na_2SO_4$ and evaporated to give the crude product, which was purified by silica gel column on silica gel (petroleum ethenediyl acetate=6:1) to give the mixture of 081-1 and 081-1A (150 mg, 25%) as a white solid.

To a stirred solution of t-BuOK (459 mg, 4.1 mmol) in BuOH (10 mL) was added of a solution of the mixture of 081-1 and 081-1A (150 mg, 0.41 mmol) in 1,2-dimethoxyethane (3 mL) under $N_2$. A solution of TosMic (162 mg, 0.83 mmol) in 1,2-dimethoxyethane was then added dropwise. The mixture was stirred at room temperature for 12 hours. The mixture was added water (20 mL) and extracted with EtOAc (20 mL×2), and the organic layer was washed with brine, dried over anhydrous $Na_2SO_4$, then concentrated to get residue, which was purified by flash column chromatography on silica gel (eluent: petroleum ether:ethyl acetate=7:1) and prep HPLC to give the 22 (31.3 mg, 20.2%) as a yellow oil. $^1$H NMR (22): (300 MHz, $CDCl_3$) δ 3.86-3.81 (m, 1H), 3.80-3.71 (m, 1H), 3.47-3.40 (m, 1H), 2.63-2.56 (m, 1H), 2.55-2.45 (m, 2H), 2.30-2.21 (m, 2H), 2.08-1.64 (m, 7H), 1.58-1.24 (m, 6H), 1.20-1.05 (m, 11H), 0.86 (s, 3H).

Example 16. Synthesis of Compound 23

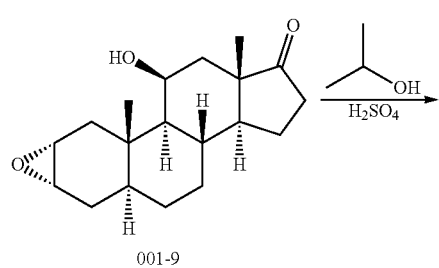

To a solution of 001-9 (500 mg, 1.64 mmol) in propan-2-ol (10 mL) was added a solution of conc. $H_2SO_4$ (0.125 mL) dropwise. The solution was stirred at room temperature for 3 h. After the TLC showed that the starting material was consumed completely. The mixture was quenched with aq. $NaHCO_3$, then the mixture was concentrated under reduced pressure. The mixture was poured into water (10 mL) and extracted with EtOAc (10 mL×3). The combined organic layers were dried over $Na_2SO_4$, concentrated to give crude product, which was purified by column chromatography on silica gel (eluent: petroleum ether:ethyl acetate=6:1) to give 077-1 (150 mg, 25.05%) as white solid. $^1$H NMR (077-1): (400 MHz, $CDCl_3$) δ 4.45-4.38 (m, 1H), 3.95-3.85 (m, 1H), 3.72-3.62 (m, 1H), 3.55-3.45 (m, 2H), 2.55-2.40 (m, 1H), 2.12-1.85 (m, 8H), 1.45-1.38 (m, 3H), 1.30-1.24 (m, 5H), 1.18-1.05 (m, 13H), 0.85-0.75 (m, 1H).

To a solution of t-BuOK (461.33 mg, 4.12 mmol) in t-BuOH (6 mL) was added a solution of 077-1 (150 mg, 0.41 mmol) in 1,2-Dimethoxyethane (2 mL) dropwise at room temperature. Then a solution of TosMic (160.80 mg, 0.82 mmol) in 1,2-Dimethoxyethane (4 mL) was added dropwise in the mixture. The reaction mixture was allowed to warm to room temperature and stirred for 4 hours. After the LCMS showed that the starting material was consumed completely, the mixture was extracted with EtOAc (10 mL×3). The combined organic phases were dried over $Na_2SO_4$, and the solvent was evaporated to afford crude product. The crude product was firstly purified by column chromatography on silica gel (eluent: petroleum ether:ethyl acetate=7:1), and then purified by prep HPLC to give 23 (16.6 mg, 11.07%) as a white powder. $^1$H NMR (23): (400 MHz, $CDCl_3$) δ 4.44-4.36 (m, 1H), 3.95-3.82 (m, 1H), 3.74-3.64 (m, 1H), 3.55-3.50 (m, 1H), 2.25-2.18 (m, 1H), 2.14-2.04 (m, 2H), 2.00-1.75 (m, 6H), 1.49-1.18 (m, 8H), 1.18-1.08 (m, 13H), 1.02-0.94 (m, 2H), 0.84-0.75 (m, 1H).

Example 17. Synthesis of Compounds 24 and 25

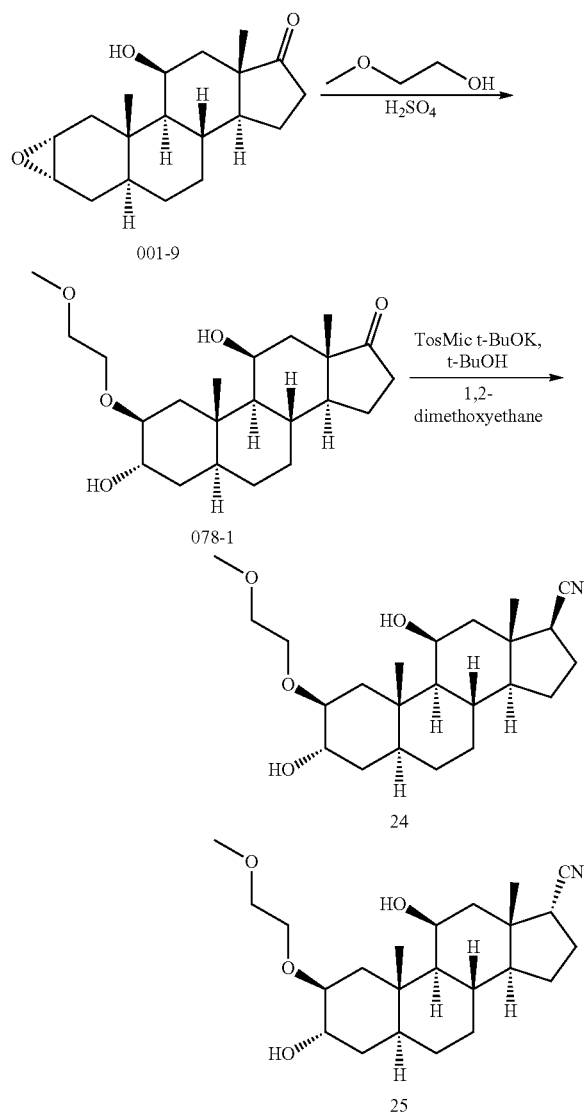

To a solution of 001-9 (500 mg, 1.64 mmol) in 2-Methoxy-ethanol (10 mL) was added fuming sulfuric acid (3 drops). The solution was stirred at room temperature for 3 hours. After TLC showed that the starting material was consumed completely, the reaction mixture was quenched with aqueous NaHCO$_3$ (30 mL) and extracted with EtOAc (10 mL×3). The combined organic layer was dried over Na$_2$SO$_4$, concentrated to give crude product, which was purified by column chromatography on silica gel (eluent: petroleum ether:ethyl acetate=6:1) to give 078-1 (270 mg, 43%) as a white solid. $^1$H NMR (078-1): (400 MHz, CDCl$_3$) δ 4.46-4.40 (m, 1H), 3.99-3.97 (m, 1H), 3.72-3.64 (m, 1H), 3.59-3.46 (m, 4H), 3.37 (s, 3H), 2.51-2.41 (m, 1H), 2.09-1.82 (m, 8H), 1.63-0.98 (m, 20H), 0.84-0.77 (m, 1H).

To a solution of t-BuOK (795.46 mg, 7.10 mmol) in t-BuOH (10 mL) was added a solution of 078-1 (270 mg, 0.71 mmol) in 1,2-Dimethoxyethane (4 mL) dropwise at room temperature. Then a solution of TosMic (277.26 mg, 1.42 mmol) in 1,2-Dimethoxyethane (6 mL) was added dropwise. Then the reaction mixture was warmed to room temperature and stirred for 4 hours. After the LC-MS showed that the starting material was consumed completely. The mixture was extracted with EtOAc (10 mL*3). The combined organic phases were dried over Na$_2$SO$_4$, and the solvent was evaporated to afford crude product. The crude product was purified by column chromatography on silica gel (eluent: petroleum ether:ethyl acetate=3:1) for 3 times to give the product 24 (22.2 mg, 7.93%) and 25 (10.6 mg, 3.79%). $^1$H NMR (25): (400 MHz, CDCl$_3$) δ 4.45-4.35 (m, 1H), 4.02-3.95 (m, 1H), 3.75-3.65 (m, 1H), 3.58-3.46 (m, 4H), 3.38 (s, 3H), 2.35-2.16 (m, 1H), 2.12-1.76 (m, 8H), 1.46-1.18 (m, 10H), 1.18-1.10 (m, 6H), 1.06-0.86 (m, 3H), 0.82-0.75 (m, 1H). $^1$H NMR (24): (400 MHz, CDCl$_3$) δ 4.55-4.45 (m, 1H), 4.05-3.95 (m, 1H), 3.75-3.65 (m, 1H), 3.60-3.50 (m, 4H), 3.38 (s, 3H), 2.58-2.52 (m, 1H), 2.26-2.14 (m, 1H), 2.12-1.92 (m, 3H), 1.88-1.72 (m, 4H), 1.40-1.10 (m, 13H), 1.06-0.98 (m, 4H), 0.95-0.86 (m, 1H).

Example 18. Synthesis of Compound 26

Synthesis of Intermediates 076-1 and 076-1A

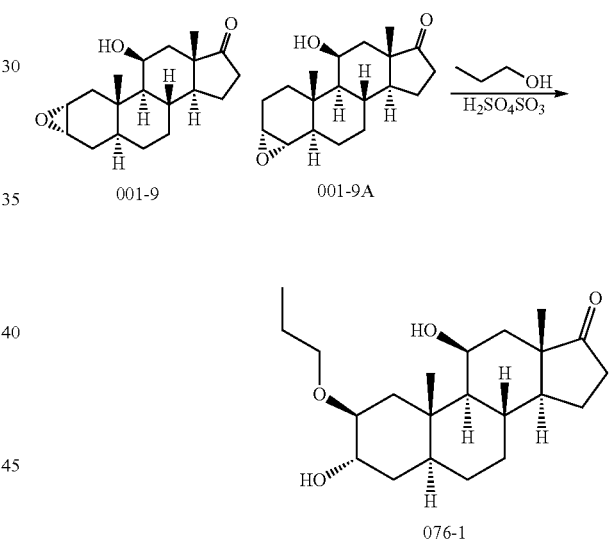

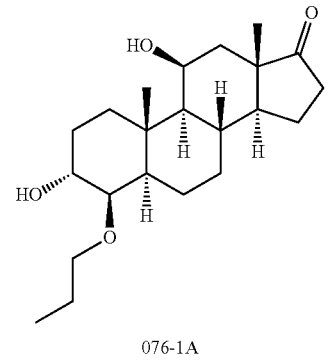

Synthesis of Compound 26

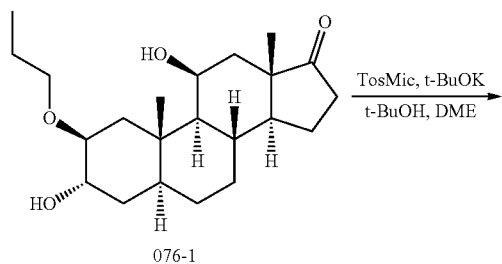

Example 19. Synthesis of Compounds 27 and 39

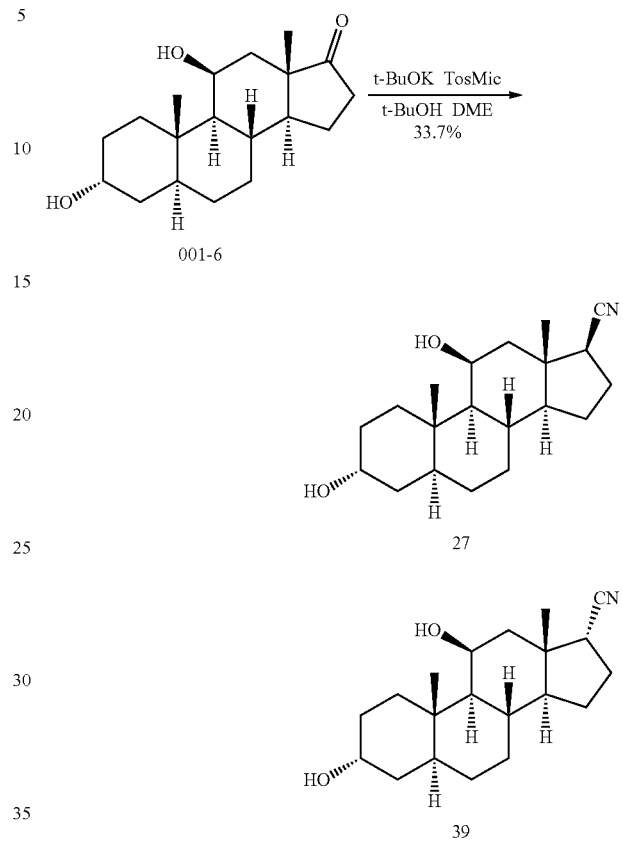

To a solution of mixture 001-9 and 001-9A (500 mg, 1.64 mmol) in Propan-1-ol (10 mL) was added a solution of fuming $H_2SO_4$ (0.125 mL) dropwise. The solution was stirred at room temperature for 3 h. After the TLC showed that the starting material was consumed completely. The mixture was quenched with aq.$NaHCO_3$ and concentrated under reduced pressure. The mixture was poured into water (10 mL) and extracted with EtOAc (10 mL×3). The combined organic layers were dried over $Na_2SO_4$, concentrated to give the crude product, which was purified by column chromatography on silica gel (eluent: petroleum ether:ethyl acetate=6:1) to give the mixture of 076-1 and 076-1A (250 mg, 41.8%) as white solid. To a solution of t-BuOK (768 mg, 6.86 mmol) in t-BuOH (10 mL) was added a solution of 076-1 (250 mg, 0.686 mmol) in 1,2-Dimethoxyethane (5 mL) dropwise at room temperature under $N_2$ atmosphere. Then a solution of TosMic (267 mg, 1.372 mmol) in 1,2-Dimethoxyethane (5 mL) was added dropwise to the mixture. The reaction mixture was stirred for 4 hours. After the LC-MS showed that the starting material was consumed completely. The mixture was extracted with EtOAc (10 mL×3). The combined organic phases were dried over $Na_2SO_4$, and concentrated. The residue was purified by column chromatography on silica gel (eluent: petroleum ether:ethyl acetate=6:1) to give crude 26 (110 mg), which was purified by prep-HPLC to afford pure 26 (36 mg, 27.9%) as white powder. $^1$H NMR (26): (400 MHz, CDCl3) δ 4.42-4.38 (m, 1H), 3.96-3.90 (m, 1H), 3.53-3.40 (m, 2H), 3.33-3.26 (m, 1H), 2.23-2.17 (m, 1H), 2.15-1.72 (m, 8H), 1.63-1.48 (m, 5H), 1.46-1.10 (m, 14H), 1.04-0.85 (m, 5H), 0.83-0.76 (m, 1H).

To a solution of t-BuOK (1.83 g, 16.32 mmol) in t-BuOH (10 mL) was added 001-6 (0.5 g, 1.63 mmol) in 1,2-dimethoxyethane (7 mL) at room temperature under $N_2$ atmosphere. The mixture was stirred at room temperature for 30 min, then the solution of TosMic (0.640 g, 3.26 mmol) in 1,2-dimethoxyethane (7 mL) was added and the solution was stirred at room temperature overnight. TLC (ethyl acetate/petroleum ether=1/3) showed the starting material was consumed completely. To the mixture was added saturate NaCl aqueous (10 mL) and extracted with dichloromethane (20 mL×3). The combined organic layers were washed with brine (15 mL×2), dried over anhydrous $Na_2SO_4$ and concentrated under vacuum to give crude product, which was purified by column chromatography on silica gel (ethyl acetate/petroleum ether=1/5) and further purified by ELSE-HPLC to afford 27 (110.6 mg, 21%) and 39 (63.8 mg, 12.3%) as a white solid. $^1$H NMR (27): (400 MHz, CDCl$_3$) δ 4.43-4.39 (m, 1H), 4.09-4.04 (m, 1H), 2.25-2.18 (m, 1H), 2.16-2.03 (m, 1H), 1.99-1.88 (m, 1H), 1.87-1.76 (m, 3H), 1.74-1.68 (m, 1H), 1.64-1.68 (m, 1H), 1.64-1.61 (m, 4H), 1.60-1.57 (m, 1H), 1.56-1.50 (m, 2H), 1.49-1.32 (m, 4H), 1.32-1.27 (m, 1H), 1.27-1.18 (m, 2H), 1.16 (s, 3H), 1.10-1.07 (m, 1H), 1.01-0.91 (m, 1H), 0.86-0.78 (m, 1H). $^1$H NMR (39): (400 MHz, CDCl$_3$) δ 4.45-4.38 (m, 1H), 4.01-3.97 (m, 1H), 2.50-2.44 (m, 1H), 2.19-2.07 (m, 1H), 1.98-1.64 (m, 7H), 1.64-1.58 (m, 1H), 1.58-1.53 (m, 1H), 1.52-1.49 (m, 4H), 1.39-1.21 (m, 4H), 1.21-1.08 (m, 3H), 1.06-0.90 (m, 7H), 0.89-0.80 (m, 1H).

Example 20. Synthesis of Compound 28

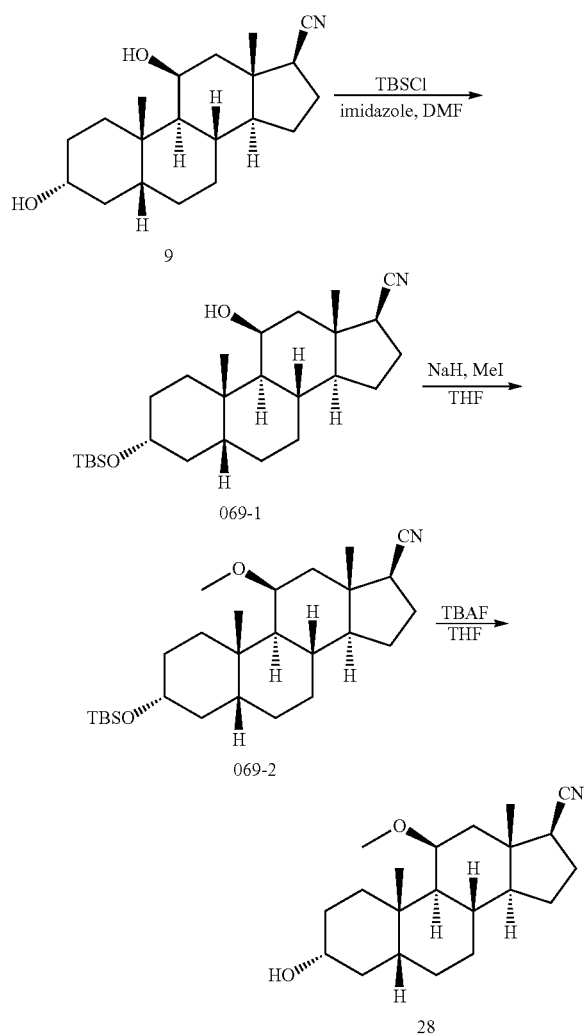

To a solution of 9 (800 mg, 2.52 mmol) in DMF (10 mL) was added TBSCl (569 mg, 3.78 mmol) and imidazole (343 mg, 5.04 mmol) at room temperature. The mixture was stirred overnight at room temperature. TLC (petroleum ether:ethyl acetate=1:1) showed that the reaction was completed. The reaction was quenched with water (50 mL) and the resulting solution was extracted with 3×30 mL of ethyl acetate and the organic layers combined and dried over anhydrous sodium sulfate. The organic phase was concentrated under vacuum. The crude product was purified by column chromatography on silica gel (petroleum ether:ethyl acetate=20:1) to give the product 069-1 (800 mg, 73%) as a white solid.

$^1$H NMR (069-1): (300 MHz, CDCl$_3$) δ 4.28-4.15 (m, 1H), 3.63-3.51 (m, 1H), 2.19-1.52 (m, 11H), 1.52-1.48 (m, 3H), 1.42-1.12 (m, 7H), 1.12 (s, 3H), 1.08 (s, 3H), 0.84 (s, 9H), 0.00 (s, 3H).

To a solution of 069-1 (800 mg, 1.86 mmol) in THF (10 mL) was added NaH (372 mg, 9.3 mmol) at 0° C. The mixture was stirred at room temperature for 30 minutes. Then MeI (528 mg, 3.72 mmol) was added dropwise and the mixture was stirred overnight at 40° C. TLC (petroleum ether:ethyl acetate=3:1) showed that the reaction was complete. The reaction was quenched with NH$_4$Cl solution (50 mL) and the resulting mixture was extracted with 3×30 mL of ethyl acetate, the organic layers combined and dried over anhydrous sodium sulfate. The organic phase was concentrated under vacuum to give the crude product (700 mg, crude) as a yellow solid, which was used in the next step directly.

To a solution of 069-2 (700 mg, crude) in THF (10 mL) was added TBAF (9 mL, 1M in THF) at room temperature. The mixture was stirred overnight at 30° C. TLC (petroleum ether:ethyl acetate=5:1) showed that the reaction was complete. The reaction was quenched with NaHCO$_3$ solution (20 mL) and the resulting solution was extracted with 3×30 mL of ethyl acetate, the organic layers combined and dried over anhydrous sodium sulfate. The organic phase was concentrated under vacuum to give the crude product which was purified by column chromatography on silica gel (petroleum ether:ethyl acetate=3:1) to give the product 28 (230 mg, 37% of two steps) as white solid. $^1$H NMR (28): (400 MHz, CDCl$_3$) δ 3.72-3.62 (m, 1H), 3.56-3.55 (m, 1H), 3.25 (s, 3H), 2.43-2.39 (m, 1H), 2.25-2.22 (m, 1H), 2.16 (m, 1H), 2.15-2.04 (m, 1H), 1.99-1.87 (m, 2H), 1.84-1.62 (m, 5H), 1.55-1.13 (m, 8H), 1.11 (s, 3H), 1.08 (s, 3H), 1.03-0.96 (m, 2H).

Example 21. Synthesis of Compounds 29 and 37

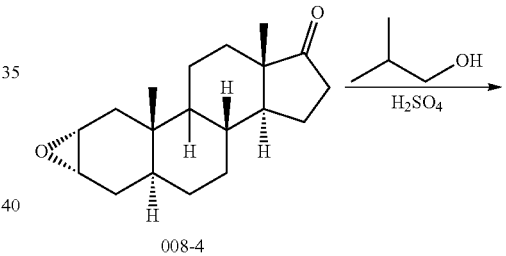

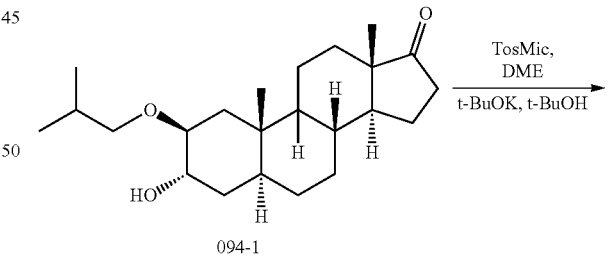

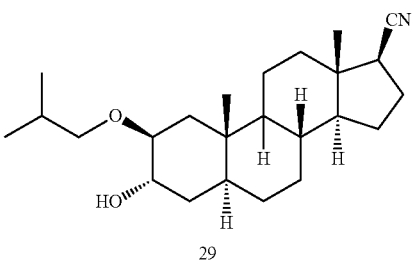

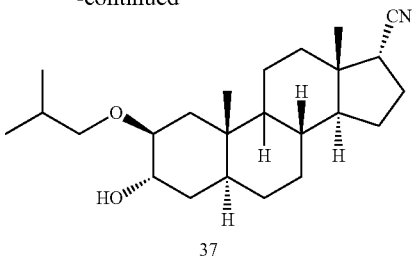

37

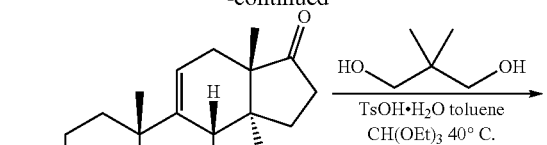

074-1

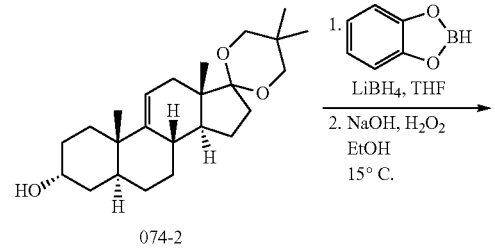

074-2

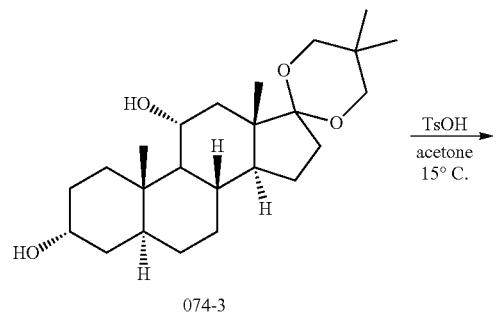

074-3

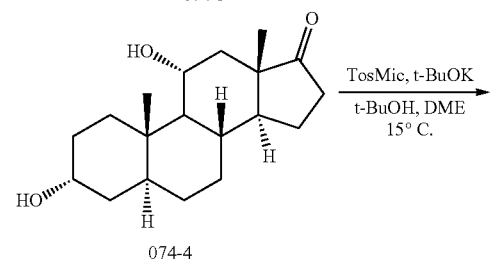

074-4

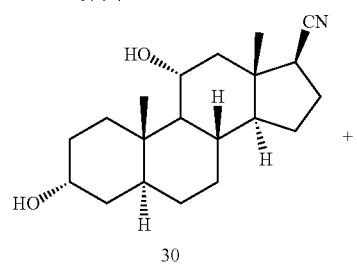

30

+

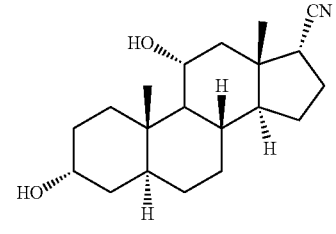

35

To a solution of 008-4 (2 g, mmol) in 2-Methyl-propan-1-ol (10 mL) was added a solution of H₂SO₄ (10 drop, 98%) dropwise. The solution was stirred at room temperature for 2 h. After the TLC showed that the starting material was consumed completely, the mixture was quenched with aq.NaHCO₃, and then was concentrated under reduced pressure. The mixture was poured into water (20 mL) and extracted with EtOAc (20 mL×3). The combined organic layers were dried over Na₂SO₄, concentrated to give crude product, which was purified by column chromatography on silica gel (eluent: petroleum ether:ethyl acetate=30:1) to give 094-1 (1 g, 40%) as white solid. $^1$H NMR (094-1): (400 MHz, CDCl₃) δ 4.00-3.90 (m, 1H), 3.40-3.35 (m, 1H), 3.30-3.24 (m, 1H), 3.15-3.06 (m, 1H), 2.50-2.36 (m, 1H), 2.14-2.00 (m, 1H), 1.98-1.60 (m, 8H), 1.50-1.10 (m, 10H), 1.10-0.92 (m, 4H), 0.92-0.80 (m, 9H), 0.80-0.70 (m, 1H).

To a solution of t-BuOK (3.1 g, 27.58 mmol) in t-BuOH (25 mL) was added a solution of 094-1 (1 g, 2.76 mmol) in 1,2-Dimethoxyethane (10 mL) dropwise at room temperature. Then a solution of TosMic (1.08 mg, 5.51 mmol) in 1,2-Dimethoxyethane (15 mL) was added dropwise in the mixture. The reaction mixture was warmed to room temperature and stirred for 4 hours. After the LCMS showed that the starting material was consumed completely, the mixture was extracted with EtOAc (10 mL×3). The combined organic phases were dried over Na₂SO₄, and the solvent was evaporated to afford crude product, which was purified by column chromatography on silica gel (eluent: petroleum ether:ethyl acetate=7:1) to give the crude product 29 and 37, then the mixture of the two products was purified by prep-HPLC respectively to give 29 (130.3 mg, 12.7%) and 37 (14.1 mg, 1.2%) as white powder. $^1$HNMR (29): (400 MHz, CDCl₃) δ 3.95-3.90 (m, 1H), 3.40-3.35 (m, 1H), 3.30-3.22 (m, 1H), 3.15-3.06 (m, 1H), 2.30-2.24 (m, 1H), 2.16-2.04 (m, 1H), 1.96-1.62 (m, 8H), 1.42-1.22 (m, 8H), 1.16-1.06 (m, 1H), 1.06-0.94 (m, 5H), 0.94-0.84 (m, 10H), 0.76-0.68 (m, 1H). $^1$HNMR (37): (400 MHz, CDCl₃) δ 3.95-3.90 (m, 1H), 3.41-3.35 (m, 1H), 3.30-3.20 (m, 1H), 3.15-3.05 (m, 1H), 2.60-2.50 (m, 1H), 2.20-2.08 (m, 1H), 2.02-1.92 (m, 1H), 1.88-1.68 (m, 8H), 1.42-1.22 (m, 9H), 1.10-0.80 (m, 15H).

Example 22. Synthesis of Compounds 30 and 35

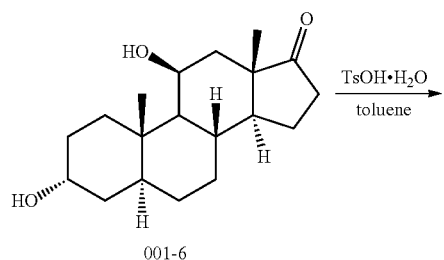

001-6

To a solution of 001-6 (4 g, 13 mmol) in toluene (80 mL) was added TsOH.H₂O (745 mg, 3.9 mmol). The mixture was stirred at 70° C. over night. The mixture was quenched with aqueous NaHCO₃ solution (100 mL) and extracted with EtOAc (100 mL×2). The organic phase was dried over Na₂SO₄ and evaporated to give the crude product, which was purified by column chromatography (petrol ether:ethyl acetate=10:1) to afford 1.5 g of 074-1 (Yield: 40%) as a white solid. ¹H NMR (074-1): (400 MHz, CDCl₃) 55.38-5.37 (m, 1H), 4.06-4.05 (m, 1H), 2.49-2.42 (m, 1H), 2.22-2.15 (m, 1H), 2.13-1.98 (m, 7H), 1.75-1.54 (m, 6H), 1.52-1.25 (m, 9H), 1.11-1.03 (m, 2H), 0.96 (s, 3H), 0.82 (s, 3H).

To a solution of 074-1 (1.5 g, 5.2 mmol) in toluene (30 mL) was added 2,2-dimethylpropane-1,3-diol (2.16 g, 20.8 mmol), CH(OEt)₃ (2.26 g, 15.6 mmol) and TsOH.H₂O (30 mg, 0.16 mmol). The mixture was stirred at 40° C. overnight. Then the mixture was quenched with NaHCO₃ solution (50 mL) and extracted with EtOAc (50 mL×2). The organic phase was dried over Na₂SO₄ and evaporated to give the crude product, which was purified by column chromatography (petrol ether:ethyl acetate=25:1) to afford 1.3 g of 074-2 (Yield: 67%) as a white solid. ¹H NMR (074-2): (400 MHz, CDCl₃) δ 5.38-5.36 (m, 1H), 4.03-4.02 (m, 1H), 3.66-3.64 (m, 1H), 3.47-3.45 (m, 1H), 3.39-3.34 (m, 2H), 2.65-2.61 (m, 1H), 2.32-2.29 (m, 1H), 2.03-2.01 (m, 1H), 1.89-1.84 (m, 1H), 1.78-1.41 (m, 14H), 1.36-1.24 (m, 5H), 1.14 (s, 3H), 1.03-0.95 (m, 2H), 0.91 (s, 3H), 0.74 (s, 3H), 0.71 (s, 3H).

To a solution of 074-2 (1.3 g, 3.47 mmol) in THF (15 mL) was added catecholorate (2.49 g, 10.4 mmol) and LiBH₄ (113 mg, 5.2 mmol). The mixture was stirred at 14° C. over night. To the mixture was added NaOH (1.6 g in 5 mL H₂O), EtOH (16 mL) and H₂O₂ (11 mL) at 0° C. and stirred at 14° C. for 5 h. The mixture was extracted with ethyl acetate (30 mL×2). The organic phase was dried over Na₂SO₄ and evaporated to give the crude product, which was purified by column chromatography (petrol ether:ethyl acetate=1:1) to afford 1.0 g of 074-3 (Yield: 76%) as a white solid. ¹H NMR (074-3): (400 MHz, CDCl₃) δ 4.01-4.00 (m, 1H), 3.93-3.92 (m, 1H), 3.63-3.62 (m, 1H), 3.44-3.41 (m, 1H), 3.36-3.34 (m, 1H), 2.28-2.20 (m, 1H), 2.16-2.10 (m, 1H), 1.85-1.81 (m, 1H), 1.76-1.32 (m, 15H), 1.21-1.15 (m, 2H), 1.12 (s, 3H), 0.91 (s, 3H), 0.90-0.85 (m, 1H), 0.79 (s, 3H), 0.70 (s, 3H).

To a solution of 074-3 (1 g, 2.55 mmol) in acetone (10 mL) was added TsOH.H₂O (485 mg, 1.27 mmol). The mixture was stirred at 15° C. for 1 h. Then the reaction mixture was quenched with NaHCO₃ solution (30 mL) and extracted with EtOAc (50 mL×2). The organic phase was dried over Na₂SO₄ and evaporated to give 750 mg of 074-4 (Yield: 94%) as a white solid. ¹H NMR (074-4): (400 MHz, CDCl₃) δ 4.01-4.00 (m, 1H), 3.93-3.92 (m, 1H), 2.48-2.40 (m, 1H), 2.14-2.05 (m, 3H), 1.95-1.48 (m, 12H), 0.93 (s, 3H), 0.91 (s, 3H), 0.84 (s, 3H).

To a solution of t-BuOK (1.65 g, 14.7 mmol) in t-BuOH (10 mL) was added a solution of 074-4 (450 mg, 1.47 mmol) in 1,2-Dimethoxyethane (5 mL) dropwise at room temperature. Then a solution of TosMic (573 mg, 2.94 mmol) in 1,2-Dimethoxyethane (5 mL) was added dropwise in the mixture. The reaction mixture was warmed to room temperature and stirred for 16 hours. After the LCMS showed that the starting material was consumed completely, the mixture was extracted with EtOAc (10 mL×3). The combined organic phases were dried over Na₂SO₄, and the solvent was evaporated to afford crude product, which was purified by column chromatography on silica gel (eluent: petroleum ether:ethyl acetate=1:1) to give 30 (220 mg, 47%) and 35 (51 mg, 12%) as a white powder. ¹H NMR (30): (400 MHz, CDCl₃) δ 4.03-4.02 (m, 1H), 4.01-3.95 (m, 1H), 2.35-2.30 (m, 1H), 2.29-2.25 (m, 1H), 2.20-2.02 (m, 2H), 2.00-1.90 (m, 1H), 1.80-1.61 (m, 5H), 1.57-1.49 (m, 2H), 1.45-1.10 (m, 10H), 0.92 (s, 3H), 0.90 (s, 3H).

¹H NMR (35): (400 MHz, CDCl₃) δ 4.03-4.01 (m, 1H), 3.95-3.93 (m, 1H), 2.57-2.55 (m, 1H), 2.19-2.00 (m, 4H), 1.90-1.80 (m, 1H), 1.75-1.50 (m, 11H), 1.50-1.08 (m, 10H), 1.57-1.49 (m, 2H), 1.45-1.10 (m, 10H), 0.93 (s, 3H), 0.82 (s, 3H).

Example 23. Synthesis of Compound 31

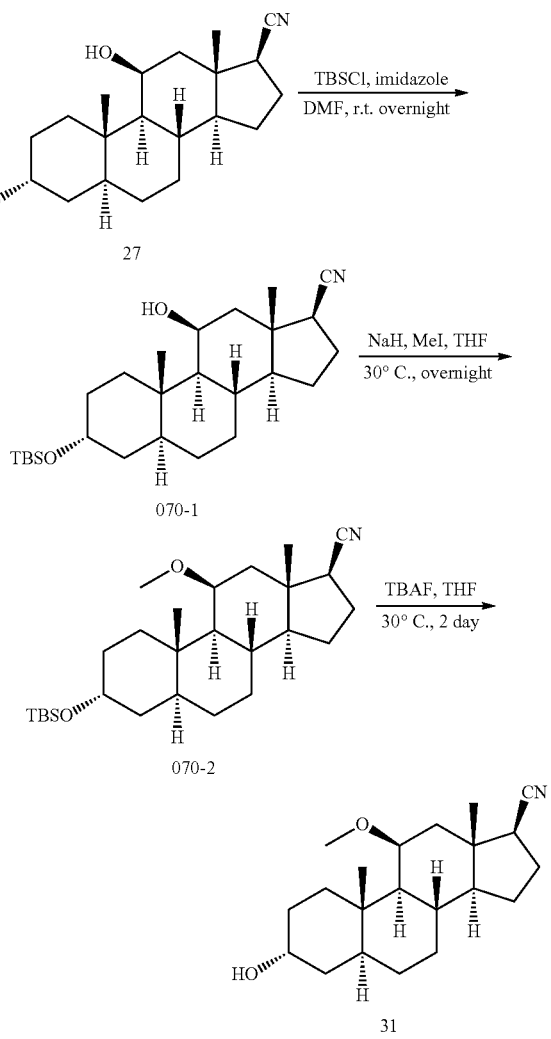

To a solution of 27 (650 mg, 2.05 mmol) and 1H-imidazole (278.77 mg, 4.09 mmol) in DMF (8 mL) was added TBSCl (462.9 mg, 4.09 mmol) in DMF (4 mL) at room temperature under N₂ atmosphere. The mixture was stirred at room temperature overnight. TLC showed the starting material was consumed completely. The resulting mixture was added saturated brine (10 mL) and the resulting solution was extracted with dichloromethane (20 mL×3). The combined organic layers were washed with saturated brine (15 mL×3) and dried over anhydrous Na₂SO₄ and concentrated under vacuum to give crude, which was purified by column chromatography eluting with (ethyl acetate/petroleum ether=1/150) to afford 070-1 (500 mg, 56.6%) as a white solid.

¹H NMR (070-1): (400 MHz, CDCl₃) δ 4.44-4.38 (m, 1H), 3.98-3.94 (m, 1H), 2.14-2.06 (m, 2H), 2.03-1.87 (m, 1H), 1.85-1.73 (m, 3H), 1.62-1.47 (m, 7H), 1.47-1.28 (m, 4H), 1.28-1.17 (m, 2H), 1.17-1.12 (m, 4H), 1.07-1.02 (m, 2H), 1.01-0.92 (m, 4H), 0.91-0.84 (m, 12H), 0.83-0.78 (m, 1H), 0.02 (s, 6H).

To a suspension of NaH (463.21 mg, 11.58 mmol) in THF (10 mL) was added dropwise a solution of compound 070-1 (0.5 g, 1.16 mmol) in THF (5 mL) at 0° C. under N₂. The mixture was stirred at 0° C. for 30 min. Then MeI (1.64 g, 11.58 mmol) was added dropwise and the mixture was stirred at 30° C. overnight. TLC showed that the reaction was complete. The reaction was quenched with aqueous NH₄Cl (10 mL), the resulting solution was extracted with ethyl acetate (15 mL×2) and the organic layers combined and dried over anhydrous Na₂SO₄, concentrated under vacuum to give crude product, which was purified by column chromatography on silica gel (ethyl acetate/petroleum ether=1/50) to give the product 070-2 (270 mg, 52.3%) as a white solid. ¹H NMR (070-2): (400 MHz, CDCl₃) δ 3.98-3.92 (m, 1H), 3.72-3.68 (m, 1H), 3.21 (s 3), 2.40-2.37 (m, 1H), 2.26-2.18 (m, 1H), 1.98-1.82 (m, 1H), 1.82-1.71 (m, 4H), 1.47-1.31 (m, 5H), 1.23-1.16 (m, 2H), 1.08 (s, 3H), 1.02-091 (m, 7H), 0.88 (s, 12H), 0.78-0.72 (m, 1H), 0.06-0.02 (m, 7H).

To a mixture of 070-2 (270 mg, 605.72 μmmol) and TBAF (1.58 g, 6.06 mmol) in THF (6 mL) was stirred at 30° C. for 2 days. TLC showed that the reaction was complete. To the reaction mixture was added saturated brine (10 mL) and the resulting solution was extracted with EtOAc (10 mL×3). The combined organic layers were washed with saturated brine (10 mL×2), dried over anhydrous Na₂SO₄ and concentrated under vacuum to give crude product, which was purified by column chromatography on silica gel (ethyl acetate/petroleum ether=1/5) to afford 31 (65.4 mg, 24.2%) as a white solid. ¹H NMR (31): (400 MHz, CDCl₃) δ 4.06-4.02 (m, 1H), 3.71-3.68 (m, 1H), 3.23 (s, 3H), 2.41-2.37 (m, 1H), 2.24-2.18 (m, 1H), 2.14-2.06 (m, 1H), 1.98-1.87 (m, 1H), 1.84-1.68 (m, 5H), 1.78-1.79 (m, 1H), 1.59-1.48 (m, 3H), 1.48-1.32 (m, 5H), 1.32-1.13 (m, 4H), 108 (s, 3H), 0.99-0.89 (m, 7H), 0.82-0.77 (m, 1H).

Example 24. Synthesis of Compound 32

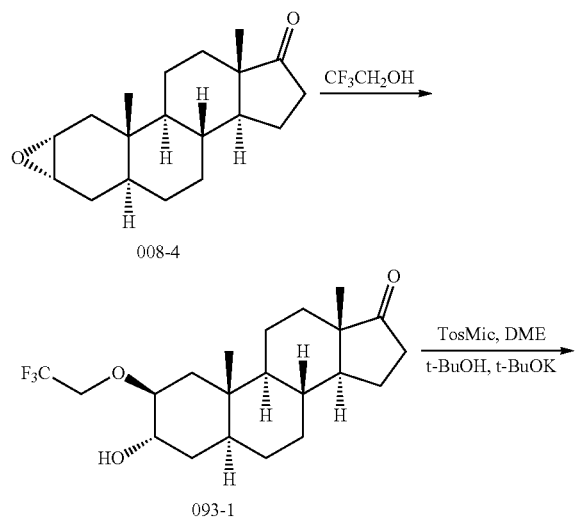

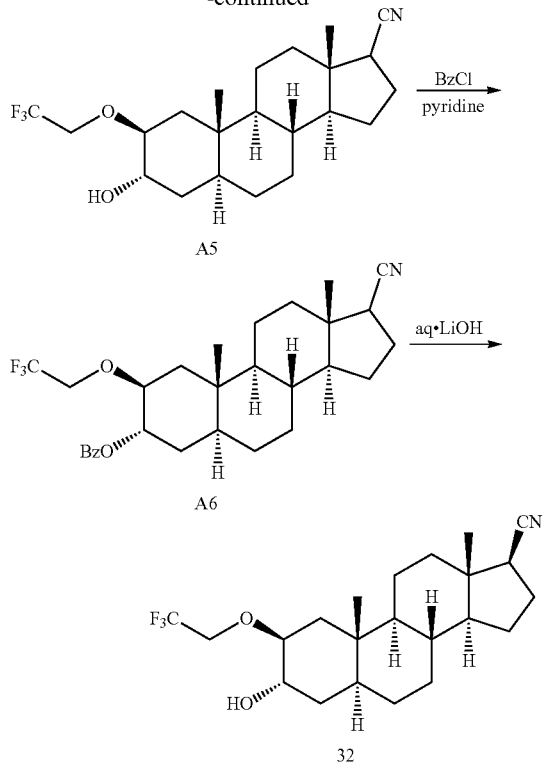

To a mixture of 008-4 (2 g, 6.934 mmol) in CF₃CH₂OH (20 mL) at room temperature under N₂ atmosphere was added a catalytic amount of conc.H₂SO₄ (a drop). The reaction mixture was stirred at room temperature for 16 h. TLC showed the reaction was complete. The reaction mixture was diluted with EtOAc (30 ml) and aq.NH₄Cl (50 ml), extracted with EtOAc (30 ml). The combined organic layers were washed with aq. NaHCO₃ (2×50 ml), dried over Na₂SO₄, and concentrated to get the crude product, which was purified by column chromatography on silica gel (Petroleum ether:EtOAc=6:1) to afford the product A5 (720 mg, 26.6% yield).

To a mixture of t-BuOK (1.73 g, 15.44 mmol) in t-BuOH (10 ml) was added a solution of 093-1 (600 mg, 1.544 mmol) in 1,2-Dimethoxyethane (5 ml) under a N₂ atmosphere. A solution of TosMic (603 mg, 3.089 mmol) in 1,2-Dimethoxyethane (5 ml) was added. The reaction mixture was stirred for 16 h at room temperature. The reaction mixture was diluted with CH₂Cl₂ (30 ml) and H₂O (50 ml) and extracted with CH₂Cl₂ (30 ml). The combined organic layers were washed with aq. NH₄Cl (50 ml) and dried over Na₂SO₄, then concentrated to get the crude product, which was purified by column chromatography on silica gel (Petroleum ether:EtOAc=10:1) to afford the crude product A5 (250 mg, 40.5% yield, mixture of 17-CN epimers).

To a suspension of A5 (300 mg, 0.751 mmol) in pyridine (10 ml) at room temperature under N₂ atmosphere was added PhCOCl (316 mg, 2.253 mmol) dropwise. The reaction mixture was heated to 100° C. and stirred for 3 h. TLC showed the reaction was complete. The reaction mixture was diluted with CH₂Cl₂ (30 ml) and H₂O (50 ml), extracted with CH₂Cl₂ (30 ml). The combined organic layers were washed with 1N HCl (30 ml×2), dried over Na₂SO4, and concentrated to get the crude product. This was purified by column chromatography on silica gel (Petroleum ether:

EtOAc=25:1) to afford the pure target product A6 (100 mg, 26.4% yield). $^1$H NMR (A6): (400 MHz, CDCl$_3$) δ 5.20 (m, 1H), 3.99-3.86 (m, 2H), 3.73 (m, 1H), 2.29-2.22 (m, 1H), 2.18-1.88 (m, 5H), 1.79-1.21 (m, 14H), 1.20-0.72 (m, 11H).

To a solution of A6 (100 mg, 0.2 mmol) in MeOH (5 ml) was added a solution of LiOH.H$_2$O (20 mg, 1 mmol) in H$_2$O (1 ml). The reaction mixture was stirred at room temperature for 16 h. TLC showed the reaction was complete. The reaction mixture was diluted with EtOAc (10 ml) and aq. NH$_4$Cl (10 ml), extracted with EtOAc (10 ml). The combined organic layers were washed with H$_2$O (10 ml), dried over Na$_2$SO$_4$, and concentrated to get the crude product. The crude product was purified by column chromatography on silica gel (Petroleum ether:EtOAc=10:1) to afford 32 (67 mg, 85% yield). $^1$H NMR (32): (400 MHz, CDCl$_3$) δ 3.99 (m, 1H), 3.89-3.70 (m, 2H), 3.58 (m, 1H), 2.30-2.22 (m, 1H), 2.15-2.02 (m, 1H), 1.97-1.60 (m, 7H), 1.44-1.20 (m, 9H), 1.18-0.70 (m, 11H).

Example 25. Synthesis of Compounds 33 and 36

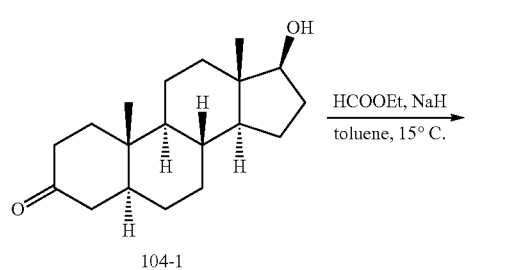

104-1

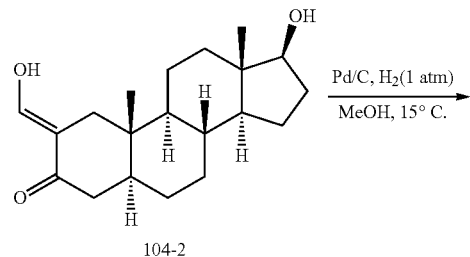

104-2

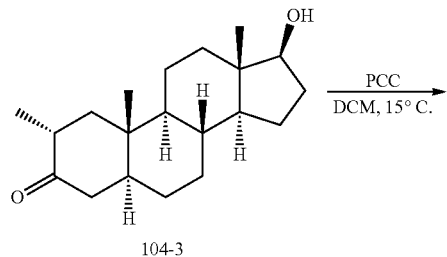

104-3

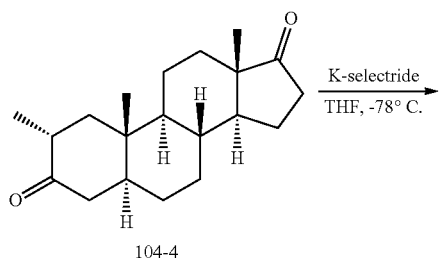

104-4

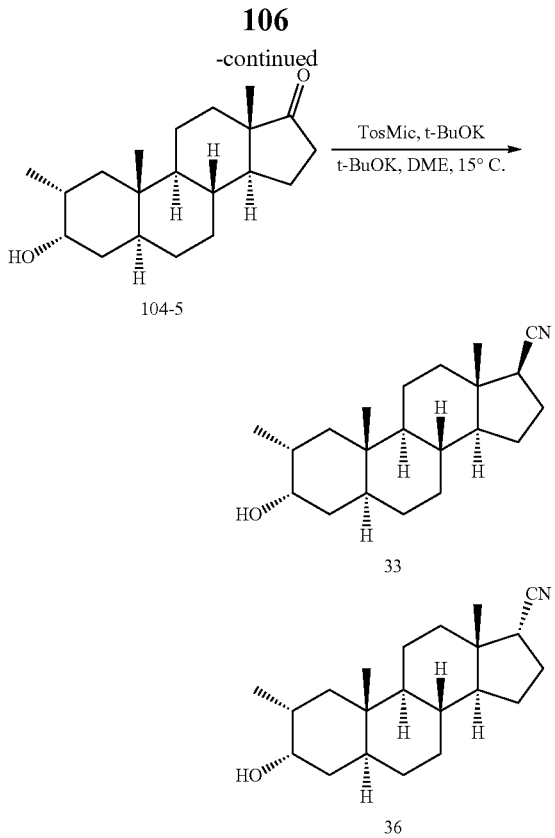

104-5

33

36

To a solution of 104-1 (10 g, 34 mmol) in toluene (100 mL) was added sodium hydride (5.2 g, 60%, 130 mmol) and ethyl formate (3.7 g, 51 mmol). The mixture was then stirred at 10° C. for 16 hours. The mixture was then filtered. The solid washed with petrol ether, added to HCl (1N, aq.), filtered and washed with water. The solid was dried under vacuum to give 20 g of crude 104-2 as a white solid. $^1$H NMR (104-2): (400 MHz, CDCl$_3$) δ 14.37 (brs, 1H), 8.62 (s, 1H), 3.64 (t, J=8.6 Hz, 1H), 2.39-2.20 (m, 2H), 2.14-1.94 (m, 3H), 1.88-1.79 (m, 1H), 1.54-1.32 (m, 7H), 1.31-1.16 (m, 3H), 1.13-0.80 (m, 5H), 0.77 (s, 3H), 0.75 (s, 3H).

To a solution of 104-2 (20 g of crude product) in methanol (400 mL) was added Pd/C (3 g). The mixture was then stirred at 10° C. for 16 hours under hydrogen (1 atm.). The mixture was then filtered, concentrated under vacuum, purified by column chromatography (petrol ether:ethyl acetate=8:1 to ethyl acetate) to give 104-3 (3.1 g, 30% above 2 steps) as a colorless oil. $^1$H NMR (104-3): (400 MHz, CDCl$_3$) δ 3.63 (t, J=8.6 Hz, 1H), 2.66-2.40 (m, 1H), 2.38-2.20 (m, 1H), 2.10-1.92 (m, 3H), 1.85-1.75 (m, 1H), 1.70-1.20 (m, 12H), 1.10-0.81 (m, 7H), 0.80-0.75 (m, 6H).

To a solution of 104-3 (3.1 g, 10.1 mmol) in dichloromethane (30 mL) was added pyridinium chlorochromate (4.8 g, 22.3 mmol) at 15° C. and stirred at 15° C. for 2 hours. To the mixture was then added water and filtered. The organic layer was then separated, dried over anhydrous sodium sulfate, concentrated under vacuum, and purified by column chromatography (petrol ether:ethyl acetate=8:1) to give 104-4 (2.6 g, 84%) as a white solid, $^1$H NMR (104-4): (400 MHz, CDCl$_3$) δ 2.67-2.55 (m, 1H), 2.48-2.41 (m, 1H), 2.32-1.24 (m, 1H), 2.12-1.95 (m, 5H), 1.83-1.79 (m, 2H), 1.58-1.36 (m, 5H), 1.32-1.23 (m, 4H), 1.03-0.98 (m, 4H), 0.88-0.76 (m, 4H), 0.78 (s, 3H).

To a solution of 104-4 (2.1 g, 7 mmol) in tetrahydrofuran (20 mL) was added K-selectride (10 mL, 1M in THF, 10 mmol) dropwise at −78° C. The mixture was stirred at −78° C. for 5 hours and hydrogen peroxide (2 mL, 30% in water) was then added dropwise at −78° C. The mixture was then warmed to 10° C. and aq. sodium thiosulfate was added. The mixture was then extracted with ethyl acatate (30 mL×3), the organic layer dried over anhydrous sodium sulfate, concentrated under vacuum and purified by column chromatography (petrol ether:ethyl acetate=4:1) to give 104-5 (700 mg, 30%) as a white solid. $^1$H NMR (104-5): (400 MHz, CDCl$_3$) δ 3.82-3.75 (m, 1H), 2.42 (dd, J=19.4 Hz, J=9.0 Hz, 1H), 2.12-2.00 (m, 1H), 1.97-1.89 (m, 1H), 1.82-1.67 (m, 4H), 1.56-1.44 (m, 5H), 1.37-1.20 (m, 7H), 1.07-0.97 (m, 2H), 0.93 (d, J=6.8 Hz, 3H), 0.85 (s, 3H), 0.81 (s, 3H), 0.79-0.73 (m, 1H).

To a solution of potassium tert-butylate (1.4 g, 13 mmol) in tert-butanol (5 mL) was added a solution of 104-5 (400 mg, 1.3 mmol) in 1,2-dimethoxyethane (5 mL) and a solution of TosMic (600 mg, 3.3 mmol) in 1,2-dimethoxyethane (5 mL). The mixture was stirred at 15° C. for 16 hours. Water was added to the mixture and extracted with ethyl acetate. The organic layer was dried over anhydrous sodium sulfate, concentrated under vacuum and the resulting crude solid purified by column chromatography (petrol ether:ethyl acetate=15:1) to give 33 (87.2 mg, 21%) and 36 (70.3 mg, 17%) as a white solid. $^1$H NMR (33): (400 MHz, CDCl$_3$) δ 3.82-3.75 (m, 1H), 2.26 (t, J=9.6 Hz, 1H), 2.18-2.04 (m, 1H), 1.98-1.87 (m, 2H), 1.79-1.62 (m, 4H), 1.56-1.40 (m, 3H), 1.39-1.10 (m, 8H), 1.10-0.95 (m, 3H), 0.93 (d, J=7.2 Hz, 3H), 0.90 (s, 3H), 0.79 (s, 3H), 0.78-0.71 (m, 1H).

$^1$H NMR (36): (400 MHz, CDCl$_3$) δ 3.81-3.75 (m, 1H), 2.55 (dd, J=9.2 Hz, J=2.0 Hz, 1H), 2.20-2.11 (m, 1H), 2.02-1.91 (m, 1H), 1.89-1.80 (m, 1H), 1.77-1.62 (m, 5H), 1.53-1.41 (m, 3H), 1.38-1.13 (m, 8H), 1.08-0.98 (m, 2H), 0.93 (d, J=6.8 Hz, 3H), 0.89-0.82 (m, 1H), 0.80 (s, 3H), 0.79 (s, 3H).

Example 26. Synthesis of Compound 34

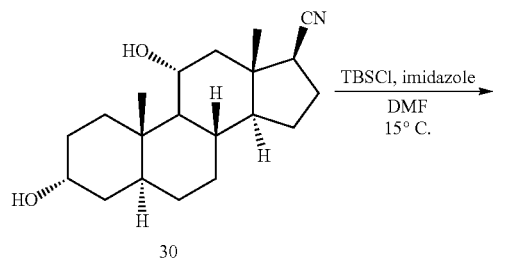

30

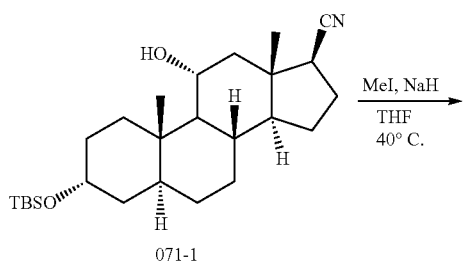

071-1

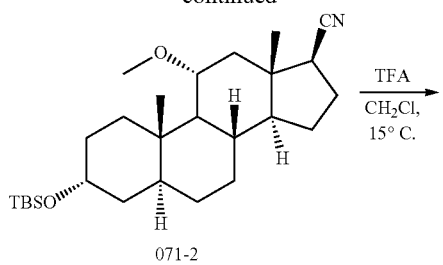

071-2

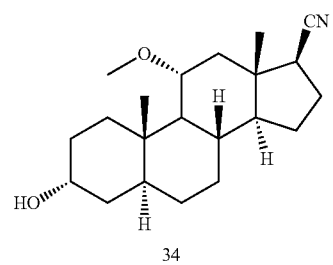

34

To a solution of 30 (170 mg, 0.53 mmol) in DMF (2 mL) was added imidazole (73 mg, 1.07 mmol) and TBSCl (121 mg, 0.80 mmol). The reaction was stirred at 15° C. for 16 h. TLC (petroleum ether:EtOAc=1:2) showed the starting material was consumed completely. The reaction was extracted with EtOAc (20 mL) and aq. NaCl (20 mL). The organic layer was dried over anhydrous sodium sulfate. The organic phase was concentrated under vacuum and was purified by silica gel chromatography eluted with ethyl acetate/petroleum ether (1/60) to give 150 mg of 071-1 (65%) as a white solid.

To a solution of 071-1 (150 mg, 0.35 mmol) in THF (2 mL) was added NaH (56 mg, 1.39 mmol). The mixture was stirred at 12° C. for 30 min. To the reaction mixture was added MeI (197 mg, 1.39 mmol) and stirred at 40° C. for 16 h. TLC (petroleum ether:EtOAc=5:1) showed the starting material was consumed completely. The reaction was quenched with aq. NH$_4$Cl (5 mL) and extracted with EtOAc (20 mL). The organic layer was dried over anhydrous sodium sulfate and the organic phase was concentrated under vacuum. The crude product was purified by silica gel chromatography eluted with ethyl acetate/petroleum ether (1/30) to give 100 mg of 071-2 (65%) as a white solid.

To a solution of 071-2 (100 mg, 0.22 mmol) in CH$_2$Cl$_2$ (3 mL) was added TFA (0.5 mL). The mixture was stirred at 15° C. for 15 min. TLC (petroleum ether:EtOAc=5:1) showed the starting material was consumed completely. The reaction was quenched with aq. NaHCO$_3$ (5 mL) and extracted with EtOAc (20 mL). The organic layer was dried over anhydrous sodium sulfate and the organic phase was concentrated under vacuum. The crude product was purified by silica gel chromatography eluted with ethyl acetate/petroleum ether (1/1) to give 66 mg of 34 (88%) as a white solid. $^1$H NMR (34): (400 MHz, CDCl$_3$) δ 4.00 (m, 1H), 3.41-3.35 (m, 1H), 2.25 (s, 3H), 2.46-2.42 (m, 1H), 2.34-2.29 (m, 1H), 2.19-2.09 (m, 1H), 2.00-1.88 (m, 1H), 1.82-1.56 (m, 7H), 1.53-0.98 (m, 12H), 0.90 (s, 3H), 0.89 (s, 3H).

Example 27. Synthesis of Compounds 40 and 49
Synthesis of Intermediates 105-7 and 105-7A
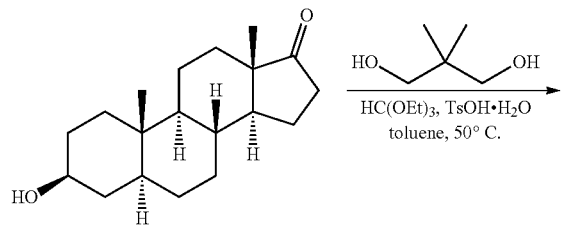
008-1
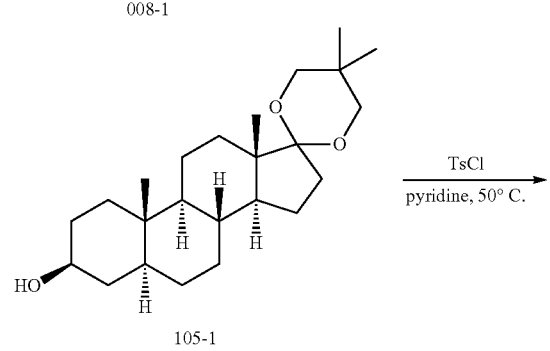
105-1
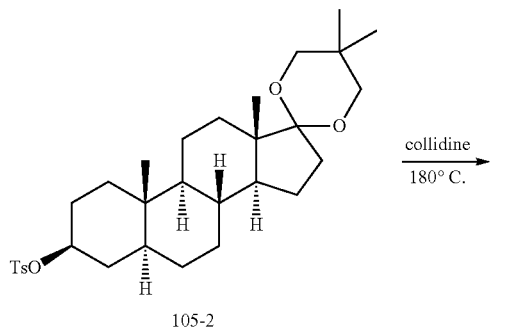
105-2
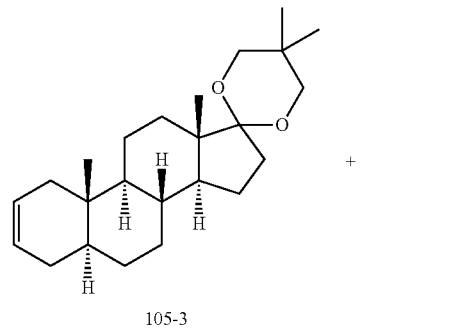
105-3
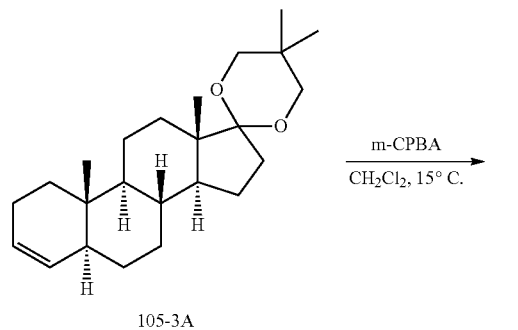
105-3A
-continued
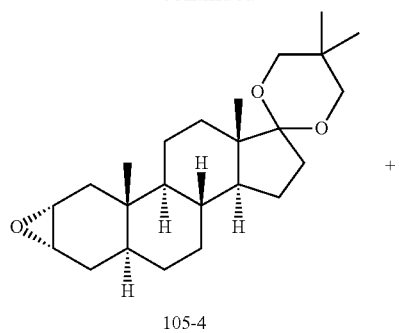
105-4
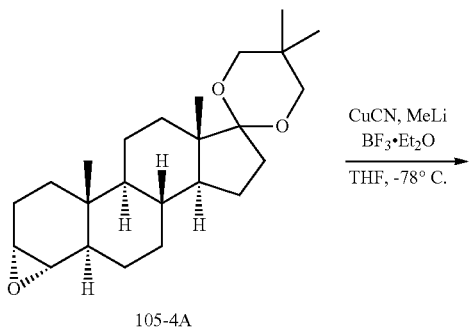
105-4A
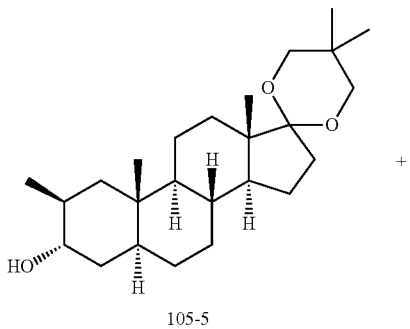
105-5
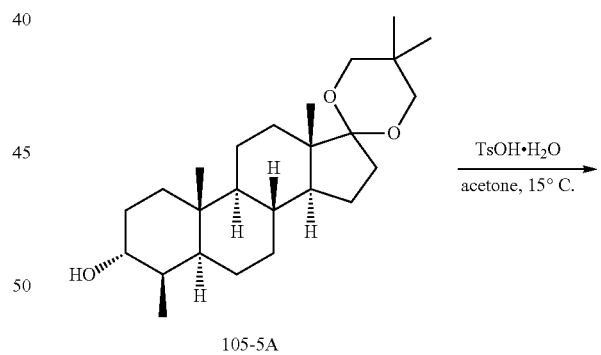
105-5A
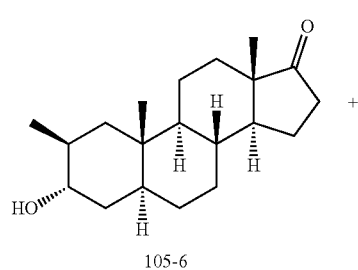
105-6

-continued

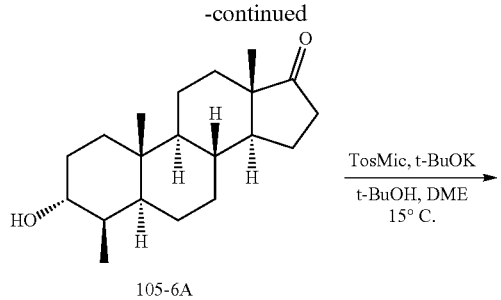
105-6A

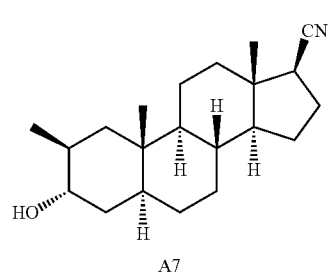
A7

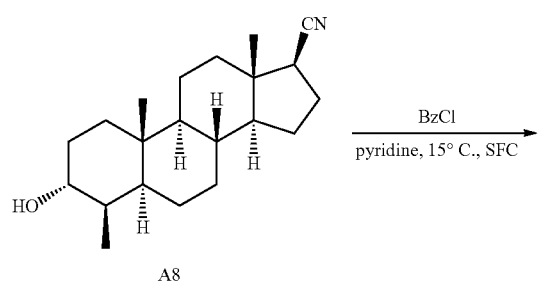
105-7

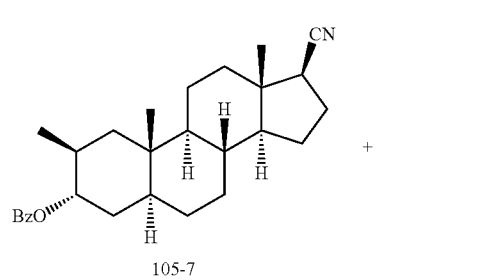
105-7A

Synthesis of Compound 40

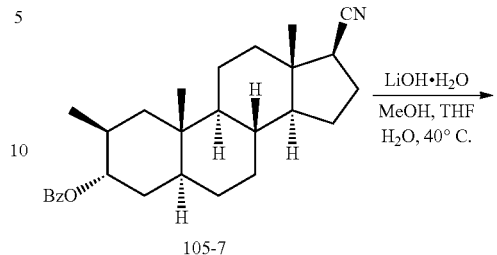
105-7

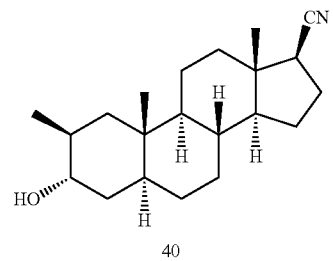
40

Synthesis of Compound 49

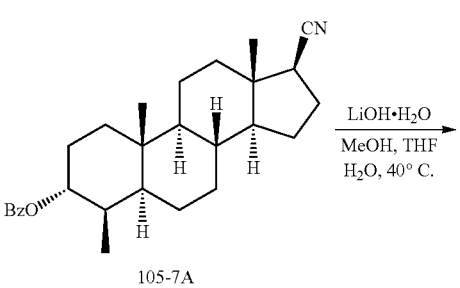
105-7A

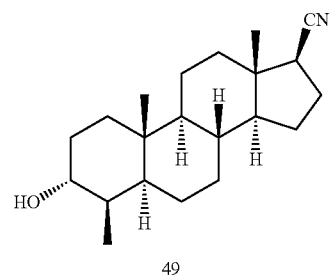
49

To a solution of 008-1 (20 g, 69 mmol) in toluene (200 mL) was added Me$_2$C(CH$_2$OH)$_2$ (22 g, 211 mmol), HC(OEt)$_3$ (40 g, 270 mmol) and TsOH·H$_2$O (2.5 g, 13 mmol). The mixture was then stirred at 50° C. for 48 hours. To the mixture was then added aq. NaHCO$_3$. The organic layer dried over Na$_2$SO$_4$, concentrated under vacuum, purified by column chromatography on silica gel (petrol ether: ethyl acetate=4:1) to give 105-1 (23 g, 88%) as a white solid.

$^1$H NMR (105-1): (400 MHz, CDCl$_3$) δ 3.65-3.30 (m, 5H), 2.25-2.15 (m, 1H), 1.84-1.18 (m, 16H), 1.15-0.62 (m, 18H).

To a solution of 105-1 (23 g, 61 mmol) in pyridine (100 mL) was added TsCl (20 g, 105 mmol). The mixture was then stirred at 50° C. for 4 hours. The mixture was then poured into water and filtered. The resulting solid was washed with water, dissolved in CH$_2$Cl$_2$, dried over Na$_2$SO$_4$ and concentrated under vacuum to give 105-2 (35 g, 100%) as an off-white solid, $^1$H NMR (105-2): (400 MHz, CDCl$_3$) δ 7.80-7.74 (m, 2H), 7.38-7.28 (m, 2H), 4.45-4.33 (m, 1H), 3.65-3.58 (m, 1H), 3.47-3.30 (m, 3H), 2.43 (s, 3H), 2.25-2.15 (m, 1H), 1.80-0.57 (m, 33H).

A solution of 105-2 (35 g, 66 mmol) in collidine (60 mL) was stirred at 180° C. for 2 hours. The mixture was then poured into water, acidified with 1N HCl to pH=3 and extracted with CH$_2$Cl$_2$. The organic layer was dried over Na$_2$SO$_4$ and concentrated under vacuum to give crude 105-3 and 105-3A (23 g, 100%) as an off-white solid. $^1$H NMR (105-3 and 105-3A): (400 MHz, CDCl$_3$) δ 5.63-5.50 (m, 1.75H, alkene-2,3-CH), 5.30-5.24 (m, 0.25H, alkene-4-CH), 3.67-3.60 (m, 1H), 3.48-3.40 (m, 1H), 3.38-3.30 (m, 2H), 2.27-2.16 (m, 1H), 2.05-1.05 (m, 16H), 0.95-0.65 (m, 15H).

To a solution of 105-3 and 105-3A (23 g, 64 mmol) in CH$_2$Cl$_2$ (100 mL) was added m-CPBA (18 g, 105 mmol). The mixture was then stirred at 15° C. for 16 hours. To the mixture was added NaHCO$_3$/Na$_2$S$_2$O$_3$ (aq.). The organic layer was dried over Na$_2$SO$_4$ and purified by column chromatography (petrol ether:ethyl acetate=20:1) to give 105-4 and 105-4A (8 g, 32%) as a white solid. $^1$H NMR (105-4 and 105-4A): (400 MHz, CDCl$_3$) δ 3.67-3.57 (m, 1H), 3.48-3.40 (m, 1H), 3.38-3.30 (m, 2H), 3.17-3.03 (m, 1.75H, epoxy-2,3-CH), 2.70-2.65 (m, 0.25H, epoxy-4-CH), 2.27-2.14 (m, 1H), 2.06-0.55 (m, 31H).

To a suspension of CuCN (2.3 g, 26 mmol) in THF (20 mL) was added MeLi (53 mL, 1M in 2-Me-THF, 53 mmol) at −78° C. dropwise. The mixture was warmed to 0° C. and then cooled to −78° C. A solution of BF$_3$.Et$_2$O (1.5 g, 10.6 mmol) in THF (10 mL) was added dropwise and then stirred at −78° C. for 30 minutes. A solution of 105-4 and 105-4A (2 g, 5.3 mmol) in THF (10 mL) was then added dropwise and stirred at −78° C. for another 3 hours. To the mixture was then added a mixture of MeOH (15 mL) and Et$_3$N (15 mL). The mixture was then warmed to 10° C. To the mixture was added NH$_4$Cl (aq.) and ethyl acetate. The mixture was then filtered. The organic layer was separated, dried over Na$_2$SO$_4$ and concentrated under vacuum to give 105-5 and 105-5A (3.1 g, crude) as light yellow oil. $^1$H NMR (105-5 and 105-5A): (400 MHz, CDCl$_3$) δ 3.72-3.67 (m, 0.4H, 3-CHOH of 4-methyl compound), 3.67-3.62 (m, 0.6H, 3-CHOH of 2-methyl compound), 3.58-3.52 (m, 1H), 3.41-3.34 (m, 1H), 3.32-3.25 (m, 2H), 2.20-2.03 (m, 2H), 1.86-0.58 (m, 35H).

To a solution of 105-5 and 105-5A (3.1 g, crude) in acetone (30 mL) was added TSOH.H$_2$O (1.5 g, 7.9 mmol). The mixture was stirred at 15° C. for 1 hour. To the mixture was added NaHCO$_3$ (aq.) to pH=7. The mixture was extracted with ethyl acetate. The organic layer was dried over Na$_2$SO$_4$, concentrated under vacuum and purified by column chromatography on silica gel (petrol ether:ethyl acetate=8:1 to 5:1) to give 105-6 and 105-6A (1.2 g, 70% of two steps) as a white solid. $^1$H NMR (105-6 and 105-6A): (400 MHz, CDCl$_3$) δ 3.72-3.67 (m, 0.4H, 3-CHOH of 4-methyl compound), 3.67-3.62 (m, 0.6H, 3-CHOH of 2-methyl compound), 2.48-2.38 (m, 1H), 2.13-1.98 (m, 1H), 1.97-1.15 (m, 18H), 1.05-0.63 (m, 11H).

To a solution of t-BuOK (2.2 g, 20 mmol) in t-BuOH (20 mL) was added a solution of TosMic (900 mg, 5 mmol) in 1,2-dimethoxyethane (10 mL) and a solution of 105-6 and 105-6A (600 mg, 2 mmol) in 1,2-dimethoxyethane (10 mL). The mixture was stirred at 15° C. for 3 hours. To the mixture was added water and that mixture was extracted with ethyl acetate. The organic layer was dried over Na$_2$SO$_4$ and purified by column chromatography (petrol ether:ethyl acetate=15:1 to 10:1) to give A7 and A8 (600 mg, crude) as white solid. $^1$H NMR (A7 and A8): (400 MHz, CDCl$_3$) δ 3.72-3.67 (m, 0.25H, 3-CHOH of 4-methyl compound), 3.67-3.62 (m, 0.75H, 3-CHOH of 2-methyl compound), 2.26 (t, J=9.2 Hz, 1H), 2.15-0.68 (m, 31H).

To a solution of A7 and A8 (600 mg, 1.9 mmol) in pyridine (6 mL) was added BzCl (1 g, 7 mmol). The mixture was then stirred at 15° C. for 3 days. To the mixture was then added NaHCO$_3$ (aq.) and then extracted with ethyl acetate. The organic layer was concentrated under vacuum and purified by prep-HPLC and then SFC to give 105-7 (90 mg) and 105-7A (40 mg, total yield of two steps: 30%) as white solids. $^1$H NMR (105-7): (400 MHz, CDCl$_3$) δ 8.08-8.03 (m, 2H), 7.61-7.55 (m, 1H), 7.51-7.44 (m, 2H), 5.08-5.00 (m, 1H), 2.29 (t, J=9.6 Hz, 1H), 2.22-0.90 (m, 29H), 0.83-0.74 (m, 1H). $^1$H NMR (105-7A): (400 MHz, CDCl$_3$) δ 8.10-8.05 (m, 2H), 7.63-7.55 (m, 1H), 7.52-7.44 (m, 2H), 5.11-5.04 (m, 1H), 2.29 (t, J=9.6 Hz, 1H), 2.23-1.13 (m, 18H), 1.07-0.88 (m, 11H), 0.85-0.75 (m, 1H).

To a solution of 105-7 (90 mg, 0.2 mmol) in THF (2 mL) was added MeOH (1 mL) and a solution of LiOH.H$_2$O (0.1 g, 2.4 mmol) in water (1 mL). The mixture was stirred at 40° C. for 16 hours. The mixture was extracted with ethyl acetate. The organic layer was dried over Na$_2$SO$_4$ and purified by column chromatography on silica gel (petrol ether:ethyl acetate=8:1 to 5:1) to give 40 (72 mg, 100%) as an off-white solid. $^1$H NMR (40): (400 MHz, CDCl$_3$) δ 3.74-3.67 (m, 1H), 2.24 (t, J=9.6 Hz, 1H), 2.24-2.00 (m, 1H), 1.97-1.81 (m, 3H), 1.78-1.45 (m, 7H), 1.43-0.75 (m, 19H), 0.75-0.65 (m, 1H).

To a solution of compound 105-7A (40 mg, 0.1 mmol) in THF (2 mL) was added MeOH (1 mL) and a solution of LiOH.H$_2$O (0.1 g, 2.4 mmol) in water (1 mL). The mixture was stirred at 40° C. for 16 hours. Then the mixture was extracted with ethyl acetate. The organic layer was dried over Na$_2$SO$_4$ and purified by column chromatography on silica gel (petrol ether:ethyl acetate=8:1 to 5:1) to give 49 (25 mg, 100%) as an off-white solid. $^1$H NMR (49): (400 MHz, CDCl$_3$) δ 3.83-3.77 (m, 1H), 2.27 (t, J=9.6 Hz, 1H), 2.17-2.03 (m, 1H), 1.99-1.50 (m, 11H), 1.50-0.73 (m, 19H).

Example 28. Synthesis of Compounds 41 and 50

Synthesis of Intermediates 107-3 and 107-3A

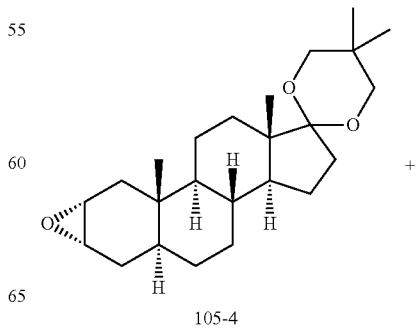

105-4

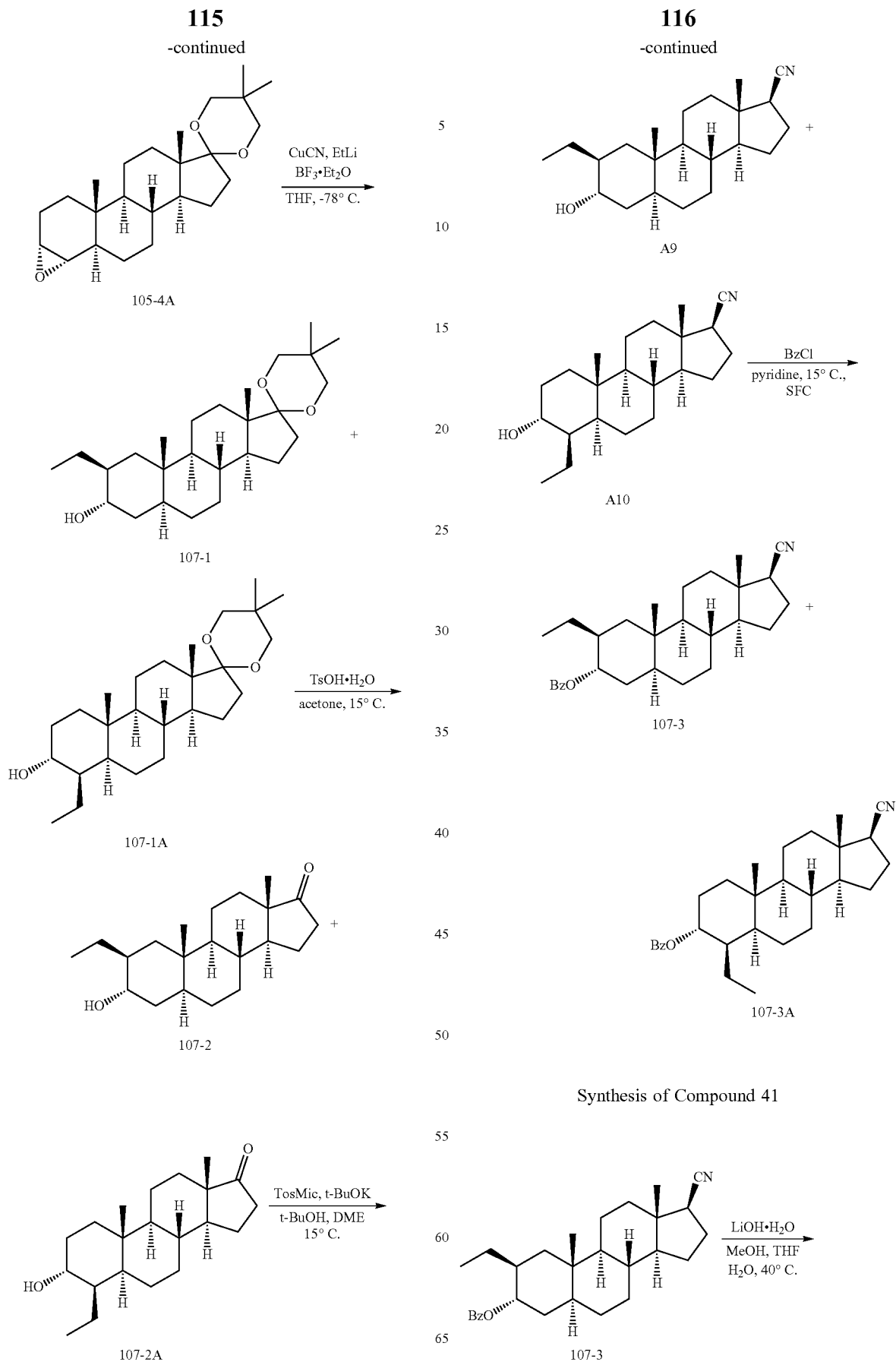
Synthesis of Compound 41

-continued

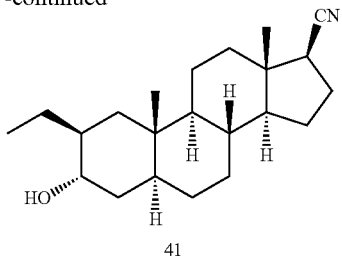

41

Synthesis of Compound 50

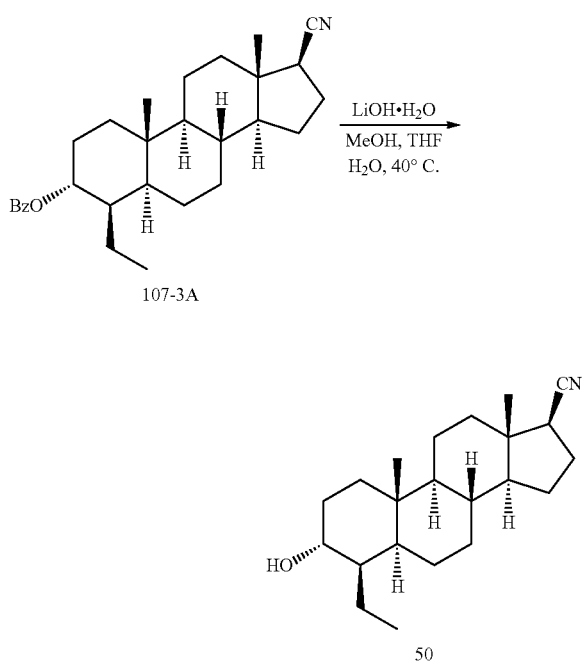

To a suspension of CuCN (1.88 g, 21.2 mmol) in THF (150 mL) was added EtLi (85 mL, 0.5M in benzene/cyclohexane, 42.5 mmol) at −78° C. dropwise. The mixture was warmed to 0° C. and then cooled to −78° C. A solution of BF$_3$.Et$_2$O (1.5 g, 10.6 mmol) in THF (10 mL) was added dropwise and stirred at −78° C. for 30 minutes. A solution of 105-4 and 105-4A (2 g, 5.3 mmol) in THF (10 mL) was added dropwise and stirred at −78° C. for another 3 hours. To the mixture was then added a mixture of MeOH (15 mL) and Et$_3$N (15 mL). The mixture was warmed to 10° C. To the mixture was added NH$_4$Cl (aq.) and ethyl acetate. The mixture was filtered and the organic layer was separated, dried over Na$_2$SO$_4$ and concentrated under vacuum to give 107-1 and 107-1A (2.5 g, crude) as a light yellow oil, a mixture of the 2β-Et, 3-αOH and 3-αOH, 4β-Et isomers. $^1$H NMR (107-1 and 107-1A): (400 MHz, CDCl$_3$) δ 3.94-3.90 (m, 0.1H, 3-CHOH of 4-ethyl compound), 3.85-3.74 (m, 0.6H, 3-CHOH of 2-ethyl compound), 3.68-3.62 (m, 1H), 3.51-3.43 (m, 1H), 3.41-3.33 (m, 2H), 2.28-2.18 (m, 1H), 1.78-0.70 (m, 38H).

To a solution of 107-1 and 107-1A (2.5 g, crude) in acetone (20 mL) was added TSOH.H$_2$O (0.5 g, 2.6 mmol). The mixture was stirred at 15° C. for 3 hours. To the mixture was added NaHCO$_3$ (aq.) to pH=7. The mixture was extracted with ethyl acetate. The organic layer was washed with brine, dried over Na$_2$SO$_4$ and concentrated under vacuum. The residue was purified by column chromatography on silica gel (petrol ether:ethyl acetate=10:1 to 5:1) to give 107-2 and 107-2A (1.2 g, 70% of two steps) as a white solid. $^1$H NMR (107-2 and 107-2A): (400 MHz, CDCl$_3$) δ 3.93-3.88 (m, 0.2H, 3-CHOH of 4-ethyl compound), 3.83-3.77 (m, 0.8H, 3-CHOH of 2-ethyl compound), 2.46-2.34 (m, 1H), 2.10-1.97 (m, 1H), 1.95-1.13 (m, 20H), 1.06-0.70 (m, 11H).

To a solution of t-BuOK (4.2 g, 38 mmol) in t-BuOH (20 mL) was added a solution of TosMic (1.8 g, 9.5 mmol) in 1,2-dimethoxyethane (20 mL) and a solution of 107-2 and 107-2A (1.2 g, 3.8 mmol) in 1,2-dimethoxyethane (20 mL). The mixture was stirred at 15° C. for 5 hours. To the mixture was added water and extracted with ethyl acetate. The organic layer was dried over Na$_2$SO$_4$ and purified by column chromatography on silica gel (petrol ether:ethyl acetate=10:1 to 8:1) to give A9 and A10 (1 g, crude) as a white solid. $^1$H NMR (A9 and A10): (400 MHz, CDCl$_3$) δ 3.97-3.93 (m, 0.15H, 3-CHOH of 4-ethyl compound), 3.87-3.80 (m, 0.8H, 3-CHOH of 2-ethyl compound), 2.28 (t, J=9.2 Hz, 1H), 2.17-2.06 (m, 1H), 1.98-1.90 (m, 2H), 1.82-0.70 (m, 30H).

To a solution of A9 and A10 (1 g, 3 mmol) in pyridine (10 mL) was added BzCl (1.5 g, 10.6 mmol). The mixture was stirred at 20° C. for 16 hours. To the mixture was added NaHCO$_3$ (aq.) and extracted with ethyl acetate. The organic layer was concentrated under vacuum, purified by prep-HPLC and then SFC to give 107-3 (450 mg) and 107-3A (80 mg, total yield of two steps: 40%) as white solids. $^1$H NMR (107-3): (400 MHz, CDCl$_3$) δ 8.07-8.00 (m, 2H), 7.59-7.52 (m, 1H), 7.50-7.42 (m, 2H), 5.15-5.10 (m, 1H), 2.27 (t, J=9.6 Hz, 1H), 2.15-2.05 (m, 1H), 1.98-0.85 (m, 30H), 0.82-0.73 (m, 1H). $^1$H NMR (107-3A): (400 MHz, CDCl$_3$) δ 8.10-8.02 (m, 2H), 7.58-7.52 (m, 1H), 7.50-7.42 (m, 2H), 5.25-5.18 (m, 1H), 2.26 (t, J=9.6 Hz, 1H), 2.18-2.05 (m, 1H), 1.98-1.50 (m, 13H), 1.45-1.10 (m, 6H), 1.07-0.84 (m, 11H), 0.84-0.74 (m, 1H).

To a solution of 107-3 (450 mg, 1 mmol) in THF (4 mL) was added MeOH (2 mL) and a solution of LiOH.H$_2$O (0.4 g, 10 mmol) in water (2 mL). The mixture was stirred at 40° C. for 16 hours. The mixture then was extracted with ethyl acetate. The organic layer was dried over Na$_2$SO$_4$, purified by column chromatography on silica gel (petrol ether:ethyl acetate=8:1 to 5:1) to give 41 (233 mg, 80%) as a white solid.

$^1$H NMR (41): (400 MHz, CDCl$_3$) δ 3.86-3.70 (m, 1H), 2.26 (t, J=9.6 Hz, 1H), 2.16-2.03 (m, 1H), 1.97-1.84 (m, 2H), 1.79-1.06 (m, 18H), 1.05-0.88 (m, 8H), 0.83 (s, 3H), 0.77-0.67 (m, 1H).

To a solution of 107-3A (80 mg, 0.2 mmol) in THF (2 mL) was added MeOH (1 mL) and a solution of LiOH.H$_2$O (0.1 g, 2.4 mmol) in water (1 mL). The mixture was stirred at 40° C. for 16 hours. The mixture was extracted with ethyl acetate. The organic layer was dried over Na$_2$SO$_4$, purified by column chromatography on silica gel (petrol ether:ethyl acetate=8:1 to 5:1) to give compound 50 (40 mg, 80%) as a white solid. $^1$H NMR (50): (400 MHz, CDCl$_3$) δ 3.95-3.90 (m, 1H), 2.26 (t, J=9.6 Hz, 1H), 2.16-2.03 (m, 1H), 1.98-0.85 (m, 28H), 1.82-0.70 (m, 4H).

Example 29. Synthesis of Compound 42

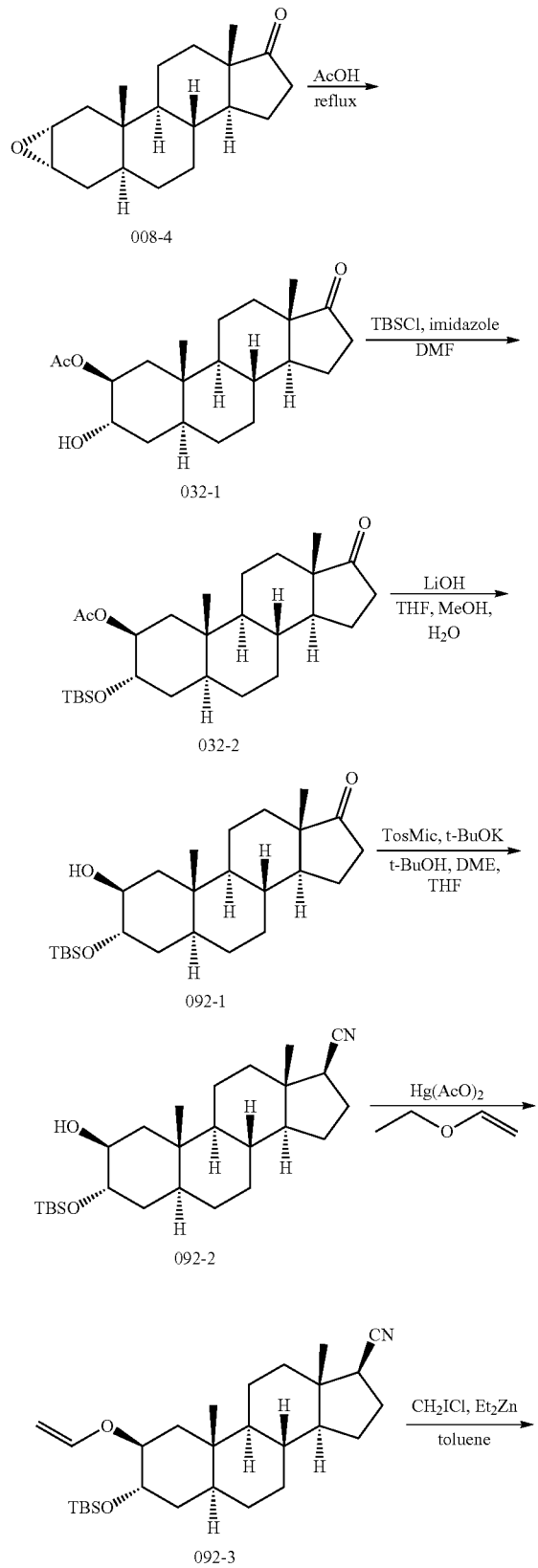

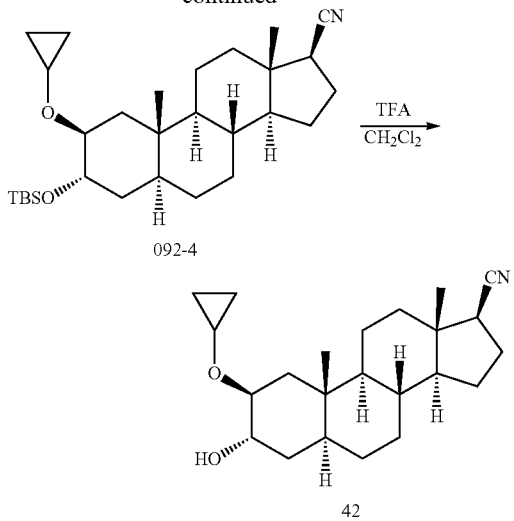

A mixture of 008-4 (20 g, 69.34 mmol) and AcOH (200 mL) was stirred at 120° C. for 3 hours. TLC showed the starting material was consumed completely. The solvent was removed, and the mixture was adjusted to pH=7 with a saturated aqueous solution of $Na_2CO_3$ (100 mL). The mixture was treated with water and extracted with EtOAc (200 mL×2). The organic phase was washed with brine, dried over anhydrous $Na_2SO_4$ and then concentrated to get the crude product. The crude product was purified by flash column chromatography on silical gel (PE:EtOAc=5:1) to afford the 032-1 (17 g, 70%) as a white solid. $^1$HNMR (032-1): (400 MHz, $CDCl_3$) δ 4.89-4.88 (m, 1H), 3.88-3.87 (m, 1H), 2.48-2.41 (m, 1H), 2.13-2.03 (m, 4H), 1.96-1.93 (m, 1H), 1.87-1.76 (m, 5H), 1.69-1.50 (m, 5H), 1.49-1.23 (m, 6H), 1.07-1.02 (m, 1H), 0.95 (s, 3H), 0.87 (s, 3H), 0.84-0.81 (m, 1H)

To a stirred solution of 032-1 (16 g, 45.6 mmol) in dry DMF (150 mL) was added imidazole (6.2 g, 91.8 mmol) and TBSCl (13.8 g, 91.8 mmol) and the mixture stirred at 50° C. for 12 hours. The mixture was treated with water and extracted with EtOAc (200 mL×2). The combined organic layer was washed with water (200 mL×4). The organic layer was dried over anhydrous $Na_2SO_4$, and concentrated to get the crude product, which was purified by flash column chromatography on silical gel (PE:EtOAc=40:1) to afford the 032-2 (18.6 g, 88%) as a white solid. $^1$HNMR (032-2): (400 MHz, $CDCl_3$) δ 4.78-4.77 (m, 1H), 3.79-3.78 (m, 1H), 2.46-2.41 (m, 1H), 2.10-2.05 (m, 4H), 1.96-1.93 (m, 1H), 1.83-1.60 (m, 6H), 1.51-1.22 (m, 9H), 1.10-1.00 (m, 1H), 0.93 (s, 3H), 0.91-0.89 (m, 9H), 0.87 (s, 3H), 0.84-0.81 (m, 1H), 0.12-0.001 (m, 6H)

To a stirred solution of 032-2 (18 g, 38.9 mmol) in THF (150 mL) was added $LiOH·H_2O$ (4.6 g, 194.6 mmol), MeOH (30 mL) and $H_2O$ (30 mL). The mixture was stirred at 50° C. for 12 hours. The solvent was removed by reduced pressure and the solid separated. The solid was filtered and the cake was washed by EtOAc, dried by vacuum. A white solid 092-1 (10.8 g, 66%) was obtained. $^1$HNMR (092-1): (400 MHz, $CDCl_3$) δ 3.82-3.80 (m, 1H), 3.79-3.76 (m, 1H), 2.46-2.41 (m, 1H), 2.10-2.05 (m, 1H), 1.95-1.92 (m, 2H), 1.83-1.80 (m, 2H), 1.79-1.64 (m, 2H), 1.54-1.51 (m, 2H), 1.41-1.20 (m, 8H) 1.11-0.98 (m, 4H), 0.95 (s, 9H), 0.93 (s, 3H), 0.80-0.72 (m, 1H), 0.0.7-0.001 (m, 6H)

To a stirred solution of t-BuOK (13.4 g, 119 mmol) in t-BuOH (80 mL) was added a solution of 092-1 (10 g, 23.8 mmol) in THF (40 mL) under nitrogen. A solution of Tosylmethyl isocyanide (9.3 g, 47.6 mmol) in 1,2-dimethoxyethane (40 mL) was added dropwise. The mixture was stirred at room temperature for 12 hours. The mixture then was treated with dilute aqueous sodium chloride followed by hydrochloric acid (1 M) until acidic. The mixture was extracted with EtOAc, and the organic layer was washed with brine, dried over anhydrous $Na_2SO_4$, concentrated to get the residue, which was purified by flash column chromatography on silical gel (PE:EtOAc=10:1) to afford 092-2 (4.2 g, 41%) as a white solid. $^1$HNMR (092-2): (400 MHz, $CDCl_3$) δ 3.82-3.80 (m, 1H), 3.79-3.76 (m, 1H), 2.30-2.23 (m, 1H), 2.20-2.00 (m, 1H), 1.94-1.88 (m, 3H), 1.80-1.61 (m, 5H), 1.52-1.23 (m, 10H), 1.15-1.04 (m, 2H), 0.99 (s, 3H), 0.97-0.89 (m, 12H), 0.73-0.65 (m, 1H), 0.0.7-0.001 (m, 6H)

To a stirred solution of 092-2 (2.0 g, 1.16 mmol) in ethoxyethylene (20 mL) was added $Hg(AcO)_2$ (2.2 g, 6.95 mmol). The mixture was stirred at 25° C. for 12 hours. The mixture was filtered, and the filtrate was evaporated to get a residue, which was purified by flash column chromatography on $Al_2O_3$ (PE:EtOAc=100:1) to afford the 092-3 (672 mg, 32%) as a white solid. $^1$HNMR (092-3): (400 MHz, $CDCl_3$) δ 6.32-6.27 (m, 1H), 4.34-4.30 (dd, $J_1$=1.6, $J_2$=14, 1H), 4.05-4.03 (dd, $J_1$=1.6, $J_2$=6.8, 1H), 3.94-3.93 (m, 1H), 3.78-3.77 (m, 1H), 2.27-2.251 (m, 1H), 2.18-2.10 (m, 1H), 2.07-1.93 (m, 1H), 1.90-1.65 (m, 5H), 1.43-1.20 (m, 10), 1.18-1.10 (m, 1H), 1.00 (s, 3H), 0.99-0.93 (m, 1H), 0.92-0.91 (m, 12H), 0.80-0.70 (m, 1H), 0.07-0.01 (m, 6H).

To a stirred solution of 092-3 (600 mg, 1.31 mmol) in dry toluene (6 mL) was added diethylzinc (3.93 mL, 3.93 mmol) at −40° C. under nitrogen. After 1 hour, chloroiodomethane (461 mg, 2.62 mmol) was added dropwise. The reaction mixture was stirred at −40° C. for 2 hours, then warmed to room temperature and stirred for 12 hours. The mixture was quenched with a saturated aqueous solution of $NH_4Cl$ (20 mL). The mixture was treated with water and extracted with EtOAc (20 mL×2). The combined organic layers were washed with brine, dried over anhydrous $Na_2SO_4$, evaporated to dryness and purified by flash column chromatography on silical gel (PE:EtOAc=200:1) to afford the 092-4 (252 mg, 41%) as a white solid. $^1$HNMR (092-4): (400 MHz, $CDCl_3$) δ 3.94-3.93 (m, 1H), 3.44-3.43 (m, 1H), 3.29-3.27 (m, 1H), 2.24-2.22 (m, 1H), 2.18-2.04 (m, 1H), 1.92-1.89 (m, 2H), 1.75-1.60 (m, 6H), 1.52-1.15 (m, 9), 1.14-1.03 (m, 2H), 1.00-0.98 (m, 5H), 0.92-0.91 (m, 12H), 0.77-0.68 (m, 1H), 0.60-0.45 (m, 4H), 0.02-0.01 (m, 6H)

To a stirred solution of 092-4 (252 mg, 0.36 mmol) in dry $CH_2Cl_2$ (3 mL) was added trifluoroacetic acid (0.27 mL, 3.6 mmol). The reaction mixture was stirred at room temperature for 3 hours. The mixture then was quenched with a saturated aqueous solution of $NaHCO_3$ (15 mL). The mixture was treated with water and extracted with $CH_2Cl_2$ (30 mL×2). The combined organic layer was washed with brine, dried over anhydrous $Na_2SO_4$ and evaporated to dryness, and purified by flash column chromatography on silical gel (PE:EtOAc=8:1) to afford 42 (38 mg, 30%) as a white solid. $^1$HNMR (42): (400 MHz, $CDCl_3$) δ 4.03-4.02 (m, 1H), 3.57-3.56 (m, 1H), 3.32-3.29 (m, 1H), 2.28-2.25 (m, 1H), 2.20-2.04 (m, 1H), 1.93-1.61 (m, 2H), 1.73-1.60 (m, 5H), 1.52-1.25 (m, 10H), 1.20-1.02 (m, 1H), 0.99 (s, 3H), 0.98-0.92 (m, 1H), 0.90 (s, 3H), 0.87-0.80 (m, 5H), 0.60-0.47 (m, 4H).

Example 30. Synthesis of Compound 43

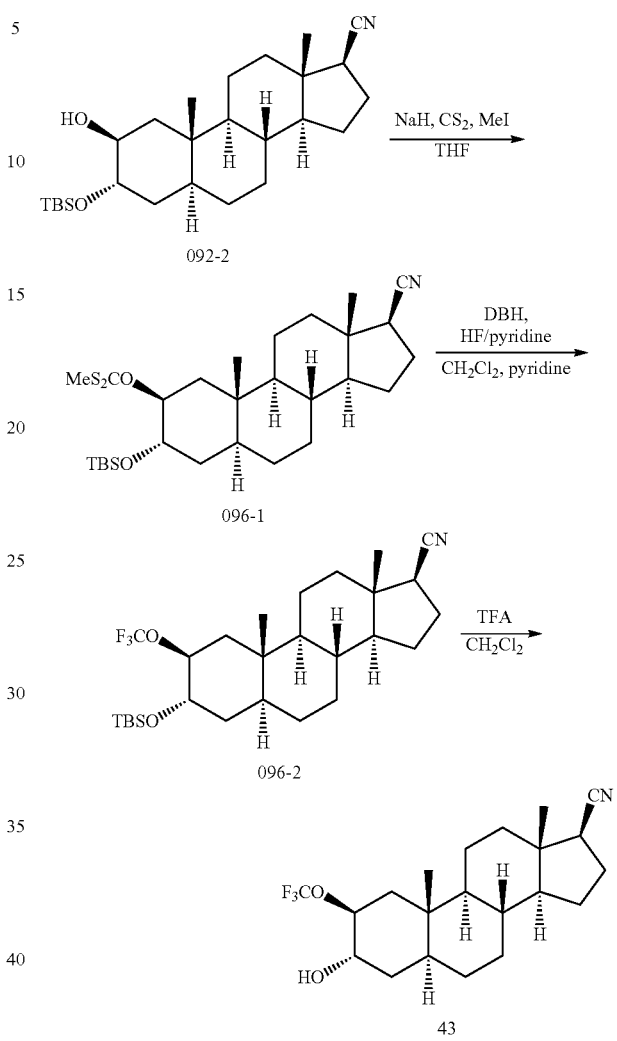

To a suspension of NaH (220 mg, 5.55 mmol) in THF (5 mL) was added dropwise a solution of 092-2 (800 mg, 1.85 mmol) in THF (5 mL). The resulting mixture was heated at reflux for 1 hour, then cooled to room temperature, and $CS_2$ (560 mg, 7.4 mmol) was added slowly to the reaction mixture. The resulting mixture was stirred for 30 min. MeI (1.31 g, 9.25 mmol) was added dropwise. The reaction mixture was stirred overnight at room temperature. Ice water was added at 0° C. and the mixture was treated with aqueous hydrochloric acid (1M, 5 mL). The mixture was extracted with EtOAc and the combined organic phase was washed with sat $NaHCO_3$ solution, then with brine, dried over anhydrous $Na_2SO_4$ and concentrated under reduced pressure. The residue was purified by flash chromatography (PE:EtOAc=150:1) to afford the 096-1 (450 mg, 46%) as a white solid. $^1$H NMR (096-1): (400 MHz, $CDCl_3$) δ 5.10-5.05 (m, 1H), 4.03-4.01 (m, 1H), 2.58 (s, 3H), 2.30-2.25 (m, 1H), 2.20-2.11 (m, 1H), 2.00-1.91 (m, 4H), 1.84-1.62 (m, 6H), 1.53-1.20 (m, 12H), 1.19-1.10 (m, 2H), 1.04 (s, 3H), 1.03-0.90 (m, 14H), 0.78-0.72 (m, 1H), 0.98 (s, 3H), 0.10 (s, 3H), 0.08 (s, 3H)

To a stirred solution of 1,3-dibromo-5,5-dimethylhydantoin (245 mg, 0.86 mmol) in dry $CH_2Cl_2$ (2 mL) was added pyridine (1.5 mL) and HF/pyridine (1.5 mL) dropwise at −78° C. The mixture was stirred at room temperature for 10 min and cooled to 0° C. A solution of 096-1 (450 mg, 0.86 mmol) in CH$_2$Cl$_2$ (2 mL) was added dropwise. The resulting mixture was stirred for 1 hour at 0° C. The mixture was quenched by a saturated aqueous solution of NaHCO$_3$ (20 mL). The mixture extracted with CH$_2$Cl$_2$ (20 mL×2) and the organic layer was washed with aqueous hydrochloric acid (0.5 M, 10 mL) then with brine. The combined organic layer was dried over anhydrous Na$_2$SO$_4$ and evaporated to dryness, and purified by flash column chromatography on silical gel (PE:EtOAc=20:1) to afford the 096-2 (120 mg, 28%) as a colorless oil. $^1$H NMR (096-2): (400 MHZ, CDCl$_3$) δ 4.13-4.11 (m, 1H), 3.95-3.94 (m, 1H), 2.26-2.23 (m, 1H), 2.11-2.08 (m, 1H), 2.00-1.58 (m, 9H), 1.55-1.01 (m, 16H), 0.98 (s, 3H), 0.92-0.80 (m, 13H), 0.78-0.70 (m, 2H), 0.10-0.02 (m, 6H).

To a stirred solution of 096-2 (120 mg, 0.24 mmol) in dry CH$_2$Cl$_2$ (3 mL) was added trifluoroacetic acid (0.09 mL, 1.2 mmol). The reaction mixture was stirred at room temperature for 3 hours. The mixture was quenched with a saturated aqueous solution of NaHCO$_3$ (10 mL). The mixture then was treated with water and extracted with CH$_2$Cl$_2$ (10 mL×2). The combined organic layers were washed with brine, dried over anhydrous Na$_2$SO$_4$ and evaporated to dryness and purified by flash column chromatography on silica gel (PE:EtOAc=20:1) to afford the 43 (31 mg, 32%) as a white solid. $^1$H NMR (43): (400 MHz, CDCl$_3$) δ 4.31-4.30 (m, 1H), 4.07-4.03 (m, 1H), 2.29-2.24 (m, 1H), 1.96-1.92 (m, 1H), 1.80-1.57 (m, 5H), 1.50-1.25 (m, 8H), 1.20-1.10 (m, 1H), 1.01 (s, 3H), 0.99-0.92 (m, 1H), 0.91 (s, 3H), 0.76-0.72 (m, 1H).

Example 31. Synthesis of Compound 44

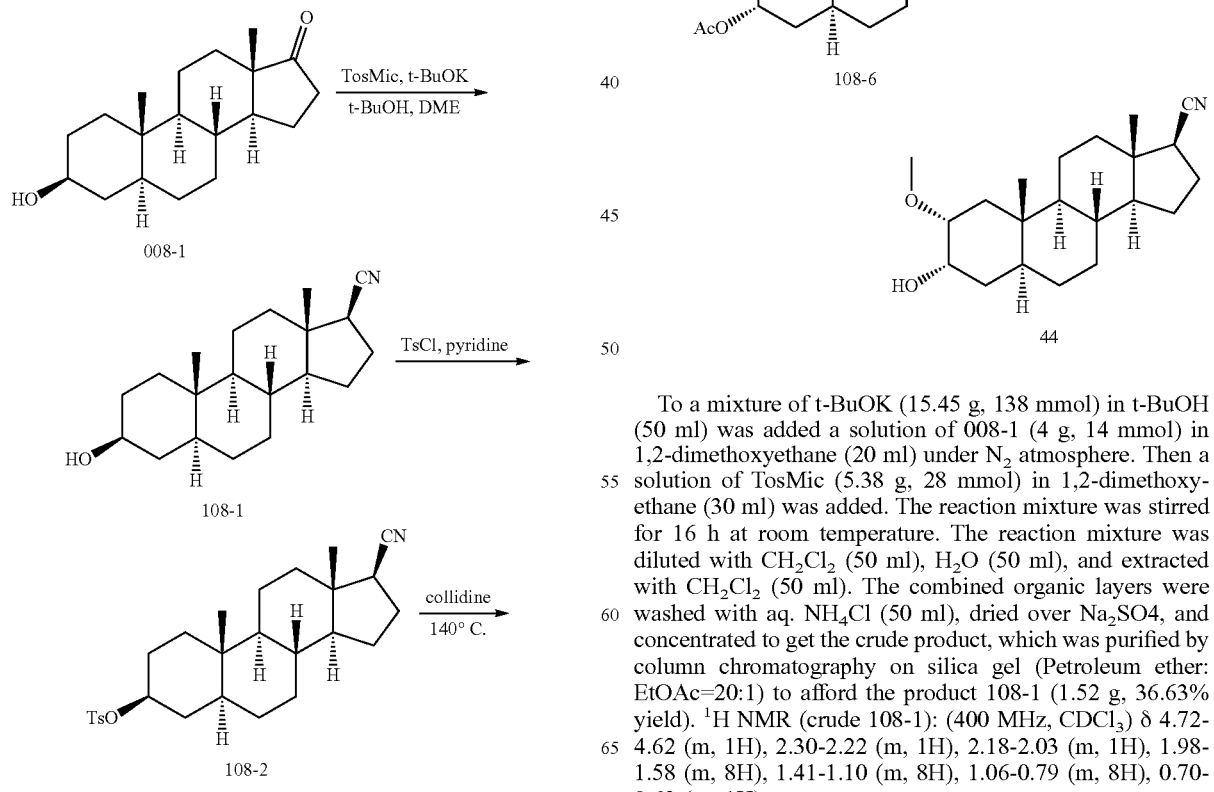

To a mixture of t-BuOK (15.45 g, 138 mmol) in t-BuOH (50 ml) was added a solution of 008-1 (4 g, 14 mmol) in 1,2-dimethoxyethane (20 ml) under N$_2$ atmosphere. Then a solution of TosMic (5.38 g, 28 mmol) in 1,2-dimethoxyethane (30 ml) was added. The reaction mixture was stirred for 16 h at room temperature. The reaction mixture was diluted with CH$_2$Cl$_2$ (50 ml), H$_2$O (50 ml), and extracted with CH$_2$Cl$_2$ (50 ml). The combined organic layers were washed with aq. NH$_4$Cl (50 ml), dried over Na$_2$SO4, and concentrated to get the crude product, which was purified by column chromatography on silica gel (Petroleum ether: EtOAc=20:1) to afford the product 108-1 (1.52 g, 36.63% yield). $^1$H NMR (crude 108-1): (400 MHz, CDCl$_3$) δ 4.72-4.62 (m, 1H), 2.30-2.22 (m, 1H), 2.18-2.03 (m, 1H), 1.98-1.58 (m, 8H), 1.41-1.10 (m, 8H), 1.06-0.79 (m, 8H), 0.70-0.62 (m, 1H).

To a solution of 108-1 (2.3 g, 7.64 mmol) in pyridine (15 ml) was added TsCl (1.7 g, 9.17 mmol). The reaction mixture was heated to 50° C. and stirred for 6 h. TLC showed the reaction was complete. The reaction mixture was concentrated to remove pyridine. The residue was diluted with H$_2$O (20 ml), extracted with EtOAc (30 ml×2). The combined organic layers were washed with 1N HCl (20 ml×2), dried over Na$_2$SO4, and concentrated to get the crude product 108-2 (3.5 g) as a yellow oil. $^1$H NMR (crude 108-2): (400 MHz, CDCl$_3$) δ 7.80-7.77 (d, 2H), 7.33-7.30 (d, 2H), 4.45-4.35 (m, 1H), 2.45 (s, 3H), 2.28-2.21 (m, 1H), 2.18-2.03 (m, 1H), 1.98-1.85 (m, 2H), 1.80-1.50 (m, 11H), 1.40-0.75 (m, 18H), 0.63-0.57 (m, 1H).

A solution of 108-2 (3.5 g, 7.68 mmol) in collidine (10 ml) was heated to 140° C. and stirred for 5 h. TLC showed the reaction was completed. After cooling, the reaction mixture was poured into 2N HCl, then extracted with EtOAc (30 ml×2). The combined organic layers were washed with 1N HCl (20 ml×2) and dried over Na$_2$SO4, then concentrated to get the crude product 108-3 (2.1 g) as a yellow oil.

To a solution of OsO$_4$ (50 mg, 1.64 mmol) and NMO (1.8 g, 15.876 mmol) in t-BuOH (20 ml), THF (20 ml) and H$_2$O (2 ml) was added a solution of 108-3 (1.5 g, 5.292 mmol) in THF (5 ml). The solution was stirred at room temperature for 3 h. After the TFC showed that the starting material was consumed completely, the mixture was quenched with aq. NaHS and extracted with EtOAc (10 mL×3). The combined organic layers were washed with aq.Na$_2$SO$_3$, dried over Na$_2$SO$_4$ and concentrated to give the crude product, which was purified by column chromatography on silica gel (eluent: petroleum ether:EtOAc=3:1) to give 108-4 (1.1 g, 65.4%) as a white solid. $^1$H NMR (crude 108-4): (400 MHz, CDCl$_3$) δ 3.98-3.93 (m, 1H), 3.81-3.75 (m, 1H), 2.30-2.23 (m, 1H), 2.15-1.50 (m, 14H), 1.49-0.78 (m, 18H).

To a mixture of 108-4 (800 mg, 2.524 mmol) in toluene (15 ml) was added Novozym 435 (2 g) and acetic acid vinyl ester (5 ml). The reaction mixture was heated to 50° C. and stirred for 3 days. The resulting mixture was filtered and the filtrate was concentrated. The residue was purified by column chromatography on silica gel (Petroleum ether: EtOAc=5:1) to afford the product 108-5 (330 mg, 36.4% yield). $^1$H NMR (crude 108-5): (400 MHz, CDCl$_3$) δ 5.13 (m, 1H), 3.88-3.81 (m, 1H), 2.30-2.22 (m, 1H), 2.18-2.05 (m, 4H), 1.98-1.52 (m, 12H), 1.43-1.10 (m, 9H), 1.03-0.78 (m, 10H).

To a solution of 108-5 (250 mg, 0.695 mmol) in THF (5 ml) was added NaH (278 mg, 6.95 mmol). The reaction mixture was stirred for 10 min. Then MeI (987 mg, 6.95 mmol) was added. The reaction mixture was stirred at room temperature for another 1 h. The reaction was quenched with aq. NH$_4$Cl (10 ml) and extracted with EtOAc (30 ml×2). The combined organic layers were washed with aq. NaCl (20 ml) and dried over Na$_2$SO4, then concentrated. The residue was purified by column chromatography on silica gel (Petroleum ether:EtOAc=10:1) to afford the crude product 108-6 (80 mg, 30.8% yield).

To a solution of 108-6 (80 mg, 0.214 mmol) in MeOH (2 ml) and THF (2 ml) was added a solution of NaOH (26 mg, 0.642 mmol) in H$_2$O (1 ml). The reaction mixture was stirred at room temperature for 16 h. TLC showed the reaction was complete. The reaction mixture was diluted with EtOAc (10 ml) and aq. NH$_4$Cl (10 ml), and extracted with EtOAc (10 ml). The combined organic layers were washed with H$_2$O (10 ml), dried over Na$_2$SO$_4$, and concentrated to get the crude product. The crude product was purified by column chromatography on silica gel (Petroleum ether:EtOAc=8:1) to afford the purified product 44 (17 mg, 23.9% yield). $^1$H NMR (44): (400 MHz, CDCl$_3$) δ 4.15-4.08 (m, 1H), 3.37 (s, 3H), 2.30-2.22 (m, 1H), 2.15-2.07 (m, 1H), 1.98-1.90 (m, 2H), 1.75-1.55 (m, 5H), 1.45-1.10 (m, 9H), 1.07-0.90 (m, 5H), 0.87-0.80 (m, 4H).

Example 32. Synthesis of Compounds 45 and 46

Synthesis of Intermediates 106-7 and 106-7A

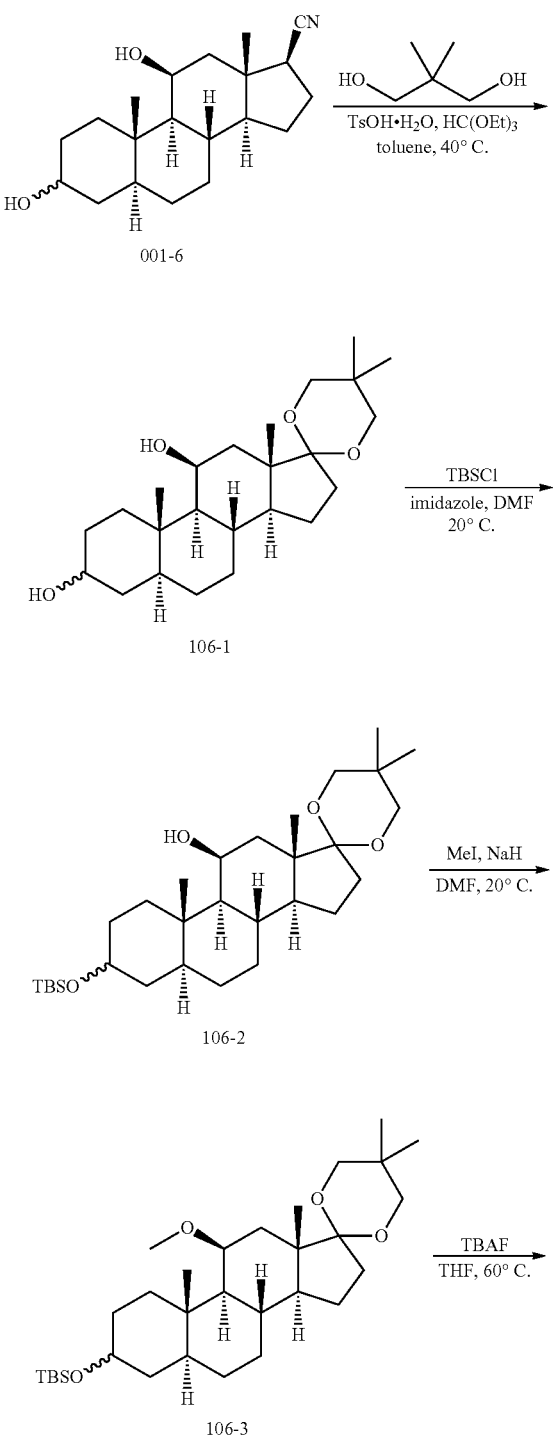

-continued

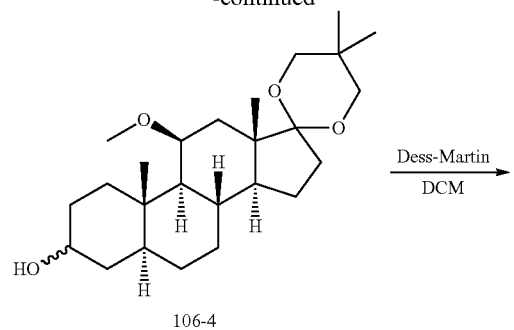

106-4

Dess-Martin
DCM
→

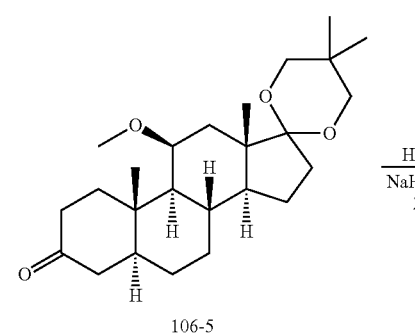

106-5

HCOOEt
NaH, toluene
20° C.
→

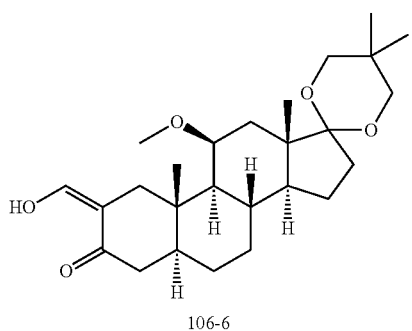

106-6

H₂ (30 psi)
Pd/C
MeOH
30° C., 43%
→

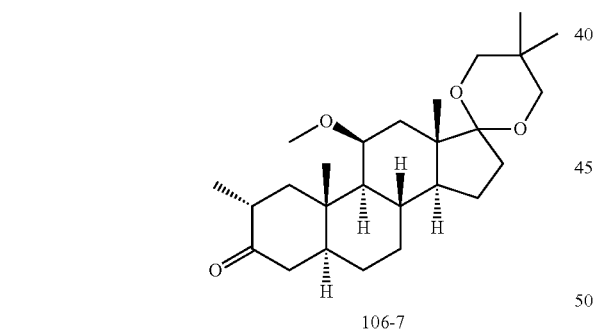

106-7

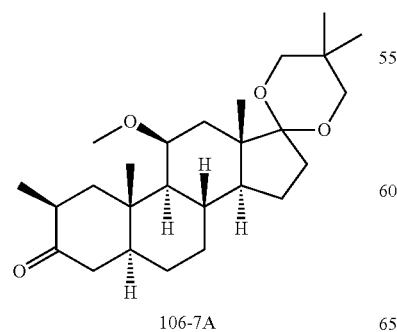

106-7A

Synthesis of Compounds 45 and 46

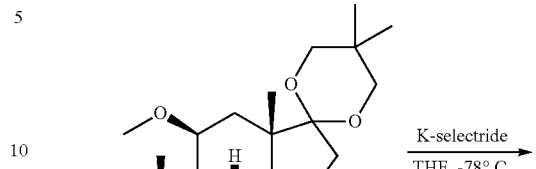

106-7

K-selectride
THF, -78° C.
→

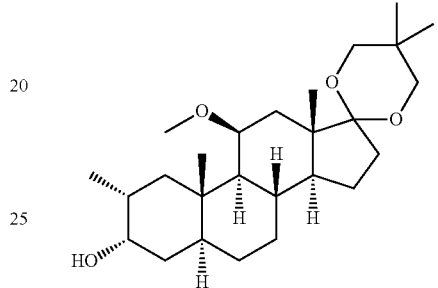

106-8

TsOH·H₂O
acetone, 25° C.
→

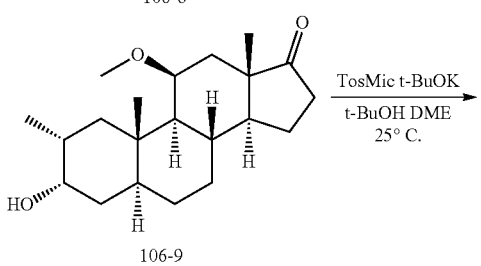

106-9

TosMic t-BuOK
t-BuOH DME
25° C.
→

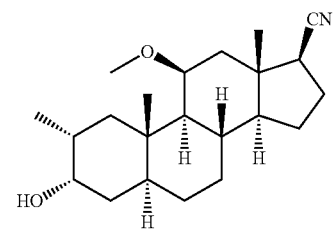

45

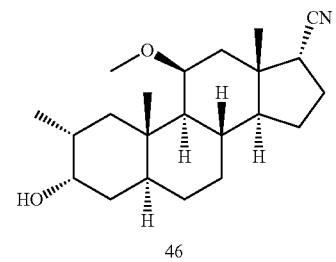

46

To a solution of 001-6 (10 g, 30 mmol) in toluene (200 mL) was added Me₂C(CH₂OH)₂ (9.4 g, 90 mmol), HC(OEt)₃ (13.3 g, 90 mmol) and TsOH·H₂O (280 mg, 1.5 mmol). The mixture was stirred at 40° C. for 3 hours. To the mixture was then added MeOH (100 ml) and a solution of LiOH·H₂O (8 g, 200 mmol) in water (100 mL). The mixture was stirred for another 4 hours at 20° C. The mixture was extracted with ethyl acetate. The combined organic layer was separated, dried over Na$_2$SO$_4$, concentrated under vacuum and purified by column chromatography (petrol ether:ethyl acetate=8:1) to give 106-1 (9 g, 70%) as a colorless oil.

$^1$H NMR (106-1): (400 MHz, CDCl$_3$) δ 4.45-4.35 (m, 1H), 3.75-3.20 (m, 5H), 2.20-2.10 (m, 1H), 1.90-0.80 (m, 30H), 0.70 (s, 3H).

To a solution of 106-1 (9 g, 23 mmol) in DMF (30 mL) was added imidazole (3.1 g, 46 mmol) and TBSCl (5.1 g, 34 mmol). The mixture was stirred at 20° C. for 5 hours. To the mixture was then added water and extracted with ethyl acetate. The organic layer was washed with water, dried over Na$_2$SO$_4$, concentrated under vacuum and purified by column chromatography (petrol ether:ethyl acetate=100:1 to 25:1) to give 106-2 (9 g, 80%) as a white solid. $^1$H NMR (106-2): (400 MHz, CDCl$_3$) δ 4.46-4.38 (m, 1H), 4.02-3.95 (m, 1H), 3.68-3.62 (m, 1H), 3.48-3.42 (m, 1H), 3.40-3.30 (m, 2H), 2.25-2.15 (m, 1H), 2.08-2.00 (m, 1H), 1.90-0.95 (m, 27H), 0.92-0.85 (m, 10H), 0.73 (s, 3H), 0.08-0.00 (m, 6H).

To a suspension of NaH (4 g, 60%, 100 mmol) in DMF (60 mL) was added a solution of 106-2 (9 g, 16 mmol) in DMF (40 mL) and tetrahydrofuran (10 mL). The mixture was stirred at 20° C. for 30 minutes. MeI (20 mL) was then added and the mixture was stirred at 40° C. for 5 hours. The mixture was poured into NH$_4$Cl (aq), extracted with petrol ether and ethyl acetate (1:1). The organic layer was separated, washed with water, dried over Na$_2$SO$_4$ and concentrated under vacuum to give 106-3 (10.6 g, crude product) as a white solid. $^1$H NMR (106-3): (400 MHz, CDCl$_3$) δ 4.00-3.95 (m, 1H), 3.78-3.72 (m, 1H), 3.70-3.65 (m, 1H), 3.50-3.35 (m, 3H), 3.25-3.20 (m, 3H), 2.25-2.15 (m, 1H), 1.80-0.80 (m, 37H), 0.75-0.70 (m, 4H).

To a solution of 106-3 (10 g, 19 mmol) in tetrahydrofuran (20 mL) was added TBAF (30 mL, 1M in tetrahydrofuran). The mixture was stirred at 60° C. for 3 days. Then the mixture was concentrated under vacuum and purified by column chromatography (petrol ether:ethyl acetate=15:1 to 10:1) to give 106-4 (6.1 g, 75% of 2 steps) as a white solid. $^1$H NMR (106-4): (400 MHz, CDCl$_3$) δ 4.10-3.30 (m, 6H), 3.22 (s, 3H), 2.23-2.15 (m, 1H), 1.98-1.92 (m, 1H), 1.85-0.80 (m, 28H), 0.70 (s, 3H).

To a solution of 106-4 (5.1 g, 12.5 mmol) in CH$_2$Cl$_2$ (50 mL) was added Dess-Matin reagent (15 g, 35 mmol). The mixture was stirred at 20° C. for 2 hours. To the mixture was added NaHCO$_3$/Na$_2$S$_2$O$_3$ (aq.). The organic layer was separated, dried over Na$_2$SO$_4$, concentrated under vacuum and purified by column chromatography (petrol ether:ethyl acetate=30:1 to 25:1) to give 106-5 (4.5 g, 75%) as a white solid. $^1$H NMR (106-5): (400 MHz, CDCl$_3$) δ 3.75-3.60 (m, 2H), 3.50-3.33 (m, 3H), 3.25 (s, 3H), 2.50-2.40 (m, 1H), 2.35-2.20 (m, 3H), 2.08-1.95 (m, 3H), 1.90-1.25 (m, 11H), 1.20 (s, 3H), 1.15 (s, 3H), 0.98 (s, 3H), 0.95-0.78 (m, 23H), 0.71 (s, 3H).

To a suspension of 106-5 (3.5 g, 8.6 mmol) in toluene (35 mL) was added NaH (1.03 g, 60%, 26 mmol) and HCOOEt (1.28 g, 17.3 mmol). The mixture was stirred at 20° C. for 16 hours. To the mixture was then added NH$_4$Cl (aq) and the mixture extracted with ethyl acetate. The combined organic layer was dried over Na$_2$SO$_4$, concentrated under vacuum and purified by column chromatography (petrol ether:ethyl acetate=30:1) to give 106-6 (3.5 g, 95%) as a white solid. $^1$H NMR (106-6): (400 MHz, CDCl$_3$) δ 14.37 (brs, 1H), 8.66 (s, 1H), 3.78-3.70 (m, 1H), 3.70-3.60 (m, 3H), 3.26 (m, 3H), 2.40-0.78 (m, 27H), 0.71 (s, 3H).

To a solution of 106-6 (4.5 g, 10 mmol) in methanol (50 mL) was added Pd/C (2 g). The mixture was then stirred at 30° C. for 3 days under hydrogen (30 psi.). The mixture was then filtered, concentrated under vacuum and purified by column chromatography (petrol ether:ethyl acetate=80:1 to 40:1) to give 106-7 (0.7 g, 20%) and compound 106-7A (0.8 g, 22%) and 0.4 g of a mixture. $^1$H NMR (106-7): (400 MHz, CDCl$_3$) δ 3.78-3.72 (m, 1H), 3.70-3.63 (m, 1H), 3.48-3.44 (m, 1H), 3.40-3.33 (m, 2H), 3.26 (s, 3H), 2.55-2.50 (m, 1H), 2.35-2.28 (m, 1H), 2.25-2.14 (m, 1H), 2.08-1.95 (m, 3H), 1.90-0.75 (m, 25H), 0.71 (s, 3H). $^1$H NMR (106-7A): (400 MHz, CDCl$_3$) δ 3.78-3.72 (m, 1H), 3.70-3.63 (m, 1H), 3.48-3.44 (m, 1H), 3.40-3.33 (m, 2H), 3.23 (s, 3H), 2.60-2.55 (m, 1H), 2.25-2.15 (m, 3H), 2.05-1.95 (m, 2H), 1.85-0.80 (m, 25H), 0.71 (s, 3H).

To a solution of 106-7 (0.7 g, 1.9 mmol) in tetrahydrofuran (12 mL) was added K-selectride (4 mL, 1M in tetrahydrofuran, 4 mmol) dropwise at −78° C. The mixture was stirred at −78° C. for 5 hours and H$_2$O$_2$ (2 mL, 30% in water) was then added dropwise at −78° C. The mixture was then warmed to 10° C. and Na$_2$S$_2$O$_3$ (aq.) was added. The mixture was extracted with ethyl acetate. The combined organic layer dried over Na$_2$SO$_4$, concentrated under vacuum and purified by column chromatography (petrol ether:ethyl acetate=40:1) to give 106-8 (600 mg, 85%) as a white solid. $^1$H NMR (106-8): (400 MHz, CDCl$_3$) δ 3.80-3.70 (m, 2H), 3.68-3.60 (m, 1H), 3.48-3.44 (m, 1H), 3.40-3.33 (m, 2H), 3.23 (s, 3H), 2.20-2.15 (m, 1H), 1.98-1.90 (m, 1H), 1.72-1.50 (m, 6H), 1.45-1.05 (m, 12H), 1.00-0.80 (m, 12H), 0.71 (s, 3H).

To a solution of 106-8 (0.66 g, 1.4 mmol) in acetone (5 mL) was added TsOH.H$_2$O (0.1 g, 0.3 mmol). The mixture was stirred at 25° C. for 1 hour. To the mixture was added NaHCO$_3$ (aq.), extracted with ethyl acetate. The organic layer was separated, combined and purified by column chromatography (petrol ether:ethyl acetate=12:1 to 8:1) to give 106-9 (0.5 g, 100%) as a white solid. $^1$H NMR (106-9): (400 MHz, CDCl$_3$) δ 3.82-3.72 (m, 2H), 3.23 (s, 3H), 2.52-2.42 (m, 1H), 2.30-2.25 (m, 1H), 2.08-1.70 (m, 5H), 1.60-1.10 (m, 9H), 1.05-0.75 (m, 13H).

To a solution of t-BuOK (0.5 g, 4.5 mmol) in t-BuOH (4 mL) was added DME (4 mL), TosMic (0.21 g. 1.07 mmol) and then 106-9 (0.15 g, 0.45 mmol). The mixture was stirred at 25° C. for 16 hours. To the mixture was added NH$_4$Cl (aq.) and extracted with ethyl acetate. The combined organic layers were separated, dried over Na$_2$SO$_4$, concentrated under vacuum and purified by column chromatography (petrol ether:ethyl acetate=10:1 to 8:1) to give 45 (67 mg, 45%) and 46 (23 mg, 15%) as white solids. $^1$H NMR (45): (400 MHz, CDCl$_3$) δ 3.82-3.74 (m, 1H), 3.73-3.68 (m, 1H), 3.25 (s, 3H), 2.44-2.35 (m, 1H), 2.25-2.18 (m, 1H), 2.10-2.00 (m, 1H), 1.98-1.88 (m, 1H), 1.85-1.60 (m, 4H), 1.56-1.50 (m, 1H), 1.48-1.06 (m, 11H), 1.00-0.90 (m, 9H), 0.78-0.75 (m, 1H). $^1$H NMR (46): (400 MHz, CDCl$_3$) δ 3.82-3.74 (m, 2H), 3.24 (s, 3H), 2.55-2.48 (m, 1H), 2.25-2.15 (m, 2H), 2.00-1.70 (m, 5H), 1.60-1.10 (m, 11H).

Example 33. Synthesis of Compounds 51 and 52

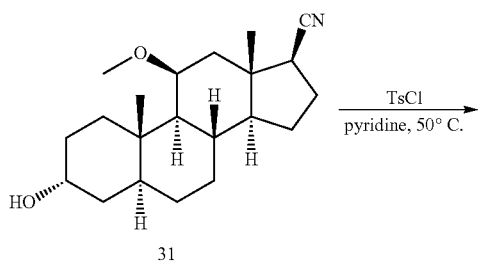

31

-continued

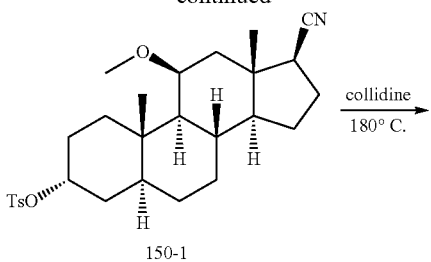
150-1

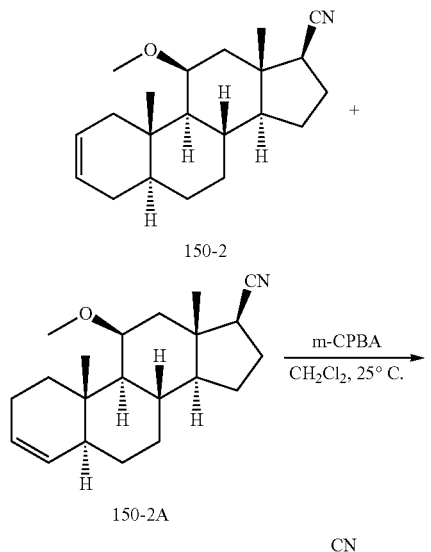
150-2

150-2A 150-3

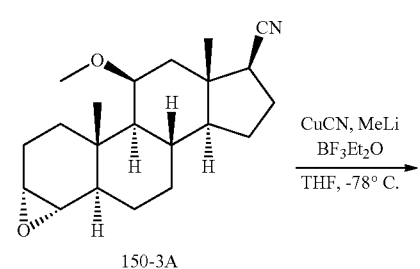
150-3A

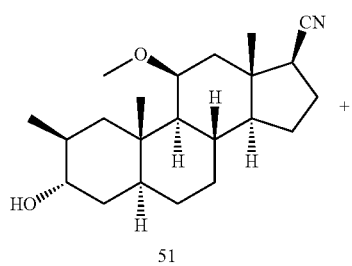
51

-continued

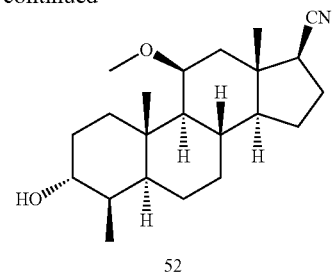
52

To a solution of 31 (1.2 g, 3.6 mmol) in pyridine (6 mL) was added TsCl (1.4 g, 7.2 mmol). The mixture was then stirred at 50° C. for 2 hours. The mixture was then poured into water, filtered. The solid was washed with water, dissolved in $CH_2Cl_2$, dried over $Na_2SO_4$, concentrated under vacuum to 150-1 (1.4 g, 80%) as an off-white solid. $^1H$ NMR (150-1): (400 MHz, $CDCl_3$) δ 7.80-7.75 (m, 2H), 7.35-7.28 (m, 2H), 4.45-4.68 (m, 1H), 3.65-3.60 (m, 1H), 3.25-3.15 (m, 3H), 2.44 (s, 3H), 2.42-2.35 (m, 1H), 2.25-2.15 (m, 1H), 2.15-0.75 (m, 25H).

A solution of 150-1 (1.4 g, 2.9 mmol) in collidine (6 mL) was stirred at 180° C. for 1 h. The mixture was then poured into $H_2SO_4$ (aq.). The mixture was extracted with $CH_2Cl_2$. The organic layer was dried over $Na_2SO_4$, concentrated under vacuum to give 150-2 and 150-2A (1 g, crude) as a light-yellow oil. $^1H$ NMR (150-2 and 150-2A): (400 MHz, $CDCl_3$) δ 5.65-5.58 (m, 1.75H, alkene-2,3-CH), 5.30-5.24 (m, 0.25H, alkene-4-CH), 3.75-3.66 (m, 1H), 3.30-3.20 (m, 3H), 2.45-2.38 (m, 1H), 2.27-2.18 (m, 1H), 2.15-1.65 (m, 8H), 1.45-0.65 (m, 15H).

To a solution of 150-2 (1 g, 3.2 mmol) in $CH_2Cl_2$ (5 mL) was added m-CPBA (1 g, 1.8 mmol). The mixture was then stirred at 25° C. for 1 hour. To the mixture was added $NaHCO_3/Na_2S_2O_3$ (aq.). The organic layer was dried over $Na_2SO_4$, purified by column chromatography (petrol ether:ethyl acetate=20:1 to 10:1) to give 150-3 and 150-3A (0.65 g, 60% of 2 steps) as a white solid. $^1H$ NMR (150-3 and 150-3A): (400 MHz, $CDCl_3$) δ 3.67-3.60 (m, 1H), 3.28-3.12 (m, 5H), 2.45-2.35 (m, 1H), 2.25-2.17 (m, 1H), 2.14-1.17 (m, 12H), 1.07-0.6 (m, 11H).

To a suspension of CuCN (667 mg, 7.5 mmol) in THF (20 mL) was added MeLi (15 mL, 1M in 2-Me-THF, 15 mmol) at −78° C. dropwise. The mixture was warmed to 0° C. and then cooled to −78° C. A solution of $BF_3.Et_2O$ (426 mg, 3 mmol) in THF (5 mL) was added dropwise and then stirred at −78° C. for 30 minutes. A solution of 150-3 and 150-3A (500 mg, 1.5 mmol) in THF (5 mL) was then added dropwise and stirred at −78° C. for another 1 hour. To the mixture was then added a mixture of MeOH (6 mL) and $Et_3N$ (6 mL). The mixture was then warmed to 10° C. To the mixture was added $NH_4Cl$ (aq.) and ethyl acetate. The mixture was then filtered. The organic layer was separated, dried over $Na_2SO_4$, concentrated under vacuum, purified by column chromatography (petrol ether:ethyl acetate=10:1 to 5:1) to give 51 and 52 (420 mg, 82%, including 4-methyl mixture) as a white solid. $^1H$ NMR (51 and 52): (400 MHz, $CDCl_3$) δ 3.78-3.66 (m, 2H), 3.27-3.20 (m, 3H), 2.42-2.35 (m, 1H), 2.24-2.16 (m, 1H), 2.14-2.02 (m, 1H), 1.97-1.63 (m, 6H), 1.55-0.70 (m, 21H).

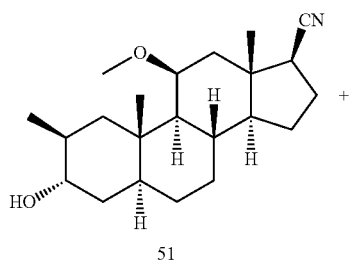

51

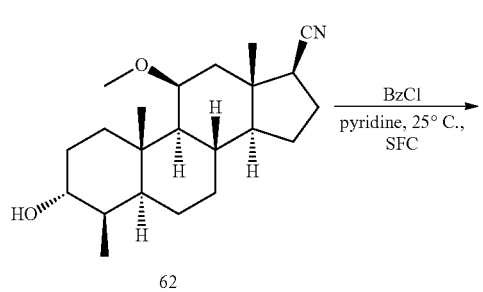

62

BzCl
pyridine, 25° C.,
SFC

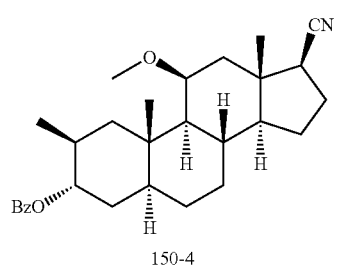

150-4

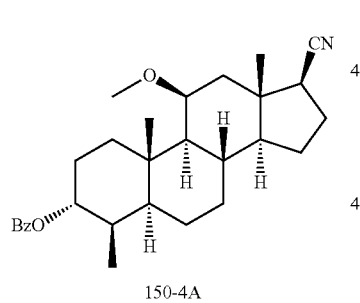

150-4A

To a solution of 51 and 52 (550 mg, 1.6 mmol) in pyridine (6 mL) was added BzCl (500 mg, 3.5 mmol). The mixture was then stirred at 25° C. for 16 hours. To the mixture was then added NaHCO$_3$ (aq.), extracted with ethyl acetate. The organic layer was concentrated under vacuum, purified by column chromatography (petrol ether:ethyl acetate=15:1) and then SFC to give 150-4 (430 mg) and 150-4A (170 mg, total yield: 85%) as white solid. $^1$H NMR (150-4): (400 MHz, CDCl$_3$) δ 8.06-8.02 (m, 2H), 7.59-7.50 (m, 1H), 7.48-7.41 (m, 2H), 5.05-5.00 (m, 1H), 3.74-3.67 (m, 1H), 3.27 (s, 3H), 2.45-2.36 (m, 1H), 2.25-1.73 (m, 7H), 1.68-1.13 (m, 12H), 1.12-0.74 (m, 9H). $^1$H NMR (150-4A): (400 MHz, CDCl$_3$) δ 8.07-8.00 (m, 2H), 7.60-7.52 (m, 1H), 7.50-7.41 (m, 2H), 5.09-5.05 (m, 1H), 3.75-3.67 (m, 1H), 3.24 (s, 3H), 2.44-2.35 (m, 1H), 2.25-2.18 (m, 7H), 2.13-0.73 (m, 27H).

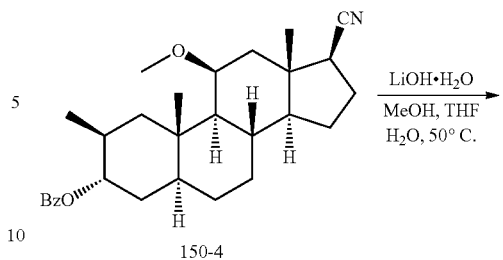

150-4

LiOH·H$_2$O
MeOH, THF
H$_2$O, 50° C.

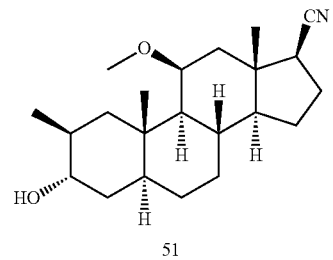

51

To a solution of 150-4 (430 mg, 0.96 mmol) in THF (2 mL) was added MeOH (1 mL) and a solution of LiOH.H$_2$O (0.2 g, 4.7 mmol) in water (1 mL). The mixture was stirred at 50° C. for 16 hours. The mixture was extracted with ethyl acetate. The organic layer was dried over Na$_2$SO$_4$, purified by column chromatography (petrol ether:ethyl acetate=8:1 to 5:1) to give 51 (236 mg, 70%) as an off-white solid. The absolute absolute configuration was confirmed by 2D-NMR. $^1$H NMR (51): (400 MHz, CDCl$_3$) δ 3.80-3.76 (m, 1H), 3.74-3.67 (m, 1H), 3.27 (s, 3H), 2.44-2.35 (m, 1H), 2.26-2.17 (m, 1H), 2.15-2.04 (m, 1H), 1.99-1.88 (m, 2H), 1.75-1.50 (m, 7H), 1.46-1.15 (m, 5H), 1.10-1.05 (m, 6H), 1.04-0.88 (m, 6H), 0.80-0.74 (m, 1H).

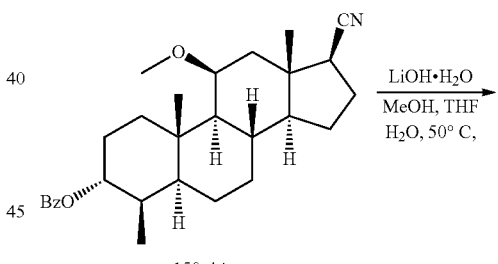

150-4A

LiOH·H$_2$O
MeOH, THF
H$_2$O, 50° C,

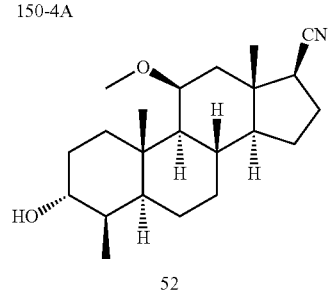

52

To a solution of 150-4A (170 mg, 0.38 mmol) in THF (2 mL) was added MeOH (1 mL) and a solution of LiOH.H$_2$O (0.2 g, 4.7 mmol) in water (1 mL). The mixture was stirred at 50° C. for 16 hours. The mixture was extracted with ethyl acetate. The organic layer was dried over Na$_2$SO$_4$, purified by column chromatography (petrol ether:ethyl acetate=8:1 to 5:1) to give 52 (79 mg, 61%) as an off-white solid. The absolute absolute configuration was confirmed by 2D-NMR.

¹H NMR (52): (400 MHz, CDCl₃) δ 3.82-3.78 (m, 1H), 3.75-3.65 (m, 1H), 3.22 (s, 3H), 2.40-2.33 (m, 1H), 2.24-2.15 (m, 1H), 2.12-2.02 (m, 1H), 1.97-1.30 (m, 13H), 1.13-1.02 (m, 7H), 1.00-0.82 (m, 6H), 0.78-0.70 (m, 1H).
Example 34. Synthesis of Compounds 53 and 54
Synthesis of Intermediates 151-5 and 151-5A
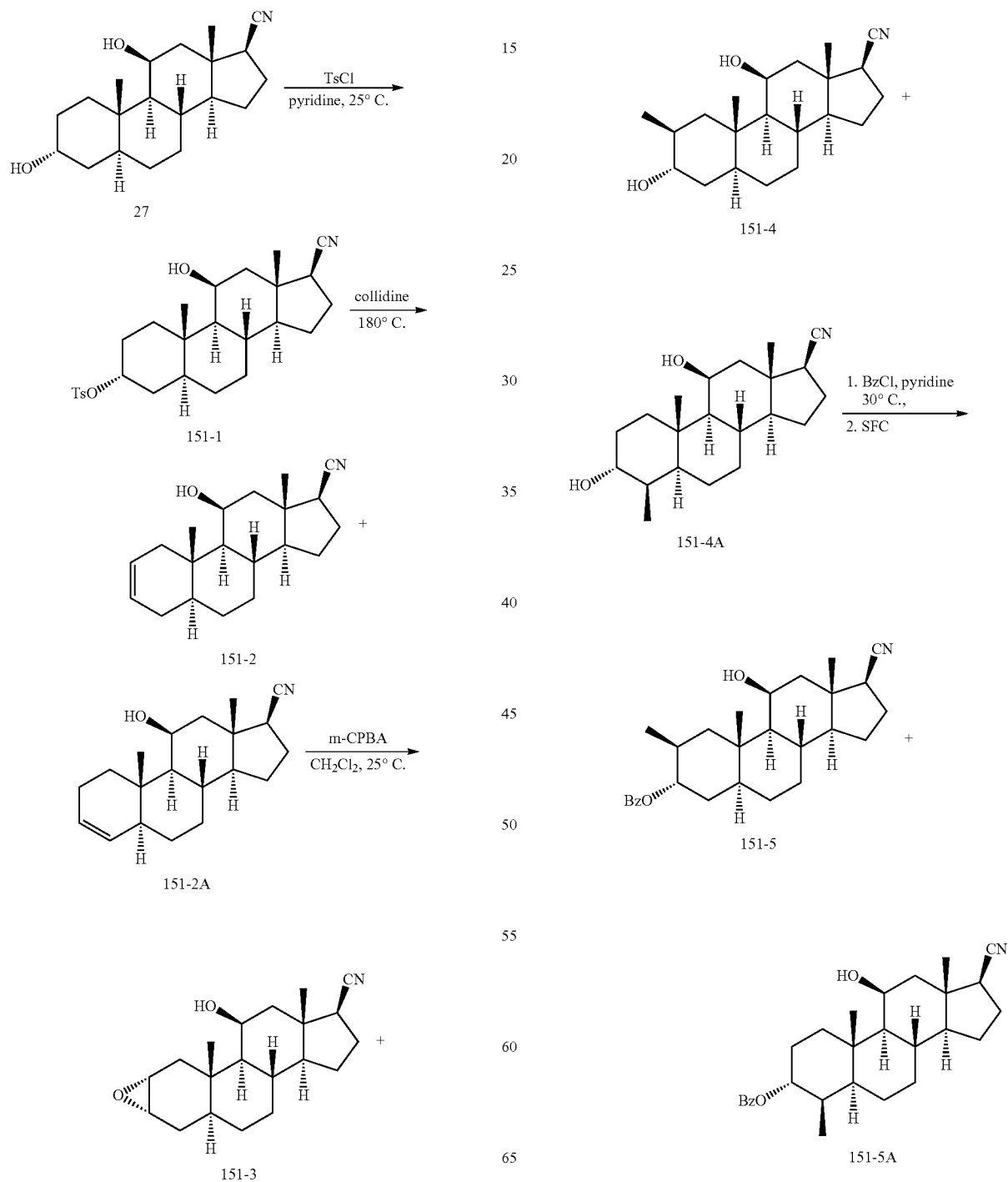

Synthesis of Compound 53

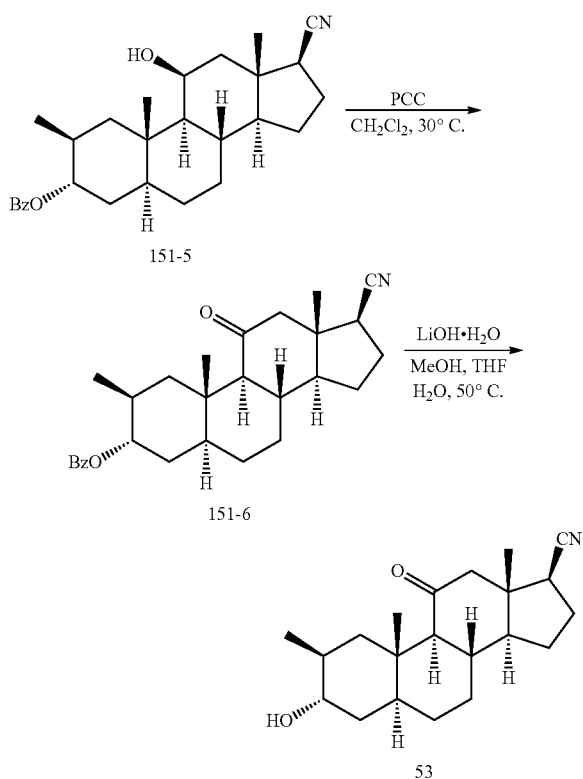

Synthesis of Compound 54

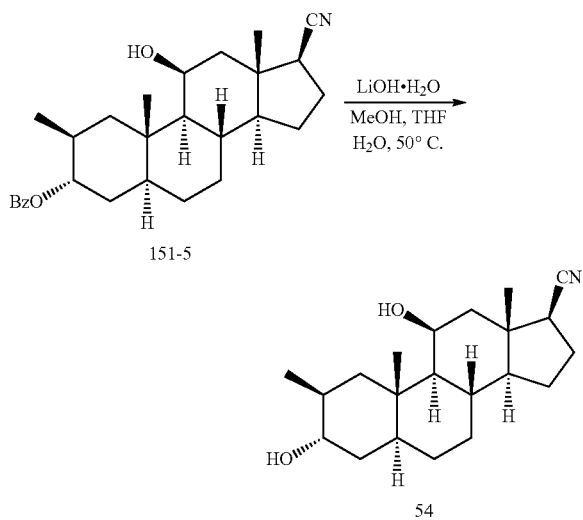

To a solution of 27 (2 g, 6.3 mmol) in pyridine (8 mL) was added TsCl (1.8 g, 9.5 mmol).

The mixture was then stirred at 25° C. for 16 hours. To the mixture was added NaHCO$_3$ (aq.), extracted with ethyl acetate. The organic layer was dried over Na$_2$SO$_4$, concentrated under vacuum to 151-1 (3.5 g, crude) as a brown solid. $^1$H NMR (151-1): (400 MHz, CDCl$_3$) δ 7.80-7.75 (m, 2H), 7.35-7.28 (m, 2H), 4.85-4.65 (m, 1H), 4.45-4.32 (m, 1H), 3.25-3.15 (m, 3H), 2.44 (s, 3H), 2.25-0.80 (m, 28H).

A solution of 151-1 (3.5 g, 6.3 mmol) in collidine (10 mL) was stirred at 180° C. for 1 hour.

To the mixture was added HCl (aq.) extracted with ethyl acetate. The organic layer was dried over Na$_2$SO$_4$, concentrated under vacuum to give 151-2 and 151-2A (2 g, 100% of two steps) as a light-yellow solid. $^1$H NMR (151-2 and 151-2A): (400 MHz, CDCl$_3$) δ 5.65-5.57 (m, 2H), 4.50-4.35 (m, 1H), 2.25-2.17 (m, 1H), 2.15-0.66 (m, 25H).

To a solution of 151-2 and 151-2A (2 g, 6.7 mmol) in CH$_2$Cl$_2$ (15 mL) was added m-CPBA (1.8 g, 10.5 mmol). The mixture was then stirred at 25° C. for 1 hour. To the mixture was added NaHCO$_3$/Na$_2$S$_2$O$_3$ (aq.). The organic layer was dried over Na$_2$SO$_4$, purified by column chromatography (petrol ether:ethyl acetate=10:1) to give 151-3 and 151-3A (1.5 g, 75%) as a white solid. $^1$H NMR (151-3 and 151-3A): (400 MHz, CDCl$_3$) δ 4.46-4.30 (m, 1H), 3.24-3.12 (m, 2H), 2.25-0.60 (m, 26H).

To a suspension of CuCN (2.1 g, 23.5 mmol) in THF (30 mL) was added MeLi (47 mL, 1M in 2-Me-THF, 47 mmol) at −78° C. dropwise. The mixture was warmed to 0° C. and then cooled to −78° C. A solution of BF$_3$.Et$_2$O (1.33 g, 9.4 mmol) in THF (10 mL) was added dropwise and then stirred at −78° C. for 30 minutes. A solution of 151-3 and 151-3A (1.5 g, 4.7 mmol) in THF (10 mL) was then added dropwise and stirred at −78° C. for another 1 hour. To the mixture was then added a mixture of MeOH (10 mL) and Et$_3$N (10 mL). The mixture was then warmed to 10° C.

To the mixture was added NH$_4$Cl (aq.) and ethyl acetate. The mixture was then filtered. The organic layer was separated, dried over Na$_2$SO$_4$, concentrated under vacuum, purified by column chromatography (petrol ether:ethyl acetate=10:1 to 5:1) to give 151-4 and 151-4A (560 mg, 33%) as a white solid. $^1$H NMR (151-4 and 151-4A): (400 MHz, CDCl$_3$) δ 4.45-4.35 (m, 1H), 3.86-3.75 (m, 1H), 2.25-2.15 (m, 1H), 2.15-0.70 (m, 30H).

To a solution of 151-4 and 151-4A (0.56 g, 1.6 mmol) in pyridine (5 mL) was added BzCl (0.5 g, 3.5 mmol). The mixture was then stirred at 30° C. for 16 hours. To the mixture was then added NaHCO$_3$ (aq.), extracted with ethyl acetate. The organic layer was concentrated under vacuum, purified by column chromatography (petrol ether:ethyl acetate=15:1 to 5:1) and then SFC to give 151-5 (310 mg) and 151-5A (170 mg, total yield: 69%) as a white solid. The absolute absolute configuration of the two compounds were confirmed by 2D-NMR. $^1$H NMR (151-5): (400 MHz, CDCl$_3$) δ 8.06-8.02 (m, 2H), 7.59-7.50 (m, 1H), 7.48-7.41 (m, 2H), 5.05-5.00 (m, 1H), 4.45-4.38 (m, 1H), 2.25-0.74 (m, 30H). $^1$H NMR (151-5A): (400 MHz, CDCl$_3$) δ 8.06-8.02 (m, 2H), 7.59-7.50 (m, 1H), 7.48-7.41 (m, 2H), 5.09-5.05 (m, 1H), 4.45-4.38 (m, 1H), 2.25-0.74 (m, 30H).

To a solution of 151-5 (20 mg, 0.46 mmol) in CH$_2$Cl$_2$ (5 mL) was added PCC (300 mg, 1.4 mmol). The mixture was stirred at 30° C. for 1 hour. To the mixture was added MgSO4, filtered.

The filtrate was concentrated under vacuum, purified by column chromatography (petrol ether:ethyl acetate=10:1) to give 151-6 (170 mg, 85%) as an off-white solid. $^1$H NMR (151-6): (400 MHz, CDCl$_3$) δ 8.06-8.02 (m, 2H), 7.59-7.50 (m, 1H), 7.48-7.41 (m, 2H), 5.03-4.95 (m, 1H), 2.55-2.45 (m, 2H), 2.30-1.65 (m, 11H), 1.60-1.40 (m, 4H), 1.35-1.10 (m, 9H), 0.89 (s, 3H).

To a solution of 151-6 (200 mg, 0.46 mmol) in THF (4 mL) was added MeOH (2 mL) and a solution of LiOH.H$_2$O (150 mg, 3.6 mmol) in water (1 mL). The mixture was stirred at 50° C. for 16 hours. The mixture was extracted with ethyl acetate. The organic layer was dried over Na$_2$SO$_4$, purified by column chromatography (petrol ether:ethyl acetate=5:1) to give 53 (112 mg, 74%) as an off-white solid. $^1$H NMR (53): (400 MHz, CDCl$_3$) δ 3.80-3.70 (m, 1H), 2.57-2.45 (m, 2H), 2.32-2.20 (m, 2H), 2.15-1.55 (m, 10H), 1.45-1.12 (m, 7H), 1.10-1.03 (m, 6H), 0.89 (s, 3H).

To a solution of 151-5 (80 mg, 0.18 mmol) in THF (2 mL) was added MeOH (2 mL) and a solution of LiOH.H$_2$O (70 mg, 1.6 mmol) in water (0.5 mL). The mixture was stirred at 50° C. for 16 hours. The mixture was extracted with ethyl acetate. The organic layer was dried over Na$_2$SO$_4$, purified by column chromatography (petrol ether:ethyl acetate=5:1) to give 54 (39 mg, 63%) as an off-white solid. $^1$H NMR (54): (400 MHz, CDCl$_3$) δ 4.42-4.37 (m, 1H), 3.82-3.75 (m, 1H), 2.25-2.17 (m, 1H), 2.15-2.05 (m, 2H), 2.00-1.88 (m, 2H), 1.85-1.50 (m, 10H), 1.45-1.18 (m, 6H), 1.15 (s, 3H), 1.10-0.90 (m, 8H), 0.82-0.74 (m, 1H).

Example 35. Synthesis of Compounds 55 and 56

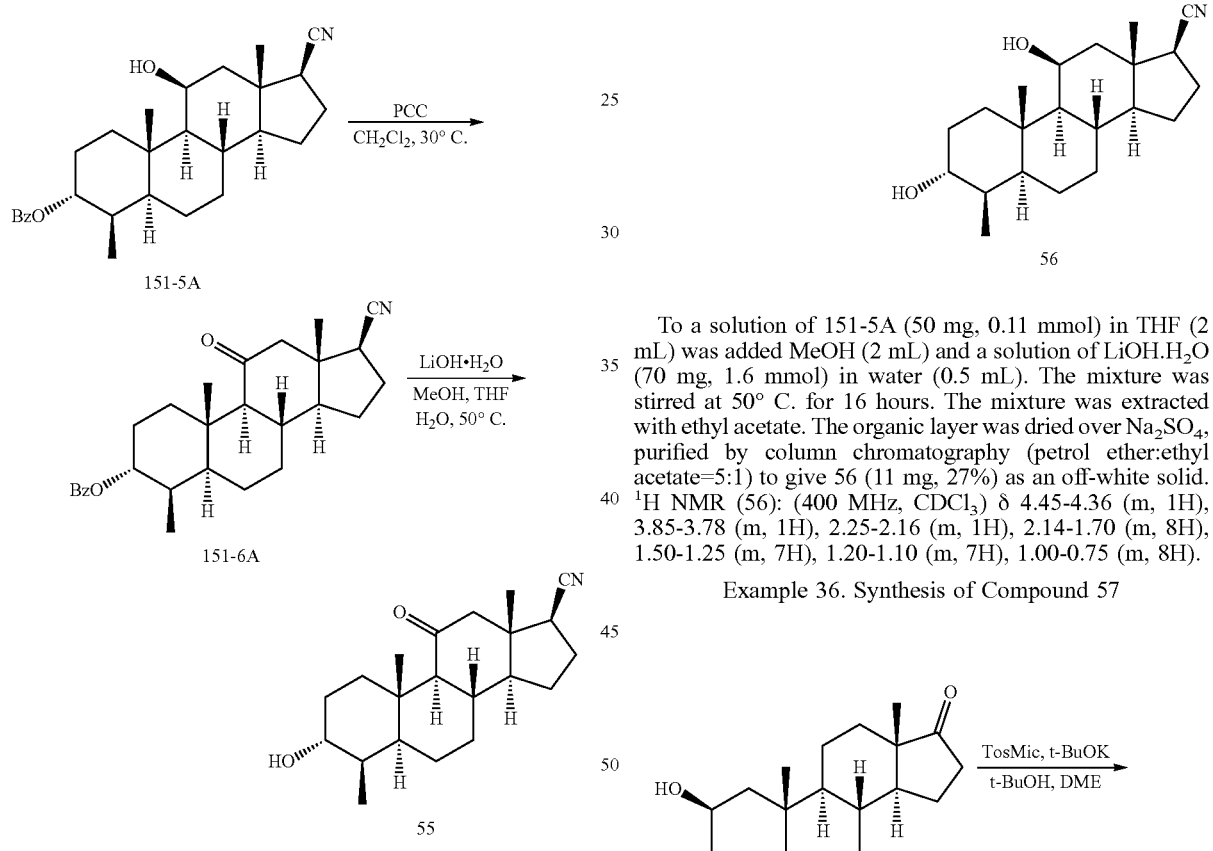

To a solution of 151-5A (120 mg, 0.28 mmol) in CH$_2$Cl$_2$ (4 mL) was added PCC (180 mg, 0.84 mmol). The mixture was stirred at 30° C. for 1 hour. To the mixture was added MgSO4, filtered. The filtrate was concentrated under vacuum, purified by column chromatography (petrol ether:ethyl acetate=10:1) to give 151-6A (110 mg, 90%) as an off-white solid. $^1$H NMR (151-6A): (400 MHz, CDCl$_3$) δ 8.06-8.02 (m, 2H), 7.59-7.50 (m, 1H), 7.48-7.41 (m, 2H), 5.05-5.00 (m, 1H), 2.55-2.45 (m, 3H), 2.30-2.20 (m, 2H), 2.05-1.85 (m, 5H), 1.80-1.60 (m, 4H), 1.50-1.10 (m, 8H), 1.03 (d, J=7.6 Hz, 3H), 0.90-0.76 (m, 4H).

To a solution of 151-6A (110 mg, 0.25 mmol) in THF (4 mL) was added MeOH (2 mL) and a solution of LiOH.H$_2$O (150 mg, 3.6 mmol) in water (1 mL). The mixture was stirred at 50° C. for 16 hours. The mixture was extracted with ethyl acetate. The organic layer was dried over Na$_2$SO$_4$, purified by column chromatography (petrol ether:ethyl acetate=5:1) to give 55 (21 mg, 26%) as an off-white solid. $^1$H NMR (55): (400 MHz, CDCl$_3$) δ 3.85-3.74 (m, 1H), 2.55-2.45 (m, 2H), 2.35-2.20 (m, 3H), 2.10-1.85 (m, 4H), 1.78-1.60 (m, 4H), 1.50-1.37 (m, 4H), 1.33-1.15 (m, 4H), 1.09 (s, 1H), 0.94 (d, J=7.6 Hz, 3H), 0.89 (s, 3H).

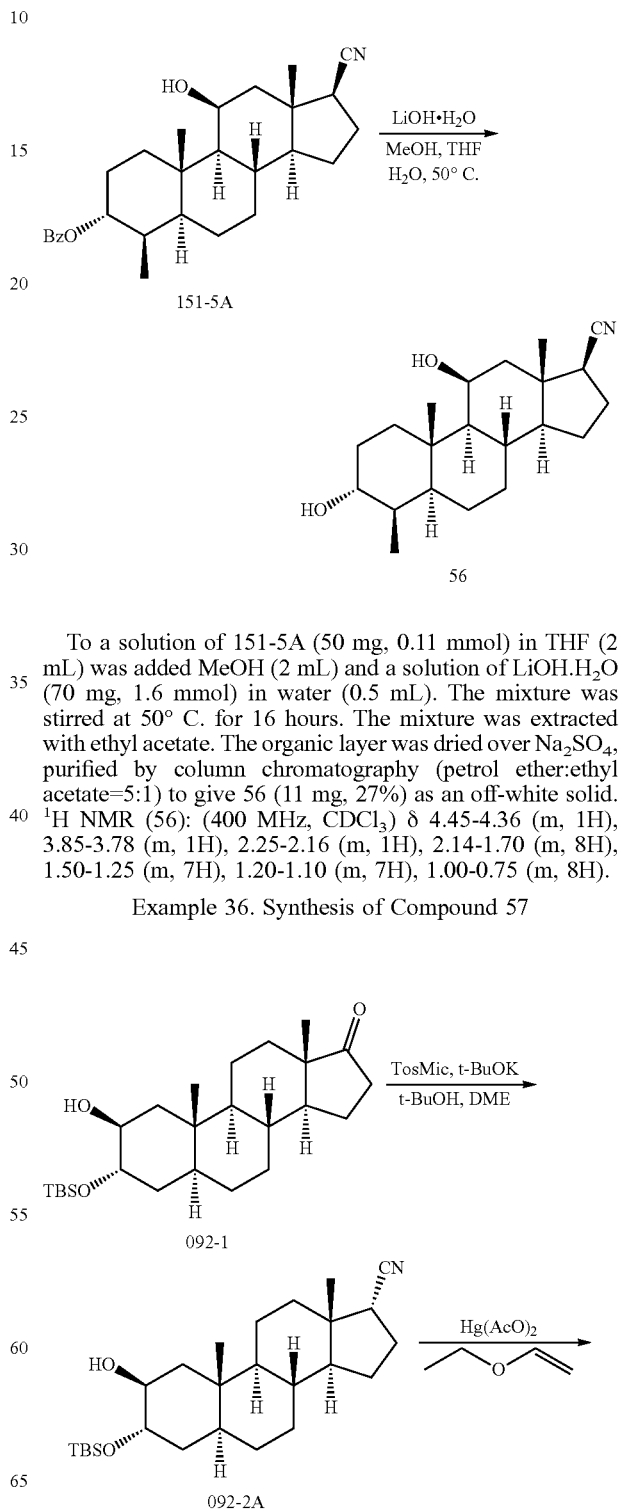

To a solution of 151-5A (50 mg, 0.11 mmol) in THF (2 mL) was added MeOH (2 mL) and a solution of LiOH.H$_2$O (70 mg, 1.6 mmol) in water (0.5 mL). The mixture was stirred at 50° C. for 16 hours. The mixture was extracted with ethyl acetate. The organic layer was dried over Na$_2$SO$_4$, purified by column chromatography (petrol ether:ethyl acetate=5:1) to give 56 (11 mg, 27%) as an off-white solid. $^1$H NMR (56): (400 MHz, CDCl$_3$) δ 4.45-4.36 (m, 1H), 3.85-3.78 (m, 1H), 2.25-2.16 (m, 1H), 2.14-1.70 (m, 8H), 1.50-1.25 (m, 7H), 1.20-1.10 (m, 7H), 1.00-0.75 (m, 8H).

Example 36. Synthesis of Compound 57

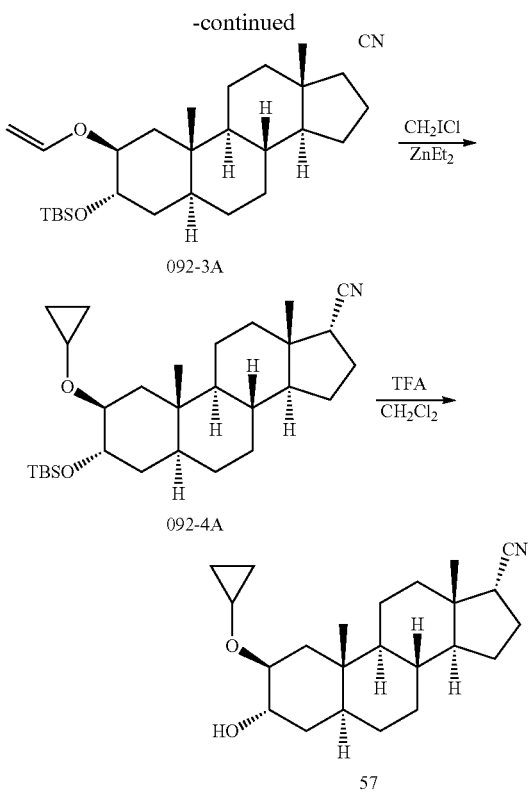

To a stirred solution of t-BuOK (4.54 g, 40.5 mmol) in t-BuOH (30 mL) was added a solution of 092-1 (3.4 g, 8.1 mmol) in THF (15 mL) under nitgen. A solution of Tosyl-methyl isocyanide (3.16 g, 16.2 mmol) in 1,2-dimethoxy-ethane (15 mL) was added dropwise. The mixture was stirred at 25° C. for 12 hours. The mixture was treated with dilute aqueous sodium chloride (50 mL) followed by hydrochloric acid (1 M) until acidic. The mixture was extracted with EtOAc (100 mL×2), and the organic layer was washed with brine (100 mL), dried over anhydrous $Na_2SO_4$, then concentrated. The residue was purified by flash column chromatography on silica gel (eluent: petroleum ether:ethyl acetate=12:1) to afford the 092-2A (530 mg, 15%) as white solid. $^1H$ NMR: (400 MHz, $CDCl_3$) δ 3.81-3.80 (m, 1H), 3.74-3.73 (m, 1H), 2.56-2.53 (m, 1H), 2.22-2.11 (m, 1H), 2.00-1.80 (m, 3H), 1.71-1.61 (m, 5H), 1.53-1.23 (m, 10H), 1.15-1.04 (m, 1H), 0.97 (s, 3H), 0.89-0.88 (m, 12H), 0.87-0.86 (m, 4H), 0.0.7-0.01 (m, 6H)

To a stirred solution of 092-2A (530 mg, 1.22 mmol) in ethoxyethene (10 mL) was added $Hg(AcO)_2$ (585.6 mg, 1.83 mmol). The mixture was stirred at 25° C. for 12 hours. The mixture was filtered, and the filtrate was evaporated. The residue was purified by flash column chromatography on $Al_2O_3$ (eluent: petroleum ether:ethyl acetate=100:1) to afford the 092-3A (230 mg, 41%) as colorless oil. $^1H$ NMR: (400 MHz, $CDCl_3$) δ 6.30-6.25 (m, 1H), 4.33-4.29 (dd, $J_1=1.6$, $J_2=14$, 1H), 4.03-4.01 (dd, $J_1=1.6$, $J_2=6.8$, 1H), 3.92-3.91 (m, 1H), 3.75-3.74 (m, 1H), 2.56-2.253 (m, 1H), 2.20-2.10 (m, 1H), 1.99-1.90 (m, 1H), 1.88-1.63 (m, 7H), 1.41-1.00 (m, 12), 0.97-0.80 (m, 13H), 0.79 (s, 3H), 0.07-0.01 (m, 6H).

To a stirred solution of 092-3A (230 mg, 0.5 mmol) in dry toluene (3 mL) was added diethylzinc (2.0 mL, 2.0 mmol) at −40° C. under nitgen. After stirring for 1 hour, chloroiodomethane (351.8 mg, 2.0 mmol) was added dropwise. The reaction mixture was stirred at −40° C. for 2 hours, then warmed to 25° C. and stirred for 12 hours. The mixture was quenched by a saturated aqueous solution of NH4Cl (20 mL), extracted with EtOAc (30 mL×2). The combined organic layer was washed with brine (30 mL), dried over anhydrous Na2SO4 and evaporated to dryness. Purification by flash column chromatography on silica gel (eluent: petroleum ether:ethyl acetate=100:1) to afford the 092-4A (100 mg, 42%) as colorless oil. $^1H$ NMR: (400 MHz, $CDCl_3$) δ 3.94-3.93 (m, 1H), 3.44-3.43 (m, 1H), 3.29-3.27 (m, 1H), 2.56-2.53 (m, 1H), 2.23-1.90 (m, 2H), 1.85-1.60 (m, 4H), 1.53-1.00 (m, 10H), 0.97-0.65 (m, 14H), 0.64-0.40 (m, 4H), 0.02-0.01 (m, 6H)

To a stirred solution of 092-4A (100 mg, 0.21 mmol) in dry $CH_2Cl_2$ (4 mL) was added 2,2,2-trifluoroacetic acid (1 mL). The reaction mixture was stirred at 25° C. for 1 hour. The mixture was quenched by a saturated aqueous solution of $NaHCO_3$ (15 mL), extracted with $CH_2Cl_2$ (20 mL×2). The combined organic layer was washed with brine (20 mL), dried over anhydrous $Na_2SO_4$ and evaporated to dryness. Purification by flash column chromatography on silica gel (eluent: petroleum ether:ethyl acetate=10:1) to afford the crude product, which was purified by prep-HPLC to afford the 57 (6 mg, 9%) as white solid. $^1H$ NMR: (400 MHz, $CDCl_3$) δ 4.06-4.05 (m, 1H), 3.58-3.57 (m, 1H), 3.33-3.30 (m, 1H), 2.58-2.55 (m, 1H), 2.16-2.10 (m, 1H), 2.01-1.90 (m, 1H), 1.85-1.58 (m, 8H), 1.50-1.25 (m, 9H), 1.01 (s, 3H), 0.90-0.82 (m, 4H), 0.60-0.48 (m, 4H)

Assay Methods

Compounds provided herein can be evaluated using various assays; examples of which are described below.

Steroid Inhibition of TBPS Binding

TBPS binding assays using rat brain cortical membranes in the presence of 5 μM GABA has been described (Gee et al, *J. Pharmacol. Exp. Then* 1987, 241, 346-353; Hawkinson et al, *Mol. Pharmacol.* 1994, 46, 977-985). Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 μL) of the membrane suspensions are incubated with 3 nM [$^{35}S$]-TBPS and 5 μL, aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Braudel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition ($IC_{50}$) of specific binding and the maximal extent of inhibition ($I_{max}$) are determined for the individual experiments with the same model used for the overall data and then the means±SEMs of the individual experiments are calculated.

Various compounds are or can be screened to determine their potential as modulators of $^{35}$S-TBPS binding in vitro. These assays are or can be performed in accordance with the above discussed procedures.

TABLE 1

$^{35}$S-TBPS displacement assay data of exemplary compounds, wherein "A" indicates an $IC_{50}$ <10 nM, "B" indicates an $IC_{50}$ of 10 nM to 50 nM, "C" indicates an $IC_{50}$ of 50 nM to 100 nM, "D" indicates an $IC_{50}$ of 100 nM to 500 nM, and "E" indicates an $IC_{50}$ >500 nM.

| Compound | $^{35}$S-TBPS Radioligand Displacement ($IC_{50}$) |
|---|---|
| 1 | E |
| 2 | B |
| 3 | E |
| 4 | B |
| 5 | A |
| 6 | E |
| 7 | E |
| 8 | E |
| 9 | E |
| 10 | E |
| 11 | E |
| 12 | D |
| 13 | E |
| 14 | E |
| 15 | E |
| 16 | A |
| 17 | E |
| 18 | E |
| 19 | C |
| 20 | E |
| 21 | B |
| 22 | C |
| 23 | D |
| 24 | E |
| 26 | D |
| 27 | E |
| 28 | D |
| 29 | A |
| 30 | E |
| 31 | B |
| 32 | B |
| 33 | B |
| 34 | D |
| 40 | B |
| 41 | A |
| 42 | E |
| 43 | E |
| 44 | E |
| 45 | C |
| 46 | D |
| 47 | B |
| 48 | E |
| 49 | D |
| 50 | E |
| 51 | B |
| 52 | E |
| 53 | D |
| 54 | D |
| 55 | E |
| 56 | E |
| 57 | E |

Patch Clamp Electrophysiology of Recombinant $\alpha_1\beta_2\gamma_2$ and $\alpha_4\beta_3\delta$ GABA Receptors Cellular electrophysiology is used to measure the pharmacological properties of the described compounds in heterologous cell systems. Each compound is tested for its ability to affect GABA mediated currents at a submaximal agonist dose (GABA $EC_{20}$=2 µM). LTK cells are stably transfected with the $\alpha_1\beta_2\gamma_2$ subunits of the GABA receptor and CHO cells are transiently transfected with the $\alpha_4\beta_3\delta$ subunits via the Lipofecalamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., Science, 1988, 242, 1306-1308). Because responses in distant cells are not adequately voltage clamped and because of uncertainties about the extent of coupling (Verdoorn et al., Neuron, 1990, 4, 919-928), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, $CaCl_2$ 1.8 mM, $MgCl_2$ 1 mM, HEPES 10 mM, D-Glucose 10 mM, pH (NaOH) 7.4. In some cases 0.005% Cremophor was also added. Intracellular (pipette) solution contained: KCl 130 mM, $MgCl_2$ 1 mM, Mg-ATP 5 mM, HEPES 10 mM, EGTA 5 mM, pH 7.2. During experiments, cells and solutions were maintained at room temperature (19° C.-30° C.). For manual patch clamp recordings, cell culture dishes were placed on the dish holder of the microscope and continuously perfused (1 ml/min) with bath solution. After formation of a Gigaohm seal between the patch electrodes and the cell (pipette resistance range: 2.5 MΩ-6.0 MΩ; seal resistance range: >1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of –80 mV. For the analysis of test articles, GABA receptors were stimulated by 2 µM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 µM in bath solution. All concentrations of test articles were tested on each cell. The relative percentage potentiation was defined as the peak amplitude in response to GABA $EC_{20}$ in the presence of the test article divided by the peak amplitude in response to GABA $EC_{20}$ alone, multiplied by 100.

TABLE 2

Electrophysiological evaluation of exemplary compounds against GABA receptors $\alpha1\beta2\gamma2$ and $\alpha4\beta3\delta$, wherein "A" indicates 10-100% efficacy, "B" indicates 100-500% efficacy, "C" indicates >500% efficacy, and D indicates the data are not available or have not been determined.

| Compound | GABA ($\alpha1\beta2\gamma2$) Qpatch in Ltk, % efficacy at 10 µM | GABA ($\alpha4\beta3\delta$) Manual patch in CHO, % efficacy at 10 µM |
|---|---|---|
| 1 | A | D |
| 2 | B | B |
| 3 | B | B |
| 4 | B | B |
| 5 | B | D |
| 8 | B | D |
| 9 | B | A |
| 10 | C | D |
| 12 | C | D |
| 16 | C | B |
| 17 | B | D |

TABLE 2-continued

Electrophysiological evaluation of exemplary compounds against GABA receptors α1β2γ2 and α4β3δ, wherein "A" indicates 10-100% efficacy, "B" indicates 100-500% efficacy, "C" indicates >500% efficacy, and D indicates the data are not available or have not been determined.

| Compound | GABA (α1β2γ2) Qpatch in Ltk, % efficacy at 10 μM | GABA (α4β3δ) Manual patch in CHO, % efficacy at 10 μM |
|---|---|---|
| 19 | C | D |
| 21 | C | D |
| 22 | B | D |
| 28 | C | D |
| 29 | C | D |
| 31 | C | B |
| 33 | B | D |
| 40 | C | D |
| 41 | C | D |
| 45 | C | D |
| 46 | A | D |
| 47 | C | C |
| 51 | C | D |

Loss of Righting Reflex in Rats

The plasma pharmacokinetics and a qualitative assessment of sedation were obtained in male Sprague Dawley rats according to the following procedure. Rats were dosed by intravenous bolus dose (60 seconds) via the foot dorsal vein at 5 mg/kg in an appropriate vehicle. In order to assess sedation, rats were gently restrained by hand to a lateral position for dose administration. If decreased muscle tone was observed during dose administration, restraint was gradually reduced. If the animal was unable to return to an upright position, the time was recorded as the onset of loss of righting reflex (LRR). In the event that LRR did not occur during dosing, the animals were evaluated at 5 minute intervals thereafter by being placed in dorsal recumbency. Sluggish or incomplete righting twice consecutively within a 30 second interval qualifies as a loss of righting reflex. After onset of LRR, animals were assessed every 5 minutes in the same manner. Recovery of righting reflex is defined as the ability of a rat to right itself completely within 20 seconds of being placed in dorsal recumbency. The duration of LRR is defined as the time interval between LRR and the return of righting reflex.

TABLE 3

Measurement of loss of righting reflex (LRR) in male Sprague Dawley rats, wherein "A" indicates the duration of LRR to be <10 min, "B" indicates the duration of LRR to be 10-20 minutes, and "C" indicates the duration of LRR to be >20 minutes.

| Compound | Duration of LRR (min) |
|---|---|
| 1 | C |
| 3 | A |
| 47 | C |
| 4 | A |
| 5 | C |
| 10 | A |
| 12 | A |
| 16 | C |
| 19 | B |
| 21 | C |
| 23 | B |
| 26 | B |
| 28 | A |
| 29 | C |
| 31 | B |
| 32 | C |
| 33 | A |
| 40 | B |
| 41 | C |
| 45 | C |
| 51 | C |

Duration of Lateral Recumbence in Dogs

The plasma pharmacokinetics and a qualitative assessment of sedation were obtained in male beagle dogs according to the following procedure. Dogs were dosed by intravenous bolus dose (60 seconds) via the cephalic vein at doses ranging from 2 to 5 mg/kg in an appropriate vehicle. In order to assess sedation, dogs were gently restrained for dose administration. If decreased muscle tone, limb weakness, or head drop was observed during dose administration, onset of lateral recumbence was recorded. In the event that lateral recumbence did not occur during dosing, the animals were evaluated at 5 minute intervals thereafter by being placed in lateral recumbence. Sluggish or incomplete righting to the sternal position qualifies as lateral recumbence. After onset of lateral recumbence, animals were assessed every 5 minutes in the same manner. The duration of lateral recumbence was recorded as the time interval between onset of lateral recumbence and the return to sternal position.

TABLE 4

Measurement of lateral recumbence in male beagle dogs, wherein "A" indicates the duration to be >20 minutes.

| Compound | Duration of Lateral Recumbence (min) |
|---|---|
| 3** | A |
| 47* | A |
| 19** | A |
| 31** | A |

*Administered at 2 mg/kg;
**administered at 5 mg/kg.

What is claimed is:

1. A compound of Formula (III):

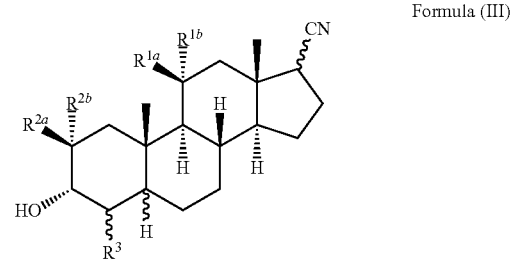

Formula (III)

wherein:
one of $R^{1a}$ and $R^{1b}$ is halo, hydroxy, alkyl, alkoxy, —C(O)$R^a$, —C(O)N($R^b$)($R^c$), —C(O)O$R^a$, —N($R^h$)($R^i$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$) and the other one is hydrogen; or $R^{1a}$ and $R^{1b}$ are taken together with the carbon to which they are attached to form C(=O);

one of $R^{2a}$ and $R^{2b}$ is chloro, fluoro, hydroxy, alkyl, alkoxy, —C(O)$R^a$, —C(O)N($R^b$)($R^c$), —C(O)O$R^a$, —N($R^f$)($R^g$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$), and the other one is hydrogen;

$R^3$ is hydrogen or $C_1$-$C_6$ alkyl;

each $R^a$ is hydrogen or $C_1$-$C_6$ alkyl;

each $R^b$ and $R^c$ is independently hydrogen or $C_1$-$C_6$ alkyl, or $R^b$ and $R^c$, taken together with the nitrogen atom to which they are attached, form a 3-7-membered heterocyclic ring;

each $R^f$ and $R^g$ is independently hydrogen or $C_1$-$C_6$ alkyl, or $R^f$ and $R^g$, taken together with the nitrogen atom to which they are attached, form a 3-7-membered heterocyclic ring optionally comprising one additional heteroatom selected from nitrogen and sulfur; and each $R^h$ is unsubstituted $C_1$-$C_4$ alkyl;

each $R^i$ is hydrogen, substituted methyl or $C_2$-$C_6$ alkyl, or $R^h$ and $R^i$, taken together with the nitrogen atom to which they are attached, form a 3-7-membered heterocyclic ring.

2. The compound of claim 1, wherein the compound is a compound of Formula (IIIb):

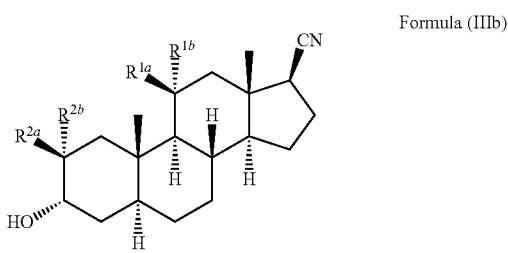

Formula (IIIb)

wherein:

one of $R^{1a}$ and $R^{1b}$ is halo, hydroxy, alkyl, alkoxy, —C(O)$R^a$, —C(O)N($R^b$)($R^c$), —C(O)O$R^a$, —N($R^h$)($R^i$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$), and the other one is hydrogen; or $R^{1a}$ and $R^{1b}$ are taken together with the carbon to which they are attached to form C(=O);

one of $R^{2a}$ and $R^{2b}$ is chloro, fluoro, hydroxy, alkyl, alkoxy, —C(O)$R^a$, —C(O)N($R^b$)($R^c$), —C(O)O$R^a$, —N($R^f$)($R^g$), —OC(O)N($R^b$)($R^c$), —OC(O)O$R^a$, —OC(O)$R^a$, —S(O)$_{0-2}R^a$, —S(O)$_{0-2}$O$R^a$, or —S(O)$_{0-2}$N($R^b$)($R^c$), and the other one is hydrogen;

each $R^a$ is hydrogen or $C_1$-$C_6$ alkyl;

each $R^b$ and $R^c$ is independently hydrogen or $C_1$-$C_6$ alkyl, or $R^b$ and $R^c$, taken together with the nitrogen atom to which they are attached to form a 3-7-membered heterocyclic ring;

each $R^f$ and $R^g$ is independently hydrogen or $C_1$-$C_6$ alkyl, or $R^f$ and $R^g$, taken together with the nitrogen atom to which they are attached to form a 3-7-membered heterocyclic ring optionally comprising one additional heteroatom selected from nitrogen and sulfur; and each $R^h$ is unsubstituted $C_1$-$C_4$ alkyl;

each $R^i$ is hydrogen, substituted methyl or $C_2$-$C_6$ alkyl, or $R^h$ and $R^i$, taken together with the nitrogen atom to which they are attached to form a 3-7-membered heterocyclic ring.

3. The compound of claim 1, wherein $R^{1a}$ and $R^{1b}$ are taken together with the carbon to which they are attached to form C(=O).

4. The compound of claim 1, wherein $R^{2a}$ or $R^{2b}$ is hydroxy, alkyl, or alkoxy.

5. The compound of claim 1, wherein $R^{1a}$ and $R^{1b}$ are taken together with the carbon to which they are attached to form C(=O) and $R^{2a}$ or $R^{2b}$ is hydroxy, alkyl, or alkoxy.

6. The compound of claim 1, wherein $R^{1a}$ or $R^{1b}$ is hydroxy, alkyl, or alkoxy.

7. The compound of claim 6, wherein $R^{1a}$ is hydroxy.

8. The compound of claim 6, wherein $R^{1a}$ is alkoxy.

9. The compound of claim 1, wherein $R^{1a}$ or $R^{1b}$ is hydroxy, alkyl, or alkoxy and $R^{2a}$ or $R^{2b}$ is hydroxy, alkyl, or alkoxy.

10. The compound of claim 4, wherein $R^{2a}$ is alkyl.

11. The compound of claim 4, wherein $R^{2a}$ is alkoxy.

12. The compound of claim 1, wherein $R^3$ is $C_1$-$C_6$ alkyl.

13. The compound of claim 1 selected from:

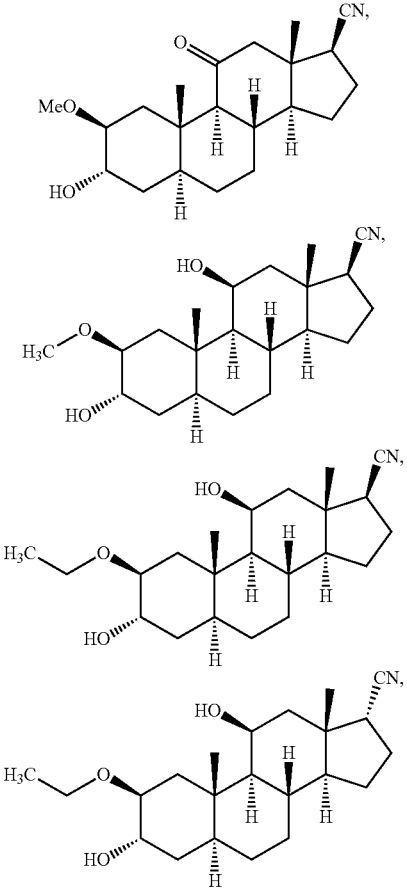

149
-continued
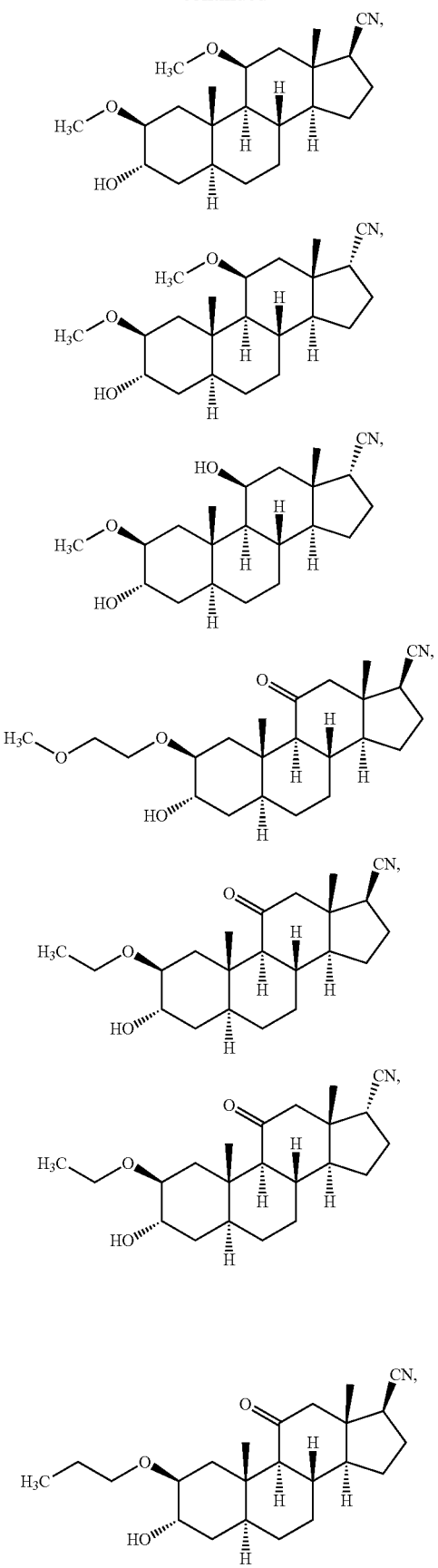
150
-continued
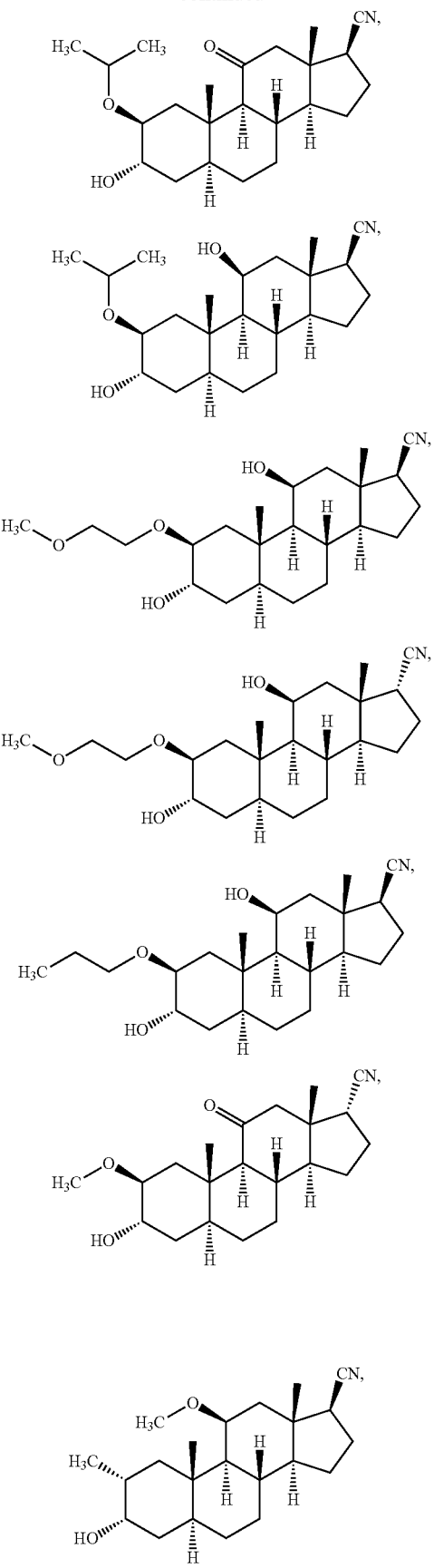

151
-continued
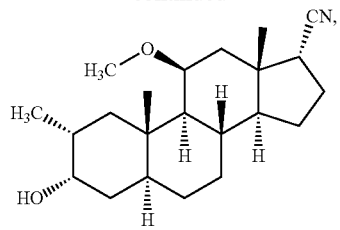
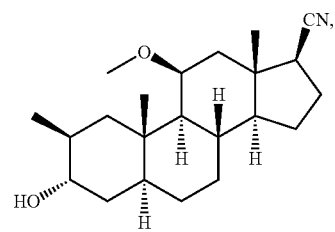
152
-continued
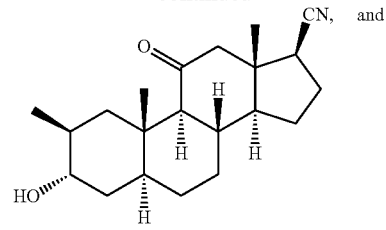
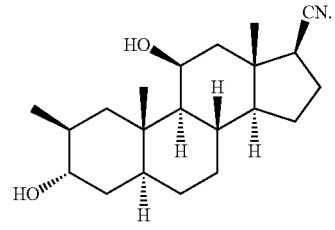
14. A pharmaceutical composition comprising a compound of claim 1, and a pharmaceutically acceptable excipient.
* * * * *